US007273698B2

(12) United States Patent
Lupski et al.

(10) Patent No.: US 7,273,698 B2
(45) Date of Patent: Sep. 25, 2007

(54) DEFECTS IN PERIAXIN ASSOCIATED WITH MYELINOPATHIES

(75) Inventors: James R. Lupski, Houston, TX (US); Cornelius F. Boerkoel, III, Houston, TX (US); Hiroshi Takashima, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 772 days.

(21) Appl. No.: 10/021,955

(22) Filed: Dec. 13, 2001

(65) Prior Publication Data

US 2003/0039987 A1 Feb. 27, 2003

Related U.S. Application Data

(60) Provisional application No. 60/255,217, filed on Dec. 13, 2000.

(51) Int. Cl.
*C12Q 1/68* (2006.01)
*C07H 21/02* (2006.01)

(52) U.S. Cl. ....................................... 435/6; 536/24.33

(58) Field of Classification Search .................... 435/6, 435/91.2; 536/22.1, 23.1, 24.33
See application file for complete search history.

(56) References Cited

U.S. PATENT DOCUMENTS

| | | | | |
|---|---|---|---|---|
| 5,306,616 | A | | 4/1994 | Lupski et al. |
| 5,420,112 | A | | 5/1995 | Lewis et al. |
| 5,569,648 | A | | 10/1996 | Lewis et al. |
| 5,599,920 | A | | 2/1997 | Patel et al. |
| 5,633,228 | A | | 5/1997 | Lewis et al. |
| 5,648,335 | A | | 7/1997 | Lewis et al. |
| 5,691,144 | A | * | 11/1997 | Boss et al. ..................... 435/6 |
| 5,723,593 | A | | 3/1998 | Lebo et al. |
| 5,780,223 | A | * | 7/1998 | Lupski et al. .................. 435/6 |
| 5,876,927 | A | | 3/1999 | Lebo et al. |
| 6,001,576 | A | | 12/1999 | Ananth et al. |
| 6,110,670 | A | | 8/2000 | Van Broeckhoven et al. |

OTHER PUBLICATIONS

Timmerman et al. Novel missense mutation in the early growth response 2 gene associated with Dejerine-Sttas syndrome phenotype. Neurology, vol. 52, pp. 1827-1832, 1999.*

Gillespie et al. Periaxin, a novel protein of myelinating schwann cells with a possible role in axonal ensheathment. Neuron, vol. 12, pp. 497-508, 1994.*

Guibot et al. A mutation in periaxin is responsible for CNT4F, an autosomal recessive form of Charcot-Marie-Tooth disease. Human Mol Genetics, vol. 10, No. 4, pp. 415-421, 2001.*

Roa et al. Dejerine-Scottas syndrome associated with point mutation in the peripheral myelin protein 22 (PMP22) gene. Nature Genetics, vol. 5, pp. 269-273, 1993.*

Kijima et al. Periaxin mutation causes early-onset but slow-progressive Charcot-Marie-Tooth disease. J Hum Genet., vol. 49, pp. 376-379, 2004.*

Takashima et al. Periaxin mutations cause a broad spectrum of demyelinating neuropathies. Ann NEurol., vol. 51, pp. 709-715 2002.*

Gillespie et al. The gene encoding the schwann cell protein periaxin localizes on mouse chromosome 7 (PRX). Geneomics, Vo 41, pp. 297-298, 1997.*

Boerkoel et al. Periaxin mutations cause recessive Dejerine-Sottas Neuropathy. Am. J. Hum. Genet., vol. 68, pp. 325-333, 2001.*

Guilbot et al. A mutation in periaxin is responsible for CMT4F, an autosomal recessive form of Charcot-Marie-Tooth disease. Human Mole.Genet., Vo. 10, No. 4, pp. 415-421, 2001.*

Gillespie et al. The gene encoding the schwann cell protein periaxin localizes on mouse chromosome 7 (PRX). Geneomics, vol. 41, pp. 297-298, 1997.*

Guilbot, Angele, et al.; A mutation in periaxin is responsible for CMT4F, an autosomal recessive form of Charcot-Marie-Tooth disease, Human Molecular Genetics, (2001) vol. 10., No. 4, pp. 415-421.

Delague, Valerie, et al.; Mapping of a new locus for autosomal recessive demyelinating charcot-marie-tooth disease to 19q13.1-13.3 in a large consanguineous lebanese family: exclusion of MAG as a candidate gene, Am. J. Hum. Genet. (2000) 67:236-243.

Williams, Anna C., et al.; The function of the periaxin gene during nerve repair in a model of CMT4F; J. Anat. (2002) 200, pp. 323-330.

Boerkoel, Cornelius F., et al.; Charcot-marie-tooth disease and related neuropathies: mutation distribution and genotype-phenotype correlation, Annals of Neurology (2002) 51:190-201.

Zhou, L., Griffin JW; Demyelinating neuropathies, Curr. Opin. Neurol. (Jun. 2003), 16:(3):307-313.p.

Martin, J.J., et al.; Neuropathology of some hereditary conditions affecting central and peripheral nervous system; Acta Neurol. Belg. (2002), 102, pp. 30-35.

Kijima, Kazuki, et al; Periaxin mutation causes early-onset but slow-progressive Charcot-Marie-Tooth disease; J. Hum. Genet., (2004) vol. 49, pp. 376-379.

Takashima, Hiroshi, et al.; Periaxin Mutations Caused a Broad Spectrum of Demyelinating Neuropathies; Ann. Neurol (2002), vol. 51, pp. 709-715.

Nagase et al., "Prediction of the Coding Sequences of Unidentified Human Genes. XVIII. The Complete Sequences of 100 New cDNA Clones from Brain Which Code for Large Proteins in vitro", DNA Res., 2000; 273-281; vol. 7.

Database NCBI Online, "Homo sapiens mRNA for KIAA1620 protein, partial ods", AB046840, Feb. 22, 2001.

Delague, Valerie, et al.; Mapping of a New Locus for Autosomal Recessive Demyelinating Charcot-Marie-Tooth Disease to 19g13. 1-13.3 in a Large Consanguineous Lebanese Family: Exclusion of MAG as a Candidate Gene; Am. J. Hum. Genet. 67:236-243,2000.

(Continued)

*Primary Examiner*—Suryaprabha Chunduru
(74) *Attorney, Agent, or Firm*—Fulbright & Jaworski, LLP

(57) ABSTRACT

The present invention relates to defects in periaxin (PRX) associated with myelinopathies, including Charcot-Marie-Tooth syndrome and/or Dejerine-Sottas syndrome. Unrelated individuals having a myelinopathy from Dejerine-Sottas syndrome have recessive PRX mutations. The PRX locus maps to a region associated with a severe autosomal recessive demyelinating neuropathy and is also syntenic to the Prx location on murine chromosome 7.

35 Claims, 9 Drawing Sheets

OTHER PUBLICATIONS

Lupski, James R., et al.; Charcot-Marie-Tooth Peripheral Neuropathies and Related Disorders; In: The Metabolic and Molecular basis of Inherited diseases, $8^{th}$ edition, McGraw-Hill, New York, Chapter 227, pp. 5759-5788, 2001.

Hayasaka, Kiyoshi, et al.; De novo mutation of the myelin Po gene in Dejerine-Sottas disease (hereditary motor and sensory neuropathy type III); Nature Genetics, vol. 5, pp. 266-268, Nov. 1993.

Lupski, James R.; Invited Editorial—Axonal Charcot-Marie-Tooth Disease and the Neurofilament Light Gene (NF-L); Am. J. Hum. Genet. 67:8-10, 2000.

Parman, Yesim, et al.; Recessive Inheritance of a New Point Mutation of the PMP22 Gene in Dejerine-Sottas Disease; Ann Neurol 1999; 45:518-522.

Roa, Benjamin B., et al.; Dejerine-Sottas syndrome associated with point mutation in the peripheral myelin protein 22 (PMP22) gene; Nature Genetics, vol. 5, pp. 269-273, Nov. 1993.

Timmerman, V., et al.; Novel missense mutation in the early growth response 2 gene associated with Dejerine-Sottas syndrome phenotype; Neurology 1999; 52:1827-1832.

Warner, Laura E., et al.; Mutations in the early growth response 2 (EGR2) gene are associated with hereditary myelinopathies; Nature Genetics, vol. 18, pp. 382-384, Apr. 1998.

Scherer, Steven S., et al.; Periaxin expression in myelinating Schwann cells: modulation by axon-glial interactions and polarized localization during development; Development 121, 4265-4273 (1995).

Gillespie, C. Stewart, et al.; Periaxin, a Novel Protein of Myelinating Schwann Cells with a Possible Role in Axonal Ensheathment; Neuron, vol. 12, 497-508, Mar. 1994.

Gillespie, C.S., et al.; The Gene Encoding the Schwann Cell Protein Periaxin Localizes on Mouse Chromosome 7 (Prx); Genomics 41, 297-298 (1997).

Gillespie, C. Stewart, et al.; Peripheral Demyelination and Neuropathic Pain Behavior in Periaxin-Deficient Mice; Neuron, vol. 26, 523-531, May 2000.

Dytrych, Lee, et al.; Two PDZ Domain Proteins Encoded by the Murine Periaxin Gene Are the Result of Alternative Intron Retention and Are Differentially Targeted in Schwann Cells; The Journal of Biological Chemistry, vol. 273 (10), pp. 5794-5800, Mar. 6, 1998.

* cited by examiner a  L-periaxin

```
                                                                                    PDZ Domain
Human    1 MEARSRSAEELRRAELVEIIVETEAQTGVSGINVAGGGKEGIFVRELREDSPAARSLSLQEGDQLLSARVFFENFKYEDALRLLQCAEPYKVSFCLK  97
Murine   1 ::::.:::::::::::::::::::::::::::::::F::::::::::::::::::K::::::::::::::::::::::::::::::::::::::::  97
Rat      1 ::..::.......::::::::::::::::::::::::F::::::::::::::::::K::::::::::::::::::::::::::::::::::::::::  97
                              NLS1                                              NLS2              NLS3
Human    RTVPTGDLALRPGTVSGYEIKGPRAKVAKLNIQSLSPVKKKKMVPGALGVPADLAPVDVEFSFPKFSRLRRGLKAEAVKGPVPAAPARRRLQLPRLRVRE  197
Murine   ::::.:.:::::::::::::M::::::::::::A::::::T::::T.:.:::::::::::::::::::::::::::D:::::::::::::::::::::  197
Rat      ::::::::::::::::::::M::::::::::::I:T:::T:::::::::::::::::::::::::::::::::::::D:::::::::::::::::::  197

Human    VAEEAQAARLAAAAPPPRKAKVEAEVAAGARFTAPQVELVGPRLPGAEVGVPQVSAPKAAPSAEAAGGFALHLPTLGLGAPAPPAVEAPAVGIQVPQVEL  297
Murine   :::::V..M:::::::::A:::A:T..G:::::I:::.::::::S:::::::::::V::GT..T:::S::::............:::P::T::.::::  297
Rat      ::-::.V..M-::::S.::.S::::T::G:-::I...::.::::S:::::::::::K::V::GT..T::S:::..........A::::P-TT::.::::  297

Human    PALPSLPTLPTLPCLETREGAVSVVVPTLDVAAPTVGVDLALPGAEVEARGEAPEVALKMPRLSFPRFGARAKEVAEAKVAKVSPEARVKGPRLRMPTFG  397
Murine   :T::::.::::::D:Q:..AV:K::::.:.:::SM.::::::::::Q::V::::::.::::.:::::I.G.:AT:::V:G::::KA::::::::::::  397
Rat      :T::::::::::::D:Q:..AV:K::::...:::S:E::::::::::Q::V::::::::::::::::::::V:G::AT:::VKG.:::KA::::::::::  397
                                                                              Repeat Domain
Human    LSLLEPRPAAPE-VVESKLKLPTIKHPSLGIGVSGPEVKVPKGPEVKLPKAPEVKLPKVPEAALPEVRLPEVELPKVSEHKLPKVPEMAVPEVRLPEVEL  496
Murine   :..::.: SG::A:A:.:. :::.L::::F::::A::::::A:T:::::::V::::::::.::::I:D:Q:::::Q...H:D.::::I::::V::D::::Q:  497
Rat      :::::S .SG::VAA::::::::L::::F::S:A::::::A::::::::V::I:-----------------------------------------:  453

Human    PKVSEMKLPKVPEMAVPEVRLPEVQLLKVSEMKLPKVPEMAVPEVRLPEVQLPKVSEMKLPEVSEVAVPEVRLPEVQLPKVPEMKLPKVPEMKLP  596
Murine   ::.P::::V:---------------------::::W::::D:H:::::P:::::M:::D:H:::D::::::::::::::::::L:::::::::::AV:  576
Rat      ::AP:AAI:------D:Q::::::P:MSD:::::I:::::D:H:::::K:::::P:::V::HKLPKI::MAV:D:H::DIQLP::::::::DMKLP:V:  545

Human    EHKLPEVQLPKV--------PEMAVPDVHLPEVQLPKVPEMKLPEMKLPKVPEMKLPKVPEMAVPEVRLPEVQLPKVPEMKLPKMPEMAVPEVRLPEVQLPKV  689
Murine   DVR.:::::::..SEVKLPKM:::::::::::L::::----------:MS:::::::M.:::::::R::::::::S:.:::::::TM.DI:::::::-  665
Rat      ::AV:D:H::DIQLPKVPEMKLPDMKLPKV..MAV:D::IPEVQLP:VS::::I:D::::R::.L:::MS.V:::I:D::::D..::::.::..:: 645

Human    SEMKLPKVPEMAVPDVHLPEVQLPKVCEMKVPDMKLPEIKLPKVPEMAVPDVHLPEVQLPKVSEIRLPEMQVPKVPDVHLPKAPEVKLPRAPEVKLKATK  788
Murine   -----------::::I-----------:::L:E:::::::::::D:::::P:::L:::::D::::::::SQ::E:Q::::M::M::SKV::::R:SAG  740
Rat      ::L:::::::::TM::IR::::::::::::::::::I::::::::::::::P:::L:::::::-----:::Q:::::::::::V::M::KV::A:R:SAG  730

Human    AEQAEGMEFGFKMPKMTHPKLGRAESPSRGKPGEAGAEVSGKLVTLPCLQPEVDGEA-HVGVPSLTLPSVELDLPGALGLQGQVPAAKMGKGERAEGPEV  887
Murine   ::::K:T::S::L:::::::::KV-----::::SI:::PD::MT:::::::GT':S::.:::S::::::::::::::::::::::E:::QE:VP::V:KP:::R:  835
Rat      :::::KT::S::L::::V:::KVT-----:::::::I::PD::LI::::::GT:VAR::::S::::::::::::::::E:::QE:VS::V'KP:.:R:  825

Human    AAGVREVGFRVPSVEIVTPQLPAVEIEEGRLEMIETKVKPSSKFSLPKFGLSGPKVAKAEAEGAGRATKLKVSKFAISLPKARVGAEAEAKGAGEAGLLP  987
Murine   :V::G:..:::::::::::::TV:V:KEQ:::V:M:::::::::::::AV:G:V::P:::::::::.T:::::A:T:::::::::::::::::::::  935
Rat      :V:TG:A::.::::::::N:::T:.:VKKEQ:::V^M:::T:::::::AV::V::P::::::::::::::R::A:TD:D:::::::::::::::  925

Human    ALDLSIPQLSLDAHLPSGKVEVAGADLKFKGPRFALPKFGVRGRDTEAAELVPGVAELEGKGWGWDGRVKMPKLKMPSFGLARGKEAEVQGDRASPGEKA  1087
Murine   :::::.:.::::Q:::::..:---:S:P.SS:::::::::K:::S::DV::A:E:::::.:::::::K::::::.:::::S::::::T:DG:V:::::L  1033
Rat      :::.:::::::Q::::::::ES:P::S:::::::AK:::S::DV::A:E::..:::::::K:::.:::::::::S::::::I:DG:V:::::L  1025
                                                                     Acidic Domain
Human    ESTAVQLKIPEVELVMTLGAQEEGRAEGAVAVSGNQLSGLKVSTARQVVTEGHDAGLRMPPLGISLPDVELTGFGEAGTPGGQAQSTVPSAEGTAGYRVQV  1187
Murine   :AI:G::::::A::::::P::TEK:::T-::::VKP::Q:::TG:::A::QESVQ::VST::::::::::::AS:::::::EIV::::::::S::::  1123
Rat      :AI:G::::::::::::P::TEK:::T-::::VKP::Q:::::::::::QEGAQ:VSS:::::::::::AS::::::EIA:::::::::::V:S:I::  1115

Human    PDVELSLFGAQVAGGELLVGEGVFKMP:TVTVPQL:ELDVGLSREAQAGEAATGEGGLRLKLPTLGARARVGGEGAEEQPPGAERTFCLSLPDVELSPSGGN  1287
Murine   ::::F:::T::::D:::::::I:::::::::::::::::::::::GH:::::::::KS:::IK:'-----GTGSR:':V:P:G:E:Q'::H::.::::TSPVSS  1221
Rat      ::::ME:::T::::D:::::::::::::::::::::::::::::::GH:::::T:KS:::K:::.::G:GGK::::::A:S:E:QH::HI::::::TSPVSS  1213

Human    HAEYQVAEGEGEAGHKLKVRLPRFGLVRAKEGAEEGEKAKSPKLRLPRVGFSQSEHVTGEGSPSPEEEEEEEEGSGEGASGRRGRVRVRLPRVGLAAPS  1387
Murine   :.:::V::D:DG::::::::L.::AK::::I:V::V:::::::::::::::S:S::::::::::::----:::::::S:::::.:::::::S.:  1317
Rat      :.:::V:D:DG:::::::::L.::A:::::I:T:::V:::::::::::::::::SAS::::::::::---::::::::::::::::::::S:.:  1309

Human    KASRGQEGDAAPKSPVREKSPKFRFPRVSLSPKARSGSGDQEEGGLRVRLPSVGFSETG------APGPARMEGAQAAAV*  1461
Murine   :V:K::::::TS:::G::::::::::::::::::::::::::::R:R:::F::::::TA------VP:.T:I':T.:::I*  1391
```

b  S-periaxin

```
                                                                                    PDZ Domain
Human    1 MEARSRSAEELRRAELVEIIVETEAQTGVSGINVAGGGKEGIFVRELREDSPAARSLSLQEGDQLLSARVFFENFKYEDALRLLQCAEPYKVSFCLK  97
Murine   1 ::::.:::::::::::::::::::::::::::::::F::::::::::::::::::K::::::::::::::::::::::::::::::::::::::::  97
Rat      1 ::..:::::::::::::::::::::::::::::::::F::::::::::::::::::K::::::::::::::::::::::::::::::::::::::::  97

Human    RTVPTGDLALRPGTVSGYEIKGPRAKVAKLVRVLSPAPALDCPSDPVSA-P*  147
Murine   ::::::::::::::::::::M::::::::::::V:VQ:S:::R:A:A:*   148
Rat      ::::::::::::::::::::M::::::::::::::::::::::A::::    147
```

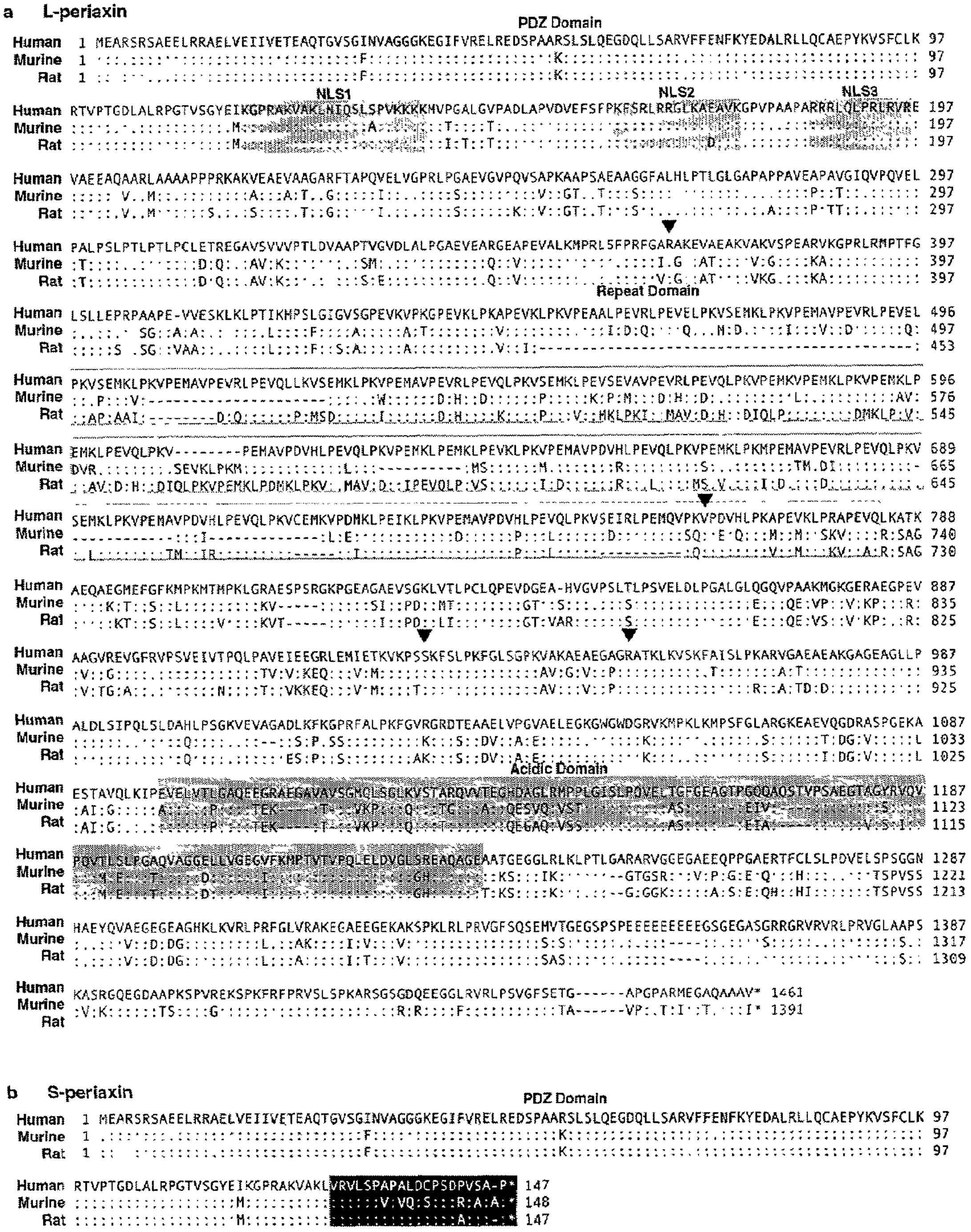

FIG. 2

| Patient | Phenotype | Pathogenic Allele 1 | Frequency | Pathogenic Allele 2 | Frequency |
|---|---|---|---|---|---|
| 851 | DSN | 2857C>T R953X | 0/190 | 2787ΔC S929fsX957 | 0/190 |
| 1461 | DSN | 1102C>T R368X | 0/178 | 2289ΔT V763fsX774 | 0/176 |
| 1136 | DSN | 2787ΔC S929fsX957 | 0/190 | 2787ΔC S929fsX957 | 0/190 |

| Patient | Phenotype | Pathogenic Allele 1 | Frequency | Pathogenic Allele 2 | Frequency |
|---|---|---|---|---|---|
| PN44.1 | CMT | C715X | 0/180 | C715X | 0/180 |
| PN44.4 | CMT | C715X | 0/180 | C715X | 0/180 |
| PN761.3 | CHN | R82fsX96 | 0/190 | R82fsX96 | 0/190 |
| 851 | DSN | R953X | 0/190 | S929fsX957 | 0/190 |
| 1461 | DSN | R368X | 0/178 | V763fsX774 | 0/176 |
| 1136 | DSN | S929fsX957 | 0/190 | S929fsX957 | 0/190 |
| CMT4F | DSN | R196X | | R196X | |

DEFECTS IN PERIAXIN ASSOCIATED WITH MYELINOPATHIES

The present invention claims priority to U.S. Provisional Patent Application 60/255,217, filed Dec. 13, 2000.

The present invention was developed with funds from the United States Government. Therefore, the United States Government may have certain rights in the invention.

FIELD OF THE INVENTION

The present invention is directed to the fields of molecular biology, molecular genetics, and neurology. More specifically, the present invention is directed to defects in periaxin related to neuropathies. More specifically, the neuropathies include recessive Dejerine-Sottas and Charcot-Marie-Tooth disease.

BACKGROUND OF THE INVENTION

Dejerine-Sottas neuropathy (DSN) and Charcot-Marie-Tooth disease type 1 (CMT1) represent genetically heterogeneous inherited peripheral myelinopathies. These conditions constitute part of a spectrum of neuropathy phenotypes ranging in severity from congenital hypomyelinating neuropathy (CHN) to adult onset hereditary neuropathy with liability to pressure palsies (HNPP) (Lupski and Garcia, 2001). At least fifteen genetic loci and six genes have been associated with these disorders; identified genetic causes include altered dosage of peripheral myelin protein 22 (PMP22) or mutations in one of the following genes: PMP22, the gap junction protein β1 gene (GJB1), the myelin protein zero gene (MPZ), the early growth response gene 2 (EGR2), the myotubularin related protein 2 gene (MTMR2), or the N-myc downstream regulated gene 1 (NDRG1)) (Lupski and Garcia, 2001). These genes encode proteins of diverse functions: compact myelin structural proteins (MPZ, PMP22), a non-compact myelin gap junction protein (GJB1), signal transduction proteins (NDRG1, MTMR2), and a transcription factor for late myelin genes (EGR2). Both dominant (PMP22, GJB1, MPZ, EGR2) and recessive (MTMR2, NDRG1, PMP22, EGR2) mutant alleles have been described. Historically considered an autosomal recessive disorder (Dejerine and Sottas, 1893), DSN has been associated predominately with de novo dominant mutations in PMP22 (Roa et al., 1993), MPZ (Hayasaka et al., 1993), or EGR2 (Timmerman et al., 1999), although rare recessive mutations in PMP22 have also been reported (Lupski, 2000; Parman et al., 1999).

In murine embryonic Schwann cells, L-periaxin is initially concentrated in the nuclei but redistributes to the plasma membrane, predominantly adaxonal, with initiation of myelination and then to the abaxonal, Schmidt-Lanterman incisures, and paranodal membranes with maturation of the myelin sheath (Scherer et al., 1995; Sherman and Brophy, 2000). In addition, L-periaxin expression recapitulates this pattern following crush injury (Scherer et al., 1995). This shift in periaxin localization after the spiralization phase of myelination suggests that periaxin participates in membrane-protein interactions that are required to stabilize the mature myelin sheath. As a cytoskeleton-associated protein, L-periaxin may mediate such stabilization by facilitating integration of extracellular signaling through the cytoskeleton which is essential for changes in Schwann cell shape and regulation of gene expression during axonal ensheathment (Fernandez-Valle et al., 1997; Tapon and Hall, 1997). Such a signaling function is supported by the observation that L-periaxin contains a PDZ motif, a domain implicated in the assembly of signaling complexes at sites of cell-cell contact, and a nuclear localization signal (Dytrych et al., 1998; Sherman and Brophy, 2000). Confirming the necessity of periaxin for maintenance of the myelin sheath, Gillespie et al. recently demonstrated that $Prx^{-/-}$ mice ensheathe and myelinate peripheral axons apparently normally but subsequently develop a severe demyelinating neuropathy associated with allodynia (pain from non-noxious stimuli) and hyperalgesia (hypersensitivity to pain) (Gillespie et al., 2000).

However, it was heretofore unknown in the art whether a relationship between the human PRX gene defects and neuropathies such as recessive DSN existed.

SUMMARY OF THE INVENTION

In an embodiment of the present invention there is a method of diagnosing myelinopathy in an individual comprising the steps of obtaining a sample containing nucleic acid from the individual; assaying the sample for an alteration in a periaxin polynucleotide, wherein the alteration is associated with the myelinopathy. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy syndrome (RLS). In another specific embodiment, the assaying step further comprises a polymerase chain reaction. In a further specific embodiment, the primers for said polymerase chain reaction are selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26. In a specific embodiment, the alteration is 3775G>A, 1216G>A, 4075-4077d, 1483G>C, 3394A>G, 3248C>G, 2763A>G, 2645C>T, 306C>T, 1491C>G, or 2655T>C.

In another embodiment of the present invention there is a method of diagnosing myelinopathy in an individual comprising the steps of obtaining a sample containing protein from the individual; assaying the sample for an alteration in a periaxin polypeptide, wherein the alteration is associated with the myelinopathy. In a specific embodiment, the alteration is E1259K, A406T, E1359delΔ, E495Q, R1132G, P1083R, I921M, A882V, T102T, P497P, P885P, R953X, R368X, S929fsX957, R196X, V763fsX774, C715X, or R82fsX96. In another specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment of the present invention there is as a composition of matter a defect of a periaxin polynucleotide of 3775G>A, 1216G>A, 4075-4077d, 1483G>C, 3394A>G, 3248C>G, 2763A>G, 2645C>T, 306C>T, 1491C>G, and 2655T>C.

In an additional embodiment of the present invention there as a composition of matter a periaxin polypeptide defect of E1259K, A406T, E1359delΔ, E495Q, R1132G, P1083R, I921M, A882V, T102T, P497P, P885P, R953X, R368X, S929fsX957, R196X, V763fsX774, C715X, or R82fsX96.

In another embodiment of the present invention there is a method of identifying a compound for the treatment of myelinopathy comprising the steps of exposing the compound to a knockout animal, wherein the animal comprises at least one defective allele of a periaxin polynucleotide and wherein the animal has at least one symptom associated with the myelinopathy; and assaying for an improvement in said at least one symptom of the myelinopathy after exposure to the compound. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In an additional embodiment of the present invention there is a method of screening for a compound for the treatment of myelinopathy comprising the steps of providing a cell lacking a functional periaxin amino acid sequence contacting the cell with the compound; and determining the effect of the compound on the cell, wherein said effect on the cell is indicative of the treatment of the myelinopathy. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In a further embodiment of the present invention there is a method of identifying an upregulator of periaxin nucleic acid sequence expression comprising the steps of administering a test compound to a transgenic animal, wherein the genome of the transgenic animal comprises a reporter nucleic acid sequence , wherein the sequence is under the control of an operably linked periaxin promoter active in eukaryotic cells; measuring the level of said periaxin expression; and comparing the level of the periaxin expression in the animal with normal periaxin expression, wherein an increase in the level following administration of the test compound indicates the test compound is an upregulator.

In another embodiment of the present invention there is a method of identifying a drug having activity in the treatment of myelinopathy, comprising the steps of obtaining a compound suspected of having extracellular signaling activity; and determining whether the compound has the extracellular signaling activity. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment of the present invention, there is a method of treating myelinopathy in an organism, comprising the step of administering to the organism a therapeutically effective amount of a periaxin nucleic acid sequence, wherein the nucleic acid sequence is administered by a vector. In a specific embodiment, the vector is selected from the group consisting of a plasmid, a viral vector, a lipid, a liposome, a polypeptide, or a combination thereof. In another specific embodiment the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment of the present invention there is a method of treating myelinopathy in an organism comprising the step of administering to said organism a therapeutically effective amount of a periaxin amino acid sequence, wherein said amino acid sequence is administered with a physiologically acceptable carrier. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In an additional embodiment of the present invention there is a method of treating an animal for a myelinopathy comprising the steps of identifying a compound which interacts with a periaxin polypeptide; and administering to the animal a therapeutically effective amount of the compound. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment of the present invention there is a method of treating a patient for a myelinopathy comprising the steps of preparing a compound obtained by a method from herein and administering the compound with a physiologically acceptable carrier to said patient.

In another embodiment of the present invention there is a kit for diagnosing a myelinopathy in an animal comprising at least two primers, wherein one primer is specific to a sense periaxin nucleic acid sequence and another primer is specific to an antisense periaxin nucleic acid sequence. In a specific embodiment the primers are SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26.

In another embodiment of the present invention there is as a composition of matter a nucleic acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26.

In an additional embodiment of the present invention, there is a method of detecting the presence or absence of a mutation associated with a myelinopathy, the method comprising a) isolating a test nucleic acid from a subject, said test nucleic acid comprising a periaxin polynucleotide; b) comparing the test nucleic acid to a reference wild-type periaxin polynucleotide; and c) determining the differences between the test nucleic acid and the reference wild-type periaxin polynucleotide, wherein the differences are mutations in the periaxin polynucleotide of the subject, and wherein the presence of a mutation in the periaxin polynucleotide of the subject is indicative of the presence of the myelinopathy in the subject.

In a specific embodiment, the mutation is in SEQ ID NO:1 and is 3775G>A, 1216G>A, 4075-4077d, 1483G>C, 3394A>G, 3248C>G, 2763A>G, 2645C>T, 306C>T, 1491C>G, 2655T>C, 2145T>A, or 247ΔC. In another specific embodiment, the mutation encodes a defect of an amino acid sequence of SEQ ID NO:2 and is E1259K, A406T, E1359delΔ, E495Q, R1132G, P1083R, I921M, A882V, T102T, P497P, P885P, R953X, R368X, S929fsX957, R196X, V763fsX774, C715X, or R82fsX96. In another specific embodiment, the periaxin polynucleotide is SEQ ID NO:1. In an additional specific embodiment, the comparing step is by DHPLC, sequencing, or hybridization.

Other and further objects, features, and advantages would be apparent and eventually more readily understood by reading the following specification and by reference to the accompanying drawings forming a part thereof, or any examples of the presently preferred embodiments of the invention are given for the purpose of the disclosure.

BRIEF DESCRIPTION OF THE FIGURES

FIG. 1*a* demonstrates that by ePCR and fluorescent in situ hybridization (FISH), BAC CTC-492K19, which contains PRX, maps between D19S324 and D19S223.

FIG. 1*b* illustrates a diagram showing the two PRX mRNAs resulting from alternative retention of intron 6. The large periaxin protein (L-PRX) is encoded by the shorter spliced mRNA and the smaller periaxin protein (S-PRX) by the longer mRNA retaining intron 6. Coding regions are shaded.

FIG. 1*c* demonstrates northern blot analysis of both the 5.1 and 5.6 kb PRX mRNAs.

FIGS. 2A through 2B demonstrate a comparison of human, murine and rat L-periaxin (2A) and S-periaxin (2B) amino acid sequences.

FIG. 2A shows human L-periaxin having approximately 78 and 73 percent sequence identity with the murine and rat proteins, respectively. The PDZ domain, tripartite nuclear localization signal (NLS1, NLS2, NLS3), repeat domain and acidic domain previously characterized in mice and rats are conserved in humans. Arrowheads indicate mutations identified in patients.

FIG. 2*b* shows S- and L-periaxin share a common amino terminal, but retention of intron 6 in the mRNA encoding S-periaxin results in a truncated protein with 20 amino acids encoded within the intron (black box). Identical amino acids are indicated by a colon (:), gaps by a dash (-) and stop codons by an asterisk (*).

In FIG. 6A, there is a transverse section showing loss of myelinated fibers of all sizes, onion bulbs (arrows) which were sometimes denervated (arrowheads) and tomacula formations. A complex of grouped, proliferated Schwann cell processes surrounded a myelinated axon (inset). (Magnification×637). In FIG. 6B, there is increased connective tissue and demyelinated (thin arrows) or thinly remyelinated (arrowheads) nerve fibers. Atrophic axons with relatively thick myelin sheaths are also apparent. A tomaculous fiber is indicated by a thick arrow, a demyelinated axon by a thin arrow, and thinly remyelinated fibers by arrowheads. (Magnification×900.)

In FIG. 7A, there is heminode showing paranodal myelin folds and a Schwann cell process separating terminal myelin loops from the axon. (Magnification×11.600.) In FIG. 7B, there are abnormalities of paranodal myelin loops and the absence of septate-like junctions or transverse bands (arrows). The myelin loops and axon are separated by a Schwann cell process (*). There were no abnormalities of the myelin packing. (Scale 0.1 μm). In FIG. 7C, normal myelin is shown. Note the well-developed septate-like junctions or transverse bands (arrows) of normal paranodal myelin. Also note the desmosome-like structures (big arrow). (Scale 0.1 μm.)

In FIGS. 8D, 8E, and 8F, nerve fibers are shown from patient PN-44.1 show staining with repeat region PRX antibody (8D), and MBP (8E) , which colocalise (8F). In FIGS. 8G, 8H, and 8I, there are nerve fibers from patient PN-44.1 show no staining with C-terminal PRX antibody (8G), but staining with MBP (8H), indicating that a truncated PRX protein is formed. In FIGS. 8J, 8K, and 8L, there are nerve fibers from a normal control show staining with the C-terminal PRX antibody (8J), and MBP (8K), which colocalise (8L). Note the organized staining of PRX in the Schmidt-Lantermann incisures, which is not present in the patient. (Scale 5 μm)

DESCRIPTION OF THE INVENTION

Figure 1:
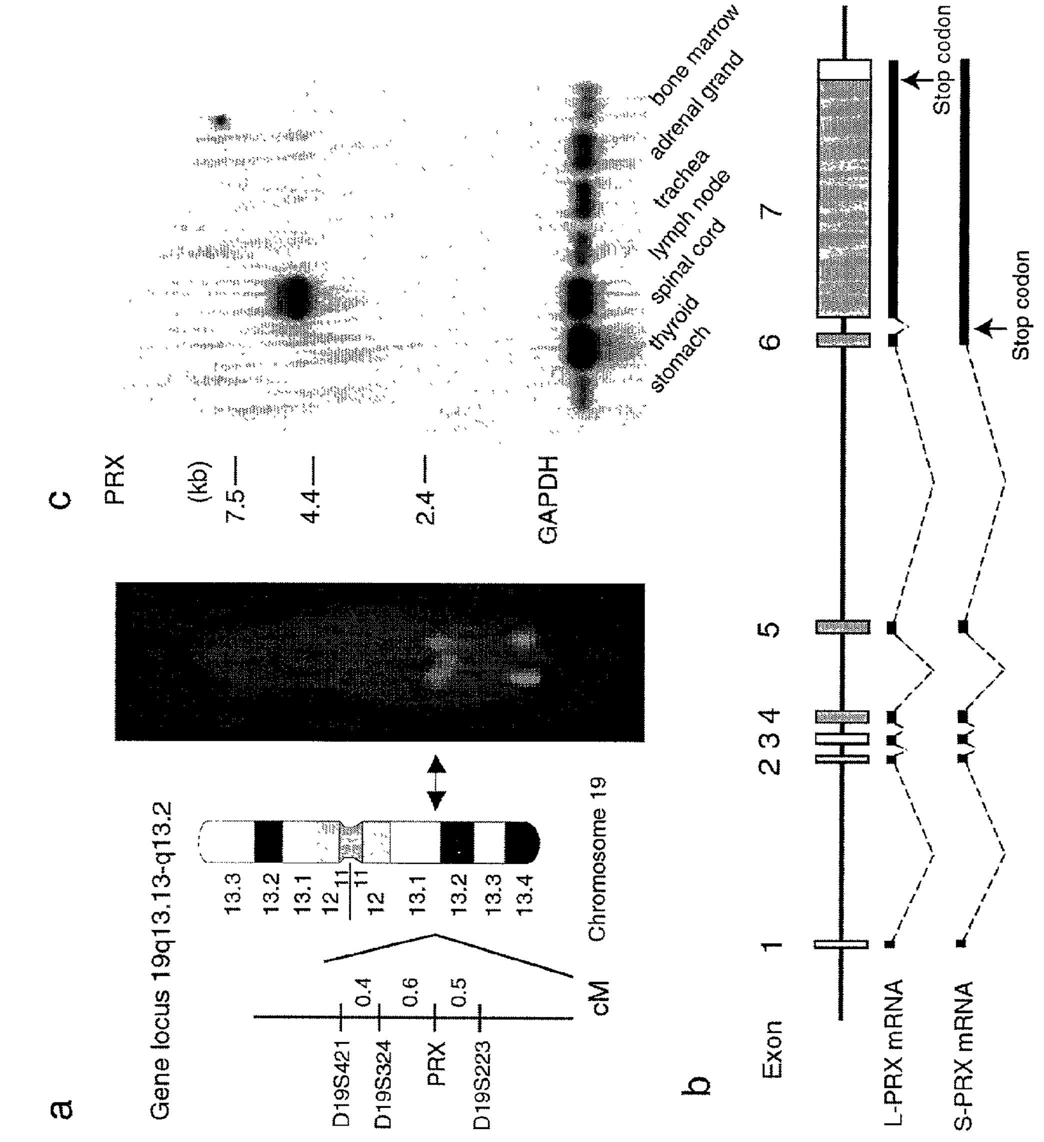
FIGS. 1*a* through 1*c* illustrate mapping of PRX and expression of PRX mRNA.

It is readily apparent to one skilled in the art that various embodiments and modifications may be made to the invention disclosed in this Application without departing from the scope and spirit of the invention.

As used in the specification, “a” or “an” may mean one or more. As used in the claim(s), when used in conjunction with the word “comprising”, the words “a” or “an” may mean one or more than one. As used herein “another” may mean at least a second or more.

I. DEFINITIONS

The term "extracellular signaling activity" as used herein is defined as the function of mediating, facilitating integration with other factors of, or contributing either directly or indirectly to signaling between a factor outside the cell and a factor inside the cell, such as the cytoskeleton. In a preferred embodiment, the extracellular signaling through the cytoskeleton is essential for changes in Schwann cell shape and regulation of gene expression during axonal ensheathment.

The term "fragments or derivatives" as used herein is defined as portions or variants of a specific nucleic acid or amino acid which retains at least one specific function of the parent sequence. For instance, if an amino acid sequence of SEQ ID NO:1 is utilized for extracellular signaling, then the fragment or derivative would also have extracellular signaling activity. Alternatively, if an amino acid sequence (such as a peptide, polypeptide or protein) of SEQ ID NO:1 is utilized for interacting with another polypeptide or nucleic acid, such as in a complex, then the fragment or derivative of SEQ ID NO:1 would likewise interact with the polypeptide or nucleic acid. The fragments may be from any location within the nucleic acid or amino acid sequence and may be of any size up to the full sequence size. Derivatives may comprise a mutation, translocation, deletion, duplication, polymorphism, such as a single nucleotide polymorphism, insertion, and others known to a skilled artisan. Derivatives of an amino acid sequence, such as a polypeptide, may contain at least one modification of at least one amino acid residue, such as methylation, phosphorylation, acetylation, or other modifications standard in the art.

The term "myelinopathy" as used herein is defined as a defect in myelin, a lipid substance which forms a sheath around nerve fibers. The defect may be absence of myelin, loss of myelin, or faulty myelin. In specific embodiments, the myelinopathy results in Charcot-Marie-Tooth (CMT) syndrome, hereditary neuropathy with liability to pressure palsies (HNPP), Dejerine-Sottas syndrome (DSS), congenital hypomyelinating neuropathy (CHN), and/or Roussy-Levy Syndrome. A skilled artisan is aware myelin is also referred to as a white substance representing membrane extensions of Schwann cells which ensheathe the peripheral nerve axon. Peripheral nerve myelinopathy refers to myelin of the peripheral nerve.

The terms "neuropathy" or "neuropathies" as used herein is defined as a functional defect or defects and/or a pathological change or changes in the peripheral nervous system. In a specific embodiment, the neuropathy is Charcot-Marie-Tooth (CMT) syndrome, hereditary neuropathy with liability to pressure palsies (HNPP), Dejerine-Sottas syndrome (DSS), congenital hypomyelinating neuropathy (CHN), and/or Roussy-Levy Syndrome.

The term "periaxin promoter" as used herein is defined as a nucleic acid sequence which under native conditions regulates expression of a periaxin nucleic acid sequence. The promoter may be from any organism.

The term "vector" is used to refer to a carrier nucleic acid molecule into which a nucleic acid sequence can be inserted for introduction into a cell where it can be replicated.

II. THE PRESENT INVENTION

A. Embodiments

In an embodiment of the present invention there is a method of diagnosing myelinopathy in an individual comprising the steps of obtaining a sample containing nucleic acid from the individual; assaying the sample for an alteration in a nucleic acid sequence of SEQ ID NO:1, wherein the alteration is associated with the myelinopathy. In a specific embodiment, the myelinopathy is selected from the group consisting of Charcot-Marie-Tooth (CMT) syndrome, hereditary neuropathy with liability to pressure palsies (HNPP), Dejerine-Scottas syndrome (DSS), congenital hypomyelinating neuropathy (CHN), and Roussy-Levy syndrome (RLS). In another specific embodiment, the assaying step further comprises a polymerase chain reaction. In a further specific embodiment, the primers for said polymerase chain reaction are selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26. In a specific embodiment, the alteration is in SEQ ID NO:1 and is selected from the group consisting of 3775G>A, 1216G>A, 4075-4077d, 1483G>C, 3394A>G, 3248C>G, 2763A>G, 2645C>T, 306C>T, 1491C>G, and 2655T>C.

In another embodiment of the present invention there is a method of diagnosing myelinopathy in an individual comprising the steps of obtaining a sample containing protein from the individual; assaying the sample for an alteration in an amino acid sequence of SEQ ID NO:2, wherein the alteration is associated with the myelinopathy. In a specific embodiment, the alteration is in SEQ ID NO:2 and is selected from the group consisting of E1259K, A406T, E1359Δ, E495Q, R1132G, P1083R, I921M, A882V, T102T, P497P, and P885P. In another specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment of the present invention there is as a composition of matter a defect of a nucleic acid sequence of SEQ ID NO:1 and is selected from the group consisting of 3775G>A, 1216G>A, 4075-4077d, 1483G>C, 3394A>G, 3248C>G, 2763A>G, 2645C>T, 306C>T, 1491C>G, and 2655T>C.

In an additional embodiment of the present invention there as a composition of matter a defect of an amino acid sequence of SEQ ID NO:2 and is selected from the group consisting of E1259K, A406T, E1359Δ, E495Q, R1132G, P1083R, I921M, A882V, T102T, P497P, and P885P.

In another embodiment of the present invention there is a method of identifying a compound for the treatment of myelinopathy comprising the steps of exposing the compound to a knockout animal, wherein the animal comprises at least one defective allele of a nucleic acid sequence of SEQ ID NO:1 and wherein the animal has at least one symptom associated with the myelinopathy; and assaying for an improvement in said at least one symptom of the myelinopathy after exposure to the compound. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In an additional embodiment of the present invention there is a method of screening for a compound for the treatment of myelinopathy comprising the steps of providing a cell lacking a functional periaxin amino acid sequence contacting the cell with the compound; and determining the effect of the compound on the cell, wherein said effect on the cell is indicative of the treatment of the myelinopathy. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In a further embodiment of the present invention there is a method of identifying an upregulator of periaxin nucleic acid sequence expression comprising the steps of administering a test compound to a transgenic animal, wherein the genome of the transgenic animal comprises a reporter nucleic acid sequence, wherein the sequence is under the control of an operably linked periaxin promoter active in eukaryotic cells; measuring the level of said periaxin expression; and comparing the level of the periaxin expression in the animal with normal periaxin expression, wherein an increase in the level following administration of the test compound indicates the test compound is an upregulator.

In another embodiment of the present invention there is a method of identifying a drug having activity in the treatment of myelinopathy, comprising the steps of obtaining a compound suspected of having extracellular signaling activity; and determining whether the compound has the extracellular signaling activity. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment of the present invention, there is a method of treating myelinopathy in an organism, comprising the step of administering to the organism a therapeutically effective amount of a periaxin nucleic acid sequence, wherein the nucleic acid sequence is administered by a vector. In a specific embodiment, the vector is selected from the group consisting of a plasmid, a viral vector, a lipid, a liposome, a polypeptide, or a combination thereof. In another specific embodiment the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment of the present invention there is a method of treating myelinopathy in an organism comprising the step of administering to said organism a therapeutically effective amount of a periaxin amino acid sequence, wherein said amino acid sequence is administered with a physiologically acceptable carrier. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In an additional embodiment of the present invention there is a method of treating an animal for a myelinopathy comprising the steps of identifying a compound which interacts with an amino acid sequence of SEQ ID NO:2; and administering to the animal a therapeutically effective amount of the compound. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment of the present invention there is a method of treating a patient for a myelinopathy comprising the steps of preparing a compound obtained by a method from herein and administering the compound with a physiologically acceptable carrier to said patient.

In another embodiment of the present invention there is a kit for diagnosing a myelinopathy in an animal comprising at least two primers, wherein one primer is specific to a sense periaxin nucleic acid sequence and another primer is specific to an antisense periaxin nucleic acid sequence. In a specific embodiment the primers are selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26.

In another embodiment of the present invention there is as a composition of matter a nucleic acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26.

In an additional embodiment of the present invention, there is a method of detecting the presence or absence of a mutation associated with a myelinopathy, the method comprising a) isolating a test nucleic acid from a subject, said test nucleic acid comprising a periaxin polynucleotide; b) comparing the test nucleic acid to a reference wild-type periaxin polynucleotide; and c) determining the differences between the test nucleic acid and the reference wild-type periaxin polynucleotide, wherein the differences are mutations in the periaxin polynucleotide of the subject, and wherein the presence of a mutation in the periaxin polynucleotide of the subject is indicative of the presence of the myelinopathy in the subject.

In a specific embodiment, the mutation is in SEQ ID NO:1 and is 3775G>A, 1216G>A, 4075-4077d, 1483G>C, 3394A>G, 3248C>G, 2763A>G, 2645C>T, 306C>T, 1491C>G, 2655T>C, 2145T>A, or 247ΔC. In another specific embodiment, the mutation encodes a defect of an amino acid sequence of SEQ ID NO:2 and is E1259K, A406T, E1359Δ, E495Q, R1132G, P1083R, I921M, A882V, T102T, P497P, P885P, C715X, or R82fsX96. In another specific embodiment, the periaxin polynucleotide is SEQ ID NO:1. In an additional specific embodiment, the comparing step is by DHPLC, sequencing, or hybridization.

In a preferred embodiment, the human orthologue of murine and rat periaxin (Prx), which expresses L- and S-periaxin by alternative intron retention (Dytrych et al., 1998), is associated with human inherited myelinopathies. The human periaxin gene (PRX) encodes two PDZ domain proteins, L- and S-periaxin, that are required for maintenance of peripheral nerve myelin. $Prx^{-/-}$ mice develop a severe demyelinating peripheral neuropathy despite apparently normal initial formation of myelin sheaths. In preferred embodiments, mutations in PRX cause human peripheral myelinopathies given that multiple unrelated Dejerine-Sottas neuropathy (DSN) patients with recessive PRX mutations, two with compound heterozygous nonsense and frameshift mutations and one with a homozygous frameshift mutation were identified. The PRX locus was mapped to 19q13.13-13.2, a region recently associated with a severe autosomal recessive demyelinating neuropathy in a Lebanese family (Delague et al. 2000) and syntenic to the location of Prx on murine chromosome 7 (Gillespie et al. 1997).

The skilled artisan is made aware of the following GenBank accession numbers and URLs for data in this article are as follows: 1) Online Mendelian Inheritance in Man: (OMIM), [http://www3.ncbi.nlm.nih.gov/Omim/] at the National Center for Biotechnology Institute's online address (for CMT1 (MIM (Mendelian Inheritance in Man) #118200), DSN (OMIM #145900), CHN (OMIM #605253), and HNPP (OMIM #162500)); 2) GenBank, [http://www.ncbi.nlm.nih.gov/Genbank] at the National Center for Biotechnology Institute's online address (for human PRX mRNA sequence encoding S-periaxin (AF321192; SEQ ID NO:64) and human PRX mRNA sequence encoding L-periaxin (AF321191; SEQ ID NO:65)); 3) HUGO Gene Nomenclature Committee, [http://www.gene.ucl.ac.uk/nomenclature/] at its online address; 4) BLAST, [http://www.ncbi.nlm.nih.gov/BLAST/] at the National Center for Biotechnology Institute's online address; 5) Chromosome 19 physical map, [http://greengenes.llnl.gov//genome/html/chrom_map.html] at the Lawrence Livermore National Laboratory's Biology and Biotechnology Research Program's online address; 6) Electronic PCR, [http://www.ncbi.nlm.nih.gov/genome/sts/epcr.cgi] at the National Center for Biotechnology Institute's online address; 7) Primer v3 program, [http://www-genome.wi.mit.edu/cgi-bin/primer/primer3_www.cgi] at the Whitehead Institute/MIT Center for Genome Research's online address.

A skilled artisan is aware that various periaxin sequences are within the scope of the compositions and methods of the present invention. Periaxin nucleic acid sequences within the scope of the present invention include: SEQ ID NO:1, BF447393 (SEQ ID NO:27); BF445684 (SEQ ID NO:28); NM_019412. (SEQ ID NO:29); BE845046 (SEQ ID NO:30); BE627424 (SEQ ID NO:31); BE625883 (SEQ ID NO:32); BE504988 (SEQ ID NO:33); BB293550 (SEQ ID NO:34); BB197351 (SEQ ID NO:35); BB095645 (SEQ ID NO:36); BB095557 (SEQ ID NO:37); BG142832 (SEQ ID NO:38); AW590908 (SEQ ID NO:39); AW337783 (SEQ ID NO:40); AW212122 (SEQ ID NO:41); AW211564 (SEQ ID NO:42); AW180312 (SEQ ID NO:43); AV313851 (SEQ ID NO:44); AV232603 (SEQ ID NO:45); AW134382 (SEQ ID NO:46); AW105547 (SEQ ID NO:47); AI447899 (SEQ ID NO:48); AI637869 (SEQ ID NO:49); AI561629 (SEQ ID NO:50); AI551992 (SEQ ID NO:51); AI466086 (SEQ ID NO:52); AI159496 (SEQ ID NO:53); AI159096 (SEQ ID NO:54); AA989929 (SEQ ID NO:55); AA984421 (SEQ ID NO:56); AJ222969 (SEQ ID NO:57); AJ222968 (SEQ ID NO:58); AA823031 (SEQ ID NO:59); AA727568 (SEQ ID NO:60); AA145455 (SEQ ID NO:61); AA105722 (SEQ ID NO:62); Z29649 (SEQ ID NO:63), BF476730 (SEQ ID NO:64), BG141436 (SEQ ID NO:65); BF940815 (SEQ ID NO:66); BF589760 (SEQ ID NO:67); .XM_068146 (SEQ ID NO:68); XM_043307 (SEQ ID NO:69); XM_047407 (SEQ ID NO:70); XM_015939 (SEQ ID NO:71); XM_047408 (SEQ ID NO:72); AY054648 (SEQ ID NO:73); BI315105 (SEQ ID NO:74); AF321192 (SEQ ID NO:75); AF321191 (SEQ ID NO:76); and/or NM_023976 (SEQ ID NO:77). A skilled artisan recognizes how to find, based on common known methods in the art, mutations of a periaxin polynucleotide listed herein in another periaxin polynucleotide sequence even if that sequence comprises a larger or smaller region of the gene.

Periaxin amino acid sequences within the scope of the present invention include: SEQ ID NO:2 (NP_066007); T49945 (SEQ ID NO:78); I58157 (SEQ ID NO:79); NP_062285 (SEQ ID NO:80); Q10018 (SEQ ID NO:81); Q63425 (SEQ ID NO:82); CAB89377 (SEQ ID NO:83); CAA11023 (SEQ ID NO:84); CAA11022 (SEQ ID NO:85); CAA82757 (SEQ ID NO:86); NP_076466 (SEQ ID NO:87); AAK19279 (SEQ ID NO:88); AAK19280 (SEQ ID NO:89); NP_196515 (SEQ ID NO:90); AAK96839 (SEQ ID NO:91); XP_047408 (SEQ ID NO:92); XP_068146 (SEQ ID NO:93).

In a specific embodiment of the present invention there is a transgenic non-human animal, wherein although the animal is not a human animal, such as a mouse, the genetic material which comprises the transgene or any related sequences to the may be derived from a human. For example, a human periaxin nucleic acid sequence, such as SEQ ID NO:1, or a fragment thereof, may be introduced into a mouse or rat.

In a specific embodiment there is a method of identifying an upregulator of PRX expression comprising the steps of administering a test compound to a transgenic non-human animal comprising a nucleic acid encoding SEQ ID NO:1, wherein said nucleic acid is under the control of a promoter active in eukaryotic cells, and wherein said nucleic acid is endogenous to an animal other than said transgenic non-human animal; measuring the level of PRX expression; and comparing the level of PRX expression in said animal with normal PRX expression, wherein an increase in said level following administration of said test compound indicates said test compound is an upregulator. The term "normal PRX expression" as used herein is defined as the basal level of expression of a PRX nucleic acid sequence. That is, the level of normal PRX expression is approximately the amount present in tissues in which it is expressed endogenously and under no atypical conditions, such as inducible stimuli including heat or stress.

In a specific embodiment of the present invention there is a method of identifying a compound for the treatment of a myelinopathy wherein the myelinopathy is Charcot-Marie-Tooth (CMT) syndrome, hereditary neuropathy with liability to pressure palsies (HNPP), Dejerine-Sottas syndrome (DSS), congenital hypomyelinating neuropathy (CHN), or Roussy-Levy Syndrome (RLS), comprising the steps of exposing a non-human knockout animal, wherein the animal comprises at least one defective allele of SEQ ID NO:1, to the compound; and assaying for an improvement of the myelinopathy A skilled artisan is aware of what would be considered an improvement of a myelinopathy. For example, an improvement of myelinopathy would comprise an increase in myelin sheathing around a nerve fiber or a decrease or complete cessation of loss of myelin sheathing around a nerve fiber, or improvement of a symptom of peripheral neuropathy.

In a specific embodiment, a reporter sequence is utilized in the methods of the present invention. In a specific embodiment, a transgenic non-human animal comprises a reporter nucleic acid, wherein said nucleic acid is under the control of a periaxin promoter active in eukaryotic cells. A reporter sequence is a nucleic acid sequence whose expression is monitored or whose gene product a nucleic acid sequence that encodes a protein or gene product which is monitored to reflect the expression of a regulatory sequence such as a promoter. Examples of reporter sequences include histological markers such as chloramphenicol acetyltransferase (CAT), green fluorescent protein (GFP), enhanced GFP, blue fluorescent protein, luciferase, β-galactosidase and -glucuronidase. A reporter gene containing an epitope tag can also be monitored. Examples of epitope tags include HA, myc and Flag.

In a specific embodiment, there is a method of diagnosing a myelinopathy in an animal, such as Charcot-Marie-Tooth disease, Dejerine-Sottas syndrome, hereditary neuropathy with liability to pressure palsies, congenital hypomyelinating neuropathy, or Roussy-Levy syndrome, comprising the step of analyzing a nucleic acid sequence of SEQ ID NO:1, wherein an alteration in the nucleic acid is associated with the myelinopathy. In another specific embodiment, the analyzing step further comprises polymerase chain reaction.

In a specific embodiment, the present invention provides a method for detecting the presence of a mutation in a periaxin polynucleotide. Detection of the presence of the mutation aids in diagnosis of a myelinopathy, such as Charcot-Marie-Tooth (CMT) syndrome, hereditary neuropathy with liability to pressure palsies (HNPP), Dejerine-Sottas syndrome (DSS), congenital hypomyelinating neuropathy (CHN), or Roussy-Levy Syndrome (RLS).

In an alternative specific embodiment, the present invention provides a method for detecting the absence of a mutation in a periaxin polynucleotide. Detection of the absence of the mutation in a periaxin polynucleotide is valuable to a health care provider by narrowing the possibilities for causes of a particular phenotype such as a myelinopathy, including one associated with Charcot-Marie-Tooth (CMT) syndrome, hereditary neuropathy with liability to pressure palsies (HNPP), Dejerine-Sottas syndrome (DSS), congenital hypomyelinating neuropathy (CHN), or Roussy-Levy Syndrome (RLS).

B. Myelinopathy

The methods and compositions of the present invention are directed to the following inherited peripheral neuropathies: Charcot-Marie-Tooth disease (Charcot and Marie, 1886; Tooth, 1886) types 1 and 2 (CMT1 and CMT2), also known as hereditary motor and sensory neuropathy types I and II (HMSNI and HMSNII) Dyck and Lambert, 1968a; Dyck and Lambert 1968b; Thomas et al., 1974); the Dejerine-Sottas syndrome (DSS) (Dejerine and Sottas, 1893), also known as hereditary motor and sensory neuropathy type III (HMSNIII); hereditary neuropathy with liability to pressure palsies (HNPP) (Windebank, 1993); congenital hypomyelinating neuropathy (CHN) (Harati and Butler, 1985; Charmas et al., 1988); and clinical variants of CMT such as Roussy-Levy syndrome (RLS) Roussy and Levy, 1926).

Charcot-Marie-Tooth (CMT) (MIM 118220) polyneuropathy syndrome represents a clinically and genetically heterogeneous group of disorders of the peripheral nerve. Two major types are distinguished by measuring motor nerve conduction velocities (NCV). CMT1 is a demyelinating neuropathy characterized by symmetrically slowed motor NCV (usually <40 meters/second). Microscopic sections of peripheral nerve in CMT1 patients reveal onion bulb formation. CMT2 is an axonal neuropathy associated with normal or near normal NCV with decreased amplitudes and axonal loss on nerve biopsy. A skilled artisan is made aware herein that although a myelinopathy in CMT2 is not to be expected, there is significant clinical overlap between CMT1 and CMT2, although the histopathology is usually defining. Thus, although a periaxin alteration resulting in CMT2 is unlikely, an individual having CMT2 may be tested for periaxin alterations in light of the difficulty in distinguishing between CMT1 and CMT2 clinically.

CMT1 which is more common and usually autosomal dominant, generally presents in the 2nd or 3rd decade, and is associated with slowly progressive symmetric distal muscle weakness and atrophy, gait disturbance, and absent stretch reflexes. CMT2 is autosomal dominant and usually manifests later in life. Different genetic subtypes of both CMT1 and CMT2 can be further delineated based on genetic linkage analysis and mapping to distinct loci.

Hereditary neuropathy with liability to pressure palsies (HNPP) (MIM 162500) is a demyelinating neuropathy whose neuropathological hallmark is sausage-like thickening of myelin sheaths (tomacula). Electrophysiologic findings include mildly slowed NCV and conduction blocks. The clinical manifestations are typically episodic, nonsymmetric palsies, that may be precipitated by trauma or compression. Multifocal neuropathies, especially entrapment neuropathies, such as carpal tunnel syndrome, may be manifestations of HNPP.

Dejerine-Sottas syndrome (DSS), or HMSNIII, was originally described as an interstitial hypertrophic neuropathy of infancy (Dejerine and Sottas, 1893). It is a more severe demyelinating neuropathy than CMT1 (Dyck et al., 1993). The disease usually begins in infancy, as evidenced by delayed motor milestones, and it is generally associated with severe pathological alterations, such as more significant slowing of NCV, more pronounced demyelination, and more numerous onion bulbs than observed in CMT, and nerve conduction velocity abnormalities (<6-12 meters/sec) (Ouvrier et al., 1987). The cerebrospinal fluid proteins can be elevated. Congenital hypomyelinating neuropathy (CHN) is distinguished from DSS by its congenital manifestation, and the histopathologic findings of hypomyelination and few onion bulbs.

Most CMT1 patients have DNA rearrangements as the molecular cause of their disease. A 1.5 Mb-tandem duplication, the CMT1A duplication, accounts for approximately 70% of CMT1 cases. A deletion of the same 1.5-Mb region in chromosome 17p12 is found in >85% of patients with HNPP. The CMT1A duplication and HNPP deletion result from unequal crossing-over and reciprocal homologous recombination involving a 24-kb repeat, CMT1A-REP, that flanks the 1.5-Mb region. A meiotic recombination hotspot occurs within CMT1A-REP. The majority of the de novo duplication and deletion events occur in meiosis of the male germ cells.

The CMT1A and HNPP phenotypes result from a gene dosage effect. CMT1A is due to trisomic overexpression of the peripheral myelin protein-22 gene, PMP22, while HNPP results from monosomic underexpression of PMP22. In rare patients without the CMT1A duplication or HNPP deletion, PMP22 point mutations can cause disease. Null alleles or haploinsufficiency cause HNPP, while gain-of-function or dominant-negative missense amino acid substitutions results in CMT1A or DSS.

Mutations in myelin protein zero (MPZ), connexin 32 (Cx32) or gap junction protein, β1 (GJB1), or early growth response 2 (EGR2, the human Krox-20 homologue), myotubularin related protein 2 (MTMR2), N-myc downstream regulated gene 1 (NDRG1) genes can also cause CMT1 (MPZ, Cx32, EGR2), DSS (MPZ, EGR2), or CHN (MPZ, EGR2). Mutation of Cx32 causes the X-linked form of CMT. Thus, these myelinopathies appear to represent a spectrum of related disorders resulting from myelin dysfunction. Each of these genes (PMP22, Cx32, MPZ, and EGR2) are expressed in myelinating Schwann cells so that mutations probably exert their effects on Schwann cells.

Clinical variability is the rule in inherited neuropathies. Discordance is even noted in identical twins with the CMT1A duplication. De novo CMT1A duplication is frequently found in sporadic CMT1. DSS and RLS can also be associated with CMT1A duplication. Multifocal neuropathy, autosomal dominant carpal tunnel syndrome, and CMT1 can also be associated with the HNPP deletion. These inherited demyelinating neuropathies can be difficult to distinguish from acquired demyelinating neuropathies. Because of the clinical heterogeneity, the clinical workup of a patient with peripheral neuropathy requires molecular definition. Determining an exact molecular etiology enables a precise and secure diagnosis, provides prognostic information, allows proper genetic counseling, and makes possible the design and implementation of rational therapeutic strategies.

Congenital hypomyelinating neuropathy (CHN) is characterized by infantile hypotonia, distal muscle weakness, areflexia, and markedly slow NCVs (<10 meters/sec). In severe cases, joint contractures or arthrogryposis multiplex congenita have been described (Charmas et al., 1988). In less severe cases it is difficult to differentiate CHN from DSS. Some have considered both DSS and CHN as forms of HMSNIII Dyck et al., 1993). The nerve biopsies show hypomyelination (few thin myelin lamellae) without active myelin breakdown products and early onion bulb formations. However, there are several histological phenotypes for DSS and CHN (Harati and Butler, 1985).

Roussy-Levy syndrome (RLS) was described in patients presenting with pes cavus, distal limb weakness, areflexia, distal sensory loss, sensory gait ataxia, and tremor (Roussy and Levy, 1926). It is controversial whether RLS represents a clinical entity distinct from CMT or a clinical variant.

C. The Periaxin Gene

The periaxin gene (PRX) encodes two PDZ domain proteins, L- and S-periaxin, that are required for the maintenance of peripheral nerve myelin. In murine embryonic Schwann cells, L-periaxin is initially concentrated in the nuclei but redistributes to the adaxonal plasma membrane with initiation of myelination and then to the abaxonal, Schmidt-Lanterman incisure, and paranodal membranes with maturation of the myelin sheath (Scherer et al., 1995; Sherman and Brophy, 2000). L-periaxin expression recapitulates this pattern following nerve crush injury (Scherer et al., 1995). This shift in periaxin localization during myelination suggests that periaxin participates in membrane-protein interactions that are required to stabilize the mature myelin sheath. As a cytoskeleton-associated protein, L-periaxin in some embodiments mediates such stabilization by facilitating integration of extracellular signaling through the cytoskeleton, a function essential for changes in Schwann cell shape and regulation of gene expression during axonal ensheathment (Fernandez-Valle et al., 1997; Tapon et al., 1997). Such a signaling function is supported by two observations: first, L-periaxin contains a nuclear localization signal and a PDZ motif, a domain implicated in the assembly of signaling complexes at sites of cell-cell contact (Sherman and Brophy, 2000; Dytrych et al., 1998); and second L-periaxin binds dystroglycan-dystrophin-related protein 2 (DRP2) which is part of a complex linking extracellular matrix proteins to the cytoskeleton and cortical signaling molecules (Sherman et al., 2001). Confirming the necessity of periaxin for maintenance of the myelin sheath, Gillespie et al demonstrated that $Prx^{-/-}$ mice ensheathe and myelinate peripheral axons normally but subsequently develop a severe demyelinating neuropathy associated with allodynia (pain from normally non-noxious stimuli) and hyperalgesia (hypersensitivity to painful stimuli) (Gillespie et al., 2000).

D. Nucleic Acid-Based Expression Systems

1. Vectors

In specific methods of the present invention, a vector is utilized to transport an exogenous nucleic acid sequence. A nucleic acid sequence is "exogenous," if it is foreign to the cell into which the vector is being introduced or if the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., yeast artificial chromosomes (YACs) or bacterial artificial chromosomes (BACs)). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

e. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

f. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

g. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the recombinant vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid of the present application encoding a gene product or a portion thereof. Further examples of selectable and screenable markers are well known to one of skill in the art.

2. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryotic host cell for replication of many vectors. Bacterial cells used as host cells for vector replication and/or expression include *E. coli* K12, DH5α, JM109, and KC8 strains, as well as a number of commercially available bacterial hosts such as SURE® Competent Cells and SOLOPACK™ Gold Cells (STRATAGENE®, La Jolla). Alternatively, bacterial cells such as *E. coli* K12 or LE392 strains could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techiques and conditions that would allow large-scale production of vectors, as well as production of the nucleic acids encoded by vectors and their cognate polypeptides, proteins, or peptides.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. Coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

E. Nucleic Acid Detection

In addition to their use in directing the expression of periaxin proteins, polypeptides and/or peptides, the nucleic acid sequences disclosed herein have a variety of other uses. For example, they have utility as probes or primers for embodiments involving nucleic acid hybridization.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Patent Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to SEQ ID NO:1 or to at least one of SEQ ID NO:27 through SEQ ID NO:53 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety.

A reverse transcriptase PCR™ (RT-PCR) amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882, 864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). Davey et al., European Application No. 329 822 disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP"), denaturing high pressure liquid chromatography (DHPLC) and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

5. Kits

All the essential materials and/or reagents required for detecting a periaxin nucleic acid sequence in a sample may be assembled together in a kit. This generally will comprise a probe or primers designed to hybridize specifically to individual nucleic acids of interest in the practice of the present invention, including SEQ ID NO:1 and/or SEQ ID NO:27 through SEQ ID NO:53. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

F. Periaxin Nucleic Acids

1. Nucleic Acids and Uses Thereof

Certain aspects of the present invention concern at least one periaxin nucleic acid. In certain aspects, the at least one periaxin nucleic acid comprises a wild-type or mutant periaxin nucleic acid. In particular aspects, the periaxin nucleic acid encodes for at least one transcribed nucleic acid. In particular aspects, the periaxin nucleic acid encodes at least one periaxin protein, polypeptide or peptide, or biologically functional equivalent thereof. In other aspects, the periaxin nucleic acid comprises at least one nucleic acid segment of SEQ ID NO:1 or one of SEQ ID NO:27 through SEQ ID NO:53, or at least one biologically functional equivalent thereof.

The present invention also concerns the isolation or creation of at least one recombinant construct or at least one recombinant host cell through the application of recombinant nucleic acid technology known to those of skill in the art or as described herein. The recombinant construct or host cell may comprise at least one periaxin nucleic acid, and may express at least one periaxin protein, polypeptide or peptide, or at least one biologically functional equivalent thereof.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e. two or more alleles exist) at a genetic locus in the individuals of a population. As used herein "mutant" refers to a change in the sequence of a nucleic acid or its encoded protein, polypeptide or peptide that is the result of the hand of man.

A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. Ser. No. 5,705,629, each incorporated herein by reference. A non-limiting example of enzymatically produced nucleic acid include one produced by enzymes in amplification reactions such as PCR™ (see for example, U.S. Pat. Nos. 4,683,202 and 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Thus, the present invention also encompasses at least one nucleic acid that is complementary to a periaxin nucleic acid. In particular embodiments, the invention encompasses at least one nucleic acid or nucleic acid segment complementary to the sequence set forth in SEQ ID NO:1 or at least one of SEQ ID NO:27 through SEQ ID NO:53. Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 75%, about 80%, about 85%, about 90%, about 95%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence of formamide, tetramethylammonium chloride or other solvent(s) in the hybridization mixture. It is generally appreciated that conditions may be rendered more stringent, such as, for example, the addition of increasing amounts of formamide.

It is also understood that these ranges, compositions and conditions for hybridization are mentioned by way of non-limiting example only, and that the desired stringency for a particular hybridization reaction is often determined empirically by comparison to one or more positive or negative controls. Depending on the application envisioned it is preferred to employ varying conditions of hybridization to achieve varying degrees of selectivity of the nucleic acid(s) towards target sequence(s). In a non-limiting example, identification or isolation of related target nucleic acid(s) that do not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

One or more nucleic acid(s) may comprise, or be composed entirely of, at least one derivative or mimic of at least one nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refers to a molecule that may or may not structurally resemble a naturally occurring molecule, but functions similarly to the naturally occurring molecule. As used herein, a "moiety" generally refers to a smaller chemical or molecular component of a larger chemical or molecular structure, and is encompassed by the term "molecule."

As used herein a "nucleobase" refers to a naturally occurring heterocyclic base, such as A, T, G, C or U ("naturally occurring nucleobase(s)"), found in at least one naturally occurring nucleic acid (i.e. DNA and RNA), and their naturally or non-naturally occurring derivatives and mimics. Non-limiting examples of nucleobases include purines and pyrimidines, as well as derivatives and mimics thereof, which generally can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

Nucleobase, nucleoside and nucleotide mimics or derivatives are well known in the art, and have been described in exemplary references such as, for example, Scheit, Nucleotide Analogs (John Wiley, New York, 1980), incorporated herein by reference. "Purine" and "pyrimidine" nucleobases encompass naturally occurring purine and pyrimidine nucleobases and also derivatives and mimics thereof, including but not limited to, those purines and pyrimidines substituted by one or more of alkyl, carboxyalkyl, amino, hydroxyl, halogen (i.e. fluoro, chloro, bromo, or iodo), thiol, or alkylthiol wherein the alkyl group comprises of from about 1, about 2, about 3, about 4, about 5, to about 6 carbon atoms. Non-limiting examples of purines and pyrimidines include deazapurines, 2,6-diaminopurine, 5-fluorouracil, xanthine, hypoxanthine, 8-bromoguanine, 8-chloroguanine, bromothymine, 8-aminoguanine 8-hydroxyguanine, 8-methylguanine, 8-thioguanine, azaguanines, 2-aminopurine, 5-ethylcytosine, 5-methylcyosine, 5-bromouracil, 5-ethyluracil, 5-iodouracil, 5-chlorouracil, 5-propyluracil, thiouracil, 2-methyladenine, methylthioadenine, N,N-diemethyladenine, azaadenines, 8-bromoadenine, 8-hydroxyadenine, 6-hydroxyaminopurine, 6-thiopurine, 4-(6-aminohexyl/cytosine), and the like. A table of exemplary, but not limiting, purine and pyrimidine derivatives and mimics is also provided herein below.

As used herein, "nucleoside" refers to an individual chemical unit comprising a nucleobase covalently attached to a nucleobase linker moiety. A non-limiting example of a "nucleobase linker moiety" is a sugar comprising 5-carbon atoms (a "5-carbon sugar"), including but not limited to deoxyribose, ribose or arabinose, and derivatives or mimics of 5-carbon sugars. Non-limiting examples of derivatives or mimics of 5-carbon sugars include 2'-fluoro-2'-deoxyribose or carbocyclic sugars where a carbon is substituted for the oxygen atom in the sugar ring. By way of non-limiting example, nucleosides comprising purine (i.e. A and G) or 7-deazapurine nucleobases typically covalently attach the 9 position of the purine or 7-deazapurine to the 1'-position of a 5-carbon sugar. In another non-limiting example, nucleosides comprising pyrimidine nucleobases (i.e. C, T or U) typically covalently attach the 1 position of the pyrimidine to 1'-position of a 5-carbon sugar (Kornberg and Baker, DNA Replication, 2nd Ed. (Freeman, San Francisco, 1992). However, other types of covalent attachments of a nucleobase to a nucleobase linker moiety are known in the art, and non-limiting examples are described herein.

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety, and non-limiting examples are described herein.

A non-limiting example of a nucleic acid comprising such nucleoside or nucleotide derivatives and mimics is a "polyether nucleic acid", described in U.S. Pat. Ser. No. 5,908,845, incorporated herein by reference, wherein one or more nucleobases are linked to chiral carbon atoms in a polyether backbone. Another example of a nucleic acid comprising nucleoside or nucleotide derivatives or mimics is a "peptide nucleic acid", also known as a "PNA", "peptide-based nucleic acid mimics" or "PENAMs", described in U.S. Pat. Ser. Nos. 5,786,461, 5,891,625, 5,773,571, 5,766,855, 5,736,336, 5,719,262, 5,714,331, 5,539,082, and WO 92/20702, each of which is incorporated herein by reference. A peptide nucleic acid generally comprises at least one nucleobase and at least one nucleobase linker moiety that is either not a 5-carbon sugar and/or at least one backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Peptide nucleic acids generally have enhanced sequence specificity, binding properties, and resistance to enzymatic degradation in comparison to molecules such as DNA and RNA (Egholm et al., Nature 1993, 365, 566; PCT/EP/01219). In addition, U.S. Pat. Nos. 5,766,855, 5,719,262, 5,714,331 and 5,736,336 describe PNAs comprising naturally and non-naturally occurring nucleobases and alkylamine side chains with further improvements in sequence specificity, solubility and binding affinity. These properties promote double or triple helix formation between a target nucleic acid and the PNA.

U.S. Pat. No. 5,641,625 describes that the binding of a PNA to a target sequence has applications including the creation of PNA probes to nucleotide sequences, modulating (i.e. enhancing or reducing) gene expression by binding of a PNA to an expressed nucleotide sequence, and cleavage of specific dsDNA molecules. In certain embodiments, nucleic acid analogues such as one or more peptide nucleic acids may be used to inhibit nucleic acid amplification, such as in PCR, to reduce false positives and discriminate between single base mutants, as described in U.S. Pat. Ser. No. 5,891,625.

U.S. Pat. No. 5,786,461 describes PNAs with amino acid side chains attached to the PNA backbone to enhance solubility. The neutrality of the PNA backbone may contribute to the thermal stability of PNA/DNA and PNA/RNA duplexes by reducing charge repulsion. The melting temperature of PNA containing duplexes, or temperature at which the strands of the duplex release into single stranded molecules, has been described as less dependent upon salt concentration.

One method for increasing amount of cellular uptake property of PNAs is to attach a lipophilic group. U.S. application Ser. No. 117,363, filed Sep. 3, 1993, describes several alkylamino functionalities and their use in the attachment of such pendant groups to oligonucleotides. U.S. application Ser. No. 07/943,516, filed Sep. 11, 1992, and its corresponding published PCT application WO 94/06815, describe other novel amine-containing compounds and their incorporation into oligonucleotides for, inter alia, the purposes of enhancing cellular uptake, increasing lipophilicity, causing greater cellular retention and increasing the distribution of the compound within the cell.

Additional non-limiting examples of nucleosides, nucleotides or nucleic acids comprising 5-carbon sugar and/or backbone moiety derivatives or mimics are well known in the art.

In certain aspect, the present invention concerns at least one nucleic acid that is an isolated nucleic acid. As used herein, the term "isolated nucleic acid" refers to at least one nucleic acid molecule that has been isolated free of, or is otherwise free of, the bulk of the total genomic and transcribed nucleic acids of one or more cells, particularly mammalian cells, and more particularly human and/or mouse and/or rat cells. In certain embodiments, "isolated nucleic acid" refers to a nucleic acid that has been isolated free of, or is otherwise free of, bulk of cellular components and macromolecules such as lipids, proteins, small biological molecules, and the like. As different species may have a RNA or a DNA containing genome, the term "isolated nucleic acid" encompasses both the terms "isolated DNA" and "isolated RNA". Thus, the isolated nucleic acid may comprise a RNA or DNA molecule isolated from, or otherwise free of, the bulk of total RNA, DNA or other nucleic acids of a particular species. As used herein, an isolated nucleic acid isolated from a particular species is referred to as a "species specific nucleic acid." When designating a nucleic acid isolated from a particular species, such as human, such a type of nucleic acid may be identified by the name of the species. For example, a nucleic acid isolated from one or more humans would be an "isolated human nucleic acid", a nucleic acid isolated from human would be an "isolated human nucleic acid", and so forth.

Of course, more than one copy of an isolated nucleic acid may be isolated from biological material, or produced in vitro, using standard techniques that are known to those of skill in the art. In particular embodiments, the isolated nucleic acid is capable of expressing a protein, polypeptide or peptide that has periaxin activity. In other embodiments, the isolated nucleic acid comprises an isolated periaxin gene.

In certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises a periaxin nucleic acid, and/or encodes a periaxin polypeptide or peptide coding sequences. The term "an amino acid sequence" as used herein may be used interchangeably with the terms protein, polypeptide, or peptide, and the like. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, and so forth. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

"Isolated substantially away from other coding sequences" means that the gene of interest, in this case the periaxin gene(s), forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

In certain embodiments, the nucleic acid is a nucleic acid segment. As used herein, the term "nucleic acid segment", are smaller fragments of a nucleic acid, such as for non-limiting example, those that encode only part of the periaxin peptide or polypeptide sequence. Thus, a "nucleic acid segment" may comprise any part of the periaxin gene sequence(s), of from about 2 nucleotides to the full length of the periaxin peptide or polypeptide encoding region. In certain embodiments, the "nucleic acid segment" encompasses the full length periaxin gene(s) sequence. In particular embodiments, the nucleic acid comprises any part of the SEQ ID NO:1 and/or one of SEQ ID NO:27 through SEQ ID NO:53 sequence(s), of from about 2 nucleotides to the full length of the sequence disclosed in SEQ ID NO:1 and/or one of SEQ ID NO:27 through SEQ ID NO:53.

Various nucleic acid segments may be designed based on a particular nucleic acid sequence, and may be of any length. In certain embodiments, the nucleic acid segment may be a probe or primer. As used herein, a "probe" is a relatively short nucleic acid sequence, such as an oligonucleotide, used to identify other nucleic acid sequences to which it hybridizes. As used herein, a "primer" is a relatively short nucleic acid sequence used as a starting molecule for polymerization to extend from, such as in polymerase chain reaction, which is a method well known in the art. A non-limiting example of this would be the creation of nucleic acid segments of various lengths and sequence composition for probes and primers based on the sequences disclosed in SEQ ID NO:1 or at least one of SEQ ID NO:27 through SEQ ID NO:53.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended recombinant nucleic acid protocol.

In a non-limiting example, one or more nucleic acid constructs may be prepared that include a contiguous stretch of nucleotides identical to or complementary to SEQ ID NO:1 or at least one of SEQ ID NO:27 through SEQ ID NO:53. A nucleic acid construct may be about 3, about 5, about 8, about 10 to about 14, or about 15, about 20, about 30, about 40, about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges", as used herein, means any length or range including or between the quoted values (i.e. all integers including and between such values).

In particular embodiments, the invention concerns one or more recombinant vector(s) comprising nucleic acid sequences that encode a periaxin protein, polypeptide or peptide that includes within its amino acid sequence a contiguous amino acid sequence in accordance with, or essentially as set forth in, SEQ ID NO:1, corresponding to human periaxin. In other embodiments, the invention concerns recombinant vector(s) comprising nucleic acid sequences that encode a mouse periaxin protein, polypeptide or peptide that includes within its amino acid sequence a contiguous amino acid sequence in accordance with, or essentially as set forth in SEQ ID NO:29. In particular aspects, the recombinant vectors are DNA vectors.

The term “a sequence essentially as set forth in SEQ ID NO:2 means that the sequence substantially corresponds to a portion of SEQ ID NO:2 and has relatively few amino acids that are not identical to, or a biologically functional equivalent of, the amino acids of SEQ ID NO:2.

The term “biologically functional equivalent” is well understood in the art and is further defined in detail herein. Accordingly, a sequence that has between about 70% and about 80%; or more preferably, between about 81% and about 90%; or even more preferably, between about 91% and about 99%; of amino acids that are identical or functionally equivalent to the amino acids of SEQ ID NO:2 or at least one of SEQ ID NO:55 through SEQ ID NO:63 will be a sequence that is “essentially as set forth in SEQ ID NO:2” or “a sequence essentially as set forth in at least one of SEQ ID NO:55 through SEQ ID NO:63”, provided the biological activity of the protein, polypeptide or peptide is maintained.

In certain other embodiments, the invention concerns at least one recombinant vector that include within its sequence a nucleic acid sequence essentially as set forth in SEQ ID NO:1 or at least one of SEQ ID NO:27 through SEQ ID NO:54. In particular embodiments, the recombinant vector comprises DNA sequences that encode protein(s), polypeptide(s) or peptide(s) exhibiting periaxin activity.

The term “functionally equivalent codon” is used herein to refer to codons that encode the same amino acid, such as the six codons for arginine and serine, and also refers to codons that encode biologically equivalent amino acids. Information on codon usage in a variety of non-human organisms is known in the art (see for example, Bennetzen and Hall, 1982; Ikemura, 1981a, 1981b, 1982; Grantham et al., 1980, 1981; Wada et al., 1990; each of these references are incorporated herein by reference in their entirety). Thus, it is contemplated that codon usage may be optimized for other animals, as well as other organisms such as fungi, plants, prokaryotes, virus and the like, as well as organelles that contain nucleic acids, such as mitochondria, chloroplasts and the like, based on the preferred codon usage as would be known to those of ordinary skill in the art.

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of SEQ ID NO:1 or at least one of SEQ ID NO:27 through SEQ ID NO:55 will be nucleic acid sequences that are “essentially as set forth in SEQ ID NO:1 or at least one of SEQ ID NO:27 through SEQ ID NO:55”.

It will also be understood that this invention is not limited to the particular nucleic acid or amino acid sequences of periaxin Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present invention encompass biologically functional equivalent periaxin proteins, polypeptides, or peptides. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide, or to test mutants in order to examine periaxin protein, polypeptide or peptide activity at the molecular level.

Fusion proteins, polypeptides or peptides may be prepared, e.g., where the periaxin coding regions are aligned within the same expression unit with other proteins, polypeptides or peptides having desired functions. Non-limiting examples of such desired functions of expression sequences include purification or immunodetection purposes for the added expression sequences, e.g., proteinaceous compositions that may be purified by affinity chromatography or the enzyme labeling of coding regions, respectively.

As used herein the term “sequence” encompasses both the terms “nucleic acid” and “proteinaceous” or “proteinaceous composition.” As used herein, the term “proteinaceous composition” encompasses the terms “protein”, “polypeptide” and “peptide.” As used herein “artificial sequence” refers to a sequence of a nucleic acid not derived from sequence naturally occurring at a genetic locus, as well as the sequence of any proteins, polypeptides or peptides encoded by such a nucleic acid. A “synthetic sequence”, refers to a nucleic acid or proteinaceous composition produced by chemical synthesis in vitro, rather than enzymatic production in vitro (i.e. an “enzymatically produced” sequence) or biological production in vivo (i.e. a “biologically produced” sequence).

G. Pharmaceutical Compositions

Aqueous compositions of the present invention comprise an effective amount of a chemical compound or pharmaceutically acceptable salts thereof or the periaxin protein, polypeptide, peptide, epitopic core region, inhibitor, and/or such like, dissolved and/or dispersed in a pharmaceutically acceptable carrier and/or aqueous medium. Aqueous compositions of gene therapy vectors expressing any of the foregoing are also contemplated.

The phrases "pharmaceutically and/or pharmacologically acceptable" refer to molecular entities and/or compositions that do not produce an adverse, allergic and/or other untoward reaction when administered to an animal, such as a human, as appropriate.

As used herein, "pharmaceutically acceptable carrier" includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For human administration, preparations should meet sterility, pyrogenicity, general safety and/or purity standards as required by FDA Office of Biologics standards.

The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or even intraperitoneal routes. The preparation of an aqueous compositions that contain an effective amount of chemical compound or pharmaceutically acceptable salts thereof or a periaxin agent as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

A chemical compound or periaxin protein, polypeptide, peptide, agonist and/or antagonist of the present invention can be formulated into a composition in a neutral and/or salt form. Pharmaceutically acceptable salts, include the acid addition salts (formed with the free amino groups of the protein) and/or which are formed with inorganic acids such as, for example, hydrochloric and/or phosphoric acids, and/or such organic acids as acetic, oxalic, tartaric, mandelic, and/or the like. Salts formed with the free carboxyl groups can also be derived from inorganic bases such as, for example, sodium, potassium, ammonium, calcium, and/or ferric hydroxides, and/or such organic bases as isopropylamine, trimethylamine, histidine, procaine and/or the like. In terms of using peptide therapeutics as active ingredients, the technology of U.S. Pat. Nos. 4,608,251; 4,601,903; 4,599,231; 4,599,230; 4,596,792; and/or 4,578,770, each incorporated herein by reference, may be used.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to the desired area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035-1038 and/or 1570-1580). Some variation in dosage will necessarily occur depending on the condition of the subject being treated. The person responsible for administration will, in any event, determine the appropriate dose for the individual subject.

The chemical compound or pharmaceutically acceptable salts thereof or the active periaxin protein-derived peptides and/or agents may be formulated within a therapeutic mixture to comprise about 0.0001 to 1.0 milligrams, and/or about 0.001 to 0.1 milligrams, and/or about 0.1 to 1.0 and/or even about 10 milligrams per dose and/or so on. Multiple doses can also be administered.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

H. Lipid Formulations and/or Nanocapsules

In certain embodiments, the use of lipid formulations and/or nanocapsules is contemplated for the introduction of a chemical compound or pharmaceutically acceptable salts thereof or periaxin protein, polypeptides, peptides and/or agents, and/or gene therapy vectors, including both wild-type and/or antisense vectors, into host cells.

Nanocapsules can generally entrap compounds in a stable and/or reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and/or such particles may be easily made.

In a preferred embodiment of the invention, the pharmaceutical may be associated with a lipid. The pharmaceutical associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/pharmaceutical-associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., diacetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer and expression of an oligonucleotide in vitro and in vivo, then they are applicable for the present invention. Where a bacterial promoter is employed in the DNA construct, it also will be desirable to include within the liposome an appropriate bacterial polymerase.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287-341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50-200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

I. Kits

Therapeutic kits of the present invention are kits comprising a chemical compound or pharmaceutically acceptable salts thereof or a periaxin protein, polypeptide, peptide, inhibitor, gene, vector and/or other periaxin effector. Such kits will generally contain, in suitable container means, a pharmaceutically acceptable formulation of a chemical compound or pharmaceutically acceptable salts thereof or a periaxin protein, polypeptide, peptide, domain, inhibitor, and/or a gene and/or vector expressing any of the foregoing in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The chemical compound or pharmaceutically acceptable salts thereof or periaxin compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the chemical compound or pharmaceutically acceptable salts thereof or periaxin protein, gene and/or inhibitory formulation are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate chemical compound or pharmaceutically acceptable salts thereof or a periaxin protein and/or gene composition within the body of an animal. Such an instrument may be a syringe, pipette, forceps, and/or any such medically approved delivery vehicle.

J. Methods of Making Transgenic Mice

A particular embodiment of the present invention provides transgenic animals that contain the transgenic constructs of interest. In a specific embodiment there is a transgenic non-human animal whose genome comprises a transgene encoding a periaxin amino acid sequence, wherein said transgene is under the control of an operably linked promoter active in eukaryotic cells. In another specific embodiment the promoter is constitutive, tissue-specific, and/or inducible. In an additional specific embodiment, the animal is a mouse.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, with standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 mg/ml in 5 mM Tris, pH 7.4 and 0.1 mM EDTA.

Other methods for purification of DNA for microinjection are described in Hogan et al. Manipulating the Mouse Embryo (Cold Spring Harbor Laboratory, Cold Spring Harbor, N.Y., 1986), in Palmiter et al. Nature 300:611 (1982); in The Qiagenologist, Application Protocols, 3rd edition, published by Qiagen, Inc., Chatsworth, Calif.; and in Sambrook et al. Molecular Cloning: A Laboratory Manual (Cold Spring Harbor Laboratory, Cold Spring Harbor, N.Y., 1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

K. Gene Therapy Administration

Where appropriate, gene therapy vectors can be formulated into preparations in solid, semisolid, liquid, or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds.

Accordingly, the pharmaceutical composition of the present invention may be delivered via various routes and to various sites in an animal body to achieve a particular effect (see, e.g., Rosenfeld et al. (1991); Rosenfeld et al., (1991a); Jaffe et al., 1992). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, and topical administration.

One skilled in the art recognizes that different methods of delivery may be utilized to administer a vector into a cell. Examples include: (1) methods utilizing physical means, such as electroporation (electricity), a gene gun (physical force), or applying large volumes of a liquid (pressure); and (2) methods wherein said vector is complexed to another entity, such as a liposome or transporter molecule.

Accordingly, the present invention provides a method of transferring a therapeutic gene to a host, which comprises administering the vector of the present invention, preferably as part of a composition, with any of the aforementioned routes of administration or alternative routes known to those skilled in the art and appropriate for a particular application. Effective gene transfer of a vector to a host cell in accordance with the present invention can be monitored in terms of a therapeutic effect (e.g., alleviation of some symptom or sign associated with the particular disease being treated) or, further, by evidence of the transferred gene or expression of the gene within the host (e.g., with the polymerase chain reaction in conjunction with sequencing, Northern or Southern hybridizations, or transcription assays to detect the nucleic acid in host cells, or with immunoblot analysis, antibody-mediated detection, mRNA, or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be approximated further through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

The following examples are offered by way of example, and are not intended to limit the scope of the invention in any manner.

EXAMPLE 1

Materials and Methods

Human Subjects

All patients had DNA isolated from the peripheral blood, and lymphoblastoid cell lines were established.

Human PRX cDNA Sequence

The human PRX cDNA sequence corresponding to L-periaxin was defined by sequencing two EST clones (AW105547, AW337783) from the IMAGE consortium, by sequencing RT-PCR and 5' RACE products from human femoral nerve total RNA, and by sequencing 150-190 control chromosomes across all coding exons. Human femoral nerve total RNA was isolated using Trizol (Life Technologies) (Chomczynski and Sacchi, 1987). Prior to using the RNA for RT-PCR (One-Step RT-PCR or Superscript II RNase H Reverse Transcriptase, Life Technologies) or 5' RACE (GeneRacer Kit, Invitrogen), it was treated with ribonuclease-free deoxyribonuclease I (Life Technologies) to remove contaminating DNA. The products of the 5'

RACE reaction were cloned into the TA vector (Invitrogen) to separate and sequence the various products.

Mapping PRX

The published rat Prx cDNA sequence (GenBank Accession Number Z29649) was screened through the high-throughput genomic sequence database using the BLAST algoritlun. BAC clone CTC-492K19 (AC010271) exhibited 83 percent identity to the cDNA sequence. Using electronic PCR, nine chromosome 19q STSs in BAC CTC-492K19 were identified and these were used to place it on the chromosome 19 physical map. The RPCI-11 BAC library was also screened with an overgo primer probe for PRX and two BACs (104E13, 4K5) were isolated containing all coding exons of PRX and were used to map PRX by fluorescence in situ hybridization (FISH).

FISH was performed on metaphase preparations of human peripheral blood lymphocytes according to a modified procedure of Shaffer et al. (1997). Briefly, 200 ng of isolated BAC (104E13, 4K5) DNA was labeled by nick translation reaction using digoxigenin and 50 ng of chromosome 19q13.4 control cosmid probe (F13141 from LLNL flow sorted chromosome 19-specific cosmid library) using biotin (Boehringer Mannheim). Biotin was detected with FITC-avidin DCS (Vector Labs) and digoxigenin was detected with rhodamine-anti-digoxigenin antibodies (Sigma). Chromosomes were counterstained with DAPI diluted in Vectashield antifade (Vector Labs). Cells were viewed under a Zeiss Axioskop fluorescence microscope equipped with an appropriate filter combination. Monochromatic images were captured and pseudocolored using MacProbe 4.2.2/Power Macintosh G4 system (Perceptive Scientific Instruments, Inc., League City, Tex. USA).

Mutation Screening

By aligning the human genomic sequence from BAC clone CTC-492K19 with the rat Prx cDNA, all coding exons were identified; each exon was confirmed following characterization of the human cDNAs. Using the Primer v3 program, primers were designed to amplify exons and intronic splice junctions and then were used to screen amplified PCR products from patient genomic DNA for mutations using the WAVE DNA-fragment analysis system (Transgenomic). Briefly, by PCR the coding region of PRX was amplified from 50 ng of patient genomic DNA using the primers listed in Table 1 and Qiagen HotStarTaq.

TABLE 1

PRIMER PAIRS USED FOR AMPLIFYING THE PRXCODING REGION AND OPTIMIZED DHPLC COLUMN TEMPERATURES FOR EACH AMPLICON

| Primer name | Primer pairs | | DHPLC column temperature (° C.) |
|---|---|---|---|
| Exon 4 F | GTAAGCATGGCCTCCACCT | (SEQ ID NO:3) | 63 |
| R | CTCCTTGCTGCCCTAGTCTG | (SEQ ID NO:4) | |
| Exon 5 F | ACCTGTTGAGCGCCAATG | (SEQ ID NO:5) | 66 |
| R | CCCAAGGCAGATTCCTAACC | (SEQ ID NO:6) | |
| Exon 6 F | CGTGCAAGTGGGCAGAACTA | (SEQ ID NO:7) | 65 |
| R | TGACAAGACAGAGGGCAAGG | (SEQ ID NO:8) | |
| Exon 7a F | AATACCAGGTGGGGCTCTTC | (SEQ ID NO:9) | 63 |
| R | CTCTAGGCAGGGAAGTGTGG | (SEQ ID NO:10) | |
| Exon 7b F | AGCCGTGGGAATCCAGGT | (SEQ ID NO:11) | 63 |
| R | TGACACTTTGGGCAGCTCTA | (SEQ ID NO:12) | |
| Exon 7c F | CAGAGGTTCGACTCCCAGAG | (SEQ ID NO:13) | 62 |
| R | GCCATCTCAGGCATTTTAGG | (SEQ ID NO:14) | |
| Exon 7d F | CTGAGGTGAAACTCCCGAAG | (SEQ ID NO:15) | 63 |
| R | GCAGAGTGAGAGAGGGGACA | (SEQ ID NO:16) | |
| Exon 7e F | AAGCTAGGGAGGGCAGAGTC | (SEQ ID NO:17) | 63 |
| R | AACTTGGGGAGAGCAAACCT | (SEQ ID NO:18) | |
| Exon 7f F | CCTCAGGCAAGGTAGAGGTG | (SEQ ID NO:19) | 63 |
| R | GTCACGGTGGGCATCTTAAA | (SEQ ID NO:20) | |
| Exon 7g F | CAGGCTACAGGGTTCAGGTG | (SEQ ID NO:21) | 65 |
| R | TTCTCTCTGACGGGGGACTT | (SEQ ID NO:22) | |
| Exon 7h F | GTCCGCTTGCCACGTG TAG | (SEQ ID NO:23) | 62 |
| R | GTACAGGCACTCCTGCCAGA | (SEQ ID NO:24) | |
| S-PRX C F | CCGAGCCTTACAAAGTCTCCT | (SEQ ID NO:25) | ND |
| S-PRX C R | AGTTTGGGGCAGAGAGGAAG | (SEQ ID NO:26) | |

ND: not determined

All forward primers had a −21 M13 primer tail (TGTAAAACGACGGCCAGT) and all reverse primers a M13 reverse tail (CAGGAAACAGCTATGACC). Each PCR product was generated, except that corresponding to exon 5, with the following conditions: 15 minutes at 95° C., 40 cycles of amplification (95° C. for 30 seconds, 60° C. for 30 seconds, 72° C. for 1 minute), and 7 minutes at 72° C. For exon 5, 1.5 U of Qiagen HotStarTaq was added following the above protocol and then an additional 15 cycles of amplification was performed. To prepare the PCR products for DHPLC analysis, the products were pooled from every two patients, denatured for 5 minutes at 95° C., and reannealed by decreasing the temperature from 95 to 20° C. over a period of 50 minutes. These PCR products were analyzed for heteroduplexes by DHPLC using a linear acetonitrile gradient (flow rate of 0.9 ml/min, 2% slope (buffer A, 0.1 M triethylammoniumacetate; buffer B 0.1M triethylammoniumacetate/25% acetonitrile), column temperatures (Table 1)); optimal column temperatures were determined empirically and potential heteroduplexes were identified by visual inspection of elution chromatograms.

Using the Qiagen 96-PCR purification kit (Qiagen), patient PCR products having an abnormal elution profile and appropriate PCR products from relatives and control chromosomes were purified and sequenced with dye-primer chemistry (Applied Biosystems) using an ABI377 automated sequencer (Applied Biosystems). The resulting sequences were aligned and mutations were evaluated with the Sequencher sequence alignment program (ACGT Codes). The PRX cDNA sequence was numbered beginning with the adenine of the presumed initiating methionine, mutations are described according to den Dunnen and Antonarakis (2000).

EXAMPLE 2

Mapping and Characterization of PRX

The PRX gene was mapped in the human genome (see Example 1). The cDNA sequence was defined, and the gene structure was characterized. The tissue expression profile of PRX mRNA was subsequently evaluated by standards well known in the art. By FISH and electronic PCR (Schuler, 1997), the BAC containing PRX (BAC CTC-492K19) maps to chromosome 19q13.13-q13.2 between D19S324 and D19S223 (FIG. 1*a*). This was confirmed by metaphase FISH; co-hybridization with BAC RPCI-11 104E13 (red) and chromosome 19 control cosmid F13141 (green) assigned PRX to 19q13.13-q13.2 (arrow, ISCN 1995) (FIG. 1*a*). This places PRX within a recently mapped interval for an autosomal recessive myelinopathy (Delague et al. 2000). Sequencing of RT-PCR and 5' RACE products from femoral nerve mRNA and available EST clones defined two PRX transcripts of 4853 and 5502 bp excluding the polyA tails. The shorter mRNA is transcribed from seven exons and the deduced coding sequence extends from exon 4 through exon 7 (FIG. 1*b*). The longer transcript arises by retention of intron six (FIGS. 1*b* and 1*c;* FIG. 2); this introduces a stop codon and results in a truncated protein with an intron encoded carboxyl terminus of 21 amino acids. The large periaxin protein (L-PRX) is encoded by the shorter spliced mRNA and the smaller periaxin protein (S-PRX) by the longer mRNA retaining intron 6. Coding regions are shaded (C).

As observed in mice and rats, the amino acid sequence deduced from the shorter cDNA sequence contains a PDZ domain (amino acids 14 to 98), a highly basic domain (amino acids 118 to 194) that functions as a nuclear localization signal in mice, a repeat domain (amino acids 400 to 700), and an acidic domain (amino acids 1098 to 1235, FIGS. 1*b* and 2) (Dytrych et al., 1998; Gillespie et al., 1994; Sherman and Brophy, 2000). The amino acid sequence deduced from the longer cDNA sequence contains only the PDZ motif. Hybridization of several Clontech multi-tissue Northems with a probe from exon 7 revealed expression of a 5.1 kb PRX mRNA in all tissues examined; spinal cord mRNA, a tissue with many peripheral nerve roots, showed strongest hybridization of 5.1 and 5.6 kb bands (FIG. 1*c*). In contrast to the nearly equal expression of each mRNA in mice (Dytrych et al., 1998), the 5.6 kb mRNA appears less abundant in humans. RT-PCR confirmed the peripheral nerve tissue predominant expression.

EXAMPLE 3

PRX Mutation Analysis in Neuropathy Patients

Figure 3:
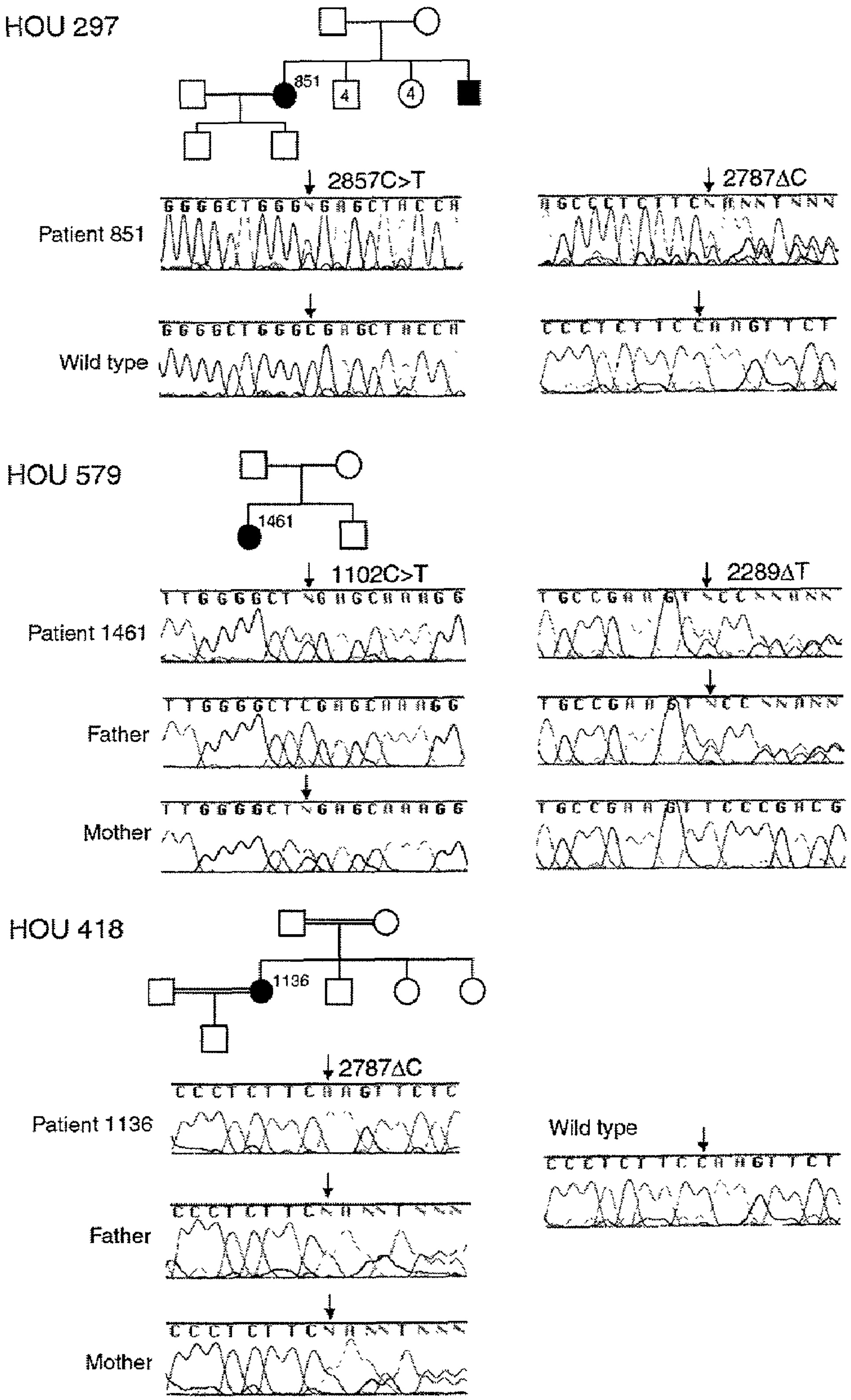
FIG. 3 illustrates chromatograms of PRX alterations identified in three families.
Figure 4:
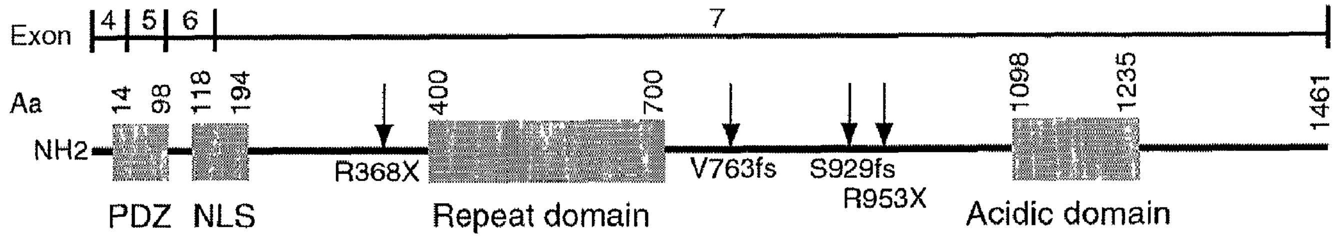
FIG. 4 demonstrates mutations identified in PRX. The location of mutations within L-periaxin is indicated in the diagram at the top by the arrows. The clinical phenotype of each patient, their mutations, and the frequency of their mutations in North American control chromosomes are listed in the table on the bottom of the figure.

Using denaturing high pressure liquid chromatography (DHPLC), each coding exon of PRX was screened for mutations in 168 peripheral neuropathy patients who had tested negative for mutations involving PMP22, MPZ, GJB1, EGR2, or MTMR2. The PCR amplicons that gave an abnormal DHPLC elution profile were sequenced by standard methods in the art. Patient 851 of family HOU297 is compound heterozygous for deletion 2787 C and transition 2857C>T. By conceptual translation, 2787 C causes a frameshift after amino acid S929 and terminates the protein at codon 957 (S929fsX957), while 2857C>T causes the nonsense mutation R953X (FIGS. 3 and 4). The 2787 C or 2857C>T defects were not observed in control chromosomes (FIG. 4). The patient 1461 in family HOU579 is compound heterozygous for deletion 2289 T and a 1102C>T transition causing the nonsense mutation R368X; 2289 T results in a frameshift after amino acid V763 and terminates the protein at codon 774 (V763fsX774, FIG. 3). The unaffected parents and son of family HOU579 are each heterozygous carriers of a PRX mutant allele (FIG. 3). Families HOU418, HOU579 and HOU297 exhibit autosomal recessive inheritance. Black symbols indicate DSN. Patient 851 from family HOU297 is compound heterozygous for mutations S929fsX957 and R953X; her older normal son is heterozygous for R953X. Patient 1461 from family HOU579 is compound heterozygous for mutations V763fsX774 and R368X; her normal brother is heterozygous for V763fsX774. Patient 1136 from family HOU418 has the homozygous mutation S929fsX957; her two normal sisters and her son are heterozygous for this mutation.

The defects 2289 T or 1102C>T were not observed in control chromosomes (FIG. 4). Patient 1136 of family HOU418 was homozygous for deletion 2787 C, the same deletion observed in patient 851 of HOU297. The unaffected parents, sisters, and son of this patient are each heterozygous carriers of this deletion on one PRX allele (FIGS. 3 and 4); although unaware of consanguinity, both parents hailed from a small village in Vietnam.

Other PRX sequence variants identified in patients and controls are shown in Table 2. In specific embodiments, these represent benign polymorphic variants. In one specific embodiment the alleles identified in only one control chromosome represent rare polymorphisms, or in an alternative embodiment a recessive carrier state.

TABLE 2

| Alterations occurring in North American control chromosomes or unaffected family members | | |
|---|---|---|
| Alteration | | Frequency in control chromosomes |
| 3775G > A | E1259K | 0/190* |
| 1216G > A | A406T | 1/178 |
| 4075-4077 | E1359 | 1/150 |
| 1483G > C | E495Q | 2/184 |
| 3394A > G | R1132G | 6/182 |
| 3248C > G | P1083R | 24/182 |
| 2763A > G | I921M | 37/190 |
| 2645C > T | A882V | 45/190 |
| 306C > T | T102T | ND |
| 1491C > G | P497P | ND |
| 2655T > C | P885P | ND |

*Observed in an unaffected sibling; ND, not determined

EXAMPLE 4

Phenotype of Patients with PRX Loss-of-Function Mutations

The clinical features of peripheral neuropathy in patients with autosomal recessive PRX mutations are comparable to those observed in the 19q13 linked family and the homozygous knockout mice (Table 3) (Delague et al., 2000; Gillespie et al., 2000). In each patient, objective findings include markedly reduced nerve conduction velocities and onion bulb formations on neuropathology. Interestingly, these patients have a more severe sensory component than usually seen with typical DSN or CMT1.

TABLE 3

| CLINICAL FEATURES OF PATIENTS WITH MYELINOPATHY SECONDARY TO PRX MUTATIONS | | | | | |
|---|---|---|---|---|---|
| Family<br>Patient | HOU297<br>851 | HOU579<br>1461 | HOU418<br>1136 | CMT4F<br>19q13.1-q13.3 | $Prx^{-/-}$<br>mice |
| Current age (years) | 46 | 6 | 31 | | |
| Sex | F | F | F | | |
| Age at onset (years) | <7 | 1.5 | 1 | Early childhood | 4-6 weeks |
| Inheritance pattern | AR | AR | AR | AR | AR |
| Motor involvement | Distal dominant, severe | Distal dominant, severe | Distal dominant, severe | Distal dominant, severe | Severe weakness |
| Sensory loss | Severe | Severe | Severe | Severe | Severe |
| Sensory ataxia | No | Yes | Yes | Yes | Unsteady gait |
| Dysesthesia | None | None | Yes | Yes | Yes |
| Foot deformity | Pes cavus | None | Pes cavus | Pes cavus, Pes equinovarus | Not described |
| Motor nerve conduction velocity | 3 m/sec | Undetectable | 2.1 m/sec in median nerve | Undetectable | Severely delayed |
| Peripheral nerve histopathology | NA | Hypomyelination, Dysmyelination OBF | NA | Severe loss of MF, OBF | Demyelination, thick and thin myelin sheaths, loss of MF, OBF |

The table utilizes the following abbreviations: F-female; AR-autosomal recessive; NA-not available; MF-myelinated fibers; and OBF-onion bulb formation.

EXAMPLE 5

Testing Individual for Myelinopathy

In an embodiment of the present invention, a myelinopathy is diagnosed by the methods and/or compositions of the present invention. In a specific embodiment, a sample containing nucleic acid is obtained from an individual. In a preferred embodiment, the nucleic acid is SEQ ID NO:1 or an RNA from SEQ ID NO:1. Examples of samples include blood, saliva, semen, urine, hair, feces, sweat, tears, cheek scrapings, body tissue, and the like. The nucleic acid is analyzed by standard molecular biology methods, such as sequencing, polymerase chain reaction, hybridization, electrophoresis, or a combination thereof. In a specific embodiment the myelinopathy is Charcot-Marie-Tooth (CMT) syndrome, hereditary neuropathy with liability to pressure palsies (HNPP), Dejerine-Sottas syndrome (DSS), congenital hypomyelinating neuropathy (CHN), or Roussy-Levy syndrome (RLS). In the embodiment wherein polymerase chain reaction is used to diagnose the myelinopathy, primers selected from SEQ ID NO:3 through SEQ ID NO:26 may be utilized. In a specific embodiment the nucleic acid comprises an alteration such as 3775G>A, 1216G>A, 4075-4077d, 1483G>C, 3394A>G, 3248C>G, 2763A>G, 2645C>T, 306C>T, 1491C>G, and/or 2655T>C.

In a specific embodiment, a sample containing an amino acid sequence is obtained from an individual. In a preferred embodiment, the nucleic acid is SEQ ID NO:2. Examples of samples include blood, saliva, semen, urine, hair, feces, sweat, tears, cheek scrapings, body tissue, and the like. The amino acid sequence is analyzed by standard molecular biology methods, such as with antibodies, electrophoresis, sequencing, or a combination thereof. In a specific embodiment the amino acid sequence comprises an alteration in SEQ ID NO:2 and may include E1259K, A406T, E1359delΔ, E495Q, R1132G, P1083R, I921M, A882V, T102T, P497P, and/or P885P. In a specific embodiment the myelinopahty is Charcot-Marie-Tooth (CMT) syndrome, hereditary neuropathy with liability to pressure palsies (HNPP), Dejerine-Sottas syndrome (DSS), congenital hypomyelinating neuropathy (CHN), or Roussy-Levy syndrome (RLS).

EXAMPLE 6

Identifying Compounds for Therapeutic Use

In a specific embodiment there is a method of identifying a compound for the treatment of myelinopathy comprising the steps of exposing said compound to a knockout animal, wherein the animal comprises at least one defective allele of a nucleic acid sequence of SEQ ID NO:1 and wherein the animal has at least one symptom associated with the myelinopathy; and assaying for an improvement in the at least one symptom of the myelinopathy after exposure to said compound. In a specific embodiment there myelinopathy is Charcot-Marie-Tooth (CMT) syndrome, hereditary neuropathy with liability to pressure palsies (HNPP), Dejerine-Sottas syndrome (DSS), congenital hypomyelinating neuropathy (CHN), or Roussy-Levy syndrome (RLS). The compound may be any biological agent, such as a protein, lipid, nucleic acid, chemical agent, and the like. In a preferred embodiment, the knockout animal comprises two defective alleles of a nucleic acid sequence of SEQ ID NO: 1.

A method of screening for a compound for the treatment of myelinopathy comprising the steps of providing a cell lacking a functional periaxin amino acid sequence contacting the cell with the compound; and determining the effect of the compound on said cell, wherein the effect on the cell is indicative of the treatment of the myelinopathy. In a specific embodiment there myelinopathy is Charcot-Marie-Tooth (CMT) syndrome, hereditary neuropathy with liability to pressure palsies (HNPP), Dejerine-Sottas syndrome (DSS), congenital hypomyelinating neuropathy (CHN), or Roussy-Levy syndrome (RLS). The compound may be any biological agent, such as a protein, lipid, nucleic acid, chemical agent, and the like.

In a specific embodiment there is a method of identifying an upregulator of periaxin nucleic acid sequence expression comprising the steps of administering a test compound to a transgenic animal, wherein the genome of said transgenic animal comprises a reporter nucleic acid sequence, wherein the sequence is under the control of an operably linked periaxin promoter active in eukaryotic cells; measuring the level of the periaxin expression; and comparing the level of the periaxin expression in the animal with normal periaxin expression, wherein an increase in the level following administration of the test compound indicates the test compound is an upregulator. The compound may be any biological agent, such as a protein, lipid, nucleic acid, chemical agent, and the like.

In another embodiment there is a method of identifying a drug having activity in the treatment of myelinopathy, comprising the steps of obtaining a compound suspected of having extracellular signaling activity; and determining whether the compound has the extracellular signaling activity. The extracellular signaling activity preferably is associated with the cytoskeleton. In a specific embodiment the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS). The compound may be any biological agent, such as a protein, lipid, nucleic acid, chemical agent, and the like.

EXAMPLE 7

Treating Myelinopathy

In an embodiment of the present invention there is a method of treating myelinopathy in an organism, comprising the step of administering to the organism a therapeutically effective amount of a periaxin nucleic acid sequence, wherein the nucleic acid sequence is administered by a vector. In a specific embodiment, the vector is selected from the group consisting of a plasmid, a viral vector, a lipid, a liposome, a polypeptide, or a combination thereof. In another specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment of the present invention there is a method of treating myelinopathy in an organism comprising the step of administering to the organism a therapeutically effective amount of a periaxin amino acid sequence, wherein the amino acid sequence is administered with a physiologically acceptable carrier.

In an additional embodiment there is a method of treating myelinopathy in an organism comprising the step of administering to the organism a therapeutically effective amount of a periaxin amino acid sequence, wherein the amino acid sequence is administered with a physiologically acceptable carrier. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment there is a method of treating an animal for a myelinopathy comprising the steps of identifying a compound which interacts with an amino acid sequence of SEQ ID NO:2; and administering to the animal a therapeutically effective amount of the compound. In a specific embodiment, the myelinopathy is selected from the group consisting of Charcot-Marie-Tooth (CMT) syndrome, hereditary neuropathy with liability to pressure palsies (HNPP), Dejerine-Sottas syndrome (DSS), congenital hypomyelinating neuropathy (CHN), and Roussy-Levy Syndrome (RLS).

In another embodiment there is a method of treating a patient for a myelinopathy comprising the steps of preparing a compound obtained by methods described herein; and administering the compound with a physiologically acceptable carrier to the patient.

EXAMPLE 7

Significance of PRX Defects

Consistent with the phenotypes of $Prx^{-/-}$ mice, the three families described in the preceding examples establish that putative loss-of-function mutations in PRX cause autosomal recessive DSN (FIG. 4). The nonsense and frameshift mutations delete the carboxyl portion of L-periaxin, including the acidic domain. In a specific embodiment, the acidic domains mediate protein-protein interactions. Loss of this domain, therefore, in a specific embodiment inhibits binding of L-periaxin to the cytoskeleton or in an alternative embodiment precludes L-periaxin from interacting with proteins essential for transmission of extracellular signals.

PRX mutations are a significant cause of apparently sporadic and autosomal recessive DSN. Three of twenty unrelated DSN patients inherited two recessive mutant PRX alleles; by comparison, four, three and two DSN patients of the twenty had de novo heterozygous causative mutations in MPZ, PMP22 and EGR2, respectively. Moreover, because HOU297, HOU579, and HOU418 are respectively of North American Hispanic, Northern European (English-German-Polish), and Vietnamese ethnicities, in a specific embodiment PRX mutations are a significant cause of DSN in most populations. Thus, identification of PRX mutations is important for the diagnosis and recurrence risk counseling of DSN patients and their families.

Mutations of the transcription factor EGR2 cause myelinopathies (Warner et al. 1998), and in a specific embodiment mutation of genes regulated by EGR2 also result in myelinopathies. In a specific embodiment, the expression of proteins interacting with L-periaxin is also regulated by EGR2.

The association of mutations in PRX with peripheral neuropathy not only identifies another genetic cause for the CMT1 spectrum of myelinopathies but also provides further insights into the molecular mechanisms for these diseases. The interaction among L-periaxin, the cytoskeleton and a membrane complex is reminiscent of the interactions among the proteins of the dystrophin-sarcoglycan complex (Cohen and Campbell, 2000) and the signaling complexes organized by other PDZ domain proteins (Montell, 2000). In a specific embodiment, mutations in cytoskeletal and membrane proteins interacting with L-periaxin also cause CMT or related neuropathies.

EXAMPLE 8

PRX Mutations Cause a Broad Spectrum of Demyelinating Neuropathies

PRX Mutation Analysis

Figure 5:
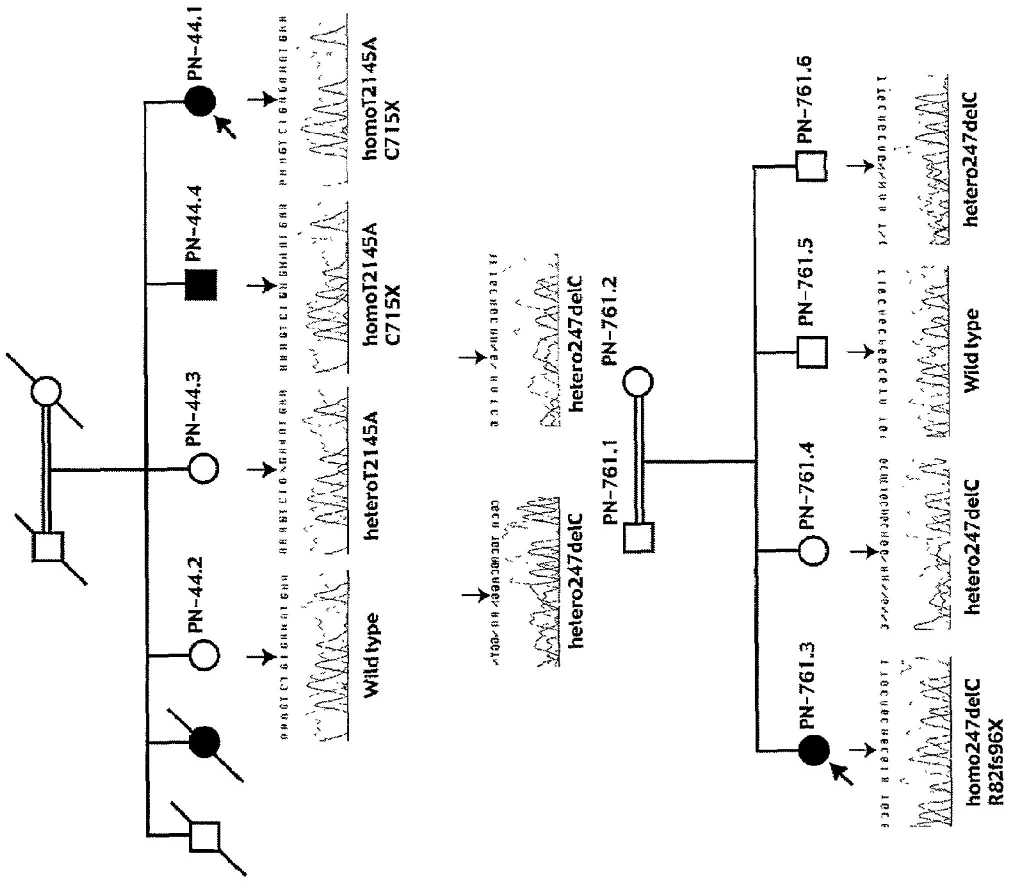
FIG. 5 shows chromatograms of PRX alterations identified in two families. Standard pedigree symbols are used; males are represented by squares, females by circles. Black filled symbols indicate patients with CMT or CHN. Families PN-44, and PN-761 exhibit autosomal recessive inheritance. Below each individual the DNA sequence chromatogram is shown with the specific mutation (vertical allows) given under the chromatogram. PN-44.1 and PN-44.4 are homozygous and their unaffected sister PN-44.3 is heterozygous for the C715X mutation. PN-761.3 is homozygous, and her parents and unaffected brother are heterozygous for the R82fsX96 mutation.

By DNA sequencing, each coding exon of PRX was screened for mutations in 29 peripheral neuropathy patients who had tested negative for mutations involving the following genes: PMP22 encoding peripheral myelin protein, MPZ encoding myelin protein zero, GJB1 encoding connexin 32, and EGR2 encoding early growth response 2 protein. Sibling patients PN-44.1 and PN-44.4 were homozygous for the mutation 2145T>A that by conceptual translation causes a nonsense stop codon at amino acid 715 that normally encodes a cysteine (C715X). Patient PN-761.3 was homozygous for 247DC that results in frameshift mutation R82fsX96. The unaffected parents, sister and brothers either did not carry the mutation or were heterozygous carriers (FIG. 5). We did not observe either 2145T>A or 247DC in 180 control chromosomes.

Histopathology

Figure 6:
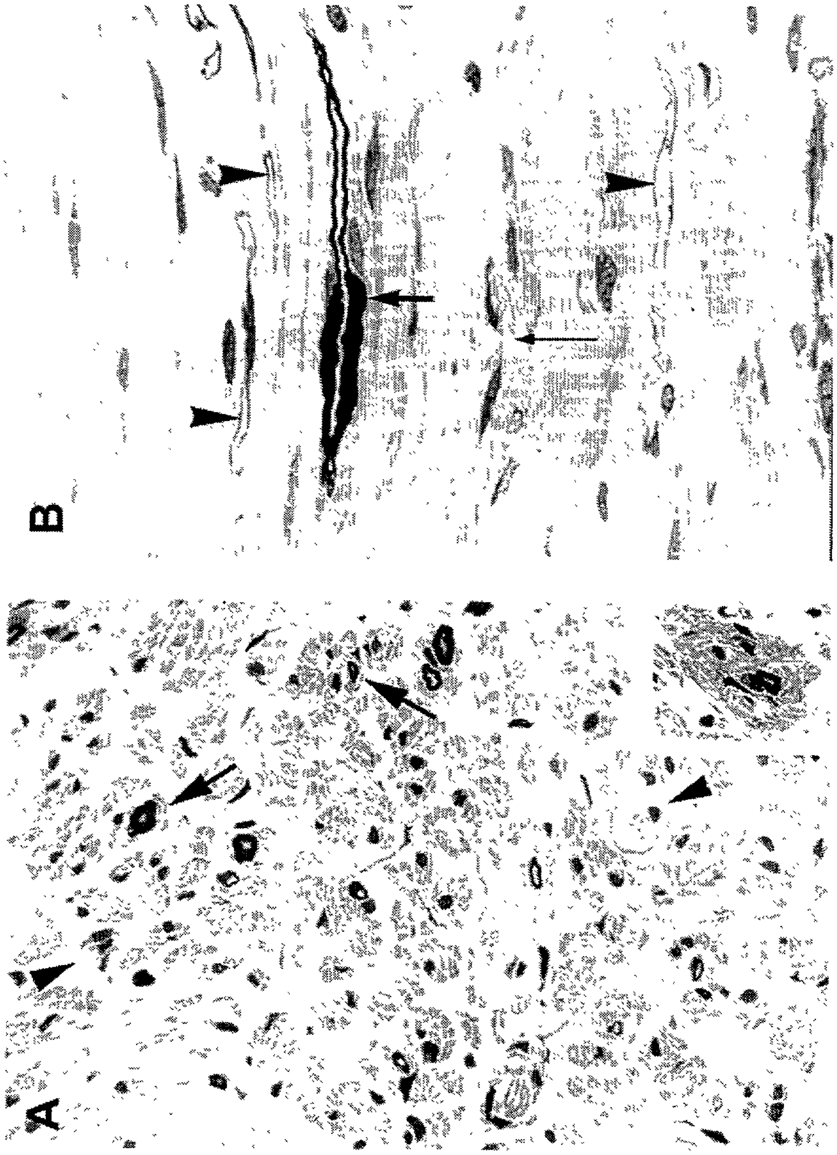
FIG. 6 demonstrates light microscopy of semi-thin resin sections from the sural nerve biopsies of patients PN-44.1 (6A) and PN-761.3 (6B).
Figure 7:
FIG. 7 shows electron microscopy of longitudinal sections in patients PN-761.3 (7A) and PN-44.1 (7B), and control sural nerve (7C).

For patient PN-44.1, light microscopy revealed a severe loss of myelinated axons of all diameters and increased connective tissue (FIG. 6A). Although some remaining myelinated fibers were normal, many showed tomacula formation or small onion bulb formations. Some onion bulbs had a central axon but many were denervated. There was no evidence of axonal regeneration. Endoneural and perineurial vessels were normal and inflammatory infiltrates were not seen. On electron microscopy, the tomacula consisted of concentric or eccentric thickenings of the myelin sheath with focally folded myelin surrounding a constricted axon. The onion bulbs were made up of concentrically arranged Schwann cell processes with or without a central axon. Multiple paranodal abnormalities were identified including a reduced number of myelin loops and an absence of septate-like junctions between the paranodal myelin and the axon (FIG. 7B). Denervated Schwann cell units of unmyelinated axons enclosed collagen pockets.

For patient PN-761.3, light microscopy revealed a severe loss of thick myelin sheaths. Numerous fibers were demyelinated or thinly remyelinated. Atrophic axons with relatively thick myelin sheaths (tomacula) were occasionally seen (FIG. 6B). Typical onion bulb formation was minimal. At the electron microscopic level, basal lamina onion bulbs with up to 6 layers were frequently encountered. As observed in patient PN-44.1, the paranodes of nerve fibers showed incomplete myelination or demyelination and separation of multiple terminal myelin loops from the axon at the paranode, sometimes with flat intervening Schwann cell processes (FIG. 7A). The unmyelinated axons were of uneven size and surrounded by Schwann cell processes that showed degenerative changes such as condensation, swelling, vacuoles, membranous cytoplasmic bodies, and dilated ergastoplasma.

Periaxin Immunofluorescence Analysis

Figure 8:
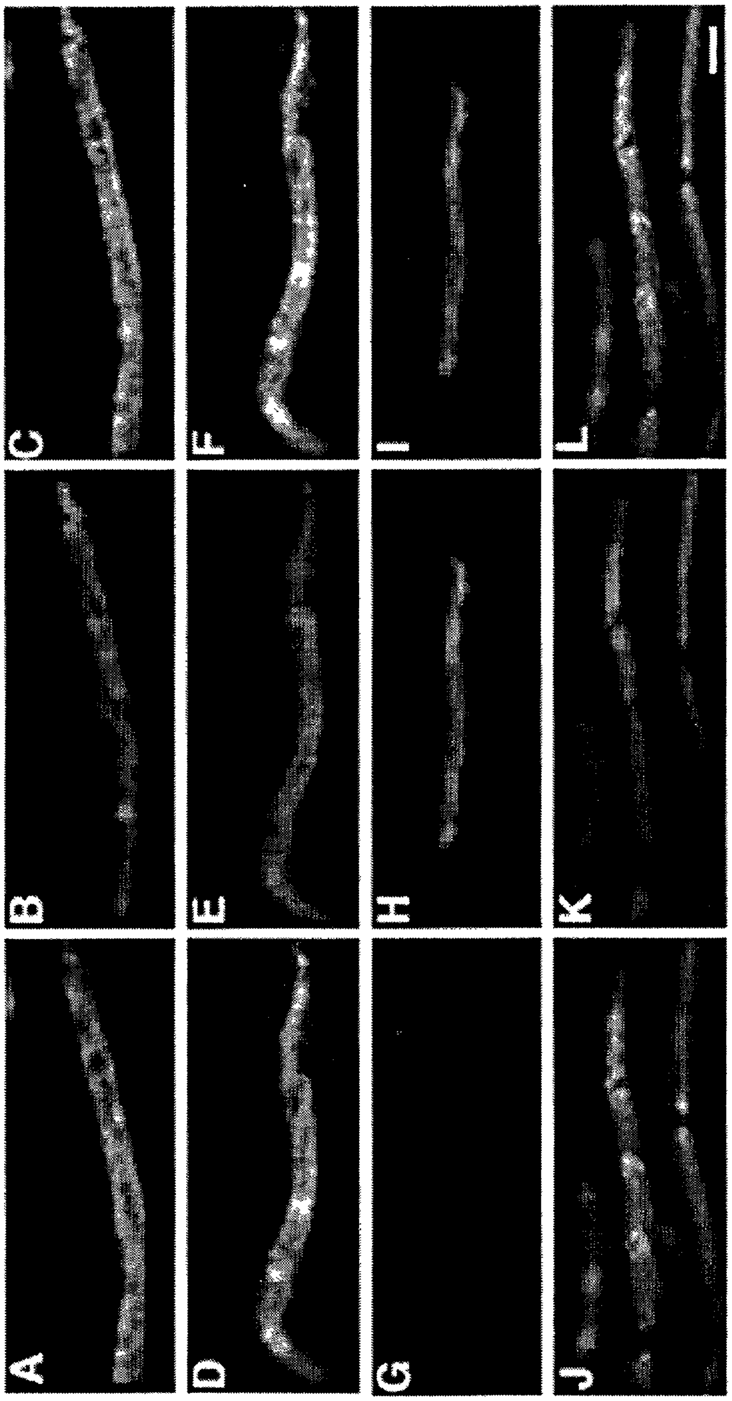
FIG. 8 demonstrates immunofluorescence analysis of sural nerve biopsy from patient PN-44.1. For FIGS. 8A, 8B, and 8C, nerve fibers from patient PN-44.1 are shown staining with N-terminal PRX antibody (8A), and MBP (8B), which colocalise (8C).

Immunofluorescence analysis of a normal human sural nerve biopsy showed positive double staining for myelin basic protein (MBP) and the anti-N-terminal, the anti-repeat region and the C-terminal L-periaxin antibodies. In patient 44.1, there is also staining for the N-terminal and repeat region antibodies, but there is no labeling with the anti-C-terminal antibody even though there is MBP-positive staining (FIG. 8). This result demonstrates that a truncated L-periaxin is made. It also indicates that the C-terminal region downstream of the repeat region has an important function. Furthermore, these data suggest that interaction with DRP2 (approximately at amino acid positions 118 to 196 in rat L-periaxin) is not sufficient for L-periaxin's function.

These two families confirm that putative loss-of-function mutations in PRX cause autosomal recessive neuropathies and broaden the spectrum of PRX-associated peripheral neuropathies. Consistent with the phenotype of $Prx^{-/-}$ mice (Gillespie et al., 2000) and previously reported patients (Boerkoel et al., 2001; Gulbot et al., 2001), all three patients reported in this study had marked sensory involvement. Such severe sensory involvement is rare among patients with mutations in other CMT-associated genes such as PMP22, MPZ, GJB1 and EGR2 and thus may be a signature clinical feature of neuropathy arising from PRX mutations. Interestingly, the sensory involvement observed in patients PN-44.1 and PN-44.4 was more severe, and their motor neuropathy was less severe, than previously reported for PRX mutations (Boerkoel et al., 2001; Gulbot et al., 2001).

Patient PN-761.3 has been the only patient reported with a PRX mutation affecting both L- and S-periaxin; all other patients have had mutations involving only L-periaxin. A thorough evaluation of her symptoms and nerve histopathology did not identify features that were distinct from those observed in other patients; therefore no specific pathology can be attributed to the frameshift mutation in S-periaxin. Because the frameshift mutation occurs in exon 6 (the penultimate exon of L-periaxin), in a specific embodiment this mutation results in complete loss of L-periaxin expression by nonsense mediated RNA decay (Lykke-Andersen, 2001). In contrast, because exon 6 is the last exon of S-periaxin, in a specific embodiment S-periaxin is expressed as an altered protein. Expression of this altered form of S-periaxin may therefore fulfill the function of S-periaxin.

The peripheral nerve pathology observed in the patients described herein include demyelination with minor remyelination, typical or basal lamina onion bulb formation with occasional tomacula, focally folded myelin, and detached terminal myelin loops. Focally folded myelin has been reported in patients with myotubularin related protein 2 (MTMR2) mutations (Houlden et al., 2001), a patient with an MPZ mutation (Nakagawa et al., 1999) and a patient with an EGR2 mutation (Timmerman et al., 1999). However, detachment of terminal paranodal myelin loops from the axon with loss of septate-like junctions and transverse bands has not yet been reported with these mutations. Therefore detached terminal myelin loops with focally folded myelin may be unique to the pathology observed with mutations of PRX. On the other hand, separation of terminal myelin loops from the axon by flat intervening Schwann cell processes was also seen in HNPP and Cockayne Syndrome (Schroder, 1996).

Recent data show that L-periaxin is an integral constituent of a dystroglycan-dystrophin-related protein 2 complex in the plasma membrane, where it presumably participates in interaction with the basal lamina surrounding the Schwann cell (Sherman et al., 2001). The importance of this complex for stabilizing the axon-Schwann cell unit is illustrated by periaxin-null mice, which show a late-onset peripheral demyelinating neuropathy (Gillespie et al., 2000) and the observation of CMT4F and Dejerine-Sottas disease among patients with PRX mutations (Boerkoel et al., 2001; Gulbot et al., 2001). A previously described patient with CMT4F and a homozygous mutation (R196X) did not express the periaxin protein (Guilbot et al., 2001). However, as described herein there is a patient with a similar demyelinating neuropathy who expresses a truncated periaxin protein lacking the C-terminal region. The interactions of this domain of the periaxin protein would seem to be critical in maintaining peripheral nerve myelination. This C-terminal domain is responsible for targeting the protein for ubiquitin-mediated proteolysis. Hence, the presence of this truncated protein in a specific embodiment reflects an enhancement of its stability. Therefore, it cannot be ruled out that, in addition to a loss-of-function caused by the absence of the C-terminal domain, this mutant protein may also disrupt interactions with the basal lamina as a result of gain-of-function effects.

Although the interaction between periaxin and DRP2 may be essential for complex formation, the disruption of the interaction between these two proteins does not appear to be essential for causation of demyelinating CMT. Immunofluorescence studies on the nerve biopsy from patient PN-44.1 showed that this patient made a stable truncated periaxin protein containing the DRP2 binding domain, and this suggests that the truncated protein can still interact with DRP2. In addition, 168 patients with CMT and related neuropathies were screened for DRP2 mutations but did not identify any nucleotide sequence variants segregating with disease. Thus these two observations suggest that mutation of DRP2 is not a prominent cause of demyelinating CMT neuropathy.

Similar to the spectrum of phenotypes observed with mutation of other genes associated with CMT and related inherited peripheral neuropathies, the clinical phenotypes manifested in patients with mutations in PRX include CMT myelinopathies and DSN. However, in contrast to mutation of other neuropathy genes, mutation of PRX causes a prominent sensory neuropathy. These observations on peripheral neuropathy due to recessive PRX mutations add to a growing body of evidence implicating specific genes/proteins in peripheral nerve function and delineating the pathological consequences of their dysfunction.

Figure 9:
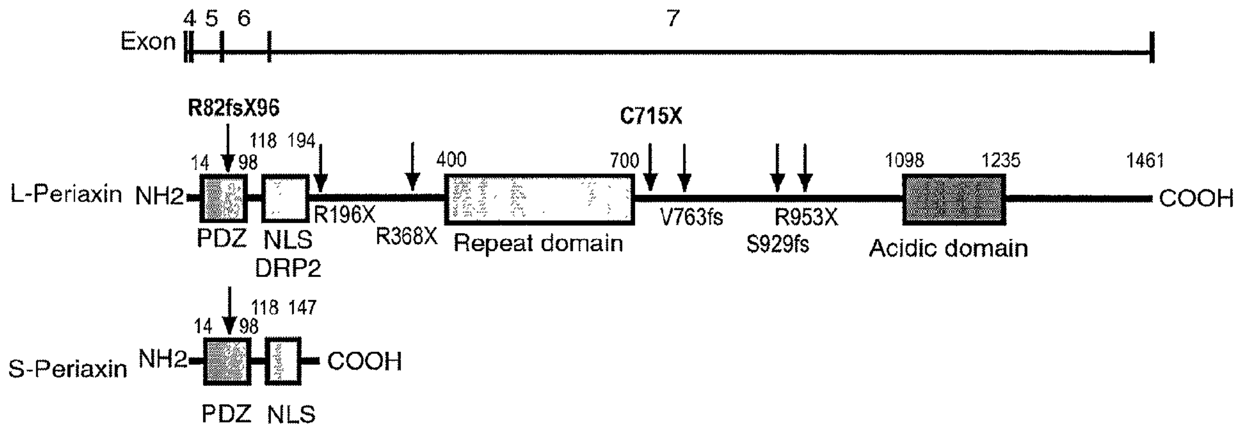
FIG. 9 provides a summary of all reported mutations identified in PRX. The top panel depicts which exons encode specific portion of the periaxin proteins. The middle panel of horizontal shaded boxes illustrates the various domains of L- and S-periaxin. Previously reported mutations are given below with the mutations reported herein shown above. The location of mutations is indicated by the vertical arrows. The mutation C715X affects only L-periaxin, and the mutation R82fsX96 affects both S- and L-periaxin. The table at the bottom lists all reported PRX mutations and their associated disease phenotypes. Abbreviations; PDZ, PDZ domain; NLS, nuclear localization signal; DRP2, DRP2 binding domain.

FIG. 9 provides a summary of all reported mutations identified in PRX. Materials and methods for this Example are as follows.

Human Subjects

DNA was isolated from the peripheral blood of each patient.

Mutation Screening

Mutation screening was performed as described (Boerkoel et al., 2001) The PRX cDNA sequence was numbered beginning with the adenine of the presumed initiating methionine and described mutations according to den Dunnen and Antonarakis (den Dunnen and Antonarakis, 2000).

Sural Nerve Pathology

Sural nerve biopsies, performed at the age of 40 years in patient PN-44.1 and at the age of 3 years in patient PN-761.3 were analyzed according to standard morphological procedures for light- and electron microscopy (Delague et al., 2000; Schroder, 1996). No morphometric studies were done.

Immunohistochemistry

Frozen sections (5 μm) of sural nerve biopsy embedded in OCT (optimal cutting temperature) were collected on 3-aminopropyltriethoxysilane-subbed slides. The sections were fixed in 4% paraformaldehyde solution. Immunofluorescence for L-periaxin, myelin basic protein, and neurofilament was then carried out as described (Dytrych et al., 1998).

Patients

Family PN-44

The proband (PN-44.1, FIG. 4) was the sixth child of healthy consanguineous parents. One brother died at the age of 3 months due to heart failure, two sisters were healthy, and one sister and one brother had a similar neurologic phenotype. The affected sister died at the age of 48 years due to a cardiomyopathy; detailed clinical information on her neurologic condition was not available. The affected brother (PN-44.4) is described below.

Beginning in the first year of life, patient PN-44.1 had signs of motor involvement with difficulty sitting and subsequently delayed acquisition of motor milestones and inability to run as fast as children of her own age; she attended a school for children with a motor handicap. She developed scoliosis in puberty. A neurological examination at the age of 50, showed a normal mental status, normal cranial nerves except for hearing loss, weakness of the intrinsic hand (5-/5), foot (5-/5) and distal leg muscles (5-/5), atrophy of the thenar and foot muscles, a steppage and ataxic gait, absent tendon reflexes, s-curved scoliosis, and pes cavus. Her strength was normal in more proximal muscles. Co-ordination tests showed slight dysmetria on the finger-nose test that could have been due to proprioceptive problems. She had severely decreased sensitivity for touch, position, vibration, pin-prick and temperature to the level of the knees and elbows. She had no palpable nerve hypertrophy. Electrophysiological studies of the median and ulnar nerves showed slow motor nerve conduction velocities (motor NCV, 3 m/sec), reduced compound muscle action potentials (CMAP, median: 1.1 mV, ulnar: 0.45 mV, control: >6 mV), and undetectable median sensory nerve action potentials.

Patient PN-44.4 had gait problems from childhood and developed a severe scoliosis at the age of 10 yrs. On the examination at the age of 54 years, he had normal mental status, normal cranial nerves excepting hearing loss, absent reflexes, weak foot and distal leg muscles, and atrophy of the hands, distal forearms and calves. His proximal muscle strength was normal. His sensation for touch, position, vibration, and pin-prick was severely reduced in both arms and legs. He had no palpable hypertrophic nerves and no pes cavus. The results of his electrophysiologic studies were unavailable.

Family PN-761

Patient PN-761.3 was the first child of healthy consanguineous parents (FIG. 4) who had normal motor nerve conduction velocities. Her three siblings were healthy. Beginning in the first year of life, she manifested delayed motor development; she sat at 10 months, crawled at 17 months, stood with support at 4 years and took her first steps at 5 years. At 6 years, she was able to walk 20-30 meters with a broad based gait and marked sensory ataxia. On examination at 2 years of age, she had absent deep tendon reflexes, weakness of her lower legs and hands, atrophy of the distal lower leg muscles, incomplete foot dorsal flexion, pes planus, and normal cranial nerves. She could stand only with Nancy Hilton orthoses. Her proximal muscle strength and head control were good, and her spine was straight. When last seen at age 6 years, she had weak proximal muscles, could not rise from a squat, walked with 'locked knees", and was unable to hop on two legs or stand on one leg. She was able to stand briefly on her toes but not on her heels. Additionally, her sensation of vibration was diminished in the distal lower legs and hands and her tongue showed fasciculations. Her electrophysiologic studies at age 20 months showed a normal sensory nerve conduction velocity (sensory NCV, 53 m/sec), latency (1.3 msec) and action potential (SNAP, 21 mV), but undetectable CMAP upon stimulation of the peroneal and tibial nerves (100 mA for 0.5 sec). Her visual evoked potential was normal and her auditory evoked potential showed a slight delay of wave I.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

PATENTS

U.S. Pat. No. 4,578,770
U.S. Pat. No. 4,596,792
U.S. Pat. No. 4,599,231
U.S. Pat. No. 4,599,230
U.S. Pat. No. 4,601,903
U.S. Pat. No. 4,608,251
U.S. Pat. No. 5,840,873, issued Nov. 24, 1998
U.S. Pat. No. 5,843,640, issued Dec. 1, 1998
U.S. Pat. No. 5,843,650, issued Dec. 1. 1998
U.S. Pat. No. 5,843,651, issued Dec. 1, 1998
U.S. Pat. No. 5,843,663, issued Dec. 1, 1998
U.S. Pat. No. 5,846,708, issued Dec. 8, 1998
U.S. Pat. No. 5,846,709, issued Dec. 8, 1998
U.S. Pat. No. 5,846,717, issued Dec. 8, 1998
U.S. Pat. No. 5,846,726, issued Dec. 8, 1998
U.S. Pat. No. 5,846,729, issued Dec. 8, 1998
U.S. Pat. No. 5,846,783, issued Dec. 8, 1998
U.S. Pat. No. 5,849,481, issued Dec. 15, 1998
U.S. Pat. No. 5,849,483, issued Dec. 15, 1998
U.S. Pat. No. 5,849,486, issued Dec. 15, 1998
U.S. Pat. No. 5,849,487, issued Dec. 15, 1998
U.S. Pat. No. 5,849,497, issued Dec. 15, 1998
U.S. Pat. No. 5,849,546, issued Dec. 15, 1998
U.S. Pat. No. 5,849,547, issued Dec. 15, 1998
U.S. Pat. No. 5,851,770, issued Dec. 22, 1998
U.S. Pat. No. 5,851,772, issued Dec. 22, 1988
U.S. Pat. No. 5,853,990, issued Dec. 29, 1998
U.S. Pat. No. 5,853,993, issued Dec. 29, 1998
U.S. Pat. No. 5,853,992, issued Dec. 29, 1998
U.S. Pat. No. 5,856,092, issued Jan. 5, 1999
U.S. Pat. No. 5,858,652, issued Jan. 12, 1999
U.S. Pat. No. 5,861,244, issued Jan. 19, 1999
U.S. Pat. No. 5,863,732, issued Jan. 26, 1999
U.S. Pat. No. 5,863,753, issued Jan. 26, 1999
U.S. Pat. No. 5,866,331, issued Feb. 2, 1999
U.S. Pat. No. 5,866,336, issued Feb. 2, 1999
U.S. Pat. No. 5,866,337, issued Feb. 2, 1999
U.S. Pat. No. 5,900,481, issued May 4, 1999
U.S. Pat. No. 5,905,024, issued May 18, 1999
U.S. Pat. No. 5,910,407, issued Jun. 8, 1999
U.S. Pat. No. 5,912,124, issued Jun. 15, 1999
U.S. Pat. No. 5,912,145, issued Jun. 15, 1999
U.S. Pat. No. 5,912,148, issued Jun. 15, 1999
U.S. Pat. No. 5,916,776, issued Jun. 29, 1999
U.S. Pat. No. 5,916,779, issued Jun. 29, 1999
U.S. Pat. No. 5,919,626, issued Jul. 6, 1999
U.S. Pat. No. 5,919,630, issued Jul. 6, 1999
U.S. Pat. No. 5,922,574, issued Jul. 13, 1999
U.S. Pat. No. 5,925,517, issued Jul. 20, 1999
U.S. Pat. No. 5,925,525, issued Jul. 20, 1999
U.S. Pat. No. 5,928,862, issued Jul. 27, 1999
U.S. Pat. No. 5,928,869, issued Jul. 27, 1999
U.S. Pat. No. 5,928,870, issued Jul. 27, 1999
U.S. Pat. No. 5,928,905, issued Jul. 27, 1999
U.S. Pat. No. 5,928,906, issued Jul. 27, 1999
U.S. Pat. No. 5,929,227, issued Jul. 27, 1999
U.S. Pat. No. 5,932,413, issued Aug. 3, 1999
U.S. Pat. No. 5,932,451, issued Aug. 3, 1999
U.S. Pat. No. 5,935,791, issued Aug. 10, 1999
U.S. Pat. No. 5,935,825, issued Aug. 10, 1999
U.S. Pat. No. 5,939,291, issued Aug. 17, 1999
U.S. Pat. No. 5,942,391, issued Aug. 24, 1999
European Application No. 320 308
European Application No. 329 822
GB Application No. 2 202 328

PCT Application No. PCT/US87/00880
PCT Application No. PCT/US89/01025
PCT Application WO 88/10315
PCT Application WO 89/06700
PCT Application WO 90/07641

PUBLICATIONS

Bangham et al., *J. Mol. Biol.,* 13:238, 1965.

Boerkoel C F, Takashima H, Lupski J R. The genetic convergence of Charcot-Marie-Tooth disease type 1 and type 2 and the role of genetics in sporadic neuropathy. Curr Neurol Neurosci Rep 2002;2: in press.

Boerkoel C F, Takashima H, Stankiewicz P, et al. Periaxin mutations cause recessive Dejerine-Sottas neuropathy. Am J Hum Genet 2001;68:325-333.

Chomczynski P, Sacchi N (1987) Single-step method of RNA isolation by acid guanidinium thiocyanate-phenol-chloroform extraction. Anal Biochem 162:156-159.

Cohen R D, Campbell K P (2000) Molecular basis of muscular dystrophies. Muscle Nerve 23:1456-1471.

Deamer and Uster, "Liposome Preparation: Methods and Mechanisms," *LIPOSOMES*, M. Ostro ed. (1983).

Dejerine J, Sottas J (1893) Sur la névrite interstitielle hypertrophique et progressive de l'enfance. Comp Rend Seanc Soc Biol 45:63-96.

Delague V, Bareil C, Tuffery S, Bouvagnet P, Chouery E, Koussa S, Maisonobe T, Loiselet J, Megarbane A, Claustres M (2000) Mapping of a new locus for autosomal recessive demyelinating Charcot-Marie-Tooth disease to 19q13.1-13.3 in a large consanguineous Lebanese family: exclusion of MAG as a candidate gene. Am J Hum Genet 67:236-243.

den Dunnen J T, Antonarakis S E (2000) Mutation nomenclature extensions and suggestions to describe complex mutations: a discussion. Hum Mutat 15:7-12.

Dyck P J, Lambert E H: Lower motor and primary sensory neuron disease with peroneal muscular atrophy I. Neurologic, genetic and electrophysiological findings in hereditary polyneuropathies. *Arch Neurol* 18:603, 1968.

Dyck P J, Lambert E H: Lower motor and primary sensory neuron disease with peroneal muscular atrophy II. Neurologic, genetic and electrophysiological findings in various neuronal degenerations. *Arch Neurol* 18:619, 1968.

Dytrych L, Sherman D L, Gillespie C S, Brophy P J. Two PDZ domain proteins encoded by the murine periaxin gene are the result of alternative intron retention and are differentially targeted in Schwann cells. J Biol Chem 1998;273:5794-5800.

Charnas L, Trapp B, Griffin J: Congenital absence of peripheral myelin: abnormal Schwann cell development causes lethal arthrogryposis multiplex congenita. *Neurology* 38:966, 1988.

Dytrych L, Sherman D L, Gillespie C S, Brophy P J (1998) Two PDZ domain proteins encoded by the murine periaxin gene are the result of alternative intron retention and are differentially targeted in Schwann cells. J Biol Chem 273:5794-5800.

Fernandez-Valle C, Gorman D, Gomez A M, Bunge M B (1997) Actin plays a role in both changes in cell shape and gene-expression associated with Schwann cell myelination. J Neurosci 17:241-250.

Ghosh and Bachhawat, "Targeting of liposomes to hepatocytes," In: Wu G. Wu C ed., Liver diseases, targeted diagnosis and therapy using specific receptors and ligands, New York: Marel Dekker, pp. 87-104, 1991.

Gillespie C S, Lee M, Fantes J F, Brophy P J (1997) The gene encoding the Schwann cell protein periaxin localizes on mouse chromosome 7 (Prx). Genomics 41:297-298.

Gillespie C S, Sherman D L, Blair G E, Brophy P J (1994) Periaxin, a novel protein of myelinating Schwann cells with a possible role in axonal ensheathment. Neuron 12:497-508.

Gillespie C S, Sherman D L, Fleetwood-Walker S M, Cottrell D F, Tait S, Garry E M, Wallace V C, Ure J, Griffiths I R, Smith A, Brophy P J (2000) Peripheral demyelination and neuropathic pain behavior in periaxin-deficient mice. Neuron 26:523-531.

Gregoriadis, *DRUG CARRIERS IN BIOLOGY AND MEDICINE,* G. Gregoriadis (ed.), 1979, pp. 287-341.

Guilbot A, Williams A, Ravisé N, et al. A mutation in periaxin is responsible for CMT4F, an autosomal recessive form of Charcot-Marie-Tooth disease. Hum Mol Genet 2001;10:415-421.

Harati Y, Butler I J: Congenital hypomyelinating neuropathy. *J Neurol Neurosurg Psychiatry* 48:1269, 1985.

Hayasaka K, Himoro M, Sawaishi Y, Nanao K, Takahashi T, Takada G, Nicholson G A, Ouvrier R A, Tachi N (1993) De novo mutation of the myelin $P_0$ gene in Dejerine-Sottas disease (hereditary motor and sensory neuropathy type III). Nat Genet 5:266-268.

Houlden H, King R H M, Wood N W, et al. Mutations in the 5' region of the myotubularin-related protein 2 (MTMR2) gene in autosomal recessive hereditary neuropathy with focally folded myelin. Brain 2001; 124:907-915.

Kaneda et al., "Increased expression of DNA cointroduced with nuclear protein in adult rat liver," *Science,* 243:375-378, 1989.

Kato et al., "Expression of hepatitis B virus surface antigen in adult rat liver," *J. Biol. Chem.,* 266:3361-3364, 1991.

Lupski J R (2000) Recessive Charcot-Marie-Tooth disease. Ann Neurol 47:6-8.

Lupski J R, Garcia C A (2001) Charcot-Marie-Tooth peripheral neuropathies and related disorders. In: Scriver C R, Beaud et al, Sly W S, Valle D, Volgelstein B, Childs B (eds) The Metabolic and Molecular Bases of Inherited Disease. McGraw-Hill, New York, pp In press.

Lykke-Andersen J. mRNA quality control: Marking the message for life or death. Current Biology 2001;11:R88-R91.

Montell C (2000) A PDZ protein ushers in new links. Nat Genet 26:6-7.

Nakagawa M, Suehara M, Saito A, et al. A novel MPZ gene mutation in dominantly inherited neuropathy with focally folded myelin sheaths. Neurology 1999;52:1271-1275.

Nicolau et al., "Liposomes as carriers for in vivo gene transfer and expression," *Methods Enzymol.,* 149:157-176, 1987.

Parman Y, Plante-Bordeneuve V, Guiochon-Mantel A, Eraksoy M, Said G (1999) Recessive inheritance of a new point mutation of the PMP22 gene in Dejerine-Sottas disease. Ann Neurol 45:518-22.

"Remington's Pharmaceutical Sciences" 15th Edition, pages 1035-1038, 1570-1580.

Roa B B, Dyck P J, Marks H G, Chance P F, Lupski J R (1993) Dejerine-Sottas syndrome associated with point mutation in the peripheral myelin protein 22 (PMP22) gene. Nat Genet 5:269-273.

Roussy G, Lévy G: Sept cas d'une maladie particulaire. *Rev Neurol* 1:427, 1926.

Sambrook, Fritsch, Maniatis, *In: Molecular Cloning: A Laboratory Manual,* Vol. 1, Cold Spring Harbor Laboratory Press, Cold Spring Harbor, N.Y., Ch. 7,7.19-17.29, 1989.

Scherer S S, Xu Y-t, Bannerman P G C, Sherman D L, Brophy P J (1995) Periaxin expression in myelinating Schwann cells: modulation by axon-glial interactions and polarized localization during development. Development 121:4265-4273.

Schröder J M. Developmental and pathological changes at the node and paranode in human sural nerves. Micr Res Techn 1996;34:422-435.

Schuler G D (1997) Sequence mapping by electronic PCR. Genome Res 7:541-550.

Shaffer L G, Kennedy G M, Spikes A S, Lupski J R (1997) Diagnosis of CMT1A duplications and HNPP deletions by interphase FISH: implications for testing in the cytogenetics laboratory. Am J Med Genet 69:325-331.

Sherman D L, Brophy P J (2000) A tripartite nuclear localization signal in the PDZ-domain protein L-periaxin. J Biol Chem 275:4537-4540.

Szoka and Papahadjopoulos, *Proc. Nat'l Acad. Sci. U.S.A.* 75:4194-98 (1978).

Tapon N, Hall A (1997) Rho, Rac and Cdc42 GTPases regulate the organization of the actin cytoskeleton. Curr Opin Cell Biol 9:86-92.

Thomas P K, Calne D B, Stewart G: Hereditary motor and sensory neuropathy (peroneal muscular atrophy). *Ann Hum Genet* 38:111, 1974.

Timmerman V, De Jonghe P, Ceuterick C, De Vriendt E, Lofgren A, Nelis E, Warner L E, Lupski J R, Martin J J, Van Broeckhoven C (1999) Novel missense mutation in the early growth response 2 gene associated with Dejerine-Sottas syndrome phenotype. Neurology 52:1827-1832.

Warner L E, Mancias P, Butler I J, McDonald C M, Keppen L, Koob K G, Lupski J R (1998) Mutations in the early growth response 2 (EGR2) gene are associated with hereditary myelinopathies. Nat Genet 18:382-384.

Windebank A J: Inherited recurrent focal neuropathies. in: Dyck P J, Thomas P K, Griffin J W, Low P A, Poduslo J F (eds): *Peripheral Neuropathy* Philadelphia, W. B. Saunders, 1993; p 1137.

Wong et al., "Appearance of β-lactamase activity in animal cells upon liposome mediated gene transfer," *Gene,* 10:87-94, 1980.

One skilled in the art to which the invention pertains readily appreciates that the patent invention is well adapted to carry out the objectives and obtain the ends and advantages mentioned as well as those inherent therein. Periaxin, periaxin mutations, methods, techniques, pharmaceutical compositions, treatments, and procedures described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A method of diagnosing myelinopathy in an individual, said myelinopathy resulting from a periaxin (PRX) alteration in the individual, comprising the step of assaying a sample from said individual for an alteration in a periaxin polynucleotide, said sample comprising periaxin polynucleotide genomic DNA having two PRX alleles, wherein said periaxin polynucleotide comprises SEQ ID NO:76 and wherein the presence of the alteration in both PRX alleles diagnoses said individual as having myelinopathy.

2. The method of claim 1, wherein said myelinopathy is selected from the group consisting of Charcot-Marie-Tooth (CMT) syndrome, hereditary neuropathy with liability to pressure palsies (HNPP), Dejerine-Sottas syndrome (DSN), congenital hypomyelinating neuropathy (CHN), and Roussy-Levy syndrome (RLS).

3. The method of claim 1, wherein said assaying step further comprises a polymerase chain reaction.

4. The method of claim 3, wherein primers for said polymerase chain reaction are selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26.

5. The method of claim 1, wherein said alteration is 3775G>A, 1216G>A, 4075-4077d, 1483G>C, 3394A>G, 3248C>G, 2763A>G, 2645C>T, 306C>T, 1491C>G, 2655T>C, 2145T>A, 1102C>T, 2289delT, 2787delC, 2857C>T, or 247ΔC.

6. A method of detecting the presence or absence of a mutation associated with a myelinopathy, said myelinopathy resulting from a periaxin mutation in the individual, the method comprising:

a) isolating a test nucleic acid from a subject, said test nucleic acid comprising a periaxin polynucleotide of SEQ ID NO:76;

b) comparing the test nucleic acid to a reference wild-type periaxin polynucleotide; and c) determining the differences between the test nucleic acid and the reference wild-type periaxin polynucleotide, wherein the differences are mutations in the periaxin polynucleotide of the subject, and wherein said detection of the presence or absence of the mutation is therein provided.

7. The method of claim 6, wherein said mutation is 2145T>A, 1102C>T, 2289delT, 2787delC, 2857C>T, or 247ΔC.

8. The method of claim 6, wherein said mutation encodes a defect of a periaxin polypeptide, wherein the defect is R953X, R368X, S929fsX957, R196X, V763fsX774, C715X, or R82fsX96.

9. The method of claim 6, wherein said comparing step is by DHPLC, sequencing, hybridization, or a combination thereof.

10. The method of claim 6, wherein the myelinopathy is Charcot-Marie-Tooth (CMT) syndrome, hereditary neuropathy with liability to pressure palsies (HNPP), Dejerine-Sottas syndrome (DSN), congenital hypomyelinating neuropathy (CHN), or Roussy-Levy Syndrome (RLS).

11. The method of claim 6, wherein said mutation encodes a defect of a periaxin polypeptide, wherein the defect is E1259K, A406T, E1359delΔ, E495Q, R1132G, P1083R, I921M, A882V, T102T, P497P, or P885P.

12. A method of diagnosing myelinopathy in an individual comprising the step of assaying a sample containing nucleic acid from said individual for an alteration in a periaxin polynucleotide, said sample comprising periaxin polynucleotide genomic DNA having two PRX alleles, wherein said periaxin polynucleotide comprises SEQ ID NO:76 and wherein said alteration is associated with said myelinopathy, and wherein said myelinopathy comprises a prominent sensory neuropathy, wherein said assay provides said diagnosis.

13. The method of claim 12, wherein said assaying step further comprises a polymerase chain reaction.

14. The method of claim 13, wherein primers for said polymerase chain reaction are selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26.

15. The method of claim 12, wherein said alteration is 3775G>A, 1216G>A, 4075-4077d, 1483G>C, 3394A>G, 3248C>G, 2763A>G, 2645C>T, 306C>T, 1491C>G, 2655T>C, 2145T>A, 1102C>T, 2289delT, 2787delC, 2857C>T, or 247ΔC.

16. A method of detecting a polymorphism or mutation in a periaxin polynucleotide of an individual, comprising the step of assaying a periaxin polynucleotide comprising SEQ ID NO:76 for the polymorphism or mutation from a sample from said individual.

17. The method of claim 1, wherein said myelinopathy is Dejerine-Sottas syndrome.

18. The method of claim 1, wherein said individual is suspected of having the myelinopathy.

19. The method of claim 1, wherein the alteration comprises a homozygous periaxin mutation.

20. The method of claim 1, wherein the alteration comprises a compound heterozygous periaxin mutation.

21. The method of claim 12, wherein the alteration comprises a homozygous periaxin mutation.

22. The method of claim 12, wherein the alteration comprises a compound heterozygous periaxin mutation.

23. A method of identifying an individual suspected of having myelinopathy or being a carrier of myelinopathy, comprising the step of assaying a sample from said individual, wherein said sample comprises nucleic acid, for an alteration in a periaxin polynucleotide, wherein said polynucleotide comprises SEQ ID NO:76 and wherein the presence of the alteration identifies said individual as having periaxin-associated myelinopathy or being a carrier of periaxin-associated myelinopathy.

24. The method of claim 23, wherein said myelinopathy comprises a prominent sensory neuropathy.

25. The method of claim 23, wherein the alteration comprises a homozygous periaxin mutation.

26. The method of claim 23, wherein the alteration comprises a compound heterozygous periaxin mutation.

27. A method of identifying an individual suspected of having myelinopathy or being a carrier of myelinopathy, comprising the step of assaying a sample from said individual, wherein the sample comprises genomic DNA having two PRX alleles, for an alteration in a periaxin polynucleotide, wherein said polynucleotide comprises SEQ ID NO:76, wherein the presence of the alteration in the periaxin polynucleotide is indicative of an alteration in at least one of the PRX alleles, wherein the presence of the alteration in both PRX alleles identifies said individual as having periaxin-associated myelinopathy and wherein the presence of the alteration in one allele identifies said individual as being a carrier of periaxin-associated myelinopathy.

28. The method of claim 1, wherein the alteration in the periaxin polynucleotide results in a loss-of-function for the corresponding periaxin polypeptide.

29. The method of claim 6, wherein the alteration in the periaxin polynucleotide results in a loss-of-function for the corresponding periaxin polypeptide.

30. The method of claim 12, wherein the alteration in the periaxin polynucleotide results in a loss-of-function for the corresponding periaxin polypeptide.

31. The method of claim 16, wherein the alteration in the periaxin polynucleotide results in a loss-of-function for the corresponding periaxin polypeptide.

32. The method of claim 23, wherein the alteration in the periaxin polynucleotide results in a loss-of-function for the corresponding periaxin polypeptide.

33. The method of claim 27, wherein the alteration in the periaxin polynucleotide results in a loss-of-function for the corresponding periaxin polypeptide.

34. A method of identifying an individual with a myelinopathy, comprising the step of assaying a sample from an individual suspected of having myelinopathy for an alteration in a periaxin polynucleotide, wherein said polynucleotide comprises SEQ ID NO:76, wherein the presence of the alteration in the periaxin polynucleotide identifies said individual as having the myelinopathy.

35. The method of claim 34, wherein the individual suspected of having myelinopathy is further defined as having one or more of a symptom selected from the group consisting of defective myelin, slowed motor nerve conduction velocity, muscle weakness, muscle atrophy, gait disturbance, onion bulb formations, palsy, areflexia, decreased sensitivity for touch, and decreased sensitivity for temperature.

* * * * *

SEQUENCE LISTING

```
<160> NUMBER OF SEQ ID NOS: 93

<210> SEQ ID NO 1
<211> LENGTH: 5502
<212> TYPE: DNA
<213> ORGANISM: human

<400> SEQUENCE: 1

gctctcgagg tgtctggagg ctcagcgagc gccggaccca ggaggcccaa ggagctggag     60

gtgaccctca ggcagcaaga accccacgga agggcgtgag ccctgcagac agctgtgcgg    120

cacctcgggc tgggctcctg ttaggaggaa gtgcctgcac ccaggcagcg gctcagaggc    180

agctgctcca tgcagaactg aagctggttc tgcagcagaa aggggagagg acacaggagc    240

ctggggtgca ggtgcctccc agcaacgcca tggaggccag gagccggagt gccgaggagc    300

tgaggcgggc ggagttggtg gaaattatcg tggagacgga ggcgcagacc ggggtcagcg    360

gcatcaacgt agcgggcggc ggcaaagagg gaatcttcgt tcgggagctg cgcgaggact    420

cacccgccgc caggagcctc agcctgcagg aaggggacca gctgctgagt gcccgagtgt    480

tcttcgagaa cttcaagtac gaggacgcac tacgcctgct gcaatgcgcc gagccttaca    540

aagtctcctt ctgcctgaag cgcactgtgc ccaccgggga cctggctctg cggcccggga    600

ccgtgtctgg ctacgagatc aagggcccgc gggccaaggt ggccaagctg gtacgcgtgc    660

ttagcccggc cccggccctg gactgcccca gcgatccggt ctctgcgccg tgagccccat    720

tccccgccat cgtgggccag ccttgccctc tgtcttgtca ctaacccaag ctaattccac    780

cctctgcccc ttcctctctg ccccaaactc ttccccggga agggggacag acccacccca    840

gcccagggcc ctcacccacc tcggagaggc gtccccacca tcggatccag gcttgctagg    900
```

-continued

```
ggtcctgaac caggctactt cgaaccagga aagccagatt ccagcctgag tgctggccca    960
attactgctg agtggccctg gacaaagttg tttctctccc tgggcctcag tttccccatc   1020
tctagaatga ggatgttggg gaaaatcccg gatcaggatc tagaagtctt gggtccccgt   1080
ccctacactc ctgttgactc atttggagat cctagatggc tgcctgcttt cctgggcact   1140
catggtgaaa tgacaggcaa gaagtgggga tgatgtttgg ggaacaagat acttgaccca   1200
gcacatcccc cgcctggtcc aataccaggt ggggctcttc ctgtccactc ccagcctccc   1260
actgtcccac cgcctcctgc ctctctcctc tctccccaga acatccagag tctgtcccct   1320
gtgaagaaga agaagatggt gcctggggct ctgggggtcc ccgctgacct ggcccctgtt   1380
gacgtcgagt tctcctttcc caagttctcc cgcctgcgtc ggggcctcaa agccgaggct   1440
gtcaagggtc ctgtcccggc tgcccctgcc cgccggcgcc tccagctgcc tcggctgcgt   1500
gtacgagaag tggccgaaga ggctcaggca gcccggctgg ccgccgccgc tcctcccccc   1560
aggaaagcca aggtggaggc tgaggtggct gcaggagctc gtttcacagc ccctcaggtg   1620
gagctggttg ggccgcggct gccaggggcg gaggtgggtg tcccccaggt ctcagccccc   1680
aaggctgccc cctcagcaga ggcagctggt ggctttgccc tccacctgcc aacccttggg   1740
ctcggagccc cggctccgcc tgctgtggag gccccagccg tgggaatcca ggtcccccag   1800
gtggagctgc ctgccttgcc ctcactgccc actctgccca cacttccctg cctagagacc   1860
cgggaagggg ctgtgtcggt agtggtgccc accctggatg tggcagcacc gactgtgggg   1920
gtggacctgg ccttgccggg tgcagaggtg gaggcccggg gagaggcacc tgaggtggcc   1980
ctgaagatgc cccgccttag ttttccccga tttggggctc gagcaaagga agttgctgag   2040
gccaaggtag ccaaggtcag ccctgaggcc agggtgaaag gtcccagact tcgaatgccc   2100
acctttgggc tttccctctt ggagccccgg cccgctgctc ctgaagttgt agagagcaag   2160
ctgaagctgc ccaccatcaa gatgccctcc cttggcatcg gagtgtcagg gcccgaggtc   2220
aaggtgccca agggacctga agtgaagctc cccaaggctc ctgaggtcaa gcttccaaaa   2280
gtgcccgagg cagcccttcc agaggttcga ctcccagagg tggagctccc caaggtgtca   2340
gagatgaaac tcccaaaggt gccagagatg gctgtgccgg aggtgcggct tccagaggta   2400
gagctgccca aagtgtcaga gatgaaactc ccaaaggtgc cagagatggc tgtgccggag   2460
gtgcggcttc cagaggtaca gctgctgaaa gtgtcggaga tgaaactccc aaaggtgcca   2520
gagatggctg tgccggaggt gcggcttcca gaggtacagc tgccgaaagt gtcagagatg   2580
aaactcccag aggtgtcaga ggtggctgtg ccagaggtgc ggcttccaga ggtgcagctg   2640
ccgaaagtgc cagagatgaa agtccctgag atgaagcttc caaaggtgcc tgagatgaaa   2700
cttcctgaga tgaaactccc tgaagtgcaa ctcccgaagg tgcccgagat ggccgtgccc   2760
gatgtgcacc tcccagaagt gcagcttcca aaagtcccag agatgaagct ccctgagatg   2820
aaactccctg aggtgaaact cccgaaggtg cccgagatgg ctgtgcccga tgtgcacctc   2880
ccggaagtgc agctcccgaa agtcccagag atgaaactcc ctaaaatgcc tgagatggct   2940
gtgccagagg ttcgactccc cgaggtgcag ctgccaaaag tctcagagat gaaactcccc   3000
aaggtgcctg aaatggccgt gcccgatgtg cacctcccag aggtgcagct gcccaaagtc   3060
tgtgaaatga aagtccctga catgaagctc ccagagataa aactccccaa ggtgcctgag   3120
atggctgtgc ccgatgtgca cctccccgag gtgcagctgc cgaaagtgtc agagattcgg   3180
ctgccggaaa tgcaagtgcc gaaggttccc gacgtgcatc ttccgaaggc accagaggtg   3240
aagctgccca gggctccgga ggtgcagcta aaggccacca aggcagaaca ggcagaaggg   3300
```

-continued atggaatttg gcttcaagat gcccaagatg accatgccca agctagggag ggcagagtcc 3360
ccatcacgtg gcaagccagg cgaggcgggt gctgaggtct cagggaagct ggtaacactt 3420
ccctgtctgc agccagaggt ggatggtgag gctcatgtgg gtgtccccctc tctcactctg 3480 ccttcagtgg agctagacct gccaggagca cttggcctgc aggggcaggt cccagccgct 3540
aaaatgggca agggagagcg ggtggagggc cctgaggtgg cagcaggggt cagggaagtg 3600
ggcttccgag tgccctctgt tgaaattgtc accccacagc tgcccgccgt ggaaattgag 3660
gaagggcggc tggagatgat agagacaaaa gtcaagccct cttccaagtt ctccttacct 3720
aagtttggac tctcggggcc aaaggtggct aaggcagagg ctgagggggc tgggcgagct 3780
accaagctga aggtatccaa atttgccatc tcactcccca aggctcgggt gggggctgag 3840
gctgaggcca aaggggctgg ggaggcaggc ctgctgcctg ccctcgatct gtccatccca 3900
cagctcagcc tggatgccca cctgccctca ggcaaggtag aggtggcagg ggccgacctc 3960
aagttcaagg ggcccaggtt tgctctcccc aagtttgggg tcagaggccg ggacactgag 4020
gcagcagaac tagtgccagg ggtggctgag ttggagggca agggctgggg ctgggatggg 4080
agggtgaaga tgcccaagct gaagatgcct tcctttgggc tggctcgagg gaaggaagca 4140
gaagttcaag gtgatcgtgc cagcccgggg gaaaaggctg agtccaccgc tgtgcagctt 4200
aagatccccg aggtggagct ggtcacgctg ggcgcccagg aggaagggag ggcagagggg 4260
gctgtggccg tcagtggaat gcagctgtca ggcctgaagg tgtccacagc caggcaggtg 4320
gtcactgagg gccatgacgc ggggctgagg atgcctccgc tgggcatctc cctgccacag 4380
gtggagctga ccggctttgg ggaggcaggt accccagggc agcaggctca gagtacagtc 4440
ccttcagcag agggcacagc aggctacagg gttcaggtgc cccaggtgac cctgtctctg 4500
cctggagccc aggttgcagg tggtgagctg ctggtgggtg agggtgtctt taagatgccc 4560
accgtgacag tgccccagct tgagctggac gtggggctaa gccgagaggc acaggcgggc 4620
gaggcggcca caggcgaggg tgggctgagg ctgaagttgc ccacactggg ggccagagct 4680
agggtggggg gcgagggtgc tgaggagcag cccccagggg ccgagcgtac cttctgcctc 4740
tcactgcccg acgtggagct ctcgccatcc gggggcaacc atgccgagta ccaggtggca 4800
gagggggagg gagaggccgg acacaagctc aaggtacggc tgccccggtt tggcctggtg 4860
cgggccaagg agggggccga ggagggtgag aaggccaaga gccccaaact caggctgccc 4920
cgagtgggct tcagccaaag tgagatggtc actggggaag ggtcccccag ccccgaggag 4980
gaggaggagg aggaggaaga gggcagtggg gaaggggcct cgggtcgccg gggccgggtc 5040
cgggtccgct tgccacgtgt aggcctggcg gccccttcta aagcctctcg gggggcaggag 5100 ggcgatgcag cccccaagtc ccccgtcaga gagaagtcac ccaagttccg cttccccagg 5160
gtgtccctaa gccccaaggc ccggagtggg agtggggacc aggaagaggg tggattgcgg 5220
gtgcggctgc ccagcgtggg gttttcagag acaggggctc caggcccggc caggatggag 5280
ggggctcagg ctgcggctgt ctgaagcccc tagtcagatg gggatccctt cttgccttcc 5340
tttctctacc ccctcgctgt tgtgtgtgtg ataactagca ctaaccctaa gagggccggg 5400
aggtgggtga ctgaccaggg ctggcaggga ggcctgctcc tgtctctctg gcaggagtgc 5460
ctgtacccca ccaagccatg tgaataaaat aatctggaag ta 5502

<210> SEQ ID NO 2
<211> LENGTH: 147
<212> TYPE: PRT

-continued

<213> ORGANISM: human

<400> SEQUENCE: 2

```
Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Ile
            20                  25                  30

Asn Val Ala Gly Gly Gly Lys Glu Gly Ile Phe Val Arg Glu Leu Arg
        35                  40                  45

Glu Asp Ser Pro Ala Ala Arg Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Ile Lys Gly Pro Arg Ala Lys Val Ala Lys Leu Val
        115                 120                 125

Arg Val Leu Ser Pro Ala Pro Ala Leu Asp Cys Pro Ser Asp Pro Val
    130                 135                 140

Ser Ala Pro
145
```

<210> SEQ ID NO 3
<211> LENGTH: 19
<212> TYPE: DNA
<213> ORGANISM: Human

<400> SEQUENCE: 3
gtaagcatgg cctccacct 19

<210> SEQ ID NO 4
<211> LENGTH: 20
<212> TYPE: DNA
<213> ORGANISM: HUMAN

<400> SEQUENCE: 4
ctccttgctg ccctagtctg 20

<210> SEQ ID NO 5
<211> LENGTH: 18
<212> TYPE: DNA
<213> ORGANISM: HUMAN

<400> SEQUENCE: 5
acctgttgag cgccaatg 18

<210> SEQ ID NO 6
<211> LENGTH: 20
<212> TYPE: DNA
<213> ORGANISM: Human

<400> SEQUENCE: 6
cccaaggcag attcctaacc 20

<210> SEQ ID NO 7
<211> LENGTH: 20
<212> TYPE: DNA
<213> ORGANISM: HUMAN

-continued

<400> SEQUENCE: 7
cgtgcaagtg ggcagaacta 20

<210> SEQ ID NO 8
<211> LENGTH: 20
<212> TYPE: DNA
<213> ORGANISM: HUMAN

<400> SEQUENCE: 8
tgacaagaca gagggcaagg 20

<210> SEQ ID NO 9
<211> LENGTH: 20
<212> TYPE: DNA
<213> ORGANISM: HUMAN

<400> SEQUENCE: 9
aataccaggt ggggctcttc 20

<210> SEQ ID NO 10
<211> LENGTH: 20
<212> TYPE: DNA
<213> ORGANISM: HUMAN

<400> SEQUENCE: 10
ctctaggcag ggaagtgtgg 20

<210> SEQ ID NO 11
<211> LENGTH: 18
<212> TYPE: DNA
<213> ORGANISM: HUMAN

<400> SEQUENCE: 11
agccgtggga atccaggt 18

<210> SEQ ID NO 12
<211> LENGTH: 20
<212> TYPE: DNA
<213> ORGANISM: HUMAN

<400> SEQUENCE: 12
tgacactttg ggcagctcta 20

<210> SEQ ID NO 13
<211> LENGTH: 20
<212> TYPE: DNA
<213> ORGANISM: HUMAN

<400> SEQUENCE: 13
cagaggttcg actcccagag 20

<210> SEQ ID NO 14
<211> LENGTH: 20
<212> TYPE: DNA
<213> ORGANISM: HUMAN

<400> SEQUENCE: 14
gccatctcag gcattttagg 20

<210> SEQ ID NO 15
<211> LENGTH: 20
<212> TYPE: DNA

-continued

<213> ORGANISM: HUMAN

<400> SEQUENCE: 15
ctgaggtgaa actcccgaag 20

<210> SEQ ID NO 16
<211> LENGTH: 20
<212> TYPE: DNA
<213> ORGANISM: Human

<400> SEQUENCE: 16
gcagagtgag agaggggaca 20

<210> SEQ ID NO 17
<211> LENGTH: 20
<212> TYPE: DNA
<213> ORGANISM: Human

<400> SEQUENCE: 17
aagctaggga gggcagagtc 20

<210> SEQ ID NO 18
<211> LENGTH: 20
<212> TYPE: DNA
<213> ORGANISM: HUMAN

<400> SEQUENCE: 18
aacttgggga gagcaaacct 20

<210> SEQ ID NO 19
<211> LENGTH: 20
<212> TYPE: DNA
<213> ORGANISM: Human

<400> SEQUENCE: 19
cctcaggcaa ggtagaggtg 20

<210> SEQ ID NO 20
<211> LENGTH: 20
<212> TYPE: DNA
<213> ORGANISM: HUMAN

<400> SEQUENCE: 20
gtcacggtgg gcatcttaaa 20

<210> SEQ ID NO 21
<211> LENGTH: 20
<212> TYPE: DNA
<213> ORGANISM: HUMAN

<400> SEQUENCE: 21
caggctacag ggttcaggtg 20

<210> SEQ ID NO 22
<211> LENGTH: 20
<212> TYPE: DNA
<213> ORGANISM: HUMAN

<400> SEQUENCE: 22
ttctctctga cgggggactt 20

<210> SEQ ID NO 23
<211> LENGTH: 19

-continued

<212> TYPE: DNA
<213> ORGANISM: HUMAN

<400> SEQUENCE: 23
gtccgcttgc cacgtgtag 19

<210> SEQ ID NO 24
<211> LENGTH: 20
<212> TYPE: DNA
<213> ORGANISM: HUMAN

<400> SEQUENCE: 24
gtacaggcac tcctgccaga 20

<210> SEQ ID NO 25
<211> LENGTH: 21
<212> TYPE: DNA
<213> ORGANISM: HUMAN

<400> SEQUENCE: 25
ccgagcctta caaagtctcc t 21

<210> SEQ ID NO 26
<211> LENGTH: 20
<212> TYPE: DNA
<213> ORGANISM: HUMAN

<400> SEQUENCE: 26
agtttggggc agagaggaag 20

<210> SEQ ID NO 27
<211> LENGTH: 384
<212> TYPE: DNA
<213> ORGANISM: Human

<400> SEQUENCE: 27
tacttccaga ttattttatt cacatggctt ggtggggtac aggcactcct gccagagaga 60
caggagcagg cctccctgcc agccctggtc agtcacccac ctcccggccc tcttagggtt 120
agtgctagtt atcacacaca caacagcgag ggggtagaga aaggaaggca agaagggatc 180
cccatctgac taggggcttc agacagccgc agcctgagcc ccctccatcc tggccgggcc 240
tggagcccct gtctctgaaa accccacgct gggcagccgc acccgcaatc caccctcttt 300
ctggtcccca ctcccactcc gggccttggg ggctaaggac acccctggga agccggaact 360
tggtgacttc tttcttgcgg ggga 384

<210> SEQ ID NO 28
<211> LENGTH: 402
<212> TYPE: DNA
<213> ORGANISM: Human
<220> FEATURE:
<221> NAME/KEY: misc_feature
<222> LOCATION: (1)..(402)
<223> OTHER INFORMATION: n equals unknown

<400> SEQUENCE: 28
tacttccaga ttattttatt cacatggctt ggtggggtac aggcactcct gccagagaga 60
caggagcagg cctccctgcc agccctggtc agtcacccac ctcccggccc tcttagggtt 120
agtgctagtt atcacacaca caacagcgag ggggtagaga aaggaaggca agaagggatc 180
cccatctgac taggggcttc agacagccgc agcctgagcc ccctccatcc tggccgggcc 240

-continued

```
tggagcccct gtctctgaaa accccacgct gggcagccgc acccgcaatc caccctcttc    300

ctggtcccca ctcccactcc gggccttggg gcttatggac accctgngga agcggaactt    360

gggtgacttc tctcttaccg gggactttgg ggcttgattt cc                       402
```

<210> SEQ ID NO 29
<211> LENGTH: 5432
<212> TYPE: DNA
<213> ORGANISM: Mouse

<400> SEQUENCE: 29

```
cagacagacc aaggagctct ggaggtgtct ggaggcccac cgagccccag acccaggagg     60

cccaggaagc tggaagtgac cctcaggcag caagacctca aaggaagagt gagattcctg    120

cttacagctg tgcatcaccc cgagtggggc tcctgtcagg agaaaaggcc atcactcaag    180

aagcggctca gcggcagctg ctccatgagg agctgaaggt ggtcctgcag cagaaggagg    240

agaggacacg ggagctcgag ccccaggtga ctctctgcag agctatggag gccaggagcc    300

gcagcgctga ggagctgaga cgggcggagt tggtggagat tatcgtggag accgaggcac    360

agaccggggt cagcggcttc aacgtagcag gcggcggcaa agaaggaatc tttgtccgtg    420

agctgcgaga ggactcaccg gcagctaaga gcctcagctt gcaagaaggg gaccagctgc    480

tgagtgcccg tgtgttcttt gagaacttca aatatgagga tgcacttcgc ctgctgcaat    540

gcgcagagcc ctacaaggtc tccttctgct tgaagcgcac tgtgcccacc ggggatctgg    600

cactgaggcc cgggacggtg tctggatacg agatgaaggg cccacgggcc aaagtggcca    660

agctggtacg cgtgcttagc ccggtcccgg tccaggacag ccccagtgac cgggtcgctg    720

ctgcgccgta aaccctactc cctttcactg tggcccactt tggccctctg tctgtcacta    780

acccgacact aattcgccct ctgccccttg ttctctgctc ctaaactcca ctcctgtcaa    840

agggtgcacc tattggcagg tggttctcac ccatccccac catgcaaccc gggctcatta    900

ggggtcatgg agtcctggaa ggccagattc tagcccaatg gctgttgggt tactgagtga    960

cccaagtttc ttttcctctc tgggtcgcag tttccccaac tctacaataa ggatgttggg   1020

ggaaattcca gaatttttgg gttcccattg ccacatccct gtcccattgc cacatcactg   1080

tgagattctg aatgactgtc attgccttcc tgaagtgaca ggcaggaagg tggatgtgtt   1140

ttgggatata ctctacccca aacttctccc agcctggtat actaggtggg ttatttttct   1200

atctactccc agcctcccac tgtcccacag cctcctgcct ctctcctctc tcctcagaac   1260

atccagagtc tggcccctgt gaagaagaag aagatggtga ctggggccct ggggacccct   1320

gcagatttgg cccctgttga cgtcgagttc tcttttccca agttctcccg actgcgtcgg   1380

ggtctcaaag ccgaggctgt caagggacct gtcccagctg cccctgcccg tcgccgcctc   1440

cagctgcctc ggctgcgtgt ccgagaagta gctgaagagg cccaggtagc ccgaatggct   1500

gctgctgctc ctcccccaag gaaggccaag gcagaagctg aggcagccac aggagctggg   1560

ttcacagccc ctcagataga gctagttggg cctcggctgc ctagtgccga ggtgggtgtc   1620

cctcaggtct cagttcccaa ggggacccca tcaacagagg cagccagcgg ctttgccctt   1680

cacctgccaa cccttgggct aggtgcccca gctgcaccgg ctgtggagcc cccagccacg   1740

ggaatccagg ttccacaagt ggaactcccc accctgccct ctctacccac gcttcccaca   1800

cttccatgcc tggacaccca ggaaggagct gcagtggtaa aagtccctac cctggatgtg   1860

gcagctccgt ctatgggggt ggacctggct ttgccgggtg cagaggtgga ggcccaggga   1920

gaggttcctg aagtggccct caagatgccc cggctcagtt tcccccgttt tgggattcgg   1980
```

-continued

```
gggaaggaag ccactgaagc caaagtagtc aagggcagcc ctgaggccaa agcaaagggt   2040
cccagacttc gaatgcccac ctttgggctt tctctcctgg aaccccggcc ctctggccct   2100
gaagctgttg ctgagagcaa gctgaagcta cccaccctca agatgccctc tttcggcatt   2160
ggtgtggctg ggcctgaagt caaggcaccc acggggcccg aagtaaagct ccctaaggtt   2220
cctgaggtca aactcccgaa agtgcccgag gcagccattc cagatgtgca actccctgag   2280
gtacagctgc ccaaaatgtc agacatgaaa cttccaaaga tccctgagat ggttgtaccc   2340
gacgttcgtc ttccggaagt gcagctgccc aaagtccctg agatgaaagt cccagagatg   2400
aagctcccga agtggcccga gatggccgtg cccgatgtac accttccaga tgtacagctc   2460
ccgaaagtcc cagagatgaa gctcccgaag gtgcccgaga tggccgtgcc cgatgtacac   2520
cttccagatg tacagctccc gaaagttcca gagatgaagc taccagagat gaagctcccg   2580
aaggtgccgg agatggccgt gccggatgta cgactcccgg aagttcagct gcccaaagtg   2640
tctgaggtga agctcccaaa gatgcctgag atggccgtgc ctgatgtcca cctcccggag   2700
ctacaacttc ccaaaatgtc cgaggtgaag ctcccaaaga tgcccgagat ggccgtgccc   2760
gatgttcgcc tcccggaagt tcagctgccc aaagtgtcag agatgaaact ccctaagatg   2820
ccagagatga ccatgcccga cattcgcctc ccagaagttc agttgcccaa agtgcctgac   2880
attaaacttc ctgaaatgaa gcttccagaa ataaaactcc ccaaagtgcc tgacatggca   2940
gtgcctgatg tccccttcc agagctgcag ctgcccaaag tgtcggacat tcggctgcct   3000
gaaatgcaag tgtcacaggt cccagaggtg cagcttccca agatgccaga gatgaagttg   3060
tccaaggttc ctgaggtaca gaggaaatct gcaggggcgg agcaggcaaa agggactgaa   3120
tttagtttca agttgcccaa gatgaccatg cccaagttgg ggaaagtggg caagcctggg   3180
gaggcaagta ttgaggttcc agacaaactc atgacacttc cctgtctgca gccagaggtg   3240
ggcactgagg catcccatgt tggtgtccct tccctctctc tcccctctgt ggagcttgac   3300
ttgcctgggg ccctgggcct ggagggacaa gtccaagaag ctgtcccagg caaagtggag   3360
aagccagagg gccccagggt agcagtgggt gttggagagg tgggctttcg tgtgccctct   3420
gtggagattg tcactcctca gctgcccaca gttgaagttg agaaagagca gctagagatg   3480
gtggagatga aagtcaaacc ctcttccaag ttctctctgc ccaaattcgg actttcaggg   3540
cccaaagctg tcaagggaga ggtggagggg cctgggcgag ccaccaagct gaaggtttcc   3600
aagtttacca tctcacttcc caaagctcga gcagggactg aggccgaagc gaagggagct   3660
ggggaagccg ggttgctgcc agcgctggat ctgtccatcc cacagctcag cctggatgcc   3720
cagctgccct caggcaaggt ggaagtagct gatagcaagc ctaaatcgtc cagatttgct   3780
ctgcccaagt ttggggtgaa aggccgggac tctgaggctg atgtactggt ggcaggggag   3840
gctgagcttg agggaaaggg ttggggctgg gatgggaagg tgaagatgcc caagctgaaa   3900
atgccatctt ttgggttgtc ccgaggaaag gaagcagaaa ctcaggatgg acgtgtcagc   3960
cccggggaaa agctggaggc catagctggg cagcttaaga tccctgcggt ggaattggtc   4020
acaccgggag ctcaggagac agagaaggtc accagtggag tgaagccgtc aggcctccag   4080
gtgtccacca ctgggcaggt ggttgcagag ggccaggaga gtgtgcagag ggtgtccaca   4140
ctaggtatct ctttgcccca ggtggaattg gccagctttg ggggaggcagg ccctgagatc   4200
gtagcccctt ctgcagaggg cacagcaggc tctagggtcc aggtgccaca ggtgatgctg   4260
gagctacctg gaacccaggt ggcagggggt gatctgttag tgggtgaggg catcttcaag   4320
```

-continued

```
atgcccacag tgacagtgcc ccagctagag ctggatgtgg ggctgggcca tgaagcccag   4380

gctggtgaag cagccaagag tgagggtggg ataaagttga agttgcccac actggggacc   4440

ggaagcagag gagagggcgt tgagccccag ggccccgagg cccagcgcac cttccacctc   4500

tcattgcccg atgtggaact cacgtcacca gtgagtagcc acgctgagta ccaggtagtt   4560

gagggtgatg ggatggtggg gcacaaactc aaggttcggc tgcccctgtt tggtctggca   4620

aaggccaagg aagggataga agttggagaa aaggttaaga gtccaaagct caggctaccc   4680

cgagtgggct tcagccagag tgagtcggtc tccggagaag gctctccaag tcctgaggag   4740

gaggaagaag gcagtgggga aggggcttcc agtcgccggg gtagggtaag ggtccgcctg   4800

cctcgggtag gcttggcttc cccttctaaa gtctctaagg gacaggaggg tgatgcaacc   4860

tccaagtccc cagttgggga gaagtcaccc aaattccgtt ttcctagggt gtccttaagc   4920

cccaaggccc ggagtgggag tagggaccgg gaagaaggtg gattcagggt ccgactgccc   4980

agtgtgggat tttcagaaac agcagttcca ggttccacca ggattgaggg aacccaggct   5040

gctgccatct gaagccccag gacagctgtg gattccccct cttgtctttc cattccccag   5100

cctagccccc cattttgtgt gtgacattac tagcactaat cctcagaggg cttgaaggtg   5160

agtaactgac tcaggcagga gccagtggcc tgtgccacct cattggccaa agtgcctgta   5220

tatcatgtca aactatggga ataaaataat tcaaaagttg tcatgtgtct tggttctcgt   5280

gggggacaca aggtctcttt atgtttcctt catctggctt gtgcagtgtt acctcagctt   5340

gaacttaaaa tcttgcagcc ttgggggctg gagaggtggc ccagaggtta agagcactgg   5400

ctgctcatgc agaggtcctg agttcaattc cc                                 5432
```

<210> SEQ ID NO 30
<211> LENGTH: 468
<212> TYPE: DNA
<213> ORGANISM: Arabidopsis

<400> SEQUENCE: 30

```
tttaagattg tgggatgggc ttcaaagtag ctgggccttc tcttcgctta aggagttccg     60

ggaacttttg ggaattccgg caacttggga agttgaggca tcgtcggtag ctctggcttt    120

ggaatctctg gaactgcagg ttttgtaatt tctggaacct tgggcagttc aggttttgga    180

acttctggaa tcttcggcag ttcaggcttt ggaatctctg gaaacttagg agcctcagac    240

tttggaacct ctggaaccgt tggcaattcg ggctttggaa cctctggcac cttcggcaac    300

tcaggcttct gaatctccgg catcttgggc aactcgggtt tcttgaatct ccggcatctt    360

aggtaactcc ggcattttgg gcaactcccg gcttctggat ctccggtacc ttaagagcct    420

caagcttggg aactcttggc aactttggca actcaaggct tttggaat                468
```

<210> SEQ ID NO 31
<211> LENGTH: 668
<212> TYPE: DNA
<213> ORGANISM: Mouse
<220> FEATURE:
<221> NAME/KEY: misc_feature
<222> LOCATION: (1)..(668)
<223> OTHER INFORMATION: n equals unknown

<400> SEQUENCE: 31

```
taacttttga attattttat tcccatagtt tgacatgata tacaggcact ttggccaatg     60

aggtggcaca ggccactggc tcctgcctga gtcagttacc caccttcaag ccctctgagg    120

attagtgcta gtaatgtcac acacaaaatg gggggctagg ctggggaatg gaaagacaag    180
```

-continued

```
aggggggaatc cacagctgtc ctggggcttc agatggcagc agcctgggtt ccctcaattc    240
ctggtggaac ctggaactgc tgtttctgaa aatcccacac tgggcagtcg gaccctgaat    300
ccaccttctt cccggtccct actcccactc cgggccttgg ggcttaagga caccctagga    360
aaacggaatt tgggtgactt ctccccaact ggggacttgg aggttgcatc accctcctgt    420
ccctagagac tttagaaggg gaagccaagc ctacccgagg caggcggacc cttaccctac    480
cccggcgact ggaagcccct tccccactgc cttcttcctc ctcctaggac ttggagagcc    540
ttctcccgag accgactcac tctggcttga acccactcng ggtagcctga gctttgactc    600
ttagcctttt ctcccacttc tatcccttcc ttgccctttg cagaccaaca agggaggcgg    660
accttgag                                                              668
```

```
<210> SEQ ID NO 32
<211> LENGTH: 433
<212> TYPE: DNA
<213> ORGANISM: Mouse
<220> FEATURE:
<221> NAME/KEY: misc_feature
<222> LOCATION: (1)..(433)
<223> OTHER INFORMATION: n equals unknown

<400> SEQUENCE: 32

cagaaactca gatggacgtg tcagccccgg ggaaaagctg gaggccatag ctgggcagct     60
taagatccct gcggtggaat tggtcacacc gggagctcag gagacagaga aggtcaccag    120
tggagtgaag ccgtcaggcc tccaggtgtc caccactggg caggtggttg cagagggcca    180
ggagagtgtg cagagggtgt ccacactagg tatctctttg ccccaggtgg aattggccag    240
ctttggggag gcaggccctg agatcgtagc cccttctgca gagggcacag caggctctag    300
ggtccaggtg ccacaggtga tgctggagct acctggaacc cacgtggcag ggggtgatct    360
gttagtgggt gagggcatct tcangatgcc ccccgtgaca gtgcccctcc ttgtgctggc    420
tgtggggctg gcc                                                       433
```

```
<210> SEQ ID NO 33
<211> LENGTH: 451
<212> TYPE: DNA
<213> ORGANISM: Human

<400> SEQUENCE: 33

acttccagat tattttattc acatggcttg gtggggtaca ggcactcctg ccagagagac     60
aggagcaggc ctccctgcca gccctggtca gtcacccacc tcccggccct cttagggtta    120
gtgctagtta tcacacacac aacagcgagg gggtagagaa aggaaggcaa gaagggatcc    180
ccatctgact aggggcttca tacagccgca gcctgagccc cctccatcct ggccgggcct    240
ggagcccctg tctctgaaaa ccccacgctg ggcagccgca cccgcaatcc accctcttcc    300
tggtccccac tcccactccg ggccttgggg cttagggaca ccctggggaa gcggaacttg    360
ggtgacttct ctctgactgg ggacttgggg gctgcatcgc cctcctgccc ccgagaggct    420
ttagaagggg ccgccaggcc tacacgtggc a                                   451
```

```
<210> SEQ ID NO 34
<211> LENGTH: 711
<212> TYPE: DNA
<213> ORGANISM: Mouse
<220> FEATURE:
<221> NAME/KEY: misc_feature
<222> LOCATION: (1)..(711)
```

-continued

<223> OTHER INFORMATION: n equals unknown

<400> SEQUENCE: 34
gcacgctgag tacaggtagt gagggtgatg ggatgggtgg cacaaactca aggttcggct 60
gcccctgttg gtctgcanaa ggccaagnga gggatagaag tggagaaaag gctaagagtc 120
caaagctcag gctaccccga gtgggcttca gccagagtga gtcggtctcc ggagaaggct 180
ctccaagtcc tgaggaggag gaagaaggca gtggggaagg ggcttccagt cgccggggta 240
gggtaagggt ccgcctgcct cgggtaggct tggcttcccc ttctaaagtc tctaagggac 300
aggagggtga tgcaacctcc aagtccccag ttggggagaa gtcacccaaa ttccgttttc 360
ctagggtgtc cttaagcccc aaggcccgga gtgggagtag ggaccgggaa gaaggtggat 420
tcagggtccg actgcccagt gtgggatttt cagaaacagc agttccaggt tccaccagga 480
ttgagggaac ccaggctgct gccatctgaa gccccaggac agctgtggat tccccctctt 540
gtctttccat tccccagcct agccccccat tttgtgtgtg acattactag cactaatcct 600
cagagggctt gaaggtgggt aactgactca ggcaggagcc agtggcctgt gccacctcat 660
tggccaaagt gcctgtatat catgtcaaac tatgggaata aaataattca a 711

<210> SEQ ID NO 35
<211> LENGTH: 239
<212> TYPE: DNA
<213> ORGANISM: Mouse
<220> FEATURE:
<221> NAME/KEY: misc_feature
<222> LOCATION: (1)..(239)
<223> OTHER INFORMATION: n equals unknown

<400> SEQUENCE: 35
ggattggggg nacccaggct cctgccttct gaacccccag gacacctgtg gattccccct 60
catgtctttc cattccccac cctacccccc cattttgtgt gtgacattac taccactagt 120
cctcagaggg cttgaaggtg ggtaactgac tcaggcagga cccagtgccc tgtgccacct 180
cattggccta agtgcctgta tttcatgtca aactatggga ataaaataat tctaaagtt 239

<210> SEQ ID NO 36
<211> LENGTH: 290
<212> TYPE: DNA
<213> ORGANISM: Mouse

<400> SEQUENCE: 36
aacttcccca tgccccactt tccgacattc agacaccgca gttccacgtt ccaccagcac 60
agagggcacc cagggcgccc caatctggag ccccaggaca cctctggatt ccccctctag 120
tctttccatt ccccacccta cccccccatt ttgtgtgtga cattactagc actattcctc 180
agagggcttg aaggtgggta actgactcag gcaggagcca gtggcctgtc ccacctcatt 240
gcccaaagtg cctgtatatc atgtcaaact atgggaataa aataattcaa 290

<210> SEQ ID NO 37
<211> LENGTH: 326
<212> TYPE: DNA
<213> ORGANISM: Mouse

<400> SEQUENCE: 37
accatacaaa gaataccctc ctggacgaac aagccttcac ggtccccccc cccaatctgc 60
gattttcagc cacaccagtt ccagttccac caggattgag ggaacccacc ctgctgcctt 120
atggatcccc aggacagttg tggattcccc cttttgtctt tccattcccc agccttcccc 180

-continued cccattttgt gtgtgacatt actaccacta atcctcagag ggcttgaagg tgggtaactg 240
actcaggcag gacccagtgt cctgtgccac ctcattggcc aaagtgcctg tatttcatgt 300
caaactatgg gaataaaata attcaa 326

<210> SEQ ID NO 38
<211> LENGTH: 633
<212> TYPE: DNA
<213> ORGANISM: Mouse

<400> SEQUENCE: 38
acgccatggc gagctctggg cgagttgccg tcttggagct ccatggcgac cccttgctgc 60
ccctcgcagg agctgagacg ggcggagttg gtggagatta tcgtggagac cgaggcacag 120
accggggtca gcggcttcaa cgtagcaggc ggcggcaaag aaggaatctt tgtccgtgag 180
ctgcgagagg actcaccggc agctaagagc ctcagcttgc aagaagggga ccagctgctg 240
agtgcccgtg tgttctttga gaacttcaaa tatgaggatg cacttcgcct gctgcaatgc 300
gcagagccct acaaagtctc cttctgcttg aagcgcactg tgcccaccgg ggatctggca 360
ctgaggcccg ggacggtgtc tggatacgag atgaagggcc cacgggccaa agtggccaag 420
ctgaacatcc agagtctggc ccctgtgaag aagaagaaga tggtgactgg ggccctgagg 480
acccctgcag atttggcccc tgttgacgtc gagttctctt tttccaagtt ctcccgactg 540
gcgtggggtc ttcaaagccg agctgtcaaa ggacctggtc cagctggccc aacccgtcgc 600
ccgcttcagc tgcctcgggt ttgggtccca gaa 633

<210> SEQ ID NO 39
<211> LENGTH: 488
<212> TYPE: DNA
<213> ORGANISM: Human

<400> SEQUENCE: 39
tttacttcca gattatttta ttcacatggc ttggtggggt acaggcactc ctgccagaga 60
gacaggagca ggcctccctg ccagccctgg tcagtcaccc acctcccggc cctcttaggg 120
ttagtgctag ttatcacaca cacaacagcg agggggtaga gaaaggaagg caagaaggga 180
tccccatctg actaggggct tcagacagcc gcagcctgag ccccctccat cctggccggg 240
cctggagccc ctgtctctga aaaccccacg ctgggcagcc gcacccgcaa tccaccctct 300
tcctggtccc cactcccact ccgggccttg gggcttaggg acaccctggg gaagcggaac 360
ttgggtgact tctctctgac gggggacatt ggggctgcat cgccctcctg cccccgagag 420
gctttagaag ggccgccag gcctacacgt ggcaagcgga cccggacccg gcccccggga 480
cccgaggc 488

<210> SEQ ID NO 40
<211> LENGTH: 372
<212> TYPE: DNA
<213> ORGANISM: Human

<400> SEQUENCE: 40
tttacttcca gattatttta ttcacatggc ttggtggggt acaggcactc ctgccagaga 60
gacaggagca ggcctccctg ccagccctgg tcagtcaccc acctcccggc cctcttaggg 120
ttagtgctag ttatcacaca cacaacagcg agggggtaga gaaaggaagg caagaaggga 180
tccccatctg actaggggct tcagacagcc gcagcctgag ccccttcat tctgggccgg 240

-continued

```
ccttgaaccc ctggtttttg aaaacccaac cttggccagc cgaccccgaa atcaaccctt    300

ttcttggtcc caactcccac tccgggcctt ggggcttagg gacaccctgg ggaagcggaa    360

cttgggtgac tt                                                        372
```

<210> SEQ ID NO 41
<211> LENGTH: 642
<212> TYPE: DNA
<213> ORGANISM: Mouse
<220> FEATURE:
<221> NAME/KEY: misc_feature
<222> LOCATION: (1)..(642)
<223> OTHER INFORMATION: n equals unknown

<400> SEQUENCE: 41

```
taacttttga attattttat tcccatagtt tgacatgata tacaggcact ttggccaatg     60

agggtggcac agggnccact ggcttcctgc ctgagtcagt taccccnnac cttcaagccc    120

tctgagggat tagtgctagt naatgtcaca cacaanaatg gggggctagg nctggggaat    180

ggaaagacaa gagggggaat ccacagctgt cctggggctt cagatggcag cagcctgggt    240

tccctcaatc ctggtggaac ctggaactgc tgtttctgaa aatcccacac tgggcagtcg    300

gaccctgaat ccaccttctt ccccgtcccc tacctccact cccggccttg gggcttaag     360

gacaccccta gaaaacggga atttgggtga cttctcccca actggggact tggaggttgc    420

atcaccctcc tgtcccttag agactttaga aggggaagcc aagcctaccc gaagcaggcg    480

gacccttacc ctacccccgc gactggaagc cccttagcca ctgctcttcc tcctcctagg    540

actggaaagc cctcttcgag accgactacc ttggctgaaa cccactcggg gtagctgagc    600

ttgggatttt taccttttt tcacttctat cctttcttgt cc                        642
```

<210> SEQ ID NO 42
<211> LENGTH: 328
<212> TYPE: DNA
<213> ORGANISM: Mouse

<400> SEQUENCE: 42

```
cccacgcgtc cgggagatga aagtcaaacc ctcttccaag ttctctctgc ccaaattcgg     60

actttcaggg cccaaagctg tcaagggaga ggtggagggg cctgggcgag ccaccaagct    120

gaaggtttcc aagtttacca tctcacttcc caaagctcga gcagggactg aggccgaagc    180

gaagggagct ggggaagccg ggttgctgcc agccctggat ctgtccatcc cacagctcag    240

cctggatgcc cagctgccct caggcaaggt ggaagtagct gatagcaagc ctaaatcgtc    300

cagatttgct ctgcccaagt ttgggggt                                       328
```

<210> SEQ ID NO 43
<211> LENGTH: 564
<212> TYPE: DNA
<213> ORGANISM: Mycosphaerella graminicola

<400> SEQUENCE: 43

```
cgctcccggc tttgacaact cccgataccc cgacactctc gacccctaag cttccatctc     60

tcagcaccac tagcattaag ctgccgccgt tctctgctcc tacactcccg gcttttacga    120

tccctaacct cccgacactc tcgaccccta agcttccatc tctcagcacc actagcatta    180

agctgccgcc gttctctgct cctacactcc cggcctttac gatccctaac ctcccgatat    240

tctcgactcc taagcttcca tctcttagca ccaccagcat taagctgccg tcgctctctg    300

ctccgagcgc tccgtctctg agcaccacta gcatcaggtt gtcgtcattc tccgctccaa    360
```

-continued

```
gcctcccgac atttatctcg agcagcgtca acttgccgtc gttctcggct ccaagcctcc    420

cgggcctccc cacgttcacc acgagcagca tcaacttgcc gtcgttctcg gctccaagcc    480

tcccgggcct ccccacgttc accacgaaca gcgtcaactt gccgtcgttc tcgggtccaa    540

gcctcccggc cctccccacg ttca                                           564
```

```
<210> SEQ ID NO 44
<211> LENGTH: 238
<212> TYPE: DNA
<213> ORGANISM: Mouse
<220> FEATURE:
<221> NAME/KEY: misc_feature
<222> LOCATION: (1)..(238)
<223> OTHER INFORMATION: n equals unknown

<400> SEQUENCE: 44

gaatgaggga acccagactt ntgccttttg aagcccccgg acagtcgtgg gttccccttc     60

tagtctttcc tttccccagc ctagcccccc attttgtgtg tgacattact agcactattc    120

ctcagagggt ttgaaggtgg gtaattgact caggcaggag ccagtggcct gtgccacctc    180

attggccaaa gtgcctgtat atcatgtcaa actatgggaa tgaaattatt caaaagtt      238
```

```
<210> SEQ ID NO 45
<211> LENGTH: 654
<212> TYPE: DNA
<213> ORGANISM: Mouse

<400> SEQUENCE: 45

aaggttaggc tgcccatgtt tggtctggca aaggccaagg aagggataga agttggagaa     60

aaggctaaga gtccaaagct caggctaccc cgagtgagct tcagccagag tgagtcggtc    120

tccggagaag gctctccaag tcctgaggag gaggaagaag gcagtgggga aggggcttcc    180

agtcgccggg gtagggtaag ggtccgcctg cctcgggtag gcttggcttc cccttctaaa    240

gtctctaagg gacaggaggg tgatgcaacc tccaagtccc cagttgggga gaagtcaccc    300

aaattccgtt ttcctagggt gtccttaagc cccaaggccc ggagtgggag tagggaccgg    360

gaagaaggtg gattcagggt ccgactgccc agtgtgggat tttcagaaac agcagttcca    420

ggttccacca ggattgaggg aacccaggct gctgccattt gaagccccag gacagctgtg    480

gattccccct cttgtctttc cattccccag cctggccccc cattttgtgt gtgacattac    540

tagcactaat cctcagaggg cttgaaggtg ggtaactgac tcaggcagga gccagtggcc    600

tgtgccacct cattggccaa agtgcctgta tatcatgtca aactatggga ataa          654
```

```
<210> SEQ ID NO 46
<211> LENGTH: 585
<212> TYPE: DNA
<213> ORGANISM: Zebrafish
<220> FEATURE:
<221> NAME/KEY: misc_feature
<222> LOCATION: (1)..(585)
<223> OTHER INFORMATION: n equals unknown

<400> SEQUENCE: 46

gggggcaga cactgacttc atcactgagg gaataactga ttctgcatga ggaaacactc     60

attaacgact ctgacagaga ggacaggggg gggaatccag aagccagagt ttcacctata    120

aacaacaaaa gacggtctcc cccctcagac aagcctccct ttggtcctca tccaagtaca    180

caccacagca tttccactga cgaacaggac agcccagaac ggattgttca gaaggaaaaa    240
```

-continued

```
ctccatgcag aactaaaaca agttttgagt cagaagagaa accagcttag agacacccaa    300

tccacttcca cagacatgga tgaaccatcc aggacagaca gtaaaaacga ggcggagaag    360

gatatgcagt tgtccgagct tgtggaagtg gttgttgaga ccgaggctga agttggagcc    420

agtggttaca gtgtggttgg tggaggggag cgaggcatct tcatcaaaga tgtcttaaaa    480

gactccccag cagcgaagca cctcagccta cagaaaggta ccaagggact gtattttaca    540

ttacaaagag caatgtcaaa tacactttan agacttgagc cactg                    585
```

<210> SEQ ID NO 47
<211> LENGTH: 232
<212> TYPE: DNA
<213> ORGANISM: Human

<400> SEQUENCE: 47

```
cagccgcagc ctgagccccc ttcatcctgg ccgggcctgg agcccctgtc tttgaaaacc     60

ccacgctggg cagccggacc cggaatccac ccttttgctg gtccccactc ccacttcggg    120

ccttgggggt gatggacacc ctggggaaac ggaacttggg tgaattcttt ttgacagggg    180

acttgtgggc tgcattcact tccttcgccc caaaagcttt aaaagggcca cc            232
```

<210> SEQ ID NO 48
<211> LENGTH: 418
<212> TYPE: DNA
<213> ORGANISM: Mouse

<400> SEQUENCE: 48

```
tttaactttt gaattatttt attcccatag tttgacatga tatacaggca ctttggccaa     60

tgaggtggca caggccactg gctcctgcct gagtcagtta cccaccttca agccctctga    120

ggattagtgc tagtaatgtc acacacaaaa tggggggcta ggctggggaa tggaaagaca    180

agagggggaa tccacagctg tcctggggct tcagatggca gcagcctggg ttccctcaat    240

cctggtggaa cctggaactg ctgtttctga aaatcccaca ctgggcagtc ggaccctgaa    300

tccaccttct tcccggtccc tactcccact ccgggccttg ggcttaagg acaccctagg     360

aaaacggaat ttgggtgact tctccccaac tggggacttg gaggttgcat caccctcc      418
```

<210> SEQ ID NO 49
<211> LENGTH: 451
<212> TYPE: DNA
<213> ORGANISM: Human

<400> SEQUENCE: 49

```
acttccagat tattttattc acatggcttg gtggggtaca ggcactcctg ccagagagac     60

aggagcaggc ctccctgcca gccctggtca gtcacccacc tcccggccct cttagggtta    120

gtgctagtta tcacacacac aacagcgagg gggtagagaa aggaaggcaa gaagggatcc    180

ccatctgact aggggcttca gacagccgca gcctgagccc cctccatcct ggccgggcct    240

ggagcccctg tctctgaaaa ccccacgctg ggcagccgca cccgcaatcc accctcttcc    300

tggtccccac tcccactccg ggccttgggg cttagggaca ccctggggaa gcggaacttg    360

ggtgacttct ctctgacggg ggacttgggg gctgcatcgc cctcctgccc ccgagaggct    420

ttagaagggg ccgccaggcc tacacgtggc a                                   451
```

<210> SEQ ID NO 50
<211> LENGTH: 498
<212> TYPE: DNA
<213> ORGANISM: Mouse

-continued

<400> SEQUENCE: 50

```
aacttttgaa ttattttatt cccatagttt gacatgatat acaggcactt tggccaatga     60
ggtggcacag gccactggct cctgcctgag tcagttaccc accttcaagc cctctgagga    120
ttagtgctag taatgtcaca cacaaaatgg ggggctaggc tggggaatgg aaagacaaga    180
gggggaatcc acagctgtcc tggggcttca gatggcagca gcctgggttc cctcaatcct    240
ggtggaacct ggaactgctg tttctgaaaa tcccacactg ggcagtcgga ccctgaatcc    300
accttcttcc cggtccctac tcccactccg ggccttgggg cttaaggaca ccctaggaaa    360
acggaatttg ggtgacttct ccccaactgg agactttgag gttgcatcac cctcctgtcc    420
cttagagact ttagaagggg aagccaagcc tacccgaggc aggcggaccc ttaccctacc    480
tcggcgactg gaagcccc                                                  498
```

<210> SEQ ID NO 51
<211> LENGTH: 409
<212> TYPE: DNA
<213> ORGANISM: Mouse

<400> SEQUENCE: 51

```
aaacagtcaa ggcaggcaca gctcctctgg cagacgtagg tcctggtgga aacggggttc     60
aggggactcc gcagccttca ccagcatgag ccatccagag gagtcaacag aggtgacact    120
gaagactgac gtggagtcag gagccagtgg ctacagtgtc acaggtggag gggatcaggg    180
gatctttgtc aagcaagtac tgaaggactc gtcggctgca aagctgttca acctgagaga    240
aggagatcaa ctgcttagtg cgaccatatt ctttgaccat atgaaatatg aagatgctct    300
taaaatcctt cagtactcag aaccatacaa agttcagttc agaatcaaac ggaaactctc    360
ggccagcaag ggagaggaag ggctgttca gcattcgcag caaggccag                 409
```

<210> SEQ ID NO 52
<211> LENGTH: 356
<212> TYPE: DNA
<213> ORGANISM: Mouse

<400> SEQUENCE: 52

```
tgagcccgca ggttgtgtga ccaagattcg caaagaaaga gagagagaga ccgatacaga     60
aagagaagaa ggaggggcgg gctcctggca aggcgtttgc tcctgagcag agtcctgcaa    120
agatggagaa ggaggaagag acaacccggg agctgctgct gcccaactgg cagggcagtg    180
gttcccacgg gctgaccatt gcccagaggg atgatggagt ctttgttcag gaggtgatgc    240
agaactcccc tgcggcccgc actggggtgg tcaaggaggg ggaccagatt gtgggtgcca    300
ccatctactt tgacaacctg cagtctggtg aggtgaccca gttgctgaat accatg        356
```

<210> SEQ ID NO 53
<211> LENGTH: 356
<212> TYPE: DNA
<213> ORGANISM: Mouse

<400> SEQUENCE: 53

```
tgagcccgca ggttgtgtga ccaagattcg caaagaaaga gagagagaga ccgatacaga     60
aagagaagaa ggaggggcgg gctcctggca aggcgtttgc tcctgagcag agtcctgcaa    120
agatggagaa ggaggaagag acaacccggg agctgctgct gcccaactgg cagggcagtg    180
gttcccacgg gctgaccatt gcccagaggg atgatggagt ctttgttcag gaggtgatgc    240
```

-continued

```
agaactcccc tgcggcccgc actggggtgg tcaaggaggg ggaccagatt gtgggtgcca    300

ccatctactt tgacaacctg cagtctggtg aggtgaccca gttgctgaat accatg        356


<210> SEQ ID NO 54
<211> LENGTH: 73
<212> TYPE: DNA
<213> ORGANISM: Mouse

<400> SEQUENCE: 54

agccaagagt gagggtggga taaagttgaa gttgcccaca ctggggaccg gaagcagagg     60

agagggcgtt gac                                                        73


<210> SEQ ID NO 55
<211> LENGTH: 342
<212> TYPE: DNA
<213> ORGANISM: Mouse

<400> SEQUENCE: 55

aagtcaccca aattccgttt tcctagggtg tccttaagcc ccaaggcccg gagtgggagt     60

agggaccggg aagaagtgtg gattcagggt ccgactgccc agtgtgggat tttcagaaac    120

agcagttcca ggttccacca ggattgaggg aacccaggct gctgcatctg aagccccagg    180

acagctgtgg attccccctc ttgtctttcc attccccagc ctagccccca ttttgtgtgt    240

gacattacta gcactaatct cagagggctt gaaggtgggt actgactcag gcaggagcag    300

tgcgctgtgc cactcattgg ccaaagtgcc tgtatatcat gt                       342


<210> SEQ ID NO 56
<211> LENGTH: 390
<212> TYPE: DNA
<213> ORGANISM: Human

<400> SEQUENCE: 56

ggggctccgg agtgcagcta aaggccacca aggcagaaca ggcagaaggg atggaatttg     60

gcttcaagat gcccaagatg accatgccca agctagggag ggcagagtcc ccatcacgtg    120

gcaagccagg cgaggcgggt gctgaggtct cagggaagct ggtaacactt ccctgtctgc    180

agccagaggt ggatggtgag gctcatgtgg gtgtccctct ctcactctgc cttcagtgga    240

gctagacctg ccaggagcac ttggcctgca ggggcaggtc ccagccgcta aaatgggcaa    300

gggagagcgg gctgagggcc cgcaggtggc agcaggggtc agggaagtgg gcttccgagt    360

gccctctgtt gaaattgtca ccccacagct                                     390


<210> SEQ ID NO 57
<211> LENGTH: 5432
<212> TYPE: DNA
<213> ORGANISM: Mouse

<400> SEQUENCE: 57

cagacagacc aaggagctct ggaggtgtct ggaggcccac cgagccccag acccaggagg     60

cccaggaagc tggaagtgac cctcaggcag caagacctca aaggaagagt gagattcctg    120

cttacagctg tgcatcaccc cgagtggggc tcctgtcagg agaaaaggcc atcactcaag    180

aagcggctca gcggcagctg ctccatgagg agctgaaggt ggtcctgcag cagaaggagg    240

agaggacacg ggagctcgag ccccaggtga ctctctgcag agctatggag gccaggagcc    300

gcagcgctga ggagctgaga cgggcggagt tggtggagat tatcgtggag accgaggcac    360

agaccggggt cagcggcttc aacgtagcag gcggcggcaa agaaggaatc tttgtccgtg    420
```

-continued

```
agctgcgaga ggactcaccg gcagctaaga gcctcagctt gcaagaaggg gaccagctgc    480
tgagtgcccg tgtgttcttt gagaacttca aatatgagga tgcacttcgc ctgctgcaat    540
gcgcagagcc ctacaaggtc tccttctgct tgaagcgcac tgtgcccacc ggggatctgg    600
cactgaggcc cgggacggtg tctggatacg agatgaaggg cccacgggcc aaagtggcca    660
agctggtacg cgtgcttagc ccggtcccgg tccaggacag ccccagtgac cgggtcgctg    720
ctgcgccgta aaccctactc cctttcactg tggcccactt tggccctctg tctgtcacta    780
acccgacact aattcgccct ctgccccttg ttctctgctc ctaaactcca ctcctgtcaa    840
agggtgcacc tattggcagg tggttctcac ccatccccac catgcaaccc gggctcatta    900
ggggtcatgg agtcctggaa ggccagattc tagcccaatg gctgttgggt tactgagtga    960
cccaagtttc ttttcctctc tgggtcgcag tttccccaac tctacaataa ggatgttggg   1020
ggaaattcca gaatttttgg gttcccattg ccacatccct gtcccattgc cacatcactg   1080
tgagattctg aatgactgtc attgccttcc tgaagtgaca ggcaggaagg tggatgtgtt   1140
ttgggatata ctctacccca aacttctccc agcctggtat actaggtggg ttatttttct   1200
atctactccc agcctcccac tgtcccacag cctcctgcct ctctcctctc tcctcagaac   1260
atccagagtc tggcccctgt gaagaagaag aagatggtga ctggggccct ggggacccct   1320
gcagatttgg cccctgttga cgtcgagttc tcttttccca agttctcccg actgcgtcgg   1380
ggtctcaaag ccgaggctgt caagggacct gtcccagctg cccctgcccg tcgccgcctc   1440
cagctgcctc ggctgcgtgt ccgagaagta gctgaagagg cccaggtagc ccgaatggct   1500
gctgctgctc ctcccccaag gaaggccaag gcagaagctg aggcagccac aggagctggg   1560
ttcacagccc ctcagataga gctagttggg cctcggctgc ctagtgccga ggtgggtgtc   1620
cctcaggtct cagttcccaa ggggacccca tcaacagagg cagccagcgg ctttgccctt   1680
cacctgccaa cccttgggct aggtgcccca gctgcaccgg ctgtggagcc cccagccacg   1740
ggaatccagg ttccacaagt ggaactcccc accctgccct ctctacccac gcttcccaca   1800
cttccatgcc tggacaccca ggaaggagct gcagtggtaa aagtccctac cctggatgtg   1860
gcagctccgt ctatgggggt ggacctggct ttgccgggtg cagaggtgga ggcccaggga   1920
gaggttcctg aagtggccct caagatgccc cggctcagtt tcccccgttt tgggattcgg   1980
gggaaggaag ccactgaagc caaagtagtc aagggcagcc ctgaggccaa agcaaagggt   2040
cccagacttc gaatgcccac ctttgggctt tctctcctgg aaccccggcc ctctggccct   2100
gaagctgttg ctgagagcaa gctgaagcta cccaccctca agatgccctc tttcggcatt   2160
ggtgtggctg ggcctgaagt caaggcaccc acggggcccg aagtaaagct ccctaaggtt   2220
cctgaggtca aactcccgaa agtgcccgag gcagccattc cagatgtgca actccctgag   2280
gtacagctgc ccaaaatgtc agacatgaaa cttccaaaga tccctgagat ggttgtaccc   2340
gacgttcgtc ttccggaagt gcagctgccc aaagtccctg agatgaaagt cccagagatg   2400
aagctcccga agtggcccga gatggccgtg cccgatgtac accttccaga tgtacagctc   2460
ccgaaagtcc cagagatgaa gctcccgaag gtgcccgaga tggccgtgcc cgatgtacac   2520
cttccagatg tacagctccc gaaagttcca gagatgaagc taccagagat gaagctcccg   2580
aaggtgccgg agatggccgt gccggatgta cgactcccgg aagttcagct gcccaaagtg   2640
tctgaggtga agctcccaaa gatgcctgag atggccgtgc ctgatgtcca cctcccggag   2700
ctacaacttc ccaaaatgtc cgaggtgaag ctcccaaaga tgcccgagat ggccgtgccc   2760
```

-continued

```
gatgttcgcc tcccggaagt tcagctgccc aaagtgtcag agatgaaact ccctaagatg   2820
ccagagatga ccatgcccga cattcgcctc ccagaagttc agttgcccaa agtgcctgac   2880
attaaacttc ctgaaatgaa gcttccagaa ataaaactcc ccaaagtgcc tgacatggca   2940
gtgcctgatg tccccttcc agagctgcag ctgcccaaag tgtcggacat tcggctgcct   3000
gaaatgcaag tgtcacaggt cccagaggtg cagcttccca agatgccaga gatgaagttg   3060
tccaaggttc ctgaggtaca gaggaaatct gcaggggcgg agcaggcaaa agggactgaa   3120
tttagtttca agttgcccaa gatgaccatg cccaagttgg ggaaagtggg caagcctggg   3180
gaggcaagta ttgaggttcc agacaaactc atgacacttc cctgtctgca gccagaggtg   3240
ggcactgagg catcccatgt tggtgtccct tccctctctc tcccctctgt ggagcttgac   3300
ttgcctgggg ccctgggcct ggagggacaa gtccaagaag ctgtcccagg caaagtggag   3360
aagccagagg gccccagggt agcagtgggt gttggagagg tgggctttcg tgtgccctct   3420
gtggagattg tcactcctca gctgcccaca gttgaagttg agaaagagca gctagagatg   3480
gtggagatga aagtcaaacc ctcttccaag ttctctctgc ccaaattcgg actttcaggg   3540
cccaaagctg tcaagggaga ggtggagggg cctgggcgag ccaccaagct gaaggtttcc   3600
aagtttacca tctcacttcc caaagctcga gcagggactg aggccgaagc gaagggagct   3660
ggggaagccg ggttgctgcc agcgctggat ctgtccatcc cacagctcag cctggatgcc   3720
cagctgccct caggcaaggt ggaagtagct gatagcaagc ctaaatcgtc cagatttgct   3780
ctgcccaagt ttggggtgaa aggccgggac tctgaggctg atgtactggt ggcaggggag   3840
gctgagcttg agggaaaggg ttggggctgg gatgggaagg tgaagatgcc caagctgaaa   3900
atgccatctt ttgggttgtc ccgaggaaag gaagcagaaa ctcaggatgg acgtgtcagc   3960
cccggggaaa agctggaggc catagctggg cagcttaaga tccctgcggt ggaattggtc   4020
acaccgggag ctcaggagac agagaaggtc accagtggag tgaagccgtc aggcctccag   4080
gtgtccacca ctgggcaggt ggttgcagag ggccaggaga gtgtgcagag ggtgtccaca   4140
ctaggtatct ctttgcccca ggtggaattg gccagctttg gggaggcagg ccctgagatc   4200
gtagcccctt ctgcagaggg cacagcaggc tctagggtcc aggtgccaca ggtgatgctg   4260
gagctacctg gaacccaggt ggcagggggt gatctgttag tgggtgaggg catcttcaag   4320
atgcccacag tgacagtgcc ccagctagag ctggatgtgg ggctgggcca tgaagcccag   4380
gctggtgaag cagccaagag tgagggtggg ataaagttga agttgcccac actggggacc   4440
ggaagcagag gagagggcgt tgagccccag ggccccgagg cccagcgcac cttccacctc   4500
tcattgcccg atgtggaact cacgtcacca gtgagtagcc acgctgagta ccaggtagtt   4560
gagggtgatg gggatggtgg gcacaaactc aaggttcggc tgcccctgtt tggtctggca   4620
aaggccaagg aagggataga agttggagaa aaggttaaga gtccaaagct caggctaccc   4680
cgagtgggct tcagccagag tgagtcggtc tccggagaag gctctccaag tcctgaggag   4740
gaggaagaag gcagtgggga aggggcttcc agtcgccggg gtagggtaag ggtccgcctg   4800
cctcgggtag gcttggcttc cccttctaaa gtctctaagg gacaggaggg tgatgcaacc   4860
tccaagtccc cagttgggga gaagtcaccc aaattccgtt ttcctagggt gtccttaagc   4920
cccaaggccc ggagtgggag tagggaccgg gaagaaggtg gattcagggt ccgactgccc   4980
agtgtgggat tttcagaaac agcagttcca ggttccacca ggattgaggg aacccaggct   5040
gctgccatct gaagccccag gacagctgtg gattccccct cttgtctttc cattccccag   5100
cctagccccc cattttgtgt gtgacattac tagcactaat cctcagaggg cttgaaggtg   5160
```

-continued

```
agtaactgac tcaggcagga gccagtggcc tgtgccacct cattggccaa agtgcctgta   5220

tatcatgtca aactatggga ataaaataat tcaaaagttg tcatgtgtct tggttctcgt   5280

gggggacaca aggtctcttt atgtttcctt catctggctt gtgcagtgtt acctcagctt   5340

gaacttaaaa tcttgcagcc ttgggggctg gagaggtggc ccagaggtta agagcactgg   5400

ctgctcatgc agaggtcctg agttcaattc cc                                 5432
```

<210> SEQ ID NO 58
<211> LENGTH: 4840
<212> TYPE: DNA
<213> ORGANISM: Mouse

<400> SEQUENCE: 58

```
cagacagacc aaggagctct ggaggtgtct ggaggcccac cgagccccag acccaggagg     60

cccaggaagc tggaagtgac cctcaggcag caagacctca aggaagagt gagattcctg    120

cttacagctg tgcatcaccc cgagtggggc tcctgtcagg agaaaaggcc atcactcaag    180

aagcggctca gcggcagctg ctccatgagg agctgaaggt ggtcctgcag cagaaggagg    240

agaggacacg ggagctcgag ccccaggtga ctctctgcag agctatggag gccaggagcc    300

gcagcgctga ggagctgaga cgggcggagt tggtggagat tatcgtggag accgaggcac    360

agaccggggt cagcggcttc aacgtagcag gcggcggcaa agaaggaatc tttgtccgtg    420

agctgcgaga ggactcaccg gcagctaaga gcctcagctt gcaagaaggg gaccagctgc    480

tgagtgcccg tgtgttcttt gagaacttca aatatgagga tgcacttcgc ctgctgcaat    540

gcgcagagcc ctacaaggtc tccttctgct tgaagcgcac tgtgcccacc ggggatctgg    600

cactgaggcc cgggacggtg tctggatacg agatgaaggg cccacgggcc aaagtggcca    660

agctgaacat ccagagtctg gcccctgtga agaagaagaa gatggtgact ggggccctgg    720

ggacccctgc agatttggcc cctgttgacg tcgagttctc ttttcccaag ttctcccgac    780

tgcgtcgggg tctcaaagcc gaggctgtca agggacctgt cccagctgcc cctgcccgtc    840

gccgcctcca gctgcctcgg ctgcgtgtcc gagaagtagc tgaagaggcc caggtagccc    900

gaatggctgc tgctgctcct cccccaagga aggccaaggc agaagctgag gcagccacag    960

gagctgggtt cacagcccct cagatagagc tagttgggcc tcggctgcct agtgccgagg   1020

tgggtgtccc tcaggtctca gttcccaagg ggaccccatc aacagaggca gccagcggct   1080

ttgcccttca cctgccaacc cttgggctag gtgccccagc tgcaccggct gtggagcccc   1140

cagccacggg aatccaggtt ccacaagtgg aactccccac cctgccctct ctacccacgc   1200

ttcccacact tccatgcctg gacacccagg aaggagctgc agtggtaaaa gtccctaccc   1260

tggatgtggc agctccgtct atgggggtgg acctggcttt gccgggtgca gaggtggagg   1320

cccagggaga ggttcctgaa gtggccctca agatgccccg gctcagtttc ccccgttttg   1380

ggattcgggg gaaggaagcc actgaagcca aagtagtcaa gggcagccct gaggccaaag   1440

caaagggtcc cagacttcga atgcccacct ttgggctttc tctcctggaa ccccggccct   1500

ctggccctga agctgttgct gagagcaagc tgaagctacc caccctcaag atgccctctt   1560

tcggcattgg tgtggctggg cctgaagtca aggcacccac ggggcccgaa gtaaagctcc   1620

ctaaggttcc tgaggtcaaa ctcccgaaag tgcccgaggc agccattcca gatgtgcaac   1680

tccctgaggt acagctgccc aaaatgtcag acatgaaact tccaaagatc cctgagatgg   1740

ttgtacccga cgttcgtctt ccggaagtgc agctgcccaa agtccctgag atgaaagtcc   1800
```

-continued

```
cagagatgaa gctcccgaag tggcccgaga tggccgtgcc cgatgtacac cttccagatg   1860
tacagctccc gaaagtccca gagatgaagc tcccgaaggt gcccgagatg gccgtgcccg   1920
atgtacacct tccagatgta cagctcccga aagttccaga gatgaagcta ccagagatga   1980
agctcccgaa ggtgccggag atggccgtgc cggatgtacg actcccggaa gttcagctgc   2040
ccaaagtgtc tgaggtgaag ctcccaaaga tgcctgagat ggccgtgcct gatgtccacc   2100
tcccggagct acaacttccc aaaatgtccg aggtgaagct cccaaagatg cccgagatgg   2160
ccgtgcccga tgttcgcctc ccggaagttc agctgcccaa agtgtcagag atgaaactcc   2220
ctaagatgcc agagatgacc atgcccgaca ttcgcctccc agaagttcag ttgcccaaag   2280
tgcctgacat taaacttcct gaaatgaagc ttccagaaat aaaactcccc aaagtgcctg   2340
acatggcagt gcctgatgtc cccctccag agctgcagct gcccaaagtg tcggacattc   2400
ggctgcctga aatgcaagtg tcacaggtcc cagaggtgca gcttcccaag atgccagaga   2460
tgaagttgtc caaggttcct gaggtacaga ggaaatctgc aggggcggag caggcaaaag   2520
ggactgaatt tagtttcaag ttgcccaaga tgaccatgcc caagttgggg aaagtgggca   2580
agcctgggga ggcaagtatt gaggttccag acaaactcat gacacttccc tgtctgcagc   2640
cagaggtggg cactgaggca tcccatgttg gtgtcccttc cctctctctc ccctctgtgg   2700
agcttgactt gcctggggcc ctgggcctgg agggacaagt ccaagaagct gtcccaggca   2760
aagtggagaa gccagagggc cccagggtag cagtgggtgt tggagaggtg ggctttcgtg   2820
tgccctctgt ggagattgtc actcctcagc tgcccacagt tgaagttgag aaagagcagc   2880
tagagatggt ggagatgaaa gtcaaaccct cttccaagtt ctctctgccc aaattcggac   2940
tttcagggcc caaagctgtc aagggagagg tggaggggcc tgggcgagcc accaagctga   3000
aggtttccaa gtttaccatc tcacttccca aagctcgagc agggactgag gccgaagcga   3060
agggagctgg ggaagccggg ttgctgccag cgctggatct gtccatccca cagctcagcc   3120
tggatgccca gctgccctca ggcaaggtgg aagtagctga tagcaagcct aaatcgtcca   3180
gatttgctct gcccaagttt ggggtgaaag gccgggactc tgaggctgat gtactggtgg   3240
caggggaggc tgagcttgag ggaaagggtt ggggctggga tgggaaggtg aagatgccca   3300
agctgaaaat gccatctttt gggttgtccc gaggaaagga agcagaaact caggatggac   3360
gtgtcagccc cggggaaaag ctggaggcca tagctgggca gcttaagatc cctgcggtgg   3420
aattggtcac accgggagct caggagacag agaaggtcac cagtggagtg aagccgtcag   3480
gcctccaggt gtccaccact gggcaggtgg ttgcagaggg ccaggagagt gtgcagaggg   3540
tgtccacact aggtatctct ttgccccagg tggaattggc cagctttggg gaggcaggcc   3600
ctgagatcgt agcccttct gcagagggca cagcaggctc tagggtccag gtgccacagg   3660
tgatgctgga gctacctgga acccaggtgg caggggggtga tctgttagtg ggtgagggca   3720
tcttcaagat gcccacagtg acagtgcccc agctagagct ggatgtgggg ctgggccatg   3780
aagcccaggc tggtgaagca gccaagagtg agggtgggat aaagttgaag ttgcccacac   3840
tggggaccgg aagcagagga gagggcgttg agccccaggg ccccgaggcc cagcgcacct   3900
tccacctctc attgcccgat gtggaactca cgtcaccagt gagtagccac gctgagtacc   3960
aggtagttga gggtgatggg gatggtgggc acaaactcaa ggttcggctg cccctgtttg   4020
gtctggcaaa ggccaaggaa gggatagaag ttggagaaaa ggttaagagt ccaaagctca   4080
ggctaccccg agtgggcttc agccagagtg agtcggtctc cggagaaggc tctccaagtc   4140
ctgaggagga ggaagaaggc agtggggaag ggcttccag tcgccggggt agggtaaggg   4200
```

-continued

```
tccgcctgcc tcgggtaggc ttggcttccc cttctaaagt ctctaaggga caggagggtg   4260

atgcaacctc caagtcccca gttggggaga agtcacccaa attccgtttt cctagggtgt   4320

ccttaagccc caaggcccgg agtgggagta gggaccggga agaaggtgga ttcagggtcc   4380

gactgcccag tgtgggattt tcagaaacag cagttccagg ttccaccagg attgagggaa   4440

cccaggctgc tgccatctga agccccagga cagctgtgga ttccccctct tgtctttcca   4500

ttccccagcc tagcccccca ttttgtgtgt gacattacta gcactaatcc tcagagggct   4560

tgaaggtgag taactgactc aggcaggagc cagtggcctg tgccacctca ttggccaaag   4620

tgcctgtata tcatgtcaaa ctatgggaat aaaataattc aaaagttgtc atgtgtcttg   4680

gttctcgtgg gggacacaag gtctctttat gtttccttca tctggcttgt gcagtgttac   4740

ctcagcttga acttaaaatc ttgcagcctt gggggctgga gaggtggccc agaggttaag   4800

agcactggct gctcatgcag aggtcctgag ttcaattccc                         4840
```

<210> SEQ ID NO 59
<211> LENGTH: 491
<212> TYPE: DNA
<213> ORGANISM: Mouse

<400> SEQUENCE: 59

```
tgagcccgca ggttgtgtga ccaagattcg caaagaaaga gagagagaga ccgatacaga     60

aagagaagaa ggaggggcgg gctcctggca aggcgtttgc tcctgagcag agtcctgcaa    120

agatggagaa ggaggaagag acaacccggg agctgctgct gcccaactgg cagggcagtg    180

gttcccacgg gctgaccatt gcccagagga gtgatggagt ctttgttcag gaggtgatgc    240

agaactcccc tgcggcccga gctggggtgg tcaaggaggg ggaccagatt gtgggtgcca    300

ccatctactt tgacaacctg cagtctggtg aggtgaccca gttgctgaat accatggggc    360

atcacactgt tggcttgaag ttgcaccgta aaggggaccg ttcccctgag cctggacaga    420

cctggaccca tgaagtcttc agttcccgta gctctgaagt ggttctgaac acggtacaac    480

cttcatccct g                                                         491
```

<210> SEQ ID NO 60
<211> LENGTH: 494
<212> TYPE: DNA
<213> ORGANISM: Mouse
<220> FEATURE:
<221> NAME/KEY: misc_feature
<222> LOCATION: (1)..(494)
<223> OTHER INFORMATION: n equals unknown

<400> SEQUENCE: 60

```
tcaggatgga cgtgtcagcc ccggggaaaa gctggaggcc atagctgggc agcttaagat     60

ccctgcggtg gaattggtca caccgggagc tcaggagaca gagaaggtca ccagtggagt    120

gaagccgtca gctccaggtg tccaccactg ggcaggtggt tgcagagggc caggagagtg    180

tgcagagggt gtccacacta ggtatctctt tgccccaggt ggaattggcc agctttgggg    240

aggcaggccc tgagatcgta gccccttctg cagagggcac agcaggctct agggtccagg    300

tgccacaggt gatgctggag ctacctggaa cccaggtggc aggggggtgat ctgttagtgg    360

gtgagggcat cttcaagatg cangcagtga cagtgcccca gctagagctg agtgtggggc    420

tgggcatgaa gcccaggctg gtgaagcagc caagagtgag ggtgggataa agttgaagtt    480

gcccacactg ggga                                                      494
```

-continued

<210> SEQ ID NO 61
<211> LENGTH: 360
<212> TYPE: DNA
<213> ORGANISM: Mouse
<220> FEATURE:
<221> NAME/KEY: misc_feature
<222> LOCATION: (1)..(360)
<223> OTHER INFORMATION: n equals unknown

<400> SEQUENCE: 61
cttggcttcc ccttctaaag tctctaaggg acaggagggt gatgcaacct ccaaggtccc 60
cnagttgggg aggaagtcac ccaaattccg ttttcctagg gtgtccttaa gccccaaggc 120
ccggagtggg agtagggacc gggaagaagg tggattcagg gtccgactgc ccagtgtggg 180
attttcagaa acagcagttc caggttccac caggattgag ggaaccaggc tgctgccatc 240
tgaagcccca ggacagctgt ggattccccc tcttgtcttt ccattcccca gcctagcccc 300
ccattttgtg tgtgacatta ctagcactaa tcctcagagg gcttgaaggt gggtaactga 360

<210> SEQ ID NO 62
<211> LENGTH: 359
<212> TYPE: DNA
<213> ORGANISM: Mouse

<400> SEQUENCE: 62
aacagtcaag gcaggcacag ctcctctggc agacgtaggt cctggtggaa acggggttca 60
ggggactccg cagccttcac cagcatgagc catccagagg agtcaacaga ggtgacactg 120
aagactgacg tggagtcagg agccagtggt acagtgtcac aggtggaggg gatcagggga 180
tctttgtcaa gcaagtactg aaggactcgt cggctgcaaa gctgttcaac ctgagagaag 240
gagatcaact gcttagtgcg accatattct ttgaccatat gaaatatgaa gatgctctta 300
aaatccttca gtactcagaa ccatacaaag ttcagttcag aatcaaacgg aaactctcg 359

<210> SEQ ID NO 63
<211> LENGTH: 4641
<212> TYPE: DNA
<213> ORGANISM: Rat

<400> SEQUENCE: 63
ggaactctgg aggtgtctgg aggcccactg agccccagac ccaggaggcc caagtagctg 60
gaactgaccc tcaggcagca agacctcaaa ggaagagtga aattccggct tacagctgta 120
catcaccccg agtggggctc ctgtcaggag aaaagaccat cacccaggaa gcggctcagc 180
ggcagctgct ccatgaggag ctgaagctgg tcctacagca gaaggaggag aggaaacagg 240
agcctgagcc ccaggtgact ctctgcagag ctatggaggc caggagccgc agcgctgagg 300
agctgagacg agcggagttg gtggagatta tcgtggagac agaggcgcag accggggtca 360
gcggcttcaa tgtagcaggc ggcggcaaag aaggaatctt tgtccgcgag ctgcgagagg 420
actcaccggc cgccaagagc ctcagtttgc aggaagggga ccaacttctg agcgcccgtg 480
tgttctttga gaacttcaaa tatgaggatg cactacgcct gctgcaatgt gccgagccct 540
acaaggtctc cttctgcttg aagcgcactg tgcccaccgg ggacctggca ctgcggcccg 600
ggacggtgtc tggatacgag atgaagggcc cgcgggccaa ggtggccaag ctgaacatcc 660
agagtctgtc ccctgtgaag aagaagaaga tggtgattgg gaccctgggg acccctgcag 720
atttggcccc tgttgacgtc gagttctctt ttcccaagtt ctcccgattg cgtcggggcc 780
ttaaagccga tgctgtcaag ggacctgtcc cagctgcccc tgcccgacga cgtctccagc 840

-continued

```
tgcctcggct acgtgtccga gaagtagctg aagaggccca ggtagcccga atggctgctg    900
ctgctcctcc ctctaggaag gccaagtcag aggctgaggt agccacaggg gctggattca    960
cagcccctca gatagagcta gttgggcctc ggctgcctag cgcagaggtg ggtgtcccta   1020
aggtctcagt tcccaaggga accccatcaa cagaggcagc cagcggcttt gcccttcacc   1080
tgccaaccct tgggctagga gccccagctg caccggctgt ggagcccccca accacaggaa   1140
tccaggtccc gcaagtggaa ctccccaccc tgccctcttt acccactctg cccacacttc   1200
cgtgcctaga tacccaggaa ggggctgcag tggtcaaagt ccccaccctg gatgtggcag   1260
ctccgtctgt ggaggtggac ctggctttgc caggtgcaga ggtggaggcc cagggagagg   1320
tacctgaagt ggctctcaag atgccccgtc tcagtttccc ccgttttggg gttcgaggga   1380
aggaagctac tgaagccaag gtagtcaagg gcagccctga ggccaaagca aagggtccca   1440
gacttcgaat gcccaccttt gggctttctc tcctggaatc ccggccctct ggccctgaag   1500
ttgctgctga gagcaagctg aagctaccca ccctcaagat gccctctttc ggcatcagcg   1560
tagctgggcc tgaggtcaag gcacccaaag ggcctgaagt gaagctcccc aaagttcctg   1620
agatcaaact cccgaaagcg ccagaggcag ccattccaga tgtgcaactc cccgaggtac   1680
agctgcccaa aatgtcagac atgaaacttc caaagatccc tgagatggct gtacccgatg   1740
ttcaccttcc ggaagtgaag ctgcccaaag tccccgagat gaaagtccca gaaatgaagc   1800
ttccgaagat cccggagatg gccgtgcctg atgtacacct tccagatata cagctcccga   1860
aagttcccga gatgaagctc ccagacatga agctcccgaa ggtgcctgag atggccgtgc   1920
ctgatgtaca ccttccagat atacagctcc cgaaagttcc cgagatgaag ctcccagaca   1980
tgaagctccc gaaggtgcct gagatggccg tgcctgatgt acgaattccg gaagttcagc   2040
tacccaaagt gtccgaggtg aagctcccga agataccgga catggccgtg cctgatgttc   2100
gcctcccaga gctgcaactg cccaaaatgt ctgaggtgaa gctcccgaag ataccggaca   2160
tggccgtacc tgatgttcgc ctcccagaag ttcagctacc caaagtgtca gagctgaagc   2220
tcccgaaggt gcctgagatg accatgcccg acattcgcct cccggaagtt cagctgccca   2280
aagtgcctga cattaaactt ccagaaataa aactccccaa agtgcctgag atggccgtgc   2340
ctgatgtccc ccttccagaa ctacagctgc ccaaagtgcc acaggtccca gacgtgcatc   2400
ttcccaaagt gccagagatg aagttgccca aggttcctga ggcacagagg aaatctgcag   2460
gggcggagca ggcagaaaag accgaattta gcttcaagtt gcccaagatg actgtgccca   2520
agttggggaa agtgaccaag cctggggagg caggtattga ggttccagac aaactcctga   2580
tacttccctg tctgcagcca gaggtgggca ctgaggtggc ccgtgttggt gtcccttccc   2640
tctctctccc ttctgtggag cttgacttgc ctggggccct gggcctggag ggacaagtcc   2700
aagaagctgt ctctggcaaa gtggagaagc cagagggccc cagggtggca gtagggactg   2760
gagaggcggg cttccgcgtg ccctctgtgg agattgtcaa tcctcagctg cccacggttg   2820
aagtcaagaa agagcagcta gagatggtgg agatgaaagt caaacccact tccaagttct   2880
ctctgcccaa atttggactt tcagggccca aagctgtcaa ggcagaggtg gaggggcctg   2940
ggcgagccac caagctgaag gtatccaagt ttgccatctc gcttcccaga gctcgagcag   3000
ggactgacgc ggacgcgaag ggagctgggg aagcggggtt gctgcctgcc ctcgatctgt   3060
ccatcccaca gctcagcctg gatgctcaac tgccctcagg caaggtggag gtagcagggg   3120
ctgagagcaa gcctaaaggg tccagatttg ctctgcccaa gtttggggcg aaaggccggg   3180
```

-continued

```
actctgaagc cgacgtactg gtggcagggg aggctgagct ggaggggaag ggttggggct   3240

gggacgggaa ggtgaagatg cccaagctga agatgccatc ttttgggctg tcccgaggaa   3300

aagaagcaga aattcaggat gggcgtgtca gcccaggaga aaagctggaa gccatagctg   3360

ggcagcttaa gatccctgag gtggaactgg tcacaccagg agctcaggag acagagaagg   3420

tcaccagtgg agtgaagcca tcaggcctcc aggtgtccac cactaggcag gtggttgcag   3480

agggccagga gggggcgcag agggtgtcct cattaggtat ctctttgccc caggtggaac   3540

tggccagctt tggggaggca ggccctgaga tcgcagcccc atctgcagag ggcacagtag   3600

gctctaggat ccaggtgcca caggtgatgc tggagttgcc gggaacccag gtggcagggg   3660

gtgatctgtt agtgggtgag ggcatcttca agatgcccac agtgacagtg ccccagttag   3720

agctggatgt ggggttgggc catgaagccc aggctggtga aacagccaag agtgagggcg   3780

ggttaaagct gaagttgccc acactggggg caggaggcaa aggagagggt gctgaggccc   3840

agagccccga ggcccagcac accttccaca tctcattgcc tgacgtagaa ctcacatcac   3900

cagtgagtag ccacgctgag taccaggtgg ttgagggcga tggggatggc gggcacaaac   3960

tcaaggtgcg gctgcccctg tttggtctgg caagggccaa ggaaggaata gaaactggag   4020

aaaaggttaa aagtccaaag ctcaggctac cccgagtggg cttcagccaa agtgagtcgg   4080

cctctggaga aggctctccc agtcctgagg aggaggaaga aggcagtggg gaaggggctt   4140

ccggtcgccg tggtcgggtc agggtccgct tgcctcgtgt aggcttggct tccccttcta   4200

aaggctctaa gggacaggag ggtgatgcgg cctccaagtc cccagttggg gagaagtccc   4260

ccaagttccg ctttcctagg gtgtccttaa gccccaaggc ccggagtggg agtaaggacc   4320

gggaagaagg tggattcagg gtccgactgc ccagtgtggg attttcagaa acagcagctc   4380

caggctccgc caggattgag gggacccagg ctgctgccat ctgaagccct gggacagctg   4440

tggattcccc ctcttgtctt cccatcccca tccctgctcc ccattttatg tgtgacatta   4500

ctagcactaa tcctcagagg gcttgaaggt gggcagctga ctcaggcagg agcggtctgt   4560

gccacctcat tggctgacgt gcctgtatat catgccaagc tctgtgaata aaataattca   4620

aaagttaaaa aaaaaaaaaa a                                             4641
```

<210> SEQ ID NO 64
<211> LENGTH: 672
<212> TYPE: DNA
<213> ORGANISM: Human
<220> FEATURE:
<221> NAME/KEY: misc_feature
<222> LOCATION: (1)..(672)
<223> OTHER INFORMATION: n equals unknown

<400> SEQUENCE: 64

```
tacttccaga ttattttatt cacatggctt ggtggggtac aggcactcct gccagagaga     60

caggagcagg cctccctgcc agccctggtc agtcacccac ctcccggccc tcttagggtt    120

agtgctagtt atcacacaca caacagcgag ggggtagaga aaggaaggca agaagggatc    180

cccatctgac taggggcttc agacagccgc agcctgagcc ccctccatcc tggccgggcc    240

tggagcccct gtctctgaaa accccacgct gggcagccgc acccgcaatc caccctcttc    300

ctggtcccca ctcccactcc gggccttggg gcttagggac accctgggga agcggaactt    360

gggtgacttc tctctgacgg gggacttggg ggctgcatcg ccctcctgcc cccgagaggc    420

tttagaaggg gccgccaggc ctacacgtgg caagcggacc cggacccggc cccggcgacc    480

cgaggcccct tccccactgc cctcttcctc ctctcctcct nctcctcggg gctggggacc    540
```

-continued

```
cttcccagtg accatctcac tttggctgaa agccactccg ggcaaccctg agttggggct    600

cttggccttc taaccttctc ggccccctcc tttggcccgc accagcccaa accggggcag    660

ccgtaccttg ac                                                        672
```

<210> SEQ ID NO 65
<211> LENGTH: 597
<212> TYPE: DNA
<213> ORGANISM: Mouse

<400> SEQUENCE: 65

```
aacttttgaa ttattttatt cccatagttt gacatgatat acaggcactt tggccaatga     60

ggtggcacag gccactggct cctgcctgag tcagttaccc accttcaagc cctctgagga    120

ttagtgctag taatgtcaca cacaaaatgg ggggctaggc tggggaatgg aaagacaaga    180

gggggaatcc acagctgtcc tggggcttca gatggcagca gcctgggttc cctcaatcct    240

ggtggaacct ggaactgctg tttctgaaaa tcccacactg ggcagtcgga ccctgaatcc    300

accttcttcc cggtccctac tcccactccg ggccttgggg cttaaggaca ccctaggaaa    360

acggaatttg ggtgacttct ccccaactgg ggacttggag gttgcatcac cctcctgtcc    420

cttaaagact ttagaagggg aagccaagcc tacccgaggc aggcggaccc ttaccctacc    480

ccggcgactg gaagcccctt ccccactggc ttcttcctcc ttctcaggac ttggagagcc    540

ttcttcggag accgacttcc tcttgctgaa acccactcgg ggaacctgag cctttga       597
```

<210> SEQ ID NO 66
<211> LENGTH: 697
<212> TYPE: DNA
<213> ORGANISM: Human
<220> FEATURE:
<221> NAME/KEY: misc_feature
<222> LOCATION: (1)..(697)
<223> OTHER INFORMATION: n equals unknown

<400> SEQUENCE: 66

```
tttttttttt ttttttactt ccaaattatt ttattcacat ggcttggggg ggtacaggca     60

cctcctgcca aaaagacagg agcaggcctc cctgccagcc ctggtcagtc acccacctcc    120

cggccctctt agggttagtg ctagttatca cacacacaac agcgaggggg tagagaaagg    180

aaggcaagaa gggatcccca tctgactagg ggcttcaaac agccgcagcc tgagcccccct   240

ccatcctggc cgggcctgga gcccctgtct ctgaaaaccc cacgctgggc aggcgcaccc    300

gcaatccacc cttttcctgg tccccactcc cactccgggc cttggggctt agggacaccc    360

tggggaagcg gaacttgggt gacttctctc tgacgggga cttgggggct gcatcgccct     420

cctgcccccg agaggcttta naagggngcc gcaggcctac acgtggcaag cggacccgga    480

cccggccccg gcgacccgag gccccctttcc cactggccta tttctcctcc tcctccttct   540

cctcnggggc tggggaccct tccccagtga ccatttcact ttggctgaag cccacttcgg    600

gcaagcctga ttttgggcct tttggcctct tacacatctt tgcccacttc ctgggcccgc    660

acaggcccaa cccgggcaag cgtacctttt acttgtg                             697
```

<210> SEQ ID NO 67
<211> LENGTH: 626
<212> TYPE: DNA
<213> ORGANISM: Human
<220> FEATURE:
<221> NAME/KEY: misc_feature
<222> LOCATION: (1)..(626)

-continued

<223> OTHER INFORMATION: n equals unknown

<400> SEQUENCE: 67
tttttttttt tttttttttt tttggctact tccaaattat tttattcaca tggcttggtg 60
gggtacaggc actcctgcca aaaaaacagg agcaggcctc cctgccagcc ctggtcagtc 120
acccacctcc cggccctctt agggttagtg ctagttatca cacacacaac agcgaggggg 180
tagaaaaagg aaggcaaaaa gggatcccca tctgactagg ggcttcaaac agccgcagcc 240
tgagccccct ccatcctggc cgggcctgga gcccctgtct ttgaaaaccc cacgctgggc 300
agccgcaccc gcaatccacc cttttcctgg tccccactcc cactccgggc cttggggctt 360
aaggacaccc tggggaaacg gaacttgggt gacttctctc tgacggggga cttgggggct 420
gcatcgccct cctgcccccg agaggcttta aaaggggccg ccaggcctac acgtggcaag 480
cggacccgga cccgggcccg gcgacccgag gccccttccc cactgccctt ttccttcctc 540
tccttcttct cctcgggggc tggggaccct tncccagtga ccatttcact tttgctgaag 600
cccactcggg gcaacctgag tttggg 626

<210> SEQ ID NO 68
<211> LENGTH: 645
<212> TYPE: DNA
<213> ORGANISM: Human

<400> SEQUENCE: 68
atggagctgt taggagaggg agcaatactg cagggcaggc gggaatcaca gatggaagca 60
gcacctggaa tccagacctg tgggcactct gctgagcttc ccagccaggg gatgggaagg 120
accagggcag agagggccac aagcccagta aggccttcta taacctggaa gataggcagc 180
ccaaaagtcg atggaaggca cacaccaatg ccattcccta gtgtttccac aggtgaagga 240
aaatcgactc tgtggatcct ttacctacac tgtttcggca gcaggaaaag ccctgacttt 300
tctactcctc caagagagcc caaatctcaa ggcatgctaa aggaacaagc gaggaaaatg 360
agaggacagc gaggaggaag ggaaggagca aagggaacac tcaagacgca gagacctcca 420
tctaaggacc aagcaccgct ggcacacgga ccgcgtgaga agcaggtccc tgccgatgag 480
tctttcctgc agaaacctcg gctccctgac ttggttaagc agcagccgaa ccgcagcctc 540
agcaccaacg tgagaggtgc cgagccctct ccttccttag ctactgagct ggttcttaag 600
aagcttgttc ctgctagtac ctgtcaagag cttcccaaaa cataa 645

<210> SEQ ID NO 69
<211> LENGTH: 5450
<212> TYPE: DNA
<213> ORGANISM: Human

<400> SEQUENCE: 69
gagcggggat gatgaggagt accagcgcat ctacaccacg aagatcaagc cacggctgaa 60
gtcggaagat ggagtggaag gagacctcgg ggagacccag agccgtacca tcacagtgac 120
cagaagggtc acggcctaca ctgtggatgt gactggccgg gaaggagcca aggacataga 180
catcagtagc cctgaattca agatcaagat tccaagacat gaactgactg aaatctccaa 240
tgtggatgtg gagacccagt ctgggaagac cgtgatcaga ctgccctcgg gctcgggggc 300
agcctctccg acaggctctg ctgtggatat ccgagcaggg gccatttctg cttcaggacc 360
agagctccaa ggtgctggcc actcgaagct ccaggtcacc atgcctggga taaaggtggg 420
aggctcaggt gtcaatgtca atgcaaaggg cttggacttg ggtggcagag gaggggtcca 480

-continued

```
agttccagca gtggacattt catcttctct tgggggtagg gcagtagagg tacagggccc    540
atctctggag agtggtgatc atggcaaaat taaatttccc accatgaaag tgccgaaatt    600
tggtgtctca acagggcgtg agggccagac accaaaggca gggctgaggg tttctgcacc    660
tgaagtctct gtggggcaca agggcggcaa gccaggcttg actatccaag cccctcagct    720
ggaagtcagt gtgccctctg ccaatattga gggccttgag gggaagctga agggccccca    780
aatcactggg ccatcacttg agggtgacct aggcctgaaa ggtgccaagc cacaggggca    840
cattggggtg gatgcctctg ctccccaaat tgggggtagc atcactggcc ccagtgtgga    900
agttcaggcc cctgacattg atgttcaggg gcctgggagc aaactgaatg tgcccaagat    960
gaaagtcccc aagttctctg tatcaggtgc aaagggagag gaaactggga ttgatgtgac   1020
actgcctaca ggtgaagtga ctgttcctgg ggtctctggg gatgtcagcc tgcctgagat   1080
tgctactggt gggctggaag gaaagatgaa aggtactaaa gtgaagactc ctgaaatgat   1140
tattcagaaa cctaaaatct ccatgcagga tgtggatctg agccttgggt ctcctaaact   1200
gaaaggagat attaaggttt ctgctcctgg ggtgcaaggt gatgttaaag gccctcaagt   1260
ggcacttaaa ggctccagag tggacataga gacaccaaac ctagagggaa ccttgacagg   1320
ccctaggctt ggcagtcctt ccgggaaaac cggaacctgt aggatctcta tgtcagaagt   1380
agacttaaat gtggccgcac ctaaagtgaa agggggtgta gatgtcacac tccccagagt   1440
agaagggaaa gtcaaagtcc ctgaagttga tgtcagaggc cccaaagtgg atgtcagtgc   1500
cccagatgtc gaagcgcatg gcccagaatg gaacctgaaa atgcccaaga tgaaaatgcc   1560
cacgttcagc actccaggag ccaaagggga aggtccagat gttcatatga ctctacccaa   1620
aggagatatc agtatttcag ggcccaaggt caatgtggaa gccccagatg tcaacttgga   1680
gggtctgggg ggaaaactta aaggccccga tgttaagctg cctgatatga gtgtcaagac   1740
accaaagatc tccatgcctg atgtagattt gcacgtgaaa ggtacaaagg tgaagggaga   1800
gtatgatgta actgtaccaa agctggaagg agaactcaaa ggcccaaaag tggacattga   1860
tgccccagat gtggatgttc atggcccaga ctggcacttg aagatgccca agatgaaaat   1920
gcccaaattc agtgtgccag ggttcaaagc agagggccca gaagtggatg tgaacctgcc   1980
caaggctgat gtggacattt ccgggcccaa gatagatgtt actgctcctg atgtgagcat   2040
tgaggaacca gaagggaaat tgaaagggcc caagtttaag atgcctgaga tgaacatcaa   2100
agtccccaag atctccatgc ctgatgtgga cttacatctg aaaggcccta acgtaaaggg   2160
agaatatgat gtcacaatgc caaaggttga aagtgagatt aaagttcctg atgttgaact   2220
taaaagtgcc aaaatggaca ttgatgtccc agatgtggag gttcaaggcc cagactggca   2280
cctgaagatg cccaagatga aaatgcccaa gttcagcatg cctggcttca aagcagaggg   2340
cccagaagtg gatgtgaacc tgcccaaggc tgatgtggac atctcaggac ccaaggtggg   2400
tgttgaagtt ccagatgtga atattgaagg acctgaagga aagctgaagg gccccaagtt   2460
caagatgcca gagatgaata tcaaggcccc caagatctcc atgcctgatg tggacttgca   2520
tatgaaaggt cctaaagtaa agggagaata tgatatgaca gtgccaaagc tggaagggga   2580
cctgaaaggc ccaaaagtag atgtcagtgc cccagatgtt gaaatgcagg gtcctgactg   2640
gaacttgaag atgccaaaga ttaaaatgcc caaatttagc atgcccagcc tcaaaggaga   2700
ggggccagaa tttgatgtga acctgtccaa agcgaatgtg gacatttctg ctacctaaag   2760
tagatactaa tgctccagat ctgagccttg aaggacctga agggaagttg aaaggcccga   2820
```

-continued

```
agtttaagat gcctgagatg cacttcagag ctcctaagat gtctttgcca gatgttgacc   2880
tggatcttaa aggacccaaa atgaaaggaa atgtagatat ctctgcacca aagatagagg   2940
gtgaaatgca ggttccagat gtggacatca gaggtcccaa ggtagatatt aaagcaccag   3000
atgtggaagg ccaaggcctg gactggagcc tgaaaatacc caagatgaaa atgcccaagt   3060
tcagcatgcc cagcctcaaa ggcgagggcc cagaagtgga tgtgaacttg cctaaggctg   3120
acgttgttgt ctcaggaccc aaggtggaca tcgaagcccc agatgtgagc ctcgaaggtc   3180
cagaagggaa gctgaagggt cccaagttta agatgcctga gatgcatttc aagacccccca   3240
agatctccat gcctgatgtg gacttacact tgaaaggccc caaagtcaaa ggggatgtgg   3300
atgtgtctgt gcccaaggta gaaggtgaaa tgaaagtgcc agatgttgaa atcaaaggac   3360
ccaaaatgga cattgatgcc ccagatgtgg aggttcaagg cccagactgg cacctgaaga   3420
tgcccaagat gaaaatgccc aagtttagca tgcctggctt caaaggagag ggccgagaag   3480
tggatgtgaa cctgcccaag gctgacattg atgtctcagg acccaaggtg gatgttgaag   3540
tcccagatgt gagccttgag ggcccggaag gaaagctgaa gggccccaag tttaagatgc   3600
ctgagatgca cttcaaggcc cccaagatct ccatgcctga tgtggacctg aatcttaagg   3660
ggccaaaatt gaagggagat gtggatgtgt ccttgcctga ggtagaaggt gaaatgaaag   3720
tgccagatgt tgacattaaa gggcccaaag ttgacattag tgctccagat gtggatgttc   3780
atggcccaga ttggcacctg aagatgccca aggtgaaaat gcccaagttc agcatgcccg   3840
gcttcaaagg agagggccct gaagtggatg tgaagctgcc caaagctgac gttgatgtct   3900
caggacccaa aatggatgct gaagttccag atgtgaatat tgaaggtcca gacgcaaaac   3960
taaaaggtcc caaattcaag atgccagaaa tgagtataaa gcctcagaag atatccatac   4020
cagatgttgg tttgcatttg aaaggtccta aaatgaaagg agattatgat gtaacagttc   4080
caaaagtaga aggagagata aaagctcctg atgttgacat caaaggcccc aaagttgata   4140
ttaatgcacc agatgtggag gttcatggcc cagactggca cctgaagatg cccaaggtaa   4200
aaatgcccaa gttcagcatg cctggcttta aggagaggg cccagaggtg gatatgaacc   4260
tgcccaaggc tgaccttggt gtttcaggac ccaaggtgga cattgatgtt ccagatgtga   4320
atcttgaagc tccagagggg aaactaaaag gccctaagtt caagatgcca agcatgaata   4380
tacagacgca caaaatctct atgcctgatg ttggacttaa tttgaaagcc cctaaactga   4440
aaactgatgt agatgtttcc cttcccaaag tggaaggaga cttgaagggt cctgaaattg   4500
atgtgaaagc ccctaagatg gatgtgaatg ttggtgatat tgatattgaa ggtccagaag   4560
ggaagttgaa gggccccaag tttaagatgc ctgagatgca tttcaaggcc cccaagatct   4620
ccatgcccga tgtggactta cacttgaaag gccccaaagt caaaggggat atggatgtgt   4680
ctgtgcccaa ggtagaaggt gaaatgaaag tgccagatgt tgacattaaa gggcccaaag   4740
tggacattga tgccccagat gtggaggttc acgacccaga ttggcacctg aaaatgccca   4800
agatgaaaat gcccaagttc agtatgcctg gcttcaaagc agagggccct gaagtggatg   4860
tgaatctgcc aaaggctgac attgatgtgt ctggacccag tgtggacact gatgctcctg   4920
atttggatat tgagggacca gaaggaaagt tgaaaggctc caaatttaag atgcccaagt   4980
tgaatataaa agctcccaag gtctccatgc cagatgtgga cttgaatttg aagggaccca   5040
aactgaaggg agagatagat gcttctgtgc cagaactgga aggtgatctc agagggccgc   5100
aagttgatgt caaaggtcct tttgtggaag cggaggtgcc cgatgttgat ctggagtgtc   5160
ctgatgcaaa gttgaaaggg cccaagttta agatgcctga gatgcacttc aaggccccca   5220
```

agatctccat gcctgatgtg gacttacacc tgaaaggccc caaagtcaaa ggggatgcgg 5280
atgtgtcggt gccaaaattg gagggagatt taacaggccc cagtgtgggt gtggaggtgc 5340
ctgatgttga gctggagtgt cctgatgcaa agttgaaagg ccctaaattt aagatgccag 5400
acatgcactt caaggccccc aagatctcca tgcctgatgt ggacttacac 5450

<210> SEQ ID NO 70
<211> LENGTH: 4790
<212> TYPE: DNA
<213> ORGANISM: Human

<400> SEQUENCE: 70
gccgctccag ggcctcggag aggccagccg gcccgcggag ctgtttaacc gttccgcggg 60
tcctagaaag ccagctgccc tcaggcttgc ttaaagggga gacgccggag tgggtgtgcc 120
ccgacgtcct gcgagggcag cgccgagggg cgtgtgccct gaaggcccgc tgaacagccg 180
cttttggccg ggcgcggtgg ctcacgcctg taatcccagc actttgggag gccgaggcgg 240
gaggatccct tgggcccagg aggagttcga gaccagcctg ggcagtgtgg cgagaccgtc 300
ccccaccccc gtctctaaat atatataaac atatatatgt atatgagcca ctgttgagcg 360
caatggcggg ctctgggcga ggtccggccc tagagcccca acgcgacacc tcgccgccct 420
ctgcaggagc tgaggcgggc ggagttggtg gaaattatcg tggagacgga ggcgcagacc 480
ggggtcagcg gcatcaacgt agcgggcggc ggcaaagagg gaatcttcgt tcgggagctg 540
cgcgaggact cacccgccgc caggagcctc agcctgcagg aaggggacca gctgctgagt 600
gcccgagtgt tcttcgagaa cttcaagtac gaggacgcac tacgcctgct gcaatgcgcc 660
gagccttaca aagtctcctt ctgcctgaag cgcactgtgc ccaccgggga cctggctctg 720
cggcccggga ccgtgtctgg ctacgagatc aagggcccgc gggccaaggt ggccaagctg 780
aacatccaga gtctgtcccc tgtgaagaag aagaagatgg tgcctggggc tctgggggtc 840
cccgctgacc tggcccctgt tgacgtcgag ttctcctttc ccaagttctc ccgcctgcgt 900
cggggcctca aagccgaggc tgtcaagggt cctgtcccgg ctgcccctgc ccgccggcgc 960
ctccagctgc ctcggctgcg tgtacgagaa gtggccgaag aggctcaggc agcccggctg 1020
gccgccgccg ctcctccccc caggaaagcc aaggtggagg ctgaggtggc tgcaggagct 1080
cgtttcacag cccctcaggt ggagctggtt gggccgcggc tgccaggggc ggaggtgggt 1140
gtcccccagg tctcagcccc caaggctgcc ccctcagcag aggcagctgg tggctttgcc 1200
ctccacctgc caacccttgg gctcggagcc ccggctccgc ctgctgtgga ggccccagcc 1260
gtgggaatcc aggtccccca ggtggagctg cctgccttgc cctcactgcc cactctgccc 1320
acacttccct gcctagagac ccgggaaggg gctgtgtcgg tagtggtgcc caccctggat 1380
gtggcagcac cgactgtggg ggtggacctg gccttgccgg gtgcagaggt ggaggcccgg 1440
ggagaggcac ctgaggtggc cctgaagatg ccccgcctta gttttccccg atttggggct 1500
cgagcaaagg aagttgctga ggccaaggta gccaaggtca gccctgaggc cagggtgaaa 1560
ggtcccagac ttcgaatgcc cacctttggg ctttccctct tggagccccg gcccgctgct 1620
cctgaagttg tagagagcaa gctgaagctg cccaccatca agatgccctc ccttggcatc 1680
ggagtgtcag ggcccgaggt caaggtgccc aagggacctg aagtgaagct ccccaaggct 1740
cctgaggtca agcttccaaa agtgcccgag gcagcccttc cagaggttcg actcccagag 1800
gtggagctcc ccaaggtgtc agagatgaaa ctcccaaagg tgccagagat ggctgtgccg 1860

-continued

```
gaggtgcggc ttccagaggt agagctgccc aaagtgtcag agatgaaact cccaaaggtg   1920
ccagagatgg ctgtgccgga ggtgcggctt ccagaggtac agctgctgaa agtgtcggag   1980
atgaaactcc caaaggtgcc agagatggct gtgccggagg tgcggcttcc agaggtacag   2040
ctgccgaaag tgtcagagat gaaactccca gaggtgtcag aggtggctgt gccagaggtg   2100
cggcttccag aggtgcagct gccgaaagtg ccagagatga aagtccctga gatgaagctt   2160
ccaaaggtgc ctgagatgaa acttcctgag atgaaactcc ctgaagtgca actcccgaag   2220
gtgcccgaga tggccgtgcc cgatgtgcac ctcccagaag tgcagcttcc aaaagtccca   2280
gagatgaagc tccctgagat gaaactccct gaggtgaaac tcccgaaggt gcccgagatg   2340
gctgtgcccg atgtgcacct cccggaagtg cagctcccga aagtcccaga gatgaaactc   2400
cctaaaatgc ctgagatggc tgtgccagag gttcgactcc ccgaggtgca gctgccaaaa   2460
gtctcagaga tgaaactccc caaggtgcct gaaatggccg tgcccgatgt gcacctccca   2520
gaggtgcagc tgcccaaagt ctgtgaaatg aaagtccctg acatgaagct cccagagata   2580
aaactcccca aggtgcctga gatggctgtg cccgatgtgc acctccccga ggtgcagctg   2640
ccgaaagtgt cagagattcg gctgccggaa atgcaagtgc cgaaggttcc cgacgtgcat   2700
cttccgaagg caccagaggt gaagctgccc agggctccgg aggtgcagct aaaggccacc   2760
aaggcagaac aggcagaagg gatggaattt ggcttcaaga tgcccaagat gaccatgccc   2820
aagctaggga gggcagagtc ccatcacgt ggcaagccag gcgaggcggg tgctgaggtc    2880
tcagggaagc tggtaacact tccctgtctg cagccagagg tggatggtga ggctcatgtg   2940
ggtgtcccct ctctcactct gccttcagtg gagctagacc tgccaggagc acttggcctg   3000
caggggcagg tcccagccgc taaaatgggc aagggagagc gggtggaggg ccctgaggtg   3060
gcagcagggg tcagggaagt gggcttccga gtgccctctg ttgaaattgt caccccacag   3120
ctgcccgccg tggaaattga ggaagggcgg ctggagatga tagagacaaa agtcaagccc   3180
tcttccaagt tctccttacc taagtttgga ctctcggggc caaaggtggc taaggcagag   3240
gctgaggggg ctgggcgagc taccaagctg aaggtatcca aatttgccat ctcactcccc   3300
aaggctcggg tgggggctga ggctgaggcc aaaggggctg gggaggcagg cctgctgcct   3360
gccctcgatc tgtccatccc acagctcagc ctggatgccc acctgccctc aggcaaggta   3420
gaggtggcag gggccgacct caagttcaag gggcccaggt ttgctctccc caagtttggg   3480
gtcagaggcc gggacactga ggcagcagaa ctagtgccag ggtggctga gttggagggc    3540
aagggctggg gctgggatgg gagggtgaag atgcccaagc tgaaggtgtc cacagccggg   3600
caggtggtca ctgagggcca tgacgcgggg ctgaggatgc ctccgctggg catctccctg   3660
ccacaggtgg agctgaccgg ctttggggag gcaggtaccc cagggcagca ggctcagagt   3720
acagtccctt cagcagaggg cacagcaggc tacagggttc aggtgcccca ggtgaccctg   3780
tctctgcctg gagcccaggt tgcaggtggt gagctgctgg tgggtgaggg tgtctttaag   3840
atgcccaccg tgacagtgcc ccagcttgag ctggacgtgg ggctaagccg agaggcacag   3900
gcgggcgagg cggccacagg cgagggtggg ctgaggctga agttgcccac actgggggcc   3960
agagctaggg tgggggcga gggtgctgag gagcagcccc caggggccga gcgtaccttc    4020
tgcctctcac tgcccgacgt ggagctctcg ccatccgggg gcaaccatgc cgagtaccag   4080
gtggcagagg gggagggaga ggccggacac aagctcaagg tacggctgcc ccggtttggc   4140
ctggtgcggg ccaaggaggg ggccgaggag ggtgagaagg ccaagagccc caaactcagg   4200
ctgccccgag tgggcttcag ccaaagtgag atggtcactg ggaagggtc ccccagcccc     4260
```

-continued

```
gaggaggagg aggaggagga ggaagagggc agtggggaag gggcctcggg tcgccggggc   4320
cgggtccggg tccgcttgcc acgtgtaggc ctggcggccc cttctaaagc ctctcggggg   4380
caggagggcg atgcagcccc caagtccccc gtcagagaga agtcacccaa gttccgcttc   4440
cccagggtgt ccctaagccc caaggcccgg agtgggagtg gggaccagga agagggtgga   4500
ttgcgggtgc ggctgcccag cgtggggttt tcagagacag gggctccagg cccggccagg   4560
atggaggggg ctcaggctgc ggctgtctga agcccctagt cagatgggga tcccttcttg   4620
ccttcctttc tctacccct cgctgttgtg tgtgtgataa ctagcactaa ccctaagagg   4680
gccgggaggt gggtgactga ccagggctgg cagggaggcc tgctcctgtc tctctggcag   4740
gagtgcctgt accccaccaa gccatgtgaa taaaataatc tggaagtagc              4790
```

<210> SEQ ID NO 71
<211> LENGTH: 4853
<212> TYPE: DNA
<213> ORGANISM: Human

<400> SEQUENCE: 71

```
gctctcgagg tgtctggagg ctcagcgagc gccggaccca ggaggcccaa ggagctggag     60
gtgaccctca ggcagcaaga accccacgga agggcgtgag ccctgcagac agctgtgcgg    120
cacctcgggc tgggctcctg ttaggaggaa gtgcctgcac ccaggcagcg gctcagaggc    180
agctgctcca tgcagaactg aagctggttc tgcagcagaa aggggagagg acacaggagc    240
ctggggtgca ggtgcctccc agcaacgcca tggaggccag gagccggagt gccgaggagc    300
tgaggcgggc ggagttggtg gaaattatcg tggagacgga ggcgcagacc ggggtcagcg    360
gcatcaacgt agcgggcggc ggcaaagagg gaatcttcgt tcgggagctg cgcgaggact    420
cacccgccgc caggagcctc agcctgcagg aaggggacca gctgctgagt gcccgagtgt    480
tcttcgagaa cttcaagtac gaggacgcac tacgcctgct gcaatgcgcc gagccttaca    540
aagtctcctt ctgcctgaag cgcactgtgc ccaccgggga cctggctctg cggcccggga    600
ccgtgtctgg ctacgagatc aagggcccgc gggccaaggt ggccaagctg aacatccaga    660
gtctgtcccc tgtgaagaag aagaagatgg tgcctggggc tctgggggtc cccgctgacc    720
tggcccctgt tgacgtcgag ttctcctttc ccaagttctc ccgcctgcgt cggggcctca    780
aagccgaggc tgtcaagggt cctgtcccgg ctgcccctgc ccgccggcgc ctccagctgc    840
ctcggctgcg tgtacgagaa gtggccgaag aggctcaggc agcccggctg gccgccgccg    900
ctcctccccc caggaaagcc aaggtggagg ctgaggtggc tgcaggagct cgtttcacag    960
cccctcaggt ggagctggtt gggccgcggc tgccaggggc ggaggtgggt gtcccccagg   1020
tctcagcccc caaggctgcc ccctcagcag aggcagctgg tggctttgcc ctccacctgc   1080
caacccttgg gctcggagcc ccggctccgc ctgctgtgga ggccccagcc gtgggaatcc   1140
aggtccccca ggtggagctg cctgccttgc cctcactgcc cactctgccc acacttccct   1200
gcctagagac ccgggaaggg gctgtgtcgg tagtggtgcc caccctggat gtggcagcac   1260
cgactgtggg ggtggacctg gccttgccgg gtgcagaggt ggaggcccgg ggagaggcac   1320
ctgaggtggc cctgaagatg ccccgcctta gttttccccg atttggggct cgagcaaagg   1380
aagttgctga ggccaaggta gccaaggtca gccctgaggc cagggtgaaa ggtcccagac   1440
ttcgaatgcc cacctttggg ctttccctct tggagccccg gcccgctgct cctgaagttg   1500
tagagagcaa gctgaagctg cccaccatca agatgccctc ccttggcatc ggagtgtcag   1560
```

-continued

```
ggcccgaggt caaggtgccc aagggacctg aagtgaagct ccccaaggct cctgaggtca   1620
agcttccaaa agtgcccgag gcagcccttc cagaggttcg actcccagag gtggagctcc   1680
ccaaggtgtc agagatgaaa ctcccaaagg tgccagagat ggctgtgccg gaggtgcggc   1740
ttccagaggt agagctgccc aaagtgtcag agatgaaact cccaaaggtg ccagagatgg   1800
ctgtgccgga ggtgcggctt ccagaggtac agctgctgaa agtgtcggag atgaaactcc   1860
caaaggtgcc agagatggct gtgccggagg tgcggcttcc agaggtacag ctgccgaaag   1920
tgtcagagat gaaactccca gaggtgtcag aggtggctgt gccagaggtg cggcttccag   1980
aggtgcagct gccgaaagtg ccagagatga aagtccctga gatgaagctt ccaaaggtgc   2040
ctgagatgaa acttcctgag atgaaactcc ctgaagtgca actcccgaag gtgcccgaga   2100
tggccgtgcc cgatgtgcac ctcccagaag tgcagcttcc aaaagtccca gagatgaagc   2160
tccctgagat gaaactccct gaggtgaaac tcccgaaggt gcccgagatg gctgtgcccg   2220
atgtgcacct cccggaagtg cagctcccga aagtcccaga gatgaaactc cctaaaatgc   2280
ctgagatggc tgtgccagag gttcgactcc ccgaggtgca gctgccaaaa gtctcagaga   2340
tgaaactccc caaggtgcct gaaatggccg tgcccgatgt gcacctccca gaggtgcagc   2400
tgcccaaagt ctgtgaaatg aaagtccctg acatgaagct cccagagata aaactcccca   2460
aggtgcctga gatggctgtg cccgatgtgc acctccccga ggtgcagctg ccgaaagtgt   2520
cagagattcg gctgccggaa atgcaagtgc cgaaggttcc cgacgtgcat cttccgaagg   2580
caccagaggt gaagctgccc agggctccgg aggtgcagct aaaggccacc aaggcagaac   2640
aggcagaagg gatggaattt ggcttcaaga tgcccaagat gaccatgccc aagctaggga   2700
gggcagagtc ccccatcacgt ggcaagccag gcgaggcggg tgctgaggtc tcagggaagc   2760
tggtaacact tccctgtctg cagccagagg tggatggtga ggctcatgtg ggtgtcccct   2820
ctctcactct gccttcagtg gagctagacc tgccaggagc acttggcctg caggggcagg   2880
tcccagccgc taaaatgggc aagggagagc gggtggaggg ccctgaggtg gcagcagggg   2940
tcagggaagt gggcttccga gtgccctctg ttgaaattgt caccccacag ctgcccgccg   3000
tggaaattga ggaagggcgg ctggagatga tagagacaaa agtcaagccc tcttccaagt   3060
tctccttacc taagtttgga ctctcggggc caaaggtggc taaggcagag gctgaggggg   3120
ctgggcgagc taccaagctg aaggtatcca aatttgccat ctcactcccc aaggctcggg   3180
tgggggctga ggctgaggcc aaaggggctg gggaggcagg cctgctgcct gccctcgatc   3240
tgtccatccc acagctcagc ctggatgccc acctgccctc aggcaaggta gaggtggcag   3300
gggccgacct caagttcaag gggcccaggt ttgctctccc caagtttggg gtcagaggcc   3360
gggacactga ggcagcagaa ctagtgccag gggtggctga gttggagggc aagggctggg   3420
gctgggatgg gagggtgaag atgcccaagc tgaagatgcc ttcctttggg ctggctcgag   3480
ggaaggaagc agaagttcaa ggtgatcgtg ccagcccggg ggaaaaggct gagtccaccg   3540
ctgtgcagct taagatcccc gaggtggagc tggtcacgct gggcgcccag gaggaaggga   3600
gggcagaggg ggctgtggcc gtcagtggaa tgcagctgtc aggcctgaag gtgtccacag   3660
ccgggcaggt ggtcactgag ggccatgacg cggggctgag gatgcctccg ctgggcatct   3720
ccctgccaca ggtggagctg accggctttg gggaggcagg taccccaggg cagcaggctc   3780
agagtacagt cccttcagca gagggcacag caggctacag ggttcaggtg ccccaggtga   3840
ccctgtctct gcctggagcc caggttgcag gtggtgagct gctggtgggt gagggtgtct   3900
ttaagatgcc caccgtgaca gtgccccagc ttgagctgga cgtggggcta agccgagagg   3960
```

-continued

```
cacaggcggg cgaggcggcc acaggcgagg gtgggctgag gctgaagttg cccacactgg   4020
gggccagagc tagggtgggg ggcgagggtg ctgaggagca gcccccaggg gccgagcgta   4080
ccttctgcct ctcactgccc gacgtggagc tctcgccatc cgggggcaac catgccgagt   4140
accaggtggc agagggggag ggagaggccg gacacaagct caaggtacgg ctgccccggt   4200
ttggcctggt gcgggccaag gagggggccg aggagggtga gaaggccaag agccccaaac   4260
tcaggctgcc ccgagtgggc ttcagccaaa gtgagatggt cactggggaa gggtccccca   4320
gccccgagga ggaggaggag gaggaggaag agggcagtgg ggaaggggcc tcgggtcgcc   4380
ggggccgggt ccgggtccgc ttgccacgtg taggcctggc ggccccttct aaagcctctc   4440
gggggcagga gggcgatgca gcccccaagt cccccgtcag agagaagtca cccaagttcc   4500
gcttccccag ggtgtcccta agccccaagg cccggagtgg gagtggggac caggaagagg   4560
gtggattgcg ggtgcggctg cccagcgtgg ggttttcaga gacaggggct ccaggcccgg   4620
ccaggatgga gggggctcag gctgcggctg tctgaagccc ctagtcagat ggggatccct   4680
tcttgccttc ctttctctac cccctcgctg ttgtgtgtgt gataactagc actaacccta   4740
agagggccgg gaggtgggtg actgaccagg gctggcaggg aggcctgctc ctgtctctct   4800
ggcaggagtg cctgtacccc accaagccat gtgaataaaa taatctggaa gta          4853
```

<210> SEQ ID NO 72
<211> LENGTH: 5502
<212> TYPE: DNA
<213> ORGANISM: Human

<400> SEQUENCE: 72

```
gctctcgagg tgtctggagg ctcagcgagc gccggaccca ggaggcccaa ggagctggag     60
gtgaccctca ggcagcaaga accccacgga agggcgtgag ccctgcagac agctgtgcgg    120
cacctcgggc tgggctcctg ttaggaggaa gtgcctgcac ccaggcagcg gctcagaggc    180
agctgctcca tgcagaactg aagctggttc tgcagcagaa aggggagagg acacaggagc    240
ctggggtgca ggtgcctccc agcaacgcca tggaggccag gagccggagt gccgaggagc    300
tgaggcgggc ggagttggtg gaaattatcg tggagacgga ggcgcagacc ggggtcagcg    360
gcatcaacgt agcgggcggc ggcaaagagg gaatcttcgt tcgggagctg cgcgaggact    420
cacccgccgc caggagcctc agcctgcagg aaggggacca gctgctgagt gcccgagtgt    480
tcttcgagaa cttcaagtac gaggacgcac tacgcctgct gcaatgcgcc gagccttaca    540
aagtctcctt ctgcctgaag cgcactgtgc ccaccgggga cctggctctg cggcccggga    600
ccgtgtctgg ctacgagatc aagggcccgc gggccaaggt ggccaagctg gtacgcgtgc    660
ttagcccggc cccggccctg gactgcccca gcgatccggt ctctgcgccg tgagccccat    720
tccccgccat cgtgggccag ccttgccctc tgtcttgtca ctaacccaag ctaattccac    780
cctctgcccc ttcctctctg ccccaaactc ttccccggga agggggacag acccacccca    840
gcccagggcc ctcacccacc tcggagaggc gtccccacca tcggatccag gcttgctagg    900
ggtcctgaac caggctactt cgaaccagga aagccagatt ccagcctgag tgctggccca    960
attactgctg agtggccctg gacaaagttg tttctctccc tgggcctcag tttccccatc   1020
tctagaatga ggatgttggg gaaaatcccg gatcaggatc tagaagtctt gggtccccgt   1080
ccctacactc ctgttgactc atttggagat cctagatggc tgcctgcttt cctgggcact   1140
catggtgaaa tgacaggcaa gaagtgggga tgatgtttgg ggaacaagat acttgaccca   1200
```

-continued

```
gcacatcccc cgcctggtcc aataccaggt ggggctcttc ctgtccactc ccagcctccc   1260

actgtcccac cgcctcctgc ctctctcctc tctccccaga acatccagag tctgtcccct   1320

gtgaagaaga agaagatggt gcctggggct ctgggggtcc ccgctgacct ggcccctgtt   1380

gacgtcgagt tctcctttcc caagttctcc cgcctgcgtc ggggcctcaa agccgaggct   1440

gtcaagggtc ctgtcccggc tgcccctgcc cgccggcgcc tccagctgcc tcggctgcgt   1500

gtacgagaag tggccgaaga ggctcaggca gcccggctgg ccgccgccgc tcctcccccc   1560

aggaaagcca aggtggaggc tgaggtggct gcaggagctc gtttcacagc cctcaggtg    1620

gagctggttg ggccgcggct gccaggggcg gaggtgggtg tcccccaggt ctcagcccc    1680

aaggctgccc cctcagcaga ggcagctggt ggctttgccc tccacctgcc aacccttggg   1740

ctcggagccc cggctccgcc tgctgtggag gccccagccg tgggaatcca ggtcccccag   1800

gtggagctgc ctgccttgcc ctcactgccc actctgccca cacttccctg cctagagacc   1860

cgggaagggg ctgtgtcggt agtggtgccc accctggatg tggcagcacc gactgtgggg   1920

gtggacctgg ccttgccggg tgcagaggtg gaggcccggg gagaggcacc tgaggtggcc   1980

ctgaagatgc cccgccttag ttttccccga tttggggctc gagcaaagga agttgctgag   2040

gccaaggtag ccaaggtcag ccctgaggcc agggtgaaag gtcccagact tcgaatgccc   2100

acctttgggc tttccctctt ggagccccgg cccgctgctc ctgaagttgt agagagcaag   2160

ctgaagctgc ccaccatcaa gatgccctcc cttggcatcg gagtgtcagg gcccgaggtc   2220

aaggtgccca agggacctga agtgaagctc cccaaggctc ctgaggtcaa gcttccaaaa   2280

gtgcccgagg cagcccttcc agaggttcga ctcccagagg tggagctccc caaggtgtca   2340

gagatgaaac tcccaaaggt gccagagatg gctgtgccgg aggtgcggct tccagaggta   2400

gagctgccca aagtgtcaga gatgaaactc ccaaaggtgc cagagatggc tgtgccggag   2460

gtgcggcttc cagaggtaca gctgctgaaa gtgtcggaga tgaaactccc aaaggtgcca   2520

gagatggctg tgccggaggt gcggcttcca gaggtacagc tgccgaaagt gtcagagatg   2580

aaactcccag aggtgtcaga ggtggctgtg ccagaggtgc ggcttccaga ggtgcagctg   2640

ccgaaagtgc cagagatgaa agtccctgag atgaagcttc caaaggtgcc tgagatgaaa   2700

cttcctgaga tgaaactccc tgaagtgcaa ctcccgaagg tgcccgagat ggccgtgccc   2760

gatgtgcacc tcccagaagt gcagcttcca aaagtcccag agatgaagct ccctgagatg   2820

aaactccctg aggtgaaact cccgaaggtg cccgagatgg ctgtgcccga tgtgcacctc   2880

ccggaagtgc agctcccgaa agtcccagag atgaaactcc ctaaaatgcc tgagatggct   2940

gtgccagagg ttcgactccc cgaggtgcag ctgccaaaag tctcagagat gaaactcccc   3000

aaggtgcctg aaatggccgt gcccgatgtg cacctcccag aggtgcagct gcccaaagtc   3060

tgtgaaatga aagtccctga catgaagctc ccagagataa aactccccaa ggtgcctgag   3120

atggctgtgc ccgatgtgca cctccccgag gtgcagctgc cgaaagtgtc agagattcgg   3180

ctgccggaaa tgcaagtgcc gaaggttccc gacgtgcatc ttccgaaggc accagaggtg   3240

aagctgccca gggctccgga ggtgcagcta aaggccacca aggcagaaca ggcagaaggg   3300

atggaatttg gcttcaagat gcccaagatg accatgccca agctagggag ggcagagtcc   3360

ccatcacgtg gcaagccagg cgaggcgggt gctgaggtct cagggaagct ggtaacactt   3420

ccctgtctgc agccagaggt ggatggtgag gctcatgtgg gtgtcccctc tctcactctg   3480

ccttcagtgg agctagacct gccaggagca cttggcctgc aggggcaggt cccagccgct   3540

aaaatgggca agggagagcg ggtggagggc cctgaggtgg cagcaggggt cagggaagtg   3600
```

-continued

```
ggcttccgag tgccctctgt tgaaattgtc accccacagc tgcccgccgt ggaaattgag   3660

gaagggcggc tggagatgat agagacaaaa gtcaagccct cttccaagtt ctccttacct   3720

aagtttggac tctcggggcc aaaggtggct aaggcagagg ctgagggggc tgggcgagct   3780

accaagctga aggtatccaa atttgccatc tcactcccca aggctcgggt gggggctgag   3840

gctgaggcca aaggggctgg ggaggcaggc ctgctgcctg ccctcgatct gtccatccca   3900

cagctcagcc tggatgccca cctgccctca ggcaaggtag aggtggcagg ggccgacctc   3960

aagttcaagg ggcccaggtt tgctctcccc aagtttgggg tcagaggccg ggacactgag   4020

gcagcagaac tagtgccagg ggtggctgag ttggagggca agggctgggg ctgggatggg   4080

agggtgaaga tgcccaagct gaagatgcct tcctttgggc tggctcgagg gaaggaagca   4140

gaagttcaag gtgatcgtgc cagcccgggg gaaaaggctg agtccaccgc tgtgcagctt   4200

aagatccccg aggtggagct ggtcacgctg ggcgcccagg aggaagggag ggcagagggg   4260

gctgtggccg tcagtggaat gcagctgtca ggcctgaagg tgtccacagc cgggcaggtg   4320

gtcactgagg gccatgacgc ggggctgagg atgcctccgc tgggcatctc cctgccacag   4380

gtggagctga ccggctttgg ggaggcaggt accccaggc  agcaggctca gagtacagtc   4440

ccttcagcag agggcacagc aggctacagg gttcaggtgc cccaggtgac cctgtctctg   4500

cctggagccc aggttgcagg tggtgagctg ctggtgggtg agggtgtctt taagatgccc   4560

accgtgacag tgccccagct tgagctggac gtggggctaa gccgagaggc acaggcgggc   4620

gaggcggcca caggcgaggg tgggctgagg ctgaagttgc ccacactggg ggccagagct   4680

agggtggggg gcgagggtgc tgaggagcag cccccagggg ccgagcgtac cttctgcctc   4740

tcactgcccg acgtggagct ctcgccatcc gggggcaacc atgccgagta ccaggtggca   4800

gagggggagg gagaggccgg acacaagctc aaggtacggc tgccccggtt tggcctggtg   4860

cgggccaagg agggggccga ggagggtgag aaggccaaga gccccaaact caggctgccc   4920

cgagtgggct tcagccaaag tgagatggtc actggggaag ggtcccccag ccccgaggag   4980

gaggaggagg aggaggaaga gggcagtggg gaaggggcct cgggtcgccg gggccgggtc   5040

cgggtccgct tgccacgtgt aggcctggcg gccccttcta aagcctctcg gggcaggag    5100

ggcgatgcag cccccaagtc cccgtcaga  gagaagtcac ccaagttccg cttccccagg   5160

gtgtccctaa gccccaaggc ccggagtggg agtggggacc aggaagaggg tggattgcgg   5220

gtgcggctgc ccagcgtggg gttttcagag acaggggctc caggcccggc caggatggag   5280

ggggctcagg ctgcggctgt ctgaagcccc tagtcagatg gggatccctt cttgccttcc   5340

tttctctacc ccctcgctgt tgtgtgtgtg ataactagca ctaaccctaa gagggccggg   5400

aggtgggtga ctgaccaggg ctggcaggga ggcctgctcc tgtctctctg gcaggagtgc   5460

ctgtacccca ccaagccatg tgaataaaat aatctggaag ta                      5502
```

```
<210> SEQ ID NO 73
<211> LENGTH: 1485
<212> TYPE: DNA
<213> ORGANISM: Arabidopsis thaliana

<400> SEQUENCE: 73

atcacaaaca caaagcaaca acaaacacca caaaagcaaa agaagaaaca aacgcaagag     60

ttctcaagca agctcaaaca tggcactaat gaagaagagt ctctctgctg ctcttctctc    120

atcaccactt ctgatcatat gtcttatcgc attgctcgct gatccgtttt cagtcggtgc    180
```

-continued

```
tcgccggtta ttggaggatc ctaaaccgga gataccaaaa ttgcctgagc tacctaaatt    240
cgaagttccc aagttgccgg agttccctaa accagagttg cccaagttac ccgaatttcc    300
aaagcctgag ttgccaaaga tcccggagat tccaaagcca gagttaccaa aggtaccgga    360
gattccaaag cctgaggaaa ctaaactgcc agatattccc aagcttgaat tgcccaagtt    420
tccggaaatt ccaaaacctg agctcccaaa gatgccagag attccaaaac ctgagttacc    480
aaaggtaccg gagattcaga agcccgagtt accaaaaatg ccggagattc caaagcctga    540
attaccaaag tttccagaga ttccaaagcc tgatttgcca aagtttccag agaattcaaa    600
gtctgaggtg cctaagctaa tggagactga aaagcctgag gctcctaagg tgccagagat    660
tccaaagcct gagttgccaa agttgccaga agttcccaag cttgaggctc ctaaggtacc    720
agagatccag aagccggagt tgcccaaaat gccggagtta cctaagatgc cggagattca    780
gaaacctgag ttgccaaagt tgccagaagt tcccaagctt gaggctccta aggtaccgga    840
gatccagaag ccggagttgc ccaaaatgcc ggagttacct aagatgccgg agattcagaa    900
acccgagttg cccaagatgc cggagattca gaagcctgag ttgccgaagg tgccagaggt    960
tccaaagccc gaattgccaa cggttccaga ggttccaaag tctgaggctc ctaagtttcc   1020
agagattcca aagcctgaac tgccgaagat tccagaagtt ccaaaacctg aactgcccaa   1080
ggttccagaa attacaaaac ctgcagttcc agagattcca aagccagagc taccgacgat   1140
gcctcaactt cccaagttgc cggaattccc aaaagttccc ggaactcctt aagcgaagag   1200
aaggcccagc tactttgaag cccatcccac aatcttaaag taccgtttta ccgttatacc   1260
atttgtctat ttgcagagat gcacttatgt ctgtctacat cattgtttcc ttagtaaaaa   1320
ccatgtcgta tggttggtct catagtcata gttcttgttt tttttgggta aagactatac   1380
acttatactt gtataattgt atcctgttat attttgtatt gtttgtttcc atacagattt   1440
cgttgtattt gatatacttt ttaattgatt atgttactta tttaa                   1485
```

<210> SEQ ID NO 74
<211> LENGTH: 421
<212> TYPE: DNA
<213> ORGANISM: Xenopus

<400> SEQUENCE: 74

```
tcactgatgt gaggctttta acagtcattt tgggcatctt ggtctttgga cccttgactt     60
ctacacttcc ggatgttggc gacactgtga catctgagga ctgtacagcc cgtttaaggc    120
agtatgagac tttgtaaggc tccatgcact gaagtaattt taaagcttct tcatatttga    180
cattttcaaa aaagacatgg gcacttagga gctggtctcc ttccaaaaga ggcaacgttt    240
tagcagcagg tgaatccttg acaacatctc tgataatcac tccctctctg ccacctccag    300
aaatgacgat gccactcatg ccagctttag cttctgtttc tacaataacc tctaccacct    360
ctgaggtttg cagcgtctcc tctttcccct tgtctgagtg tcagtgctgg agcgtggttg    420
a                                                                    421
```

<210> SEQ ID NO 75
<211> LENGTH: 5502
<212> TYPE: DNA
<213> ORGANISM: Human

<400> SEQUENCE: 75

```
gctctcgagg tgtctggagg ctcagcgagc gccggaccca ggaggcccaa ggagctggag     60
gtgaccctca ggcagcaaga accccacgga agggcgtgag ccctgcagac agctgtgcgg    120
```

-continued

```
cacctcgggc tgggctcctg ttaggaggaa gtgcctgcac ccaggcagcg gctcagaggc    180
agctgctcca tgcagaactg aagctggttc tgcagcagaa aggggagagg acacaggagc    240
ctggggtgca ggtgcctccc agcaacgcca tggaggccag gagccggagt gccgaggagc    300
tgaggcgggc ggagttggtg gaaattatcg tggagacgga ggcgcagacc ggggtcagcg    360
gcatcaacgt agcgggcggc ggcaaagagg gaatcttcgt tcgggagctg cgcgaggact    420
cacccgccgc caggagcctc agcctgcagg aaggggacca gctgctgagt gcccgagtgt    480
tcttcgagaa cttcaagtac gaggacgcac tacgcctgct gcaatgcgcc gagccttaca    540
aagtctcctt ctgcctgaag cgcactgtgc ccaccgggga cctggctctg cggcccggga    600
ccgtgtctgg ctacgagatc aagggcccgc gggccaaggt ggccaagctg gtacgcgtgc    660
ttagcccggc cccggccctg gactgcccca gcgatccggt ctctgcgccg tgagccccat    720
tccccgccat cgtgggccag ccttgccctc tgtcttgtca ctaacccaag ctaattccac    780
cctctgcccc ttcctctctg ccccaaactc ttccccggga aggggacag acccacccca     840
gcccagggcc ctcacccacc tcggagaggc gtccccacca tcggatccag gcttgctagg    900
ggtcctgaac caggctactt cgaaccagga aagccagatt ccagcctgag tgctggccca    960
attactgctg agtggccctg gacaaagttg tttctctccc tgggcctcag tttccccatc   1020
tctagaatga ggatgttggg gaaaatcccg gatcaggatc tagaagtctt gggtccccgt   1080
ccctacactc ctgttgactc atttggagat cctagatggc tgcctgcttt cctgggcact   1140
catggtgaaa tgacaggcaa gaagtgggga tgatgtttgg ggaacaagat acttgaccca   1200
gcacatcccc cgcctggtcc aataccaggt ggggctcttc ctgtccactc ccagcctccc   1260
actgtcccac cgcctcctgc ctctctcctc tctccccaga acatccagag tctgtcccct   1320
gtgaagaaga agaagatggt gcctggggct ctgggggtcc ccgctgacct ggcccctgtt   1380
gacgtcgagt tctcctttcc caagttctcc cgcctgcgtc ggggcctcaa agccgaggct   1440
gtcaagggtc ctgtcccggc tgcccctgcc cgccggcgcc tccagctgcc tcggctgcgt   1500
gtacgagaag tggccgaaga ggctcaggca gcccggctgg ccgccgccgc tcctcccccc   1560
aggaaagcca aggtggaggc tgaggtggct gcaggagctc gtttcacagc ccctcaggtg   1620
gagctggttg ggccgcggct gccaggggcg gaggtgggtg tcccccaggt ctcagcccc    1680
aaggctgccc cctcagcaga ggcagctggt ggctttgccc tccacctgcc aacccttggg   1740
ctcggagccc cggctccgcc tgctgtggag gccccagccg tggggaatcca ggtcccccag  1800
gtggagctgc ctgccttgcc ctcactgccc actctgccca cacttccctg cctagagacc   1860
cgggaagggg ctgtgtcggt agtggtgccc accctggatg tggcagcacc gactgtgggg   1920
gtggacctgg ccttgccggg tgcagaggtg gaggcccggg gagaggcacc tgaggtggcc   1980
ctgaagatgc cccgccttag ttttccccga tttggggctc gagcaaagga agttgctgag   2040
gccaaggtag ccaaggtcag ccctgaggcc agggtgaaag gtcccagact tcgaatgccc   2100
acctttgggc tttccctctt ggagccccgg cccgctgctc ctgaagttgt agagagcaag   2160
ctgaagctgc ccaccatcaa gatgccctcc cttggcatcg gagtgtcagg gcccgaggtc   2220
aaggtgccca agggacctga agtgaagctc cccaaggctc ctgaggtcaa gcttccaaaa   2280
gtgcccgagg cagcccttcc agaggttcga ctcccagagg tggagctccc caaggtgtca   2340
gagatgaaac tcccaaaggt gccagagatg gctgtgccgg aggtgcggct tccagaggta   2400
gagctgccca aagtgtcaga gatgaaactc ccaaaggtgc cagagatggc tgtgccggag   2460
```

-continued

```
gtgcggcttc cagaggtaca gctgctgaaa gtgtcggaga tgaaactccc aaaggtgcca   2520
gagatggctg tgccggaggt gcggcttcca gaggtacagc tgccgaaagt gtcagagatg   2580
aaactcccag aggtgtcaga ggtggctgtg ccagaggtgc ggcttccaga ggtgcagctg   2640
ccgaaagtgc cagagatgaa agtccctgag atgaagcttc caaaggtgcc tgagatgaaa   2700
cttcctgaga tgaaactccc tgaagtgcaa ctcccgaagg tgcccgagat ggccgtgccc   2760
gatgtgcacc tcccagaagt gcagcttcca aaagtcccag agatgaagct ccctgagatg   2820
aaactccctg aggtgaaact cccgaaggtg cccgagatgg ctgtgcccga tgtgcacctc   2880
ccggaagtgc agctcccgaa agtcccagag atgaaactcc ctaaaatgcc tgagatggct   2940
gtgccagagg ttcgactccc cgaggtgcag ctgccaaaag tctcagagat gaaactcccc   3000
aaggtgcctg aaatggccgt gcccgatgtg cacctcccag aggtgcagct gcccaaagtc   3060
tgtgaaatga aagtccctga catgaagctc ccagagataa aactccccaa ggtgcctgag   3120
atggctgtgc ccgatgtgca cctccccgag gtgcagctgc cgaaagtgtc agagattcgg   3180
ctgccggaaa tgcaagtgcc gaaggttccc gacgtgcatc ttccgaaggc accagaggtg   3240
aagctgccca gggctccgga ggtgcagcta aaggccacca aggcagaaca ggcagaaggg   3300
atggaatttg gcttcaagat gcccaagatg accatgccca agctagggag ggcagagtcc   3360
ccatcacgtg gcaagccagg cgaggcgggt gctgaggtct cagggaagct ggtaacactt   3420
ccctgtctgc agccagaggt ggatggtgag gctcatgtgg gtgtcccctc tctcactctg   3480
ccttcagtgg agctagacct gccaggagca cttggcctgc aggggcaggt cccagccgct   3540
aaaatgggca agggagagcg ggtggagggc cctgaggtgg cagcaggggt cagggaagtg   3600
ggcttccgag tgccctctgt tgaaattgtc accccacagc tgcccgccgt ggaaattgag   3660
gaagggcggc tggagatgat agagacaaaa gtcaagccct cttccaagtt ctccttacct   3720
aagtttggac tctcggggcc aaaggtggct aaggcagagg ctgagggggc tgggcgagct   3780
accaagctga aggtatccaa atttgccatc tcactcccca aggctcgggt gggggctgag   3840
gctgaggcca aaggggctgg ggaggcaggc ctgctgcctg ccctcgatct gtccatccca   3900
cagctcagcc tggatgccca cctgccctca ggcaaggtag aggtggcagg ggccgacctc   3960
aagttcaagg ggcccaggtt tgctctcccc aagtttgggg tcagaggccg ggacactgag   4020
gcagcagaac tagtgccagg ggtggctgag ttggagggca agggctgggg ctgggatggg   4080
agggtgaaga tgcccaagct gaagatgcct tcctttgggc tggctcgagg gaaggaagca   4140
gaagttcaag gtgatcgtgc cagcccgggg gaaaaggctg agtccaccgc tgtgcagctt   4200
aagatccccg aggtggagct ggtcacgctg ggcgcccagg aggaagggag ggcagagggg   4260
gctgtggccg tcagtggaat gcagctgtca ggcctgaagg tgtccacagc caggcaggtg   4320
gtcactgagg gccatgacgc ggggctgagg atgcctccgc tgggcatctc cctgccacag   4380
gtggagctga ccggctttgg ggaggcaggt accccagggc agcaggctca gagtacagtc   4440
ccttcagcag agggcacagc aggctacagg gttcaggtgc cccaggtgac cctgtctctg   4500
cctggagccc aggttgcagg tggtgagctg ctggtgggtg agggtgtctt taagatgccc   4560
accgtgacag tgccccagct tgagctggac gtggggctaa gccgagaggc acaggcgggc   4620
gaggcggcca caggcgaggg tgggctgagg ctgaagttgc ccacactggg ggccagagct   4680
agggtggggg gcgagggtgc tgaggagcag cccccagggg ccgagcgtac cttctgcctc   4740
tcactgcccg acgtggagct ctcgccatcc gggggcaacc atgccgagta ccaggtggca   4800
gagggggagg gagaggccgg acacaagctc aaggtacggc tgccccggtt tggcctggtg   4860
```

-continued

```
cgggccaagg agggggccga ggagggtgag aaggccaaga gccccaaact caggctgccc   4920
cgagtgggct tcagccaaag tgagatggtc actggggaag ggtcccccag ccccgaggag   4980
gaggaggagg aggaggaaga gggcagtggg gaaggggcct cgggtcgccg gggccgggtc   5040
cgggtccgct tgccacgtgt aggcctggcg gcccccttcta aagcctctcg ggggcaggag  5100
ggcgatgcag cccccaagtc ccccgtcaga gagaagtcac ccaagttccg cttccccagg   5160
gtgtccctaa gccccaaggc ccggagtggg agtggggacc aggaagaggg tggattgcgg   5220
gtgcggctgc ccagcgtggg gttttcagag acaggggctc caggcccggc caggatggag   5280
ggggctcagg ctgcggctgt ctgaagcccc tagtcagatg gggatccctt cttgccttcc   5340
tttctctacc ccctcgctgt tgtgtgtgtg ataactagca ctaaccctaa gagggccggg   5400
aggtgggtga ctgaccaggg ctggcaggga ggcctgctcc tgtctctctg gcaggagtgc   5460
ctgtacccca ccaagccatg tgaataaaat aatctggaag ta                      5502
```

```
<210> SEQ ID NO 76
<211> LENGTH: 4853
<212> TYPE: DNA
<213> ORGANISM: Human

<400> SEQUENCE: 76
```

```
gctctcgagg tgtctggagg ctcagcgagc gccggaccca ggaggcccaa ggagctggag     60
gtgaccctca ggcagcaaga accccacgga agggcgtgag ccctgcagac agctgtgcgg    120
cacctcgggc tgggctcctg ttaggaggaa gtgcctgcac ccaggcagcg gctcagaggc    180
agctgctcca tgcagaactg aagctggttc tgcagcagaa aggggagagg acacaggagc    240
ctggggtgca ggtgcctccc agcaacgcca tggaggccag gagccggagt gccgaggagc    300
tgaggcgggc ggagttggtg gaaattatcg tggagacgga ggcgcagacc ggggtcagcg    360
gcatcaacgt agcgggcggc ggcaaagagg gaatcttcgt tcgggagctg cgcgaggact    420
cacccgccgc caggagcctc agcctgcagg aaggggacca gctgctgagt gcccgagtgt    480
tcttcgagaa cttcaagtac gaggacgcac tacgcctgct gcaatgcgcc gagccttaca    540
aagtctcctt ctgcctgaag cgcactgtgc ccaccgggga cctggctctg cggcccggga    600
ccgtgtctgg ctacgagatc aagggcccgc gggccaaggt ggccaagctg aacatccaga    660
gtctgtcccc tgtgaagaag aagaagatgg tgcctggggc tctgggggtc cccgctgacc    720
tggcccctgt tgacgtcgag ttctcctttc ccaagttctc ccgcctgcgt cggggcctca    780
aagccgaggc tgtcaagggt cctgtcccgg ctgcccctgc ccgccggcgc ctccagctgc    840
ctcggctgcg tgtacgagaa gtggccgaag aggctcaggc agcccggctg gccgccgccg    900
ctcctccccc caggaaagcc aaggtggagg ctgaggtggc tgcaggagct cgtttcacag    960
cccctcaggt ggagctggtt gggccgcggc tgccaggggc ggaggtgggt gtcccccagg   1020
tctcagcccc caaggctgcc ccctcagcag aggcagctgg tggctttgcc ctccacctgc   1080
caacccttgg gctcggagcc ccggctccgc ctgctgtgga ggccccagcc gtgggaatcc   1140
aggtccccca ggtggagctg cctgccttgc cctcactgcc cactctgccc acacttccct   1200
gcctagagac ccgggaaggg gctgtgtcgg tagtggtgcc caccctggat gtggcagcac   1260
cgactgtggg ggtggacctg gccttgccgg gtgcagaggt ggaggcccgg ggagaggcac   1320
ctgaggtggc cctgaagatg ccccgcctta gttttccccg atttggggct cgagcaaagg   1380
aagttgctga ggccaaggta gccaaggtca gccctgaggc cagggtgaaa ggtcccagac   1440
```

-continued

```
ttcgaatgcc cacctttggg ctttccctct tggagccccg gcccgctgct cctgaagttg   1500
tagagagcaa gctgaagctg cccaccatca agatgccctc ccttggcatc ggagtgtcag   1560
ggcccgaggt caaggtgccc aagggacctg aagtgaagct ccccaaggct cctgaggtca   1620
agcttccaaa agtgcccgag gcagcccttc cagaggttcg actcccagag gtggagctcc   1680
ccaaggtgtc agagatgaaa ctcccaaagg tgccagagat ggctgtgccg gaggtgcggc   1740
ttccagaggt agagctgccc aaagtgtcag agatgaaact cccaaaggtg ccagagatgg   1800
ctgtgccgga ggtgcggctt ccagaggtac agctgctgaa agtgtcggag atgaaactcc   1860
caaaggtgcc agagatggct gtgccggagg tgcggcttcc agaggtacag ctgccgaaag   1920
tgtcagagat gaaactccca gaggtgtcag aggtggctgt gccagaggtg cggcttccag   1980
aggtgcagct gccgaaagtg ccagagatga aagtccctga gatgaagctt ccaaaggtgc   2040
ctgagatgaa acttcctgag atgaaactcc ctgaagtgca actcccgaag gtgcccgaga   2100
tggccgtgcc cgatgtgcac ctcccagaag tgcagcttcc aaaagtccca gagatgaagc   2160
tccctgagat gaaactccct gaggtgaaac tcccgaaggt gcccgagatg gctgtgcccg   2220
atgtgcacct cccggaagtg cagctcccga aagtcccaga gatgaaactc cctaaaatgc   2280
ctgagatggc tgtgccagag gttcgactcc ccgaggtgca gctgccaaaa gtctcagaga   2340
tgaaactccc caaggtgcct gaaatggccg tgcccgatgt gcacctccca gaggtgcagc   2400
tgcccaaagt ctgtgaaatg aaagtccctg acatgaagct cccagagata aaactcccca   2460
aggtgcctga gatggctgtg cccgatgtgc acctccccga ggtgcagctg ccgaaagtgt   2520
cagagattcg gctgccggaa atgcaagtgc cgaaggttcc cgacgtgcat cttccgaagg   2580
caccagaggt gaagctgccc agggctccgg aggtgcagct aaaggccacc aaggcagaac   2640
aggcagaagg gatggaattt ggcttcaaga tgcccaagat gaccatgccc aagctaggga   2700
gggcagagtc ccccatcacgt ggcaagccag gcgaggcggg tgctgaggtc tcagggaagc   2760
tggtaacact tccctgtctg cagccagagg tggatggtga ggctcatgtg ggtgtcccct   2820
ctctcactct gccttcagtg gagctagacc tgccaggagc acttggcctg caggggcagg   2880
tcccagccgc taaaatgggc aagggagagc gggtggaggg ccctgaggtg gcagcagggg   2940
tcagggaagt gggcttccga gtgccctctg ttgaaattgt caccccacag ctgcccgccg   3000
tggaaattga ggaagggcgg ctggagatga tagagacaaa agtcaagccc tcttccaagt   3060
tctccttacc taagtttgga ctctcggggc caaaggtggc taaggcagag gctgaggggg   3120
ctgggcgagc taccaagctg aaggtatcca aatttgccat ctcactcccc aaggctcggg   3180
tgggggctga ggctgaggcc aaaggggctg gggaggcagg cctgctgcct gccctcgatc   3240
tgtccatccc acagctcagc ctggatgccc acctgccctc aggcaaggta gaggtggcag   3300
gggccgacct caagttcaag gggcccaggt ttgctctccc caagtttggg gtcagaggcc   3360
gggacactga ggcagcagaa ctagtgccag ggtggctga gttggaggc aagggctggg   3420
gctgggatgg gagggtgaag atgcccaagc tgaagatgcc ttcctttggg ctggctcgag   3480
ggaaggaagc agaagttcaa ggtgatcgtg ccagcccggg ggaaaaggct gagtccaccg   3540
ctgtgcagct taagatcccc gaggtggagc tggtcacgct gggcgcccag gaggaaggga   3600
gggcagaggg ggctgtggcc gtcagtggaa tgcagctgtc aggcctgaag gtgtccacag   3660
ccaggcaggt ggtcactgag ggccatgacg cggggctgag gatgcctccg ctgggcatct   3720
ccctgccaca ggtggagctg accggctttg gggaggcagg taccccaggg cagcaggctc   3780
agagtacagt cccttcagca gagggcacag caggctacag ggttcaggtg ccccaggtga   3840
```

-continued

```
ccctgtctct gcctggagcc caggttgcag gtggtgagct gctggtgggt gagggtgtct   3900
ttaagatgcc caccgtgaca gtgccccagc ttgagctgga cgtggggcta agccgagagg   3960
cacaggcggg cgaggcggcc acaggcgagg gtgggctgag gctgaagttg cccacactgg   4020
gggccagagc tagggtgggg ggcgagggtg ctgaggagca gcccccaggg gccgagcgta   4080
ccttctgcct ctcactgccc gacgtggagc tctcgccatc cgggggcaac catgccgagt   4140
accaggtggc agagggggag ggagaggccg gacacaagct caaggtacgg ctgccccggt   4200
ttggcctggt gcgggccaag gagggggccg aggagggtga gaaggccaag agccccaaac   4260
tcaggctgcc ccgagtgggc ttcagccaaa gtgagatggt cactggggaa gggtccccca   4320
gccccgagga ggaggaggag gaggaggaag agggcagtgg ggaaggggcc tcgggtcgcc   4380
ggggccgggt ccgggtccgc ttgccacgtg taggcctggc ggccccttct aaagcctctc   4440
gggggcagga gggcgatgca gcccccaagt cccccgtcag agagaagtca cccaagttcc   4500
gcttccccag ggtgtcccta agccccaagg cccggagtgg gagtggggac caggaagagg   4560
gtggattgcg ggtgcggctg cccagcgtgg ggttttcaga gacaggggct ccaggcccgg   4620
ccaggatgga gggggctcag gctgcggctg tctgaagccc ctagtcagat ggggatccct   4680
tcttgccttc ctttctctac cccctcgctg ttgtgtgtgt gataactagc actaacccta   4740
agagggccgg gaggtgggtg actgaccagg gctggcaggg aggcctgctc ctgtctctct   4800
ggcaggagtg cctgtacccc accaagccat gtgaataaaa taatctggaa gta          4853
```

<210> SEQ ID NO 77
<211> LENGTH: 4641
<212> TYPE: DNA
<213> ORGANISM: Rat

<400> SEQUENCE: 77

```
ggaactctgg aggtgtctgg aggcccactg agccccagac ccaggaggcc caagtagctg     60
gaactgaccc tcaggcagca agacctcaaa ggaagagtga aattccggct tacagctgta    120
catcaccccg agtggggctc ctgtcaggag aaaagaccat cacccaggaa gcggctcagc    180
ggcagctgct ccatgaggag ctgaagctgg tcctacagca gaaggaggag aggaaacagg    240
agcctgagcc ccaggtgact ctctgcagag ctatggaggc caggagccgc agcgctgagg    300
agctgagacg agcggagttg gtggagatta tcgtggagac agaggcgcag accggggtca    360
gcggcttcaa tgtagcaggc ggcggcaaag aaggaatctt tgtccgcgag ctgcgagagg    420
actcaccggc cgccaagagc ctcagtttgc aggaagggga ccaacttctg agcgcccgtg    480
tgttctttga gaacttcaaa tatgaggatg cactacgcct gctgcaatgt gccgagccct    540
acaaggtctc cttctgcttg aagcgcactg tgcccaccgg ggacctggca ctgcggcccg    600
ggacggtgtc tggatacgag atgaagggcc cgcgggccaa ggtggccaag ctgaacatcc    660
agagtctgtc ccctgtgaag aagaagaaga tggtgattgg gaccctgggg accccctgcag   720
atttggcccc tgttgacgtc gagttctctt ttcccaagtt ctcccgattg cgtcggggcc    780
ttaaagccga tgctgtcaag ggacctgtcc cagctgcccc tgcccgacga cgtctccagc    840
tgcctcggct acgtgtccga gaagtagctg aagaggccca ggtagcccga atggctgctg    900
ctgctcctcc ctctaggaag gccaagtcag aggctgaggt agccacaggg gctggattca    960
cagcccctca gatagagcta gttgggcctc ggctgcctag cgcagaggtg ggtgtcccta   1020
aggtctcagt tcccaaggga accccatcaa cagaggcagc cagcggcttt gcccttcacc   1080
```

-continued tgccaaccct tgggctagga gccccagctg caccggctgt ggagccccca accacaggaa 1140
tccaggtccc gcaagtggaa ctccccaccc tgccctcttt acccactctg cccacacttc 1200
cgtgcctaga tacccaggaa ggggctgcag tggtcaaagt ccccaccctg gatgtggcag 1260
ctccgtctgt ggaggtggac ctggctttgc caggtgcaga ggtggaggcc cagggagagg 1320
tacctgaagt ggctctcaag atgccccgtc tcagtttccc ccgttttggg gttcgaggga 1380
aggaagctac tgaagccaag gtagtcaagg gcagccctga ggccaaagca aagggtccca 1440
gacttcgaat gcccaccttt gggctttctc tcctggaatc ccggccctct ggccctgaag 1500
ttgctgctga gagcaagctg aagctaccca ccctcaagat gccctctttc ggcatcagcg 1560
tagctgggcc tgaggtcaag gcacccaaag ggcctgaagt gaagctcccc aaagttcctg 1620
agatcaaact cccgaaagcg ccagaggcag ccattccaga tgtgcaactc cccgaggtac 1680
agctgcccaa aatgtcagac atgaaacttc caaagatccc tgagatggct gtacccgatg 1740
ttcaccttcc ggaagtgaag ctgcccaaag tccccgagat gaaagtccca gaaatgaagc 1800
ttccgaagat cccggagatg gccgtgcctg atgtacacct tccagatata cagctcccga 1860
aagttcccga gatgaagctc ccagacatga agctcccgaa ggtgcctgag atggccgtgc 1920
ctgatgtaca ccttccagat atacagctcc cgaaagttcc cgagatgaag ctcccagaca 1980
tgaagctccc gaaggtgcct gagatggccg tgcctgatgt acgaattccg gaagttcagc 2040
tacccaaagt gtccgaggtg aagctcccga agataccgga catggccgtg cctgatgttc 2100
gcctcccaga gctgcaactg cccaaaatgt ctgaggtgaa gctcccgaag ataccggaca 2160
tggccgtacc tgatgttcgc ctcccagaag ttcagctacc caaagtgtca gagctgaagc 2220
tcccgaaggt gcctgagatg accatgcccg acattcgcct cccggaagtt cagctgccca 2280
aagtgcctga cattaaactt ccagaaataa aactccccaa agtgcctgag atggccgtgc 2340
ctgatgtccc ccttccagaa ctacagctgc ccaaagtgcc acaggtccca gacgtgcatc 2400
ttcccaaagt gccagagatg aagttgccca aggttcctga ggcacagagg aaatctgcag 2460
gggcggagca ggcagaaaag accgaattta gcttcaagtt gcccaagatg actgtgccca 2520
agttggggaa agtgaccaag cctggggagg caggtattga ggttccagac aaactcctga 2580
tacttccctg tctgcagcca gaggtgggca ctgaggtggc ccgtgttggt gtcccttccc 2640
tctctctccc ttctgtggag cttgacttgc ctggggccct gggcctggag ggacaagtcc 2700
aagaagctgt ctctggcaaa gtggagaagc cagagggccc cagggtggca gtagggactg 2760
gagaggcggg cttccgcgtg ccctctgtgg agattgtcaa tcctcagctg cccacggttg 2820
aagtcaagaa agagcagcta gagatggtgg agatgaaagt caaacccact tccaagttct 2880
ctctgcccaa atttggactt tcagggccca aagctgtcaa ggcagaggtg gaggggcctg 2940
ggcgagccac caagctgaag gtatccaagt ttgccatctc gcttcccaga gctcgagcag 3000
ggactgacgc ggacgcgaag ggagctgggg aagcggggtt gctgcctgcc ctcgatctgt 3060
ccatcccaca gctcagcctg gatgctcaac tgccctcagg caaggtggag gtagcagggg 3120
ctgagagcaa gcctaaaggg tccagatttg ctctgcccaa gtttggggcg aaaggccggg 3180
actctgaagc cgacgtactg gtggcagggg aggctgagct ggaggggaag ggttggggct 3240
gggacgggaa ggtgaagatg cccaagctga agatgccatc ttttgggctg tcccgaggaa 3300
aagaagcaga aattcaggat gggcgtgtca gcccaggaga aaagctggaa gccatagctg 3360
ggcagcttaa gatccctgag gtggaactgg tcacaccagg agctcaggag acagagaagg 3420
tcaccagtgg agtgaagcca tcaggcctcc aggtgtccac cactaggcag gtggttgcag 3480

-continued

```
agggccagga gggggcgcag agggtgtcct cattaggtat ctctttgccc caggtggaac   3540
tggccagctt tggggaggca ggccctgaga tcgcagcccc atctgcagag ggcacagtag   3600
gctctaggat ccaggtgcca caggtgatgc tggagttgcc gggaacccag gtggcagggg   3660
gtgatctgtt agtgggtgag ggcatcttca agatgcccac agtgacagtg ccccagttag   3720
agctggatgt ggggttgggc catgaagccc aggctggtga aacagccaag agtgagggcg   3780
ggttaaagct gaagttgccc acactggggg caggaggcaa aggagagggt gctgaggccc   3840
agagccccga ggcccagcac accttccaca tctcattgcc tgacgtagaa ctcacatcac   3900
cagtgagtag ccacgctgag taccaggtgg ttgagggcga tggggatggc gggcacaaac   3960
tcaaggtgcg gctgcccctg tttggtctgg caagggccaa ggaaggaata gaaactggag   4020
aaaaggttaa aagtccaaag ctcaggctac cccgagtggg cttcagccaa agtgagtcgg   4080
cctctggaga aggctctccc agtcctgagg aggaggaaga aggcagtggg gaaggggctt   4140
ccggtcgccg tggtcgggtc agggtccgct tgcctcgtgt aggcttggct tccccttcta   4200
aaggctctaa gggacaggag ggtgatgcgg cctccaagtc cccagttggg gagaagtccc   4260
ccaagttccg ctttcctagg gtgtccttaa gccccaaggc ccggagtggg agtaaggacc   4320
gggaagaagg tggattcagg gtccgactgc ccagtgtggg attttcagaa acagcagctc   4380
caggctccgc caggattgag gggacccagg ctgctgccat ctgaagccct gggacagctg   4440
tggattcccc ctcttgtctt cccatcccca tccctgctcc ccattttatg tgtgacatta   4500
ctagcactaa tcctcagagg gcttgaaggt gggcagctga ctcaggcagg agcggtctgt   4560
gccacctcat tggctgacgt gcctgtatat catgccaagc tctgtgaata aaataattca   4620
aaagttaaaa aaaaaaaaaa a                                             4641
```

<210> SEQ ID NO 78
<211> LENGTH: 370
<212> TYPE: PRT
<213> ORGANISM: Arabidopsisthaliana

<400> SEQUENCE: 78

```
Met Ala Leu Met Lys Lys Ser Leu Ser Ala Ala Leu Leu Ser Ser Pro
1               5                   10                  15

Leu Leu Ile Ile Cys Leu Ile Ala Leu Leu Ala Asp Pro Phe Ser Val
            20                  25                  30

Gly Ala Arg Arg Leu Leu Glu Asp Pro Lys Pro Glu Ile Pro Lys Leu
        35                  40                  45

Pro Glu Leu Pro Lys Phe Glu Val Pro Lys Leu Pro Glu Phe Pro Lys
    50                  55                  60

Pro Glu Leu Pro Lys Leu Pro Glu Phe Pro Lys Pro Glu Leu Pro Lys
65                  70                  75                  80

Ile Pro Glu Ile Pro Lys Pro Glu Leu Pro Lys Val Pro Glu Ile Pro
                85                  90                  95

Lys Pro Glu Glu Thr Lys Leu Pro Asp Ile Pro Lys Leu Glu Leu Pro
            100                 105                 110

Lys Phe Pro Glu Ile Pro Lys Pro Glu Leu Pro Lys Met Pro Glu Ile
        115                 120                 125

Pro Lys Pro Glu Leu Pro Lys Val Pro Glu Ile Gln Lys Pro Glu Leu
    130                 135                 140

Pro Lys Met Pro Glu Ile Pro Lys Pro Glu Leu Pro Lys Phe Pro Glu
145                 150                 155                 160
```

-continued

```
Ile Pro Lys Pro Asp Leu Pro Lys Phe Pro Glu Asn Ser Lys Pro Glu
                165                 170                 175

Val Pro Lys Leu Met Glu Thr Glu Lys Pro Glu Ala Pro Lys Val Pro
            180                 185                 190

Glu Ile Pro Lys Pro Glu Leu Pro Lys Leu Pro Glu Val Pro Lys Leu
        195                 200                 205

Glu Ala Pro Lys Val Pro Glu Ile Gln Lys Pro Glu Leu Pro Lys Met
    210                 215                 220

Pro Glu Leu Pro Lys Met Pro Glu Ile Gln Lys Pro Glu Leu Pro Lys
225                 230                 235                 240

Leu Pro Glu Val Pro Lys Leu Glu Ala Pro Lys Val Pro Glu Ile Gln
                245                 250                 255

Lys Pro Glu Leu Pro Lys Met Pro Glu Leu Pro Lys Met Pro Glu Ile
            260                 265                 270

Gln Lys Pro Glu Leu Pro Lys Met Pro Glu Ile Gln Lys Pro Glu Leu
        275                 280                 285

Pro Lys Val Pro Glu Val Pro Lys Pro Glu Leu Pro Thr Val Pro Glu
    290                 295                 300

Val Pro Lys Ser Glu Ala Pro Lys Phe Pro Glu Ile Pro Lys Pro Glu
305                 310                 315                 320

Leu Pro Lys Ile Pro Glu Val Pro Lys Pro Glu Leu Pro Lys Val Pro
                325                 330                 335

Glu Ile Thr Lys Pro Ala Val Pro Glu Ile Pro Lys Pro Glu Leu Pro
            340                 345                 350

Thr Met Pro Gln Leu Pro Lys Leu Pro Glu Phe Pro Lys Val Pro Gly
        355                 360                 365

Thr Pro
    370


<210> SEQ ID NO 79
<211> LENGTH: 1389
<212> TYPE: PRT
<213> ORGANISM: Rat

<400> SEQUENCE: 79

Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Phe
            20                  25                  30

Asn Val Ala Gly Gly Gly Lys Glu Gly Ile Phe Val Arg Glu Leu Arg
        35                  40                  45

Glu Asp Ser Pro Ala Ala Lys Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Met Lys Gly Pro Arg Ala Lys Val Ala Lys Leu Asn
        115                 120                 125

Ile Gln Ser Leu Ser Pro Val Lys Lys Lys Lys Met Val Ile Gly Thr
    130                 135                 140

Leu Gly Thr Pro Ala Asp Leu Ala Pro Val Asp Val Glu Phe Ser Phe
145                 150                 155                 160
```

-continued

```
Pro Lys Phe Ser Arg Leu Arg Arg Gly Leu Lys Ala Asp Ala Val Lys
                165                 170                 175

Gly Pro Val Pro Ala Ala Pro Ala Arg Arg Arg Leu Gln Leu Pro Arg
            180                 185                 190

Leu Arg Val Arg Glu Val Ala Glu Glu Ala Gln Val Ala Arg Met Ala
        195                 200                 205

Ala Ala Ala Pro Pro Ser Arg Lys Ala Lys Ser Glu Ala Glu Val Ala
    210                 215                 220

Thr Gly Ala Gly Phe Thr Ala Pro Gln Ile Glu Leu Val Gly Pro Arg
225                 230                 235                 240

Leu Pro Ser Ala Glu Val Gly Val Pro Lys Val Ser Val Pro Lys Gly
                245                 250                 255

Thr Pro Ser Thr Glu Ala Ala Ser Gly Phe Ala Leu His Leu Pro Thr
            260                 265                 270

Leu Gly Leu Gly Ala Pro Ala Ala Pro Ala Val Glu Pro Pro Thr Thr
        275                 280                 285

Gly Ile Gln Val Pro Gln Val Glu Leu Pro Thr Leu Pro Ser Leu Pro
    290                 295                 300

Thr Leu Pro Thr Leu Pro Cys Leu Asp Thr Gln Glu Gly Ala Ala Val
305                 310                 315                 320

Val Lys Val Pro Thr Leu Asp Val Ala Ala Pro Ser Val Glu Val Asp
                325                 330                 335

Leu Ala Leu Pro Gly Ala Glu Val Glu Ala Gln Gly Glu Val Pro Glu
            340                 345                 350

Val Ala Leu Lys Met Pro Arg Leu Ser Phe Pro Arg Phe Gly Val Arg
        355                 360                 365

Gly Lys Glu Ala Thr Glu Ala Lys Val Val Lys Gly Ser Pro Glu Ala
    370                 375                 380

Lys Ala Lys Gly Pro Arg Leu Arg Met Pro Thr Phe Gly Leu Ser Leu
385                 390                 395                 400

Leu Glu Ser Arg Pro Ser Gly Pro Glu Val Ala Ala Glu Ser Lys Leu
                405                 410                 415

Lys Leu Pro Thr Leu Lys Met Pro Ser Phe Gly Ile Ser Val Ala Gly
            420                 425                 430

Pro Glu Val Lys Ala Pro Lys Gly Pro Glu Val Lys Leu Pro Lys Val
        435                 440                 445

Pro Glu Ile Lys Leu Pro Lys Ala Pro Glu Ala Ala Ile Pro Asp Val
    450                 455                 460

Gln Leu Pro Glu Val Gln Leu Pro Lys Met Ser Asp Met Lys Leu Pro
465                 470                 475                 480

Lys Ile Pro Glu Met Ala Val Pro Asp Val His Leu Pro Glu Val Lys
                485                 490                 495

Leu Pro Lys Val Pro Glu Met Lys Val Pro Glu Met Lys Leu Pro Lys
            500                 505                 510

Ile Pro Glu Met Ala Val Pro Asp Val His Leu Pro Asp Ile Gln Leu
        515                 520                 525

Pro Lys Val Pro Glu Met Lys Leu Pro Asp Met Lys Leu Pro Lys Val
    530                 535                 540

Pro Glu Met Ala Val Pro Asp Val His Leu Pro Asp Ile Gln Leu Pro
545                 550                 555                 560

Lys Val Pro Glu Met Lys Leu Pro Asp Met Lys Leu Pro Lys Val Pro
                565                 570                 575
```

-continued

```
Glu Met Ala Val Pro Asp Val Arg Ile Pro Glu Val Gln Leu Pro Lys
            580                 585                 590

Val Ser Glu Val Lys Leu Pro Lys Ile Pro Asp Met Ala Val Pro Asp
        595                 600                 605

Val Arg Leu Pro Glu Leu Gln Leu Pro Lys Met Ser Glu Val Lys Leu
    610                 615                 620

Pro Lys Ile Pro Asp Met Ala Val Pro Asp Val Arg Leu Pro Glu Val
625                 630                 635                 640

Gln Leu Pro Lys Val Ser Glu Leu Lys Leu Pro Lys Val Pro Glu Met
                645                 650                 655

Thr Met Pro Asp Ile Arg Leu Pro Glu Val Gln Leu Pro Lys Val Pro
            660                 665                 670

Asp Ile Lys Leu Pro Glu Ile Lys Leu Pro Lys Val Pro Glu Met Ala
        675                 680                 685

Val Pro Asp Val Pro Leu Pro Glu Leu Gln Leu Pro Lys Val Pro Gln
    690                 695                 700

Val Pro Asp Val His Leu Pro Lys Val Pro Glu Met Lys Leu Pro Lys
705                 710                 715                 720

Val Pro Glu Ala Gln Arg Lys Ser Ala Gly Ala Glu Gln Ala Glu Lys
                725                 730                 735

Thr Glu Phe Ser Phe Lys Leu Pro Lys Met Thr Val Pro Lys Leu Gly
            740                 745                 750

Lys Val Thr Lys Pro Gly Glu Ala Gly Ile Glu Val Pro Asp Lys Leu
        755                 760                 765

Leu Ile Leu Pro Cys Leu Gln Pro Glu Val Gly Thr Glu Val Ala Arg
    770                 775                 780

Val Gly Val Pro Ser Leu Ser Leu Pro Ser Val Glu Leu Asp Leu Pro
785                 790                 795                 800

Gly Ala Leu Gly Leu Glu Gly Gln Val Gln Glu Ala Val Ser Gly Lys
                805                 810                 815

Val Glu Lys Pro Glu Gly Pro Arg Val Ala Val Gly Thr Gly Glu Ala
            820                 825                 830

Gly Phe Arg Val Pro Ser Val Glu Ile Val Asn Pro Gln Leu Pro Thr
        835                 840                 845

Val Glu Val Lys Lys Glu Gln Leu Glu Met Val Glu Met Lys Val Lys
    850                 855                 860

Pro Thr Ser Lys Phe Ser Leu Pro Lys Phe Gly Leu Ser Gly Pro Lys
865                 870                 875                 880

Ala Val Lys Ala Glu Val Glu Gly Pro Gly Arg Ala Thr Lys Leu Lys
                885                 890                 895

Val Ser Lys Phe Ala Ile Ser Leu Pro Arg Ala Arg Ala Gly Thr Asp
            900                 905                 910

Ala Asp Ala Lys Gly Ala Gly Glu Ala Gly Leu Leu Pro Ala Leu Asp
        915                 920                 925

Leu Ser Ile Pro Gln Leu Ser Leu Asp Ala Gln Leu Pro Ser Gly Lys
    930                 935                 940

Val Glu Val Ala Gly Ala Glu Ser Lys Pro Lys Gly Ser Arg Phe Ala
945                 950                 955                 960

Leu Pro Lys Phe Gly Ala Lys Gly Arg Asp Ser Glu Ala Asp Val Leu
                965                 970                 975

Val Ala Gly Glu Ala Glu Leu Glu Gly Lys Gly Trp Gly Trp Asp Gly
            980                 985                 990

Lys Val Lys Met Pro Lys Leu Lys  Met Pro Ser Phe Gly  Leu Ser Arg
```

-continued

```
995                 1000                1005

Gly Lys  Glu Ala Glu Ile Gln  Asp Gly Arg Val Ser  Pro Gly Glu
    1010                 1015                 1020

Lys Leu  Glu Ala Ile Ala Gly  Gln Leu Lys Ile Pro  Glu Val Glu
    1025                 1030                 1035

Leu Val  Thr Pro Gly Ala Gln  Glu Thr Glu Lys Val  Thr Ser Gly
    1040                 1045                 1050

Val Lys  Pro Ser Gly Leu Gln  Val Ser Thr Thr Arg  Gln Val Val
    1055                 1060                 1065

Ala Glu  Gly Gln Glu Gly Ala  Gln Arg Val Ser Ser  Leu Gly Ile
    1070                 1075                 1080

Ser Leu  Pro Gln Val Glu Leu  Ala Ser Phe Gly Glu  Ala Gly Pro
    1085                 1090                 1095

Glu Ile  Ala Ala Pro Ser Ala  Glu Gly Thr Val Gly  Ser Arg Ile
    1100                 1105                 1110

Gln Val  Pro Gln Val Met Leu  Glu Leu Pro Gly Thr  Gln Val Ala
    1115                 1120                 1125

Gly Gly  Asp Leu Leu Val Gly  Glu Gly Ile Phe Lys  Met Pro Thr
    1130                 1135                 1140

Val Thr  Val Pro Gln Leu Glu  Leu Asp Val Gly Leu  Gly His Glu
    1145                 1150                 1155

Ala Gln  Ala Gly Glu Thr Ala  Lys Ser Glu Gly Gly  Leu Lys Leu
    1160                 1165                 1170

Lys Leu  Pro Thr Leu Gly Ala  Gly Gly Lys Gly Glu  Gly Ala Glu
    1175                 1180                 1185

Ala Gln  Ser Pro Glu Ala Gln  His Thr Phe His Ile  Ser Leu Pro
    1190                 1195                 1200

Asp Val  Glu Leu Thr Ser Pro  Val Ser Ser His Ala  Glu Tyr Gln
    1205                 1210                 1215

Val Val  Glu Gly Asp Gly Asp  Gly Gly His Lys Leu  Lys Val Arg
    1220                 1225                 1230

Leu Pro  Leu Phe Gly Leu Ala  Arg Ala Lys Glu Gly  Ile Glu Thr
    1235                 1240                 1245

Gly Glu  Lys Val Lys Ser Pro  Lys Leu Arg Leu Pro  Arg Val Gly
    1250                 1255                 1260

Phe Ser  Gln Ser Glu Ser Ala  Ser Gly Glu Gly Ser  Pro Ser Pro
    1265                 1270                 1275

Glu Glu  Glu Glu Glu Gly Ser  Gly Glu Gly Ala Ser  Gly Arg Arg
    1280                 1285                 1290

Gly Arg  Val Arg Val Arg Leu  Pro Arg Val Gly Leu  Ala Ser Pro
    1295                 1300                 1305

Ser Lys  Gly Ser Lys Gly Gln  Glu Gly Asp Ala Ala  Ser Lys Ser
    1310                 1315                 1320

Pro Val  Gly Glu Lys Ser Pro  Lys Phe Arg Phe Pro  Arg Val Ser
    1325                 1330                 1335

Leu Ser  Pro Lys Ala Arg Ser  Gly Ser Lys Asp Arg  Glu Glu Gly
    1340                 1345                 1350

Gly Phe  Arg Val Arg Leu Pro  Ser Val Gly Pro Thr  Ala Gln Cys
    1355                 1360                 1365

Gly Ile  Phe Arg Asn Ser Ser  Ser Ser Ser Ala Arg  Ile Glu Gly
    1370                 1375                 1380

Thr Gln  Ala Ala Ala Ile
    1385
```

-continued

<210> SEQ ID NO 80
<211> LENGTH: 148
<212> TYPE: PRT
<213> ORGANISM: Mouse

<400> SEQUENCE: 80

```
Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Phe
            20                  25                  30

Asn Val Ala Gly Gly Gly Lys Glu Gly Ile Phe Val Arg Glu Leu Arg
        35                  40                  45

Glu Asp Ser Pro Ala Ala Lys Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Met Lys Gly Pro Arg Ala Lys Val Ala Lys Leu Val
        115                 120                 125

Arg Val Leu Ser Pro Val Pro Val Gln Asp Ser Pro Ser Asp Arg Val
    130                 135                 140

Ala Ala Ala Pro
145
```

<210> SEQ ID NO 81
<211> LENGTH: 377
<212> TYPE: PRT
<213> ORGANISM: Caenorhabditiselegans

<400> SEQUENCE: 81

```
Met Ser Val Phe Arg Phe Leu Leu Phe Leu Ser Leu Leu Val Gly Ser
1               5                   10                  15

Asn Ala Phe Val Lys Pro Gln Tyr Asn Val Thr Gly Gln Ile Asp Ser
            20                  25                  30

Ala Leu Gln Arg Phe Phe Gly Ile Thr Leu Pro Ser Leu Lys Ile Pro
        35                  40                  45

Asp Leu Leu Asn Pro Asp Lys Lys Arg Asn Pro Pro Ser Val Gly Gln
    50                  55                  60

Leu Lys Lys Thr Ser Phe Pro Leu Cys Asn Val Asn Leu Pro Pro Ile
65                  70                  75                  80

Phe Phe Thr Ile Ser Leu Phe Arg Ile Lys Leu Pro Asn Leu Ile Pro
                85                  90                  95

Thr Ala Leu Pro Val Ile Lys Leu Pro Thr Ile Lys Ile Pro Asn Ile
            100                 105                 110

Leu Pro Thr Leu Pro Thr Ile Lys Val Pro Thr Ile Lys Ile Pro Asp
        115                 120                 125

Ile Ile Pro Ile Thr Leu Pro Thr Ile Lys Ile Pro Glu Val Val Pro
    130                 135                 140

Thr Asn Leu Pro Thr Val Glu Ile Pro His Phe Ile Pro Lys Thr Leu
145                 150                 155                 160

Pro Thr Val Lys Ile Pro Asn Ile Ile Pro Thr Asn Phe Pro Thr Ile
                165                 170                 175
```

-continued

Glu Thr Pro Asp Ile Ile Pro Lys Ile Leu Pro Thr Ile Lys Ile Pro
180 185 190

Glu Ile Ile Pro Leu Thr Leu Pro Thr Val Lys Ile Pro Asp Ile Ile
195 200 205

Pro Ile Thr Leu Pro Thr Ile Lys Ile Pro Glu Ile Val Pro Thr Lys
210 215 220

Leu Pro Thr Val Glu Val Pro Asp Thr Ile Pro Lys Thr Leu Pro Thr
225 230 235 240

Thr Lys Ile Pro Asp Ile Val Pro Ile Thr Ser Pro Thr Val Lys Ile
245 250 255

Pro Gln Ile Ile Pro Thr Ile Lys Ile Pro Asp Ile Ile Pro Lys Asn
260 265 270

Leu Ser Thr Leu Gly Pro Ile Lys Leu Pro Thr Ile Lys Leu Pro Thr
275 280 285

Gly Asn Met Val Cys Asp Ile Cys Glu Lys Val Ile Gly Val Leu Thr
290 295 300

Thr Arg Leu Leu Glu Ile Ile Gln Lys Phe Arg Val Glu Ala Asp Lys
305 310 315 320

Phe Leu Thr Lys Leu Cys Thr Ser Leu Thr Ser Asn Pro Lys Thr Leu
325 330 335

Thr Val Gly Thr Met Cys Val Met Phe Lys Gly Asn Ile Met Asp Thr
340 345 350

Ile Phe Lys Gly Phe Asp Gly Leu Lys Lys Asn Leu Glu Pro Val Ser
355 360 365

Phe Cys Lys His Val Pro Phe Cys Lys
370 375

<210> SEQ ID NO 82
<211> LENGTH: 1383
<212> TYPE: PRT
<213> ORGANISM: Rat

<400> SEQUENCE: 82

Met Glu Ala Arg Ser Arg Ser Ala Glu Glu Leu Arg Arg Ala Glu Leu
1 5 10 15

Val Glu Ile Ile Val Glu Thr Glu Ala Gln Thr Gly Val Ser Gly Phe
20 25 30

Asn Val Ala Gly Gly Gly Lys Glu Gly Ile Phe Val Arg Glu Leu Arg
35 40 45

Glu Asp Ser Pro Ala Ala Lys Ser Leu Ser Leu Gln Glu Gly Asp Gln
50 55 60

Leu Leu Ser Ala Arg Val Phe Phe Glu Asn Phe Lys Tyr Glu Asp Ala
65 70 75 80

Leu Arg Leu Leu Gln Cys Ala Glu Pro Tyr Lys Val Ser Phe Cys Leu
85 90 95

Lys Arg Thr Val Pro Thr Gly Asp Leu Ala Leu Arg Pro Gly Thr Val
100 105 110

Ser Gly Tyr Glu Met Lys Gly Pro Arg Ala Lys Val Ala Lys Leu Asn
115 120 125

Ile Gln Ser Leu Ser Pro Val Lys Lys Lys Lys Met Val Ile Gly Thr
130 135 140

Leu Gly Thr Pro Ala Asp Leu Ala Pro Val Asp Val Glu Phe Ser Phe
145 150 155 160

Pro Lys Phe Ser Arg Leu Arg Arg Gly Leu Lys Ala Asp Ala Val Lys

-continued

```
                165                 170                 175

Gly Pro Val Pro Ala Ala Pro Ala Arg Arg Arg Leu Gln Leu Pro Arg
            180                 185                 190

Leu Arg Val Arg Glu Val Ala Glu Glu Ala Gln Val Ala Arg Met Ala
        195                 200                 205

Ala Ala Ala Pro Pro Ser Arg Lys Ala Lys Ser Glu Ala Glu Val Ala
    210                 215                 220

Thr Gly Ala Gly Phe Thr Ala Pro Gln Ile Glu Leu Val Gly Pro Arg
225                 230                 235                 240

Leu Pro Ser Ala Glu Val Gly Val Pro Lys Val Ser Val Pro Lys Gly
                245                 250                 255

Thr Pro Ser Thr Glu Ala Ala Ser Gly Phe Ala Leu His Leu Pro Thr
            260                 265                 270

Leu Gly Leu Gly Ala Pro Ala Ala Pro Ala Val Glu Pro Pro Thr Thr
        275                 280                 285

Gly Ile Gln Val Pro Gln Val Glu Leu Pro Thr Leu Pro Ser Leu Pro
    290                 295                 300

Thr Leu Pro Thr Leu Pro Cys Leu Asp Thr Gln Glu Gly Ala Ala Val
305                 310                 315                 320

Val Lys Val Pro Thr Leu Asp Val Ala Ala Pro Ser Val Glu Val Asp
                325                 330                 335

Leu Ala Leu Pro Gly Ala Glu Val Glu Ala Gln Gly Glu Val Pro Glu
            340                 345                 350

Val Ala Leu Lys Met Pro Arg Leu Ser Phe Pro Arg Phe Gly Val Arg
        355                 360                 365

Gly Lys Glu Ala Thr Glu Ala Lys Val Val Lys Gly Ser Pro Glu Ala
    370                 375                 380

Lys Ala Lys Gly Pro Arg Leu Arg Met Pro Thr Phe Gly Leu Ser Leu
385                 390                 395                 400

Leu Glu Ser Arg Pro Ser Gly Pro Glu Val Ala Ala Glu Ser Lys Leu
                405                 410                 415

Lys Leu Pro Thr Leu Lys Met Pro Ser Phe Gly Ile Ser Val Ala Gly
            420                 425                 430

Pro Glu Val Lys Ala Pro Lys Gly Pro Glu Val Lys Leu Pro Lys Val
        435                 440                 445

Pro Glu Ile Lys Leu Pro Lys Ala Pro Glu Ala Ala Ile Pro Asp Val
    450                 455                 460

Gln Leu Pro Glu Val Gln Leu Pro Lys Met Ser Asp Met Lys Leu Pro
465                 470                 475                 480

Lys Ile Pro Glu Met Ala Val Pro Asp Val His Leu Pro Glu Val Lys
                485                 490                 495

Leu Pro Lys Val Pro Glu Met Lys Val Pro Glu Met Lys Leu Pro Lys
            500                 505                 510

Ile Pro Glu Met Ala Val Pro Asp Val His Leu Pro Asp Ile Gln Leu
        515                 520                 525

Pro Lys Val Pro Glu Met Lys Leu Pro Asp Met Lys Leu Pro Lys Val
    530                 535                 540

Pro Glu Met Ala Val Pro Asp Val His Leu Pro Asp Ile Gln Leu Pro
545                 550                 555                 560

Lys Val Pro Glu Met Lys Leu Pro Asp Met Lys Leu Pro Lys Val Pro
                565                 570                 575

Glu Met Ala Val Pro Asp Val Arg Ile Pro Glu Val Gln Leu Pro Lys
            580                 585                 590
```

-continued

```
Val Ser Glu Val Lys Leu Pro Lys Ile Pro Asp Met Ala Val Pro Asp
        595                 600                 605

Val Arg Leu Pro Glu Leu Gln Leu Pro Lys Met Ser Glu Val Lys Leu
    610                 615                 620

Pro Lys Ile Pro Asp Met Ala Val Pro Asp Val Arg Leu Pro Glu Val
625                 630                 635                 640

Gln Leu Pro Lys Val Ser Glu Leu Lys Leu Pro Lys Val Pro Glu Met
                645                 650                 655

Thr Met Pro Asp Ile Arg Leu Pro Glu Val Gln Leu Pro Lys Val Pro
            660                 665                 670

Asp Ile Lys Leu Pro Glu Ile Lys Leu Pro Lys Val Pro Glu Met Ala
        675                 680                 685

Val Pro Asp Val Pro Leu Pro Glu Leu Gln Leu Pro Lys Val Pro Gln
    690                 695                 700

Val Pro Asp Val His Leu Pro Lys Val Pro Glu Met Lys Leu Pro Lys
705                 710                 715                 720

Val Pro Glu Ala Gln Arg Lys Ser Ala Gly Ala Glu Gln Ala Glu Lys
                725                 730                 735

Thr Glu Phe Ser Phe Lys Leu Pro Lys Met Thr Val Pro Lys Leu Gly
            740                 745                 750

Lys Val Thr Lys Pro Gly Glu Ala Gly Ile Glu Val Pro Asp Lys Leu
        755                 760                 765

Leu Ile Leu Pro Cys Leu Gln Pro Glu Val Gly Thr Glu Val Ala Arg
    770                 775                 780

Val Gly Val Pro Ser Leu Ser Leu Pro Ser Val Glu Leu Asp Leu Pro
785                 790                 795                 800

Gly Ala Leu Gly Leu Glu Gly Gln Val Gln Glu Ala Val Ser Gly Lys
                805                 810                 815

Val Glu Lys Pro Glu Gly Pro Arg Val Ala Val Gly Thr Gly Glu Ala
            820                 825                 830

Gly Phe Arg Val Pro Ser Val Glu Ile Val Asn Pro Gln Leu Pro Thr
        835                 840                 845

Val Glu Val Lys Lys Glu Gln Leu Glu Met Val Glu Met Lys Val Lys
    850                 855                 860

Pro Thr Ser Lys Phe Ser Leu Pro Lys Phe Gly Leu Ser Gly Pro Lys
865                 870                 875                 880

Ala Val Lys Ala Glu Val Glu Gly Pro Gly Arg Ala Thr Lys Leu Lys
                885                 890                 895

Val Ser Lys Phe Ala Ile Ser Leu Pro Arg Ala Arg Ala Gly Thr Asp
            900                 905                 910

Ala Asp Ala Lys Gly Ala Gly Glu Ala Gly Leu Leu Pro Ala Leu Asp
        915                 920                 925

Leu Ser Ile Pro Gln Leu Ser Leu Asp Ala Gln Leu Pro Ser Gly Lys
    930                 935                 940

Val Glu Val Ala Gly Ala Glu Ser Lys Pro Lys Gly Ser Arg Phe Ala
945                 950                 955                 960

Leu Pro Lys Phe Gly Ala Lys Gly Arg Asp Ser Glu Ala Asp Val Leu
                965                 970                 975

Val Ala Gly Glu Ala Glu Leu Glu Gly Lys Gly Trp Gly Trp Asp Gly
            980                 985                 990

Lys Val Lys Met Pro Lys Leu Lys  Met Pro Ser Phe Gly  Leu Ser Arg
        995                 1000                 1005
```

-continued

```
Gly Lys  Glu Ala Glu Ile Gln  Asp Gly Arg Val Ser  Pro Gly Glu
    1010                 1015                 1020

Lys Leu  Glu Ala Ile Ala Gly  Gln Leu Lys Ile Pro  Glu Val Glu
    1025                 1030                 1035

Leu Val  Thr Pro Gly Ala Gln  Glu Thr Glu Lys Val  Thr Ser Gly
    1040                 1045                 1050

Val Lys  Pro Ser Gly Leu Gln  Val Ser Thr Thr Arg  Gln Val Val
    1055                 1060                 1065

Ala Glu  Gly Gln Glu Gly Ala  Gln Arg Val Ser Ser  Leu Gly Ile
    1070                 1075                 1080

Ser Leu  Pro Gln Val Glu Leu  Ala Ser Phe Gly Glu  Ala Gly Pro
    1085                 1090                 1095

Glu Ile  Ala Ala Pro Ser Ala  Glu Gly Thr Val Gly  Ser Arg Ile
    1100                 1105                 1110

Gln Val  Pro Gln Val Met Leu  Glu Leu Pro Gly Thr  Gln Val Ala
    1115                 1120                 1125

Gly Gly  Asp Leu Leu Val Gly  Glu Gly Ile Phe Lys  Met Pro Thr
    1130                 1135                 1140

Val Thr  Val Pro Gln Leu Glu  Leu Asp Val Gly Leu  Gly His Glu
    1145                 1150                 1155

Ala Gln  Ala Gly Glu Thr Ala  Lys Ser Glu Gly Gly  Leu Lys Leu
    1160                 1165                 1170

Lys Leu  Pro Thr Leu Gly Ala  Gly Gly Lys Gly Glu  Gly Ala Glu
    1175                 1180                 1185

Ala Gln  Ser Pro Glu Ala Gln  His Thr Phe His Ile  Ser Leu Pro
    1190                 1195                 1200

Asp Val  Glu Leu Thr Ser Pro  Val Ser Ser His Ala  Glu Tyr Gln
    1205                 1210                 1215

Val Val  Glu Gly Asp Gly Asp  Gly Gly His Lys Leu  Lys Val Arg
    1220                 1225                 1230

Leu Pro  Leu Phe Gly Leu Ala  Arg Ala Lys Glu Gly  Ile Glu Thr
    1235                 1240                 1245

Gly Glu  Lys Val Lys Ser Pro  Lys Leu Arg Leu Pro  Arg Val Gly
    1250                 1255                 1260

Phe Ser  Gln Ser Glu Ser Ala  Ser Gly Glu Gly Ser  Pro Ser Pro
    1265                 1270                 1275

Glu Glu  Glu Glu Glu Gly Ser  Gly Glu Gly Ala Ser  Gly Arg Arg
    1280                 1285                 1290

Gly Arg  Val Arg Val Arg Leu  Pro Arg Val Gly Leu  Ala Ser Pro
    1295                 1300                 1305

Ser Lys  Gly Ser Lys Gly Gln  Glu Gly Asp Ala Ala  Ser Lys Ser
    1310                 1315                 1320

Pro Val  Gly Glu Lys Ser Pro  Lys Phe Arg Phe Pro  Arg Val Ser
    1325                 1330                 1335

Leu Ser  Pro Lys Ala Arg Ser  Gly Ser Lys Asp Arg  Glu Glu Gly
    1340                 1345                 1350

Gly Phe  Arg Val Arg Leu Pro  Ser Val Gly Phe Ser  Glu Thr Ala
    1355                 1360                 1365

Ala Pro  Gly Ser Ala Arg Ile  Glu Gly Thr Gln Ala  Ala Ala Ile
    1370                 1375                 1380
```

<210> SEQ ID NO 83
<211> LENGTH: 370
<212> TYPE: PRT

-continued

<213> ORGANISM: Arabidopsisthaliana

<400> SEQUENCE: 83

```
Met Ala Leu Met Lys Lys Ser Leu Ser Ala Ala Leu Leu Ser Ser Pro
1               5                   10                  15

Leu Leu Ile Ile Cys Leu Ile Ala Leu Leu Ala Asp Pro Phe Ser Val
            20                  25                  30

Gly Ala Arg Arg Leu Leu Glu Asp Pro Lys Pro Glu Ile Pro Lys Leu
        35                  40                  45

Pro Glu Leu Pro Lys Phe Glu Val Pro Lys Leu Pro Glu Phe Pro Lys
    50                  55                  60

Pro Glu Leu Pro Lys Leu Pro Glu Phe Pro Lys Pro Glu Leu Pro Lys
65                  70                  75                  80

Ile Pro Glu Ile Pro Lys Pro Glu Leu Pro Lys Val Pro Glu Ile Pro
                85                  90                  95

Lys Pro Glu Glu Thr Lys Leu Pro Asp Ile Pro Lys Leu Glu Leu Pro
            100                 105                 110

Lys Phe Pro Glu Ile Pro Lys Pro Glu Leu Pro Lys Met Pro Glu Ile
        115                 120                 125

Pro Lys Pro Glu Leu Pro Lys Val Pro Glu Ile Gln Lys Pro Glu Leu
    130                 135                 140

Pro Lys Met Pro Glu Ile Pro Lys Pro Glu Leu Pro Lys Phe Pro Glu
145                 150                 155                 160

Ile Pro Lys Pro Asp Leu Pro Lys Phe Pro Glu Asn Ser Lys Pro Glu
                165                 170                 175

Val Pro Lys Leu Met Glu Thr Glu Lys Pro Glu Ala Pro Lys Val Pro
            180                 185                 190

Glu Ile Pro Lys Pro Glu Leu Pro Lys Leu Pro Glu Val Pro Lys Leu
        195                 200                 205

Glu Ala Pro Lys Val Pro Glu Ile Gln Lys Pro Glu Leu Pro Lys Met
    210                 215                 220

Pro Glu Leu Pro Lys Met Pro Glu Ile Gln Lys Pro Glu Leu Pro Lys
225                 230                 235                 240

Leu Pro Glu Val Pro Lys Leu Glu Ala Pro Lys Val Pro Glu Ile Gln
                245                 250                 255

Lys Pro Glu Leu Pro Lys Met Pro Glu Leu Pro Lys Met Pro Glu Ile
            260                 265                 270

Gln Lys Pro Glu Leu Pro Lys Met Pro Glu Ile Gln Lys Pro Glu Leu
        275                 280                 285

Pro Lys Val Pro Glu Val Pro Lys Pro Glu Leu Pro Thr Val Pro Glu
    290                 295                 300

Val Pro Lys Ser Glu Ala Pro Lys Phe Pro Glu Ile Pro Lys Pro Glu
305                 310                 315                 320

Leu Pro Lys Ile Pro Glu Val Pro Lys Pro Glu Leu Pro Lys Val Pro
                325                 330                 335

Glu Ile Thr Lys Pro Ala Val Pro Glu Ile Pro Lys Pro Glu Leu Pro
            340                 345                 350

Thr Met Pro Gln Leu Pro Lys Leu Pro Glu Phe Pro Lys Val Pro Gly
        355                 360                 365

Thr Pro
    370
```

<210> SEQ ID NO 84
<211> LENGTH: 148

-continued

<212> TYPE: PRT
<213> ORGANISM: Mouse

<400> SEQUENCE: 84

Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Phe
            20                  25                  30

Asn Val Ala Gly Gly Gly Lys Glu Gly Ile Phe Val Arg Glu Leu Arg
        35                  40                  45

Glu Asp Ser Pro Ala Ala Lys Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Met Lys Gly Pro Arg Ala Lys Val Ala Lys Leu Val
        115                 120                 125

Arg Val Leu Ser Pro Val Pro Val Gln Asp Ser Pro Ser Asp Arg Val
    130                 135                 140

Ala Ala Ala Pro
145

<210> SEQ ID NO 85
<211> LENGTH: 1391
<212> TYPE: PRT
<213> ORGANISM: Mouse

<400> SEQUENCE: 85

Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Phe
            20                  25                  30

Asn Val Ala Gly Gly Gly Lys Glu Gly Ile Phe Val Arg Glu Leu Arg
        35                  40                  45

Glu Asp Ser Pro Ala Ala Lys Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Met Lys Gly Pro Arg Ala Lys Val Ala Lys Leu Asn
        115                 120                 125

Ile Gln Ser Leu Ala Pro Val Lys Lys Lys Lys Met Val Thr Gly Ala
    130                 135                 140

Leu Gly Thr Pro Ala Asp Leu Ala Pro Val Asp Val Glu Phe Ser Phe
145                 150                 155                 160

Pro Lys Phe Ser Arg Leu Arg Arg Gly Leu Lys Ala Glu Ala Val Lys
                165                 170                 175

Gly Pro Val Pro Ala Ala Pro Ala Arg Arg Arg Leu Gln Leu Pro Arg
            180                 185                 190

-continued

```
Leu Arg Val Arg Glu Val Ala Glu Glu Ala Gln Val Ala Arg Met Ala
        195                 200                 205

Ala Ala Ala Pro Pro Pro Arg Lys Ala Lys Ala Glu Ala Glu Ala Ala
    210                 215                 220

Thr Gly Ala Gly Phe Thr Ala Pro Gln Ile Glu Leu Val Gly Pro Arg
225                 230                 235                 240

Leu Pro Ser Ala Glu Val Gly Val Pro Gln Val Ser Val Pro Lys Gly
                245                 250                 255

Thr Pro Ser Thr Glu Ala Ala Ser Gly Phe Ala Leu His Leu Pro Thr
            260                 265                 270

Leu Gly Leu Gly Ala Pro Ala Ala Pro Ala Val Glu Pro Pro Ala Thr
        275                 280                 285

Gly Ile Gln Val Pro Gln Val Glu Leu Pro Thr Leu Pro Ser Leu Pro
    290                 295                 300

Thr Leu Pro Thr Leu Pro Cys Leu Asp Thr Gln Glu Gly Ala Ala Val
305                 310                 315                 320

Val Lys Val Pro Thr Leu Asp Val Ala Ala Pro Ser Met Gly Val Asp
                325                 330                 335

Leu Ala Leu Pro Gly Ala Glu Val Glu Ala Gln Gly Glu Val Pro Glu
            340                 345                 350

Val Ala Leu Lys Met Pro Arg Leu Ser Phe Pro Arg Phe Gly Ile Arg
        355                 360                 365

Gly Lys Glu Ala Thr Glu Ala Lys Val Val Lys Gly Ser Pro Glu Ala
    370                 375                 380

Lys Ala Lys Gly Pro Arg Leu Arg Met Pro Thr Phe Gly Leu Ser Leu
385                 390                 395                 400

Leu Glu Pro Arg Pro Ser Gly Pro Glu Ala Val Ala Glu Ser Lys Leu
                405                 410                 415

Lys Leu Pro Thr Leu Lys Met Pro Ser Phe Gly Ile Gly Val Ala Gly
            420                 425                 430

Pro Glu Val Lys Ala Pro Thr Gly Pro Glu Val Lys Leu Pro Lys Val
        435                 440                 445

Pro Glu Val Lys Leu Pro Lys Val Pro Glu Ala Ala Ile Pro Asp Val
    450                 455                 460

Gln Leu Pro Glu Val Gln Leu Pro Lys Met Ser Asp Met Lys Leu Pro
465                 470                 475                 480

Lys Ile Pro Glu Met Val Val Pro Asp Val Arg Leu Pro Glu Val Gln
                485                 490                 495

Leu Pro Lys Val Pro Glu Met Lys Val Pro Glu Met Lys Leu Pro Lys
            500                 505                 510

Trp Pro Glu Met Ala Val Pro Asp Val His Leu Pro Asp Val Gln Leu
        515                 520                 525

Pro Lys Val Pro Glu Met Lys Leu Pro Lys Val Pro Glu Met Ala Val
    530                 535                 540

Pro Asp Val His Leu Pro Asp Val Gln Leu Pro Lys Val Pro Glu Met
545                 550                 555                 560

Lys Leu Pro Glu Met Lys Leu Pro Lys Val Pro Glu Met Ala Val Pro
                565                 570                 575

Asp Val Arg Leu Pro Glu Val Gln Leu Pro Lys Val Ser Glu Val Lys
            580                 585                 590

Leu Pro Lys Met Pro Glu Met Ala Val Pro Asp Val His Leu Pro Glu
        595                 600                 605

Leu Gln Leu Pro Lys Met Ser Glu Val Lys Leu Pro Lys Met Pro Glu
```

-continued

```
    610                 615                 620

Met Ala Val Pro Asp Val Arg Leu Pro Glu Val Gln Leu Pro Lys Val
625                 630                 635                 640

Ser Glu Met Lys Leu Pro Lys Met Pro Glu Met Thr Met Pro Asp Ile
                645                 650                 655

Arg Leu Pro Glu Val Gln Leu Pro Lys Val Pro Asp Ile Lys Leu Pro
            660                 665                 670

Glu Met Lys Leu Pro Glu Ile Lys Leu Pro Lys Val Pro Asp Met Ala
        675                 680                 685

Val Pro Asp Val Pro Leu Pro Glu Leu Gln Leu Pro Lys Val Ser Asp
    690                 695                 700

Ile Arg Leu Pro Glu Met Gln Val Ser Gln Val Pro Glu Val Gln Leu
705                 710                 715                 720

Pro Lys Met Pro Glu Met Lys Leu Ser Lys Val Pro Glu Val Gln Arg
                725                 730                 735

Lys Ser Ala Gly Ala Glu Gln Ala Lys Gly Thr Glu Phe Ser Phe Lys
            740                 745                 750

Leu Pro Lys Met Thr Met Pro Lys Leu Gly Lys Val Gly Lys Pro Gly
        755                 760                 765

Glu Ala Ser Ile Glu Val Pro Asp Lys Leu Met Thr Leu Pro Cys Leu
    770                 775                 780

Gln Pro Glu Val Gly Thr Glu Ala Ser His Val Gly Val Pro Ser Leu
785                 790                 795                 800

Ser Leu Pro Ser Val Glu Leu Asp Leu Pro Gly Ala Leu Gly Leu Glu
                805                 810                 815

Gly Gln Val Gln Glu Ala Val Pro Gly Lys Val Glu Lys Pro Glu Gly
            820                 825                 830

Pro Arg Val Ala Val Gly Val Gly Glu Val Gly Phe Arg Val Pro Ser
        835                 840                 845

Val Glu Ile Val Thr Pro Gln Leu Pro Thr Val Glu Val Glu Lys Glu
    850                 855                 860

Gln Leu Glu Met Val Glu Met Lys Val Lys Pro Ser Ser Lys Phe Ser
865                 870                 875                 880

Leu Pro Lys Phe Gly Leu Ser Gly Pro Lys Ala Val Lys Gly Glu Val
                885                 890                 895

Glu Gly Pro Gly Arg Ala Thr Lys Leu Lys Val Ser Lys Phe Thr Ile
            900                 905                 910

Ser Leu Pro Lys Ala Arg Ala Gly Thr Glu Ala Glu Ala Lys Gly Ala
        915                 920                 925

Gly Glu Ala Gly Leu Leu Pro Ala Leu Asp Leu Ser Ile Pro Gln Leu
    930                 935                 940

Ser Leu Asp Ala Gln Leu Pro Ser Gly Lys Val Glu Val Ala Asp Ser
945                 950                 955                 960

Lys Pro Lys Ser Ser Arg Phe Ala Leu Pro Lys Phe Gly Val Lys Gly
                965                 970                 975

Arg Asp Ser Glu Ala Asp Val Leu Val Ala Gly Glu Ala Glu Leu Glu
            980                 985                 990

Gly Lys Gly Trp Gly Trp Asp Gly  Lys Val Lys Met Pro  Lys Leu Lys
        995                 1000                1005

Met Pro  Ser Phe Gly Leu Ser  Arg Gly Lys Glu Ala  Glu Thr Gln
    1010                1015                1020

Asp Gly  Arg Val Ser Pro Gly  Glu Lys Leu Glu Ala  Ile Ala Gly
    1025                1030                1035
```

-continued

```
Gln Leu  Lys Ile Pro Ala Val  Glu Leu Val Thr Pro  Gly Ala Gln
    1040                 1045                 1050

Glu Thr  Glu Lys Val Thr Ser  Gly Val Lys Pro Ser  Gly Leu Gln
    1055                 1060                 1065

Val Ser  Thr Thr Gly Gln Val  Val Ala Glu Gly Gln  Glu Ser Val
    1070                 1075                 1080

Gln Arg  Val Ser Thr Leu Gly  Ile Ser Leu Pro Gln  Val Glu Leu
    1085                 1090                 1095

Ala Ser  Phe Gly Glu Ala Gly  Pro Glu Ile Val Ala  Pro Ser Ala
    1100                 1105                 1110

Glu Gly  Thr Ala Gly Ser Arg  Val Gln Val Pro Gln  Val Met Leu
    1115                 1120                 1125

Glu Leu  Pro Gly Thr Gln Val  Ala Gly Gly Asp Leu  Leu Val Gly
    1130                 1135                 1140

Glu Gly  Ile Phe Lys Met Pro  Thr Val Thr Val Pro  Gln Leu Glu
    1145                 1150                 1155

Leu Asp  Val Gly Leu Gly His  Glu Ala Gln Ala Gly  Glu Ala Ala
    1160                 1165                 1170

Lys Ser  Glu Gly Gly Ile Lys  Leu Lys Leu Pro Thr  Leu Gly Thr
    1175                 1180                 1185

Gly Ser  Arg Gly Glu Gly Val  Glu Pro Gln Gly Pro  Glu Ala Gln
    1190                 1195                 1200

Arg Thr  Phe His Leu Ser Leu  Pro Asp Val Glu Leu  Thr Ser Pro
    1205                 1210                 1215

Val Ser  Ser His Ala Glu Tyr  Gln Val Val Glu Gly  Asp Gly Asp
    1220                 1225                 1230

Gly Gly  His Lys Leu Lys Val  Arg Leu Pro Leu Phe  Gly Leu Ala
    1235                 1240                 1245

Lys Ala  Lys Glu Gly Ile Glu  Val Gly Glu Lys Val  Lys Ser Pro
    1250                 1255                 1260

Lys Leu  Arg Leu Pro Arg Val  Gly Phe Ser Gln Ser  Glu Ser Val
    1265                 1270                 1275

Ser Gly  Glu Gly Ser Pro Ser  Pro Glu Glu Glu Glu  Glu Gly Ser
    1280                 1285                 1290

Gly Glu  Gly Ala Ser Ser Arg  Arg Gly Arg Val Arg  Val Arg Leu
    1295                 1300                 1305

Pro Arg  Val Gly Leu Ala Ser  Pro Ser Lys Val Ser  Lys Gly Gln
    1310                 1315                 1320

Glu Gly  Asp Ala Thr Ser Lys  Ser Pro Val Gly Glu  Lys Ser Pro
    1325                 1330                 1335

Lys Phe  Arg Phe Pro Arg Val  Ser Leu Ser Pro Lys  Ala Arg Ser
    1340                 1345                 1350

Gly Ser  Arg Asp Arg Glu Glu  Gly Gly Phe Arg Val  Arg Leu Pro
    1355                 1360                 1365

Ser Val  Gly Phe Ser Glu Thr  Ala Val Pro Gly Ser  Thr Arg Ile
    1370                 1375                 1380

Glu Gly  Thr Gln Ala Ala Ala  Ile
    1385                 1390
```

<210> SEQ ID NO 86
<211> LENGTH: 1383
<212> TYPE: PRT
<213> ORGANISM: Rat

-continued

<400> SEQUENCE: 86

```
Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Phe
            20                  25                  30

Asn Val Ala Gly Gly Gly Lys Glu Gly Ile Phe Val Arg Glu Leu Arg
        35                  40                  45

Glu Asp Ser Pro Ala Ala Lys Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Met Lys Gly Pro Arg Ala Lys Val Ala Lys Leu Asn
        115                 120                 125

Ile Gln Ser Leu Ser Pro Val Lys Lys Lys Lys Met Val Ile Gly Thr
    130                 135                 140

Leu Gly Thr Pro Ala Asp Leu Ala Pro Val Asp Val Glu Phe Ser Phe
145                 150                 155                 160

Pro Lys Phe Ser Arg Leu Arg Arg Gly Leu Lys Ala Asp Ala Val Lys
                165                 170                 175

Gly Pro Val Pro Ala Ala Pro Ala Arg Arg Arg Leu Gln Leu Pro Arg
            180                 185                 190

Leu Arg Val Arg Glu Val Ala Glu Glu Ala Gln Val Ala Arg Met Ala
        195                 200                 205

Ala Ala Ala Pro Pro Ser Arg Lys Ala Lys Ser Glu Ala Glu Val Ala
    210                 215                 220

Thr Gly Ala Gly Phe Thr Ala Pro Gln Ile Glu Leu Val Gly Pro Arg
225                 230                 235                 240

Leu Pro Ser Ala Glu Val Gly Val Pro Lys Val Ser Val Pro Lys Gly
                245                 250                 255

Thr Pro Ser Thr Glu Ala Ala Ser Gly Phe Ala Leu His Leu Pro Thr
            260                 265                 270

Leu Gly Leu Gly Ala Pro Ala Ala Pro Ala Val Glu Pro Pro Thr Thr
        275                 280                 285

Gly Ile Gln Val Pro Gln Val Glu Leu Pro Thr Leu Pro Ser Leu Pro
    290                 295                 300

Thr Leu Pro Thr Leu Pro Cys Leu Asp Thr Gln Glu Gly Ala Ala Val
305                 310                 315                 320

Val Lys Val Pro Thr Leu Asp Val Ala Ala Pro Ser Val Glu Val Asp
                325                 330                 335

Leu Ala Leu Pro Gly Ala Glu Val Glu Ala Gln Gly Glu Val Pro Glu
            340                 345                 350

Val Ala Leu Lys Met Pro Arg Leu Ser Phe Pro Arg Phe Gly Val Arg
        355                 360                 365

Gly Lys Glu Ala Thr Glu Ala Lys Val Val Lys Gly Ser Pro Glu Ala
    370                 375                 380

Lys Ala Lys Gly Pro Arg Leu Arg Met Pro Thr Phe Gly Leu Ser Leu
385                 390                 395                 400

Leu Glu Ser Arg Pro Ser Gly Pro Glu Val Ala Ala Glu Ser Lys Leu
                405                 410                 415
```

-continued

```
Lys Leu Pro Thr Leu Lys Met Pro Ser Phe Gly Ile Ser Val Ala Gly
            420                 425                 430

Pro Glu Val Lys Ala Pro Lys Gly Pro Glu Val Lys Leu Pro Lys Val
        435                 440                 445

Pro Glu Ile Lys Leu Pro Lys Ala Pro Glu Ala Ala Ile Pro Asp Val
    450                 455                 460

Gln Leu Pro Glu Val Gln Leu Pro Lys Met Ser Asp Met Lys Leu Pro
465                 470                 475                 480

Lys Ile Pro Glu Met Ala Val Pro Asp Val His Leu Pro Glu Val Lys
            485                 490                 495

Leu Pro Lys Val Pro Glu Met Lys Val Pro Glu Met Lys Leu Pro Lys
            500                 505                 510

Ile Pro Glu Met Ala Val Pro Asp Val His Leu Pro Asp Ile Gln Leu
        515                 520                 525

Pro Lys Val Pro Glu Met Lys Leu Pro Asp Met Lys Leu Pro Lys Val
    530                 535                 540

Pro Glu Met Ala Val Pro Asp Val His Leu Pro Asp Ile Gln Leu Pro
545                 550                 555                 560

Lys Val Pro Glu Met Lys Leu Pro Asp Met Lys Leu Pro Lys Val Pro
            565                 570                 575

Glu Met Ala Val Pro Asp Val Arg Ile Pro Glu Val Gln Leu Pro Lys
            580                 585                 590

Val Ser Glu Val Lys Leu Pro Lys Ile Pro Asp Met Ala Val Pro Asp
        595                 600                 605

Val Arg Leu Pro Glu Leu Gln Leu Pro Lys Met Ser Glu Val Lys Leu
    610                 615                 620

Pro Lys Ile Pro Asp Met Ala Val Pro Asp Val Arg Leu Pro Glu Val
625                 630                 635                 640

Gln Leu Pro Lys Val Ser Glu Leu Lys Leu Pro Lys Val Pro Glu Met
            645                 650                 655

Thr Met Pro Asp Ile Arg Leu Pro Glu Val Gln Leu Pro Lys Val Pro
            660                 665                 670

Asp Ile Lys Leu Pro Glu Ile Lys Leu Pro Lys Val Pro Glu Met Ala
        675                 680                 685

Val Pro Asp Val Pro Leu Pro Glu Leu Gln Leu Pro Lys Val Pro Gln
    690                 695                 700

Val Pro Asp Val His Leu Pro Lys Val Pro Glu Met Lys Leu Pro Lys
705                 710                 715                 720

Val Pro Glu Ala Gln Arg Lys Ser Ala Gly Ala Glu Gln Ala Glu Lys
            725                 730                 735

Thr Glu Phe Ser Phe Lys Leu Pro Lys Met Thr Val Pro Lys Leu Gly
            740                 745                 750

Lys Val Thr Lys Pro Gly Glu Ala Gly Ile Glu Val Pro Asp Lys Leu
        755                 760                 765

Leu Ile Leu Pro Cys Leu Gln Pro Glu Val Gly Thr Glu Val Ala Arg
    770                 775                 780

Val Gly Val Pro Ser Leu Ser Leu Pro Ser Val Glu Leu Asp Leu Pro
785                 790                 795                 800

Gly Ala Leu Gly Leu Glu Gly Gln Val Gln Glu Ala Val Ser Gly Lys
            805                 810                 815

Val Glu Lys Pro Glu Gly Pro Arg Val Ala Val Gly Thr Gly Glu Ala
            820                 825                 830
```

-continued

```
Gly Phe Arg Val Pro Ser Val Glu Ile Val Asn Pro Gln Leu Pro Thr
        835                 840                 845

Val Glu Val Lys Lys Glu Gln Leu Glu Met Val Glu Met Lys Val Lys
    850                 855                 860

Pro Thr Ser Lys Phe Ser Leu Pro Lys Phe Gly Leu Ser Gly Pro Lys
865                 870                 875                 880

Ala Val Lys Ala Glu Val Glu Gly Pro Gly Arg Ala Thr Lys Leu Lys
                885                 890                 895

Val Ser Lys Phe Ala Ile Ser Leu Pro Arg Ala Arg Ala Gly Thr Asp
            900                 905                 910

Ala Asp Ala Lys Gly Ala Gly Glu Ala Gly Leu Leu Pro Ala Leu Asp
        915                 920                 925

Leu Ser Ile Pro Gln Leu Ser Leu Asp Ala Gln Leu Pro Ser Gly Lys
    930                 935                 940

Val Glu Val Ala Gly Ala Glu Ser Lys Pro Lys Gly Ser Arg Phe Ala
945                 950                 955                 960

Leu Pro Lys Phe Gly Ala Lys Gly Arg Asp Ser Glu Ala Asp Val Leu
                965                 970                 975

Val Ala Gly Glu Ala Glu Leu Glu Gly Lys Gly Trp Gly Trp Asp Gly
            980                 985                 990

Lys Val Lys Met Pro Lys Leu Lys  Met Pro Ser Phe Gly  Leu Ser Arg
        995                 1000                1005

Gly Lys  Glu Ala Glu Ile Gln  Asp Gly Arg Val Ser  Pro Gly Glu
    1010                 1015                 1020

Lys Leu  Glu Ala Ile Ala Gly  Gln Leu Lys Ile Pro  Glu Val Glu
    1025                 1030                 1035

Leu Val  Thr Pro Gly Ala Gln  Glu Thr Glu Lys Val  Thr Ser Gly
    1040                 1045                 1050

Val Lys  Pro Ser Gly Leu Gln  Val Ser Thr Thr Arg  Gln Val Val
    1055                 1060                 1065

Ala Glu  Gly Gln Glu Gly Ala  Gln Arg Val Ser Ser  Leu Gly Ile
    1070                 1075                 1080

Ser Leu  Pro Gln Val Glu Leu  Ala Ser Phe Gly Glu  Ala Gly Pro
    1085                 1090                 1095

Glu Ile  Ala Ala Pro Ser Ala  Glu Gly Thr Val Gly  Ser Arg Ile
    1100                 1105                 1110

Gln Val  Pro Gln Val Met Leu  Glu Leu Pro Gly Thr  Gln Val Ala
    1115                 1120                 1125

Gly Gly  Asp Leu Leu Val Gly  Glu Gly Ile Phe Lys  Met Pro Thr
    1130                 1135                 1140

Val Thr  Val Pro Gln Leu Glu  Leu Asp Val Gly Leu  Gly His Glu
    1145                 1150                 1155

Ala Gln  Ala Gly Glu Thr Ala  Lys Ser Glu Gly Gly  Leu Lys Leu
    1160                 1165                 1170

Lys Leu  Pro Thr Leu Gly Ala  Gly Gly Lys Gly Glu  Gly Ala Glu
    1175                 1180                 1185

Ala Gln  Ser Pro Glu Ala Gln  His Thr Phe His Ile  Ser Leu Pro
    1190                 1195                 1200

Asp Val  Glu Leu Thr Ser Pro  Val Ser Ser His Ala  Glu Tyr Gln
    1205                 1210                 1215

Val Val  Glu Gly Asp Gly Asp  Gly Gly His Lys Leu  Lys Val Arg
    1220                 1225                 1230

Leu Pro  Leu Phe Gly Leu Ala  Arg Ala Lys Glu Gly  Ile Glu Thr
```

-continued

```
    1235                1240                1245

Gly Glu  Lys Val Lys Ser Pro  Lys Leu Arg Leu Pro  Arg Val Gly
    1250                1255                1260

Phe Ser  Gln Ser Glu Ser Ala  Ser Gly Glu Gly Ser  Pro Ser Pro
    1265                1270                1275

Glu Glu  Glu Glu Glu Gly Ser  Gly Glu Gly Ala Ser  Gly Arg Arg
    1280                1285                1290

Gly Arg  Val Arg Val Arg Leu  Pro Arg Val Gly Leu  Ala Ser Pro
    1295                1300                1305

Ser Lys  Gly Ser Lys Gly Gln  Glu Gly Asp Ala Ala  Ser Lys Ser
    1310                1315                1320

Pro Val  Gly Glu Lys Ser Pro  Lys Phe Arg Phe Pro  Arg Val Ser
    1325                1330                1335

Leu Ser  Pro Lys Ala Arg Ser  Gly Ser Lys Asp Arg  Glu Glu Gly
    1340                1345                1350

Gly Phe  Arg Val Arg Leu Pro  Ser Val Gly Phe Ser  Glu Thr Ala
    1355                1360                1365

Ala Pro  Gly Ser Ala Arg Ile  Glu Gly Thr Gln Ala  Ala Ala Ile
    1370                1375                1380


<210> SEQ ID NO 87
<211> LENGTH: 1383
<212> TYPE: PRT
<213> ORGANISM: Rat

<400> SEQUENCE: 87

Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Phe
            20                  25                  30

Asn Val Ala Gly Gly Gly Lys Glu Gly Ile Phe Val Arg Glu Leu Arg
        35                  40                  45

Glu Asp Ser Pro Ala Ala Lys Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Met Lys Gly Pro Arg Ala Lys Val Ala Lys Leu Asn
        115                 120                 125

Ile Gln Ser Leu Ser Pro Val Lys Lys Lys Lys Met Val Ile Gly Thr
    130                 135                 140

Leu Gly Thr Pro Ala Asp Leu Ala Pro Val Asp Val Glu Phe Ser Phe
145                 150                 155                 160

Pro Lys Phe Ser Arg Leu Arg Arg Gly Leu Lys Ala Asp Ala Val Lys
                165                 170                 175

Gly Pro Val Pro Ala Ala Pro Ala Arg Arg Arg Leu Gln Leu Pro Arg
            180                 185                 190

Leu Arg Val Arg Glu Val Ala Glu Glu Ala Gln Val Ala Arg Met Ala
        195                 200                 205

Ala Ala Ala Pro Pro Ser Arg Lys Ala Lys Ser Glu Ala Glu Val Ala
    210                 215                 220
```

-continued

```
Thr Gly Ala Gly Phe Thr Ala Pro Gln Ile Glu Leu Val Gly Pro Arg
225                 230                 235                 240

Leu Pro Ser Ala Glu Val Gly Val Pro Lys Val Ser Val Pro Lys Gly
                245                 250                 255

Thr Pro Ser Thr Glu Ala Ala Ser Gly Phe Ala Leu His Leu Pro Thr
            260                 265                 270

Leu Gly Leu Gly Ala Pro Ala Ala Pro Ala Val Glu Pro Pro Thr Thr
        275                 280                 285

Gly Ile Gln Val Pro Gln Val Glu Leu Pro Thr Leu Pro Ser Leu Pro
    290                 295                 300

Thr Leu Pro Thr Leu Pro Cys Leu Asp Thr Gln Glu Gly Ala Ala Val
305                 310                 315                 320

Val Lys Val Pro Thr Leu Asp Val Ala Ala Pro Ser Val Glu Val Asp
                325                 330                 335

Leu Ala Leu Pro Gly Ala Glu Val Glu Ala Gln Gly Glu Val Pro Glu
            340                 345                 350

Val Ala Leu Lys Met Pro Arg Leu Ser Phe Pro Arg Phe Gly Val Arg
        355                 360                 365

Gly Lys Glu Ala Thr Glu Ala Lys Val Val Lys Gly Ser Pro Glu Ala
    370                 375                 380

Lys Ala Lys Gly Pro Arg Leu Arg Met Pro Thr Phe Gly Leu Ser Leu
385                 390                 395                 400

Leu Glu Ser Arg Pro Ser Gly Pro Glu Val Ala Ala Glu Ser Lys Leu
                405                 410                 415

Lys Leu Pro Thr Leu Lys Met Pro Ser Phe Gly Ile Ser Val Ala Gly
            420                 425                 430

Pro Glu Val Lys Ala Pro Lys Gly Pro Glu Val Lys Leu Pro Lys Val
        435                 440                 445

Pro Glu Ile Lys Leu Pro Lys Ala Pro Glu Ala Ala Ile Pro Asp Val
    450                 455                 460

Gln Leu Pro Glu Val Gln Leu Pro Lys Met Ser Asp Met Lys Leu Pro
465                 470                 475                 480

Lys Ile Pro Glu Met Ala Val Pro Asp Val His Leu Pro Glu Val Lys
                485                 490                 495

Leu Pro Lys Val Pro Glu Met Lys Val Pro Glu Met Lys Leu Pro Lys
            500                 505                 510

Ile Pro Glu Met Ala Val Pro Asp Val His Leu Pro Asp Ile Gln Leu
        515                 520                 525

Pro Lys Val Pro Glu Met Lys Leu Pro Asp Met Lys Leu Pro Lys Val
    530                 535                 540

Pro Glu Met Ala Val Pro Asp Val His Leu Pro Asp Ile Gln Leu Pro
545                 550                 555                 560

Lys Val Pro Glu Met Lys Leu Pro Asp Met Lys Leu Pro Lys Val Pro
                565                 570                 575

Glu Met Ala Val Pro Asp Val Arg Ile Pro Glu Val Gln Leu Pro Lys
            580                 585                 590

Val Ser Glu Val Lys Leu Pro Lys Ile Pro Asp Met Ala Val Pro Asp
        595                 600                 605

Val Arg Leu Pro Glu Leu Gln Leu Pro Lys Met Ser Glu Val Lys Leu
    610                 615                 620

Pro Lys Ile Pro Asp Met Ala Val Pro Asp Val Arg Leu Pro Glu Val
625                 630                 635                 640

Gln Leu Pro Lys Val Ser Glu Leu Lys Leu Pro Lys Val Pro Glu Met
```

-continued

```
                645                 650                 655

Thr Met Pro Asp Ile Arg Leu Pro Glu Val Gln Leu Pro Lys Val Pro
            660                 665                 670

Asp Ile Lys Leu Pro Glu Ile Lys Leu Pro Lys Val Pro Glu Met Ala
        675                 680                 685

Val Pro Asp Val Pro Leu Pro Glu Leu Gln Leu Pro Lys Val Pro Gln
    690                 695                 700

Val Pro Asp Val His Leu Pro Lys Val Pro Glu Met Lys Leu Pro Lys
705                 710                 715                 720

Val Pro Glu Ala Gln Arg Lys Ser Ala Gly Ala Glu Gln Ala Glu Lys
                725                 730                 735

Thr Glu Phe Ser Phe Lys Leu Pro Lys Met Thr Val Pro Lys Leu Gly
            740                 745                 750

Lys Val Thr Lys Pro Gly Glu Ala Gly Ile Glu Val Pro Asp Lys Leu
        755                 760                 765

Leu Ile Leu Pro Cys Leu Gln Pro Glu Val Gly Thr Glu Val Ala Arg
    770                 775                 780

Val Gly Val Pro Ser Leu Ser Leu Pro Ser Val Glu Leu Asp Leu Pro
785                 790                 795                 800

Gly Ala Leu Gly Leu Glu Gly Gln Val Gln Glu Ala Val Ser Gly Lys
                805                 810                 815

Val Glu Lys Pro Glu Gly Pro Arg Val Ala Val Gly Thr Gly Glu Ala
            820                 825                 830

Gly Phe Arg Val Pro Ser Val Glu Ile Val Asn Pro Gln Leu Pro Thr
        835                 840                 845

Val Glu Val Lys Lys Glu Gln Leu Glu Met Val Glu Met Lys Val Lys
    850                 855                 860

Pro Thr Ser Lys Phe Ser Leu Pro Lys Phe Gly Leu Ser Gly Pro Lys
865                 870                 875                 880

Ala Val Lys Ala Glu Val Glu Gly Pro Gly Arg Ala Thr Lys Leu Lys
                885                 890                 895

Val Ser Lys Phe Ala Ile Ser Leu Pro Arg Ala Arg Ala Gly Thr Asp
            900                 905                 910

Ala Asp Ala Lys Gly Ala Gly Glu Ala Gly Leu Leu Pro Ala Leu Asp
        915                 920                 925

Leu Ser Ile Pro Gln Leu Ser Leu Asp Ala Gln Leu Pro Ser Gly Lys
    930                 935                 940

Val Glu Val Ala Gly Ala Glu Ser Lys Pro Lys Gly Ser Arg Phe Ala
945                 950                 955                 960

Leu Pro Lys Phe Gly Ala Lys Gly Arg Asp Ser Glu Ala Asp Val Leu
                965                 970                 975

Val Ala Gly Glu Ala Glu Leu Glu Gly Lys Gly Trp Gly Trp Asp Gly
            980                 985                 990

Lys Val Lys Met Pro Lys Leu Lys  Met Pro Ser Phe Gly  Leu Ser Arg
        995                 1000                1005

Gly Lys  Glu Ala Glu Ile Gln  Asp Gly Arg Val Ser  Pro Gly Glu
    1010                1015                1020

Lys Leu  Glu Ala Ile Ala Gly  Gln Leu Lys Ile Pro  Glu Val Glu
    1025                1030                1035

Leu Val  Thr Pro Gly Ala Gln  Glu Thr Glu Lys Val  Thr Ser Gly
    1040                1045                1050

Val Lys  Pro Ser Gly Leu Gln  Val Ser Thr Thr Arg  Gln Val Val
    1055                1060                1065
```

-continued

```
Ala Glu  Gly Gln Glu Gly Ala  Gln Arg Val Ser Ser  Leu Gly Ile
    1070                 1075                 1080

Ser Leu  Pro Gln Val Glu Leu  Ala Ser Phe Gly Glu  Ala Gly Pro
    1085                 1090                 1095

Glu Ile  Ala Ala Pro Ser Ala  Glu Gly Thr Val Gly  Ser Arg Ile
    1100                 1105                 1110

Gln Val  Pro Gln Val Met Leu  Glu Leu Pro Gly Thr  Gln Val Ala
    1115                 1120                 1125

Gly Gly  Asp Leu Leu Val Gly  Glu Gly Ile Phe Lys  Met Pro Thr
    1130                 1135                 1140

Val Thr  Val Pro Gln Leu Glu  Leu Asp Val Gly Leu  Gly His Glu
    1145                 1150                 1155

Ala Gln  Ala Gly Glu Thr Ala  Lys Ser Glu Gly Gly  Leu Lys Leu
    1160                 1165                 1170

Lys Leu  Pro Thr Leu Gly Ala  Gly Gly Lys Gly Glu  Gly Ala Glu
    1175                 1180                 1185

Ala Gln  Ser Pro Glu Ala Gln  His Thr Phe His Ile  Ser Leu Pro
    1190                 1195                 1200

Asp Val  Glu Leu Thr Ser Pro  Val Ser Ser His Ala  Glu Tyr Gln
    1205                 1210                 1215

Val Val  Glu Gly Asp Gly Asp  Gly Gly His Lys Leu  Lys Val Arg
    1220                 1225                 1230

Leu Pro  Leu Phe Gly Leu Ala  Arg Ala Lys Glu Gly  Ile Glu Thr
    1235                 1240                 1245

Gly Glu  Lys Val Lys Ser Pro  Lys Leu Arg Leu Pro  Arg Val Gly
    1250                 1255                 1260

Phe Ser  Gln Ser Glu Ser Ala  Ser Gly Glu Gly Ser  Pro Ser Pro
    1265                 1270                 1275

Glu Glu  Glu Glu Glu Gly Ser  Gly Glu Gly Ala Ser  Gly Arg Arg
    1280                 1285                 1290

Gly Arg  Val Arg Val Arg Leu  Pro Arg Val Gly Leu  Ala Ser Pro
    1295                 1300                 1305

Ser Lys  Gly Ser Lys Gly Gln  Glu Gly Asp Ala Ala  Ser Lys Ser
    1310                 1315                 1320

Pro Val  Gly Glu Lys Ser Pro  Lys Phe Arg Phe Pro  Arg Val Ser
    1325                 1330                 1335

Leu Ser  Pro Lys Ala Arg Ser  Gly Ser Lys Asp Arg  Glu Glu Gly
    1340                 1345                 1350

Gly Phe  Arg Val Arg Leu Pro  Ser Val Gly Phe Ser  Glu Thr Ala
    1355                 1360                 1365

Ala Pro  Gly Ser Ala Arg Ile  Glu Gly Thr Gln Ala  Ala Ala Ile
    1370                 1375                 1380

<210> SEQ ID NO 88
<211> LENGTH: 1461
<212> TYPE: PRT
<213> ORGANISM: Human

<400> SEQUENCE: 88

Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Ile
            20                  25                  30

Asn Val Ala Gly Gly Gly Lys Glu Gly Ile Phe Val Arg Glu Leu Arg
```

-continued

```
        35                  40                  45

Glu Asp Ser Pro Ala Ala Arg Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Ile Lys Gly Pro Arg Ala Lys Val Ala Lys Leu Asn
        115                 120                 125

Ile Gln Ser Leu Ser Pro Val Lys Lys Lys Lys Met Val Pro Gly Ala
    130                 135                 140

Leu Gly Val Pro Ala Asp Leu Ala Pro Val Asp Val Glu Phe Ser Phe
145                 150                 155                 160

Pro Lys Phe Ser Arg Leu Arg Arg Gly Leu Lys Ala Glu Ala Val Lys
                165                 170                 175

Gly Pro Val Pro Ala Ala Pro Ala Arg Arg Arg Leu Gln Leu Pro Arg
            180                 185                 190

Leu Arg Val Arg Glu Val Ala Glu Glu Ala Gln Ala Ala Arg Leu Ala
        195                 200                 205

Ala Ala Ala Pro Pro Pro Arg Lys Ala Lys Val Glu Ala Glu Val Ala
    210                 215                 220

Ala Gly Ala Arg Phe Thr Ala Pro Gln Val Glu Leu Val Gly Pro Arg
225                 230                 235                 240

Leu Pro Gly Ala Glu Val Gly Val Pro Gln Val Ser Ala Pro Lys Ala
                245                 250                 255

Ala Pro Ser Ala Glu Ala Ala Gly Gly Phe Ala Leu His Leu Pro Thr
            260                 265                 270

Leu Gly Leu Gly Ala Pro Ala Pro Pro Ala Val Glu Ala Pro Ala Val
        275                 280                 285

Gly Ile Gln Val Pro Gln Val Glu Leu Pro Ala Leu Pro Ser Leu Pro
    290                 295                 300

Thr Leu Pro Thr Leu Pro Cys Leu Glu Thr Arg Glu Gly Ala Val Ser
305                 310                 315                 320

Val Val Val Pro Thr Leu Asp Val Ala Ala Pro Thr Val Gly Val Asp
                325                 330                 335

Leu Ala Leu Pro Gly Ala Glu Val Glu Ala Arg Gly Glu Ala Pro Glu
            340                 345                 350

Val Ala Leu Lys Met Pro Arg Leu Ser Phe Pro Arg Phe Gly Ala Arg
        355                 360                 365

Ala Lys Glu Val Ala Glu Ala Lys Val Ala Lys Val Ser Pro Glu Ala
    370                 375                 380

Arg Val Lys Gly Pro Arg Leu Arg Met Pro Thr Phe Gly Leu Ser Leu
385                 390                 395                 400

Leu Glu Pro Arg Pro Ala Ala Pro Glu Val Val Glu Ser Lys Leu Lys
                405                 410                 415

Leu Pro Thr Ile Lys Met Pro Ser Leu Gly Ile Gly Val Ser Gly Pro
            420                 425                 430

Glu Val Lys Val Pro Lys Gly Pro Glu Val Lys Leu Pro Lys Ala Pro
        435                 440                 445

Glu Val Lys Leu Pro Lys Val Pro Glu Ala Ala Leu Pro Glu Val Arg
    450                 455                 460
```

-continued

Leu Pro Glu Val Glu Leu Pro Lys Val Ser Glu Met Lys Leu Pro Lys
465 470 475 480

Val Pro Glu Met Ala Val Pro Glu Val Arg Leu Pro Glu Val Glu Leu
485 490 495

Pro Lys Val Ser Glu Met Lys Leu Pro Lys Val Pro Glu Met Ala Val
500 505 510

Pro Glu Val Arg Leu Pro Glu Val Gln Leu Leu Lys Val Ser Glu Met
515 520 525

Lys Leu Pro Lys Val Pro Glu Met Ala Val Pro Glu Val Arg Leu Pro
530 535 540

Glu Val Gln Leu Pro Lys Val Ser Glu Met Lys Leu Pro Glu Val Ser
545 550 555 560

Glu Val Ala Val Pro Glu Val Arg Leu Pro Glu Val Gln Leu Pro Lys
565 570 575

Val Pro Glu Met Lys Val Pro Glu Met Lys Leu Pro Lys Val Pro Glu
580 585 590

Met Lys Leu Pro Glu Met Lys Leu Pro Glu Val Gln Leu Pro Lys Val
595 600 605

Pro Glu Met Ala Val Pro Asp Val His Leu Pro Glu Val Gln Leu Pro
610 615 620

Lys Val Pro Glu Met Lys Leu Pro Glu Met Lys Leu Pro Glu Val Lys
625 630 635 640

Leu Pro Lys Val Pro Glu Met Ala Val Pro Asp Val His Leu Pro Glu
645 650 655

Val Gln Leu Pro Lys Val Pro Glu Met Lys Leu Pro Lys Met Pro Glu
660 665 670

Met Ala Val Pro Glu Val Arg Leu Pro Glu Val Gln Leu Pro Lys Val
675 680 685

Ser Glu Met Lys Leu Pro Lys Val Pro Glu Met Ala Val Pro Asp Val
690 695 700

His Leu Pro Glu Val Gln Leu Pro Lys Val Cys Glu Met Lys Val Pro
705 710 715 720

Asp Met Lys Leu Pro Glu Ile Lys Leu Pro Lys Val Pro Glu Met Ala
725 730 735

Val Pro Asp Val His Leu Pro Glu Val Gln Leu Pro Lys Val Ser Glu
740 745 750

Ile Arg Leu Pro Glu Met Gln Val Pro Lys Val Pro Asp Val His Leu
755 760 765

Pro Lys Ala Pro Glu Val Lys Leu Pro Arg Ala Pro Glu Val Gln Leu
770 775 780

Lys Ala Thr Lys Ala Glu Gln Ala Glu Gly Met Glu Phe Gly Phe Lys
785 790 795 800

Met Pro Lys Met Thr Met Pro Lys Leu Gly Arg Ala Glu Ser Pro Ser
805 810 815

Arg Gly Lys Pro Gly Glu Ala Gly Ala Glu Val Ser Gly Lys Leu Val
820 825 830

Thr Leu Pro Cys Leu Gln Pro Glu Val Asp Gly Glu Ala His Val Gly
835 840 845

Val Pro Ser Leu Thr Leu Pro Ser Val Glu Leu Asp Leu Pro Gly Ala
850 855 860

Leu Gly Leu Gln Gly Gln Val Pro Ala Ala Lys Met Gly Lys Gly Glu
865 870 875 880

-continued

```
Arg Val Glu Gly Pro Glu Val Ala Ala Gly Val Arg Glu Val Gly Phe
                885                 890                 895

Arg Val Pro Ser Val Glu Ile Val Thr Pro Gln Leu Pro Ala Val Glu
            900                 905                 910

Ile Glu Glu Gly Arg Leu Glu Met Ile Glu Thr Lys Val Lys Pro Ser
        915                 920                 925

Ser Lys Phe Ser Leu Pro Lys Phe Gly Leu Ser Gly Pro Lys Val Ala
    930                 935                 940

Lys Ala Glu Ala Glu Gly Ala Gly Arg Ala Thr Lys Leu Lys Val Ser
945                 950                 955                 960

Lys Phe Ala Ile Ser Leu Pro Lys Ala Arg Val Gly Ala Glu Ala Glu
                965                 970                 975

Ala Lys Gly Ala Gly Glu Ala Gly Leu Leu Pro Ala Leu Asp Leu Ser
            980                 985                 990

Ile Pro Gln Leu Ser Leu Asp Ala  His Leu Pro Ser Gly  Lys Val Glu
        995                 1000                1005

Val Ala  Gly Ala Asp Leu Lys  Phe Lys Gly Pro Arg  Phe Ala Leu
    1010                1015                1020

Pro Lys  Phe Gly Val Arg Gly  Arg Asp Thr Glu Ala  Ala Glu Leu
    1025                1030                1035

Val Pro  Gly Val Ala Glu Leu  Glu Gly Lys Gly Trp  Gly Trp Asp
    1040                1045                1050

Gly Arg  Val Lys Met Pro Lys  Leu Lys Met Pro Ser  Phe Gly Leu
    1055                1060                1065

Ala Arg  Gly Lys Glu Ala Glu  Val Gln Gly Asp Arg  Ala Ser Pro
    1070                1075                1080

Gly Glu  Lys Ala Glu Ser Thr  Ala Val Gln Leu Lys  Ile Pro Glu
    1085                1090                1095

Val Glu  Leu Val Thr Leu Gly  Ala Gln Glu Glu Gly  Arg Ala Glu
    1100                1105                1110

Gly Ala  Val Ala Val Ser Gly  Met Gln Leu Ser Gly  Leu Lys Val
    1115                1120                1125

Ser Thr  Ala Arg Gln Val Val  Thr Glu Gly His Asp  Ala Gly Leu
    1130                1135                1140

Arg Met  Pro Pro Leu Gly Ile  Ser Leu Pro Gln Val  Glu Leu Thr
    1145                1150                1155

Gly Phe  Gly Glu Ala Gly Thr  Pro Gly Gln Gln Ala  Gln Ser Thr
    1160                1165                1170

Val Pro  Ser Ala Glu Gly Thr  Ala Gly Tyr Arg Val  Gln Val Pro
    1175                1180                1185

Gln Val  Thr Leu Ser Leu Pro  Gly Ala Gln Val Ala  Gly Gly Glu
    1190                1195                1200

Leu Leu  Val Gly Glu Gly Val  Phe Lys Met Pro Thr  Val Thr Val
    1205                1210                1215

Pro Gln  Leu Glu Leu Asp Val  Gly Leu Ser Arg Glu  Ala Gln Ala
    1220                1225                1230

Gly Glu  Ala Ala Thr Gly Glu  Gly Gly Leu Arg Leu  Lys Leu Pro
    1235                1240                1245

Thr Leu  Gly Ala Arg Ala Arg  Val Gly Gly Glu Gly  Ala Glu Glu
    1250                1255                1260

Gln Pro  Pro Gly Ala Glu Arg  Thr Phe Cys Leu Ser  Leu Pro Asp
    1265                1270                1275

Val Glu  Leu Ser Pro Ser Gly  Gly Asn His Ala Glu  Tyr Gln Val
```

-continued

```
    1280                1285                1290

Ala Glu  Gly Glu Gly Glu Ala  Gly His Lys Leu Lys  Val Arg Leu
    1295                1300                1305

Pro Arg  Phe Gly Leu Val Arg  Ala Lys Glu Gly Ala  Glu Glu Gly
    1310                1315                1320

Glu Lys  Ala Lys Ser Pro Lys  Leu Arg Leu Pro Arg  Val Gly Phe
    1325                1330                1335

Ser Gln  Ser Glu Met Val Thr  Gly Glu Gly Ser Pro  Ser Pro Glu
    1340                1345                1350

Glu Glu  Glu Glu Glu Glu Glu  Glu Gly Ser Gly Glu  Gly Ala Ser
    1355                1360                1365

Gly Arg  Arg Gly Arg Val Arg  Val Arg Leu Pro Arg  Val Gly Leu
    1370                1375                1380

Ala Ala  Pro Ser Lys Ala Ser  Arg Gly Gln Glu Gly  Asp Ala Ala
    1385                1390                1395

Pro Lys  Ser Pro Val Arg Glu  Lys Ser Pro Lys Phe  Arg Phe Pro
    1400                1405                1410

Arg Val  Ser Leu Ser Pro Lys  Ala Arg Ser Gly Ser  Gly Asp Gln
    1415                1420                1425

Glu Glu  Gly Gly Leu Arg Val  Arg Leu Pro Ser Val  Gly Phe Ser
    1430                1435                1440

Glu Thr  Gly Ala Pro Gly Pro  Ala Arg Met Glu Gly  Ala Gln Ala
    1445                1450                1455

Ala Ala  Val
    1460


<210> SEQ ID NO 89
<211> LENGTH: 147
<212> TYPE: PRT
<213> ORGANISM: Human

<400> SEQUENCE: 89

Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Ile
            20                  25                  30

Asn Val Ala Gly Gly Gly Lys Glu Gly Ile Phe Val Arg Glu Leu Arg
        35                  40                  45

Glu Asp Ser Pro Ala Ala Arg Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Ile Lys Gly Pro Arg Ala Lys Val Ala Lys Leu Val
        115                 120                 125

Arg Val Leu Ser Pro Ala Pro Ala Leu Asp Cys Pro Ser Asp Pro Val
    130                 135                 140

Ser Ala Pro
145


<210> SEQ ID NO 90
<211> LENGTH: 370
```

-continued

<212> TYPE: PRT
<213> ORGANISM: Arabidopsisthaliana

<400> SEQUENCE: 90

```
Met Ala Leu Met Lys Lys Ser Leu Ser Ala Ala Leu Leu Ser Ser Pro
1               5                   10                  15

Leu Leu Ile Ile Cys Leu Ile Ala Leu Leu Ala Asp Pro Phe Ser Val
            20                  25                  30

Gly Ala Arg Arg Leu Leu Glu Asp Pro Lys Pro Glu Ile Pro Lys Leu
        35                  40                  45

Pro Glu Leu Pro Lys Phe Glu Val Pro Lys Leu Pro Glu Phe Pro Lys
    50                  55                  60

Pro Glu Leu Pro Lys Leu Pro Glu Phe Pro Lys Pro Glu Leu Pro Lys
65                  70                  75                  80

Ile Pro Glu Ile Pro Lys Pro Glu Leu Pro Lys Val Pro Glu Ile Pro
                85                  90                  95

Lys Pro Glu Glu Thr Lys Leu Pro Asp Ile Pro Lys Leu Glu Leu Pro
            100                 105                 110

Lys Phe Pro Glu Ile Pro Lys Pro Glu Leu Pro Lys Met Pro Glu Ile
        115                 120                 125

Pro Lys Pro Glu Leu Pro Lys Val Pro Glu Ile Gln Lys Pro Glu Leu
    130                 135                 140

Pro Lys Met Pro Glu Ile Pro Lys Pro Glu Leu Pro Lys Phe Pro Glu
145                 150                 155                 160

Ile Pro Lys Pro Asp Leu Pro Lys Phe Pro Glu Asn Ser Lys Pro Glu
                165                 170                 175

Val Pro Lys Leu Met Glu Thr Glu Lys Pro Glu Ala Pro Lys Val Pro
            180                 185                 190

Glu Ile Pro Lys Pro Glu Leu Pro Lys Leu Pro Glu Val Pro Lys Leu
        195                 200                 205

Glu Ala Pro Lys Val Pro Glu Ile Gln Lys Pro Glu Leu Pro Lys Met
    210                 215                 220

Pro Glu Leu Pro Lys Met Pro Glu Ile Gln Lys Pro Glu Leu Pro Lys
225                 230                 235                 240

Leu Pro Glu Val Pro Lys Leu Glu Ala Pro Lys Val Pro Glu Ile Gln
                245                 250                 255

Lys Pro Glu Leu Pro Lys Met Pro Glu Leu Pro Lys Met Pro Glu Ile
            260                 265                 270

Gln Lys Pro Glu Leu Pro Lys Met Pro Glu Ile Gln Lys Pro Glu Leu
        275                 280                 285

Pro Lys Val Pro Glu Val Pro Lys Pro Glu Leu Pro Thr Val Pro Glu
    290                 295                 300

Val Pro Lys Ser Glu Ala Pro Lys Phe Pro Glu Ile Pro Lys Pro Glu
305                 310                 315                 320

Leu Pro Lys Ile Pro Glu Val Pro Lys Pro Glu Leu Pro Lys Val Pro
                325                 330                 335

Glu Ile Thr Lys Pro Ala Val Pro Glu Ile Pro Lys Pro Glu Leu Pro
            340                 345                 350

Thr Met Pro Gln Leu Pro Lys Leu Pro Glu Phe Pro Lys Val Pro Gly
        355                 360                 365

Thr Pro
    370
```

<210> SEQ ID NO 91

-continued

```
<211> LENGTH: 370
<212> TYPE: PRT
<213> ORGANISM: Arabidopsisthaliana

<400> SEQUENCE: 91

Met Ala Leu Met Lys Lys Ser Leu Ser Ala Ala Leu Leu Ser Ser Pro
1               5                   10                  15

Leu Leu Ile Ile Cys Leu Ile Ala Leu Leu Ala Asp Pro Phe Ser Val
            20                  25                  30

Gly Ala Arg Arg Leu Leu Glu Asp Pro Lys Pro Glu Ile Pro Lys Leu
        35                  40                  45

Pro Glu Leu Pro Lys Phe Glu Val Pro Lys Leu Pro Glu Phe Pro Lys
    50                  55                  60

Pro Glu Leu Pro Lys Leu Pro Glu Phe Pro Lys Pro Glu Leu Pro Lys
65                  70                  75                  80

Ile Pro Glu Ile Pro Lys Pro Glu Leu Pro Lys Val Pro Glu Ile Pro
                85                  90                  95

Lys Pro Glu Glu Thr Lys Leu Pro Asp Ile Pro Lys Leu Glu Leu Pro
            100                 105                 110

Lys Phe Pro Glu Ile Pro Lys Pro Glu Leu Pro Lys Met Pro Glu Ile
        115                 120                 125

Pro Lys Pro Glu Leu Pro Lys Val Pro Glu Ile Gln Lys Pro Glu Leu
    130                 135                 140

Pro Lys Met Pro Glu Ile Pro Lys Pro Glu Leu Pro Lys Phe Pro Glu
145                 150                 155                 160

Ile Pro Lys Pro Asp Leu Pro Lys Phe Pro Glu Asn Ser Lys Ser Glu
                165                 170                 175

Val Pro Lys Leu Met Glu Thr Glu Lys Pro Glu Ala Pro Lys Val Pro
            180                 185                 190

Glu Ile Pro Lys Pro Glu Leu Pro Lys Leu Pro Glu Val Pro Lys Leu
        195                 200                 205

Glu Ala Pro Lys Val Pro Glu Ile Gln Lys Pro Glu Leu Pro Lys Met
    210                 215                 220

Pro Glu Leu Pro Lys Met Pro Glu Ile Gln Lys Pro Glu Leu Pro Lys
225                 230                 235                 240

Leu Pro Glu Val Pro Lys Leu Glu Ala Pro Lys Val Pro Glu Ile Gln
                245                 250                 255

Lys Pro Glu Leu Pro Lys Met Pro Glu Leu Pro Lys Met Pro Glu Ile
            260                 265                 270

Gln Lys Pro Glu Leu Pro Lys Met Pro Glu Ile Gln Lys Pro Glu Leu
        275                 280                 285

Pro Lys Val Pro Glu Val Pro Lys Pro Glu Leu Pro Thr Val Pro Glu
    290                 295                 300

Val Pro Lys Ser Glu Ala Pro Lys Phe Pro Glu Ile Pro Lys Pro Glu
305                 310                 315                 320

Leu Pro Lys Ile Pro Glu Val Pro Lys Pro Glu Leu Pro Lys Val Pro
                325                 330                 335

Glu Ile Thr Lys Pro Ala Val Pro Glu Ile Pro Lys Pro Glu Leu Pro
            340                 345                 350

Thr Met Pro Gln Leu Pro Lys Leu Pro Glu Phe Pro Lys Val Pro Gly
        355                 360                 365

Thr Pro
    370
```

-continued

<210> SEQ ID NO 92
<211> LENGTH: 147
<212> TYPE: PRT
<213> ORGANISM: Human

<400> SEQUENCE: 92

```
Met Glu Ala Arg Ser Arg Ser Ala Glu Glu Leu Arg Arg Ala Glu Leu
1               5                   10                  15

Val Glu Ile Ile Val Glu Thr Glu Ala Gln Thr Gly Val Ser Gly Ile
            20                  25                  30

Asn Val Ala Gly Gly Gly Lys Glu Gly Ile Phe Val Arg Glu Leu Arg
        35                  40                  45

Glu Asp Ser Pro Ala Ala Arg Ser Leu Ser Leu Gln Glu Gly Asp Gln
    50                  55                  60

Leu Leu Ser Ala Arg Val Phe Phe Glu Asn Phe Lys Tyr Glu Asp Ala
65                  70                  75                  80

Leu Arg Leu Leu Gln Cys Ala Glu Pro Tyr Lys Val Ser Phe Cys Leu
                85                  90                  95

Lys Arg Thr Val Pro Thr Gly Asp Leu Ala Leu Arg Pro Gly Thr Val
            100                 105                 110

Ser Gly Tyr Glu Ile Lys Gly Pro Arg Ala Lys Val Ala Lys Leu Val
        115                 120                 125

Arg Val Leu Ser Pro Ala Pro Ala Leu Asp Cys Pro Ser Asp Pro Val
    130                 135                 140

Ser Ala Pro
145
```

<210> SEQ ID NO 93
<211> LENGTH: 214
<212> TYPE: PRT
<213> ORGANISM: Human

<400> SEQUENCE: 93

```
Met Glu Leu Leu Gly Glu Gly Ala Ile Leu Gln Gly Arg Arg Glu Ser
1               5                   10                  15

Gln Met Glu Ala Ala Pro Gly Ile Gln Thr Cys Gly His Ser Ala Glu
            20                  25                  30

Leu Pro Ser Gln Gly Met Gly Arg Thr Arg Ala Glu Arg Ala Thr Ser
        35                  40                  45

Pro Val Arg Pro Ser Ile Thr Trp Lys Ile Gly Ser Pro Lys Val Asp
    50                  55                  60

Gly Arg His Thr Pro Met Pro Phe Pro Ser Val Ser Thr Gly Glu Gly
65                  70                  75                  80

Lys Ser Thr Leu Trp Ile Leu Tyr Leu His Cys Phe Gly Ser Arg Lys
                85                  90                  95

Ser Pro Asp Phe Ser Thr Pro Pro Arg Glu Pro Lys Ser Gln Gly Met
            100                 105                 110

Leu Lys Glu Gln Ala Arg Lys Met Arg Gly Gln Arg Gly Gly Arg Glu
        115                 120                 125

Gly Ala Lys Gly Thr Leu Lys Thr Gln Arg Pro Pro Ser Lys Asp Gln
    130                 135                 140

Ala Pro Leu Ala His Gly Pro Arg Glu Lys Gln Val Pro Ala Asp Glu
145                 150                 155                 160

Ser Phe Leu Gln Lys Pro Arg Leu Pro Asp Leu Val Lys Gln Gln Pro
                165                 170                 175

Asn Arg Ser Leu Ser Thr Asn Val Arg Gly Ala Glu Pro Ser Pro Ser
```

-continued

```
        180                 185                 190

Leu Ala Thr Glu Leu Val Leu Lys Lys Leu Val Pro Ala Ser Thr Cys
        195                 200                 205

Gln Glu Leu Pro Lys Thr
    210
```